(12) United States Patent
Mueller et al.

(10) Patent No.: US 7,625,886 B2
(45) Date of Patent: *Dec. 1, 2009

(54) SELECTED CGRP ANTAGONISTS, PROCESSES FOR PREPARING THEM AND THEIR USE AS PHARMACEUTICAL COMPOSITIONS

(75) Inventors: Stephan Georg Mueller, Warthausen (DE); Klaus Rudolf, Warthausen (DE); Philipp Lustenberger, Basel (CH); Gerhard Schaenzle, Biberach (DE); Dirk Stenkamp, Biberach (DE); Henri Doods, Warthausen (DE); Kirsten Arndt, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/550,979

(22) Filed: Oct. 19, 2006

(65) Prior Publication Data

US 2007/0099903 A1 May 3, 2007

(30) Foreign Application Priority Data

Oct. 21, 2005 (DE) ........................ 10 2005 050 892

(51) Int. Cl.
*C07D 243/10* (2006.01)
*A61K 31/551* (2006.01)
(52) U.S. Cl. .................. 514/211.05; 540/500
(58) Field of Classification Search ................. 540/500; 514/211.05
See application file for complete search history.

(56) References Cited

U.S. PATENT DOCUMENTS

| 6,344,449 | B1 | 2/2002 | Rudolf et al. |
| 6,521,609 | B1 | 2/2003 | Doods et al. |
| 7,479,488 | B2 | 1/2009 | Mueller et al. |
| 7,491,717 | B2 | 2/2009 | Mueller et al. |
| 7,439,237 | B2 | 4/2009 | Rudolf et al. |
| 2004/0192729 | A1 | 9/2004 | Rudolf et al. |
| 2005/0227968 | A1 | 10/2005 | Lustenberger et al. |
| 2006/0079504 | A1 | 4/2006 | Rudolf et al. |
| 2006/0252931 | A1 | 11/2006 | Mueller et al. |
| 2007/0244099 | A1 | 10/2007 | Rudolf et al. |

FOREIGN PATENT DOCUMENTS

| CA | 2503455 A1 | 5/2004 |
| CA | 2503462 A1 | 5/2004 |
| CA | 2558889 A1 | 10/2005 |
| CA | 2562526 A1 | 10/2005 |
| CA | 2565219 A1 | 11/2005 |
| WO | WO 01/32649 | * 5/2001 |
| WO | 2004037810 A1 | 5/2004 |
| WO | 2004037811 A1 | 5/2004 |
| WO | 2004063171 A1 | 7/2004 |
| WO | 2005084672 A1 | 9/2005 |
| WO | 2005092880 A1 | 10/2005 |
| WO | 2005100343 A1 | 10/2005 |
| WO | 2005103037 A2 | 11/2005 |
| WO | 2006100009 A1 | 9/2006 |

OTHER PUBLICATIONS

Silverman, R.B. The Organic Chemistry of Drug Design and Drug Action 1992, Academic: New York, p. 19.*
Mueller et al.; Selected CGRP-antagonists, process for preparing them and their use as pharmaceutical compositions; U.S. Appl. No. 12/246,067, filed Oct. 6, 2008.
Mueller et al.; New CGRP-antagonists, process for preparing them and their use as pharmaceutical compositions; U.S. Appl. No. 12/363,175, filed on Jan. 30, 2009.
Mueller et al.; Selected CGRP-antagonists, process for preparing them and their use as pharmaceutical compositions; U.S. Appl. No. 12/186,005, filed Aug. 5, 2008.

* cited by examiner

*Primary Examiner*—Rita J Desai
*Assistant Examiner*—David K O'Dell
(74) *Attorney, Agent, or Firm*—Michael P. Morris; Mary-Ellen M. Devlin; Alan R. Stempel

(57) ABSTRACT

The present invention relates to the CGRP antagonists of general formula I

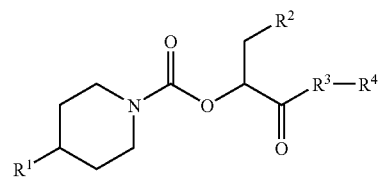

wherein $R^1$, $R^2$, $R^3$ and $R^4$ are defined as in claim 1, the tautomers, the isomers, the diastereomers, the enantiomers, the hydrates thereof, the mixtures thereof and the salts thereof and the hydrates of the salts thereof, particularly the physiologically acceptable salts thereof with inorganic or organic acids or bases, as well as those compounds of general formula I wherein one or more hydrogen atoms are replaced by deuterium, pharmaceutical compositions containing these compounds, their use and processes for preparing them.

3 Claims, No Drawings

SELECTED CGRP ANTAGONISTS, PROCESSES FOR PREPARING THEM AND THEIR USE AS PHARMACEUTICAL COMPOSITIONS

The present invention relates to the CGRP antagonists of general formula I

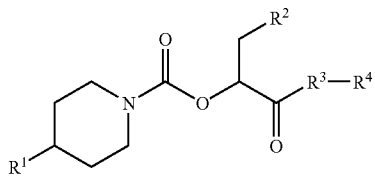

wherein $R^1$, $R^2$, $R^3$ and $R^4$ are as defined herein, the tautomers, the isomers, the diastereomers, the enantiomers, the hydrates thereof, the mixtures thereof and the salts thereof and the hydrates of the salts thereof, particularly the physiologically acceptable salts thereof with inorganic or organic acids or bases, as well as those compounds of general formula I wherein one or more hydrogen atoms are replaced by deuterium, pharmaceutical compositions containing these compounds, their use and processes for preparing them.

PRIOR ART

CGRP antagonists for the treatment of migraine have already been described in International Patent Applications PCT/EP97/04862 and PCT/EP03/11762.

DETAILED DESCRIPTION OF THE INVENTION

In the above general formula I in a first embodiment $R^1$ denotes a group selected from

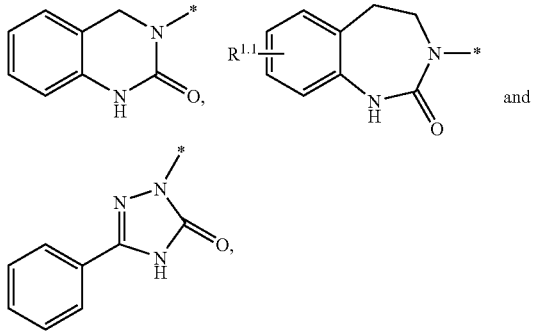

wherein
$R^{1.1}$ denotes H or $H_3C\text{---}O\text{---}$,
$R^2$ denotes a group selected from

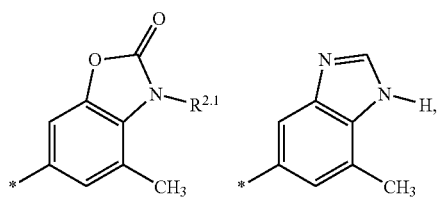

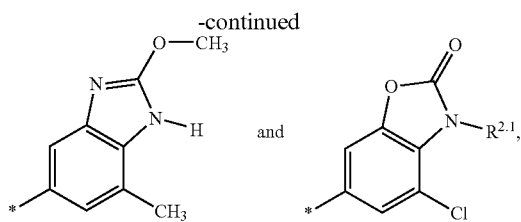

wherein
$R^{2.1}$ denotes H or $H_3C\text{---}$,
$R^3$ denotes a group of general formulae II

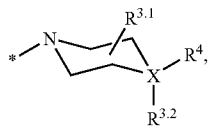

wherein
x denotes N or C,
$R^{3.1}$ denotes H or $C_{1-3}$-alkyl,
$R^{3.2}$ denotes a free pair of electrons, if X=N, or
$R^{3.2}$ denotes H or $C_{1-3}$-alkyl, if X=C,
$R^4$ denotes phenyl or
$R^4$ denotes a group of general formulae III

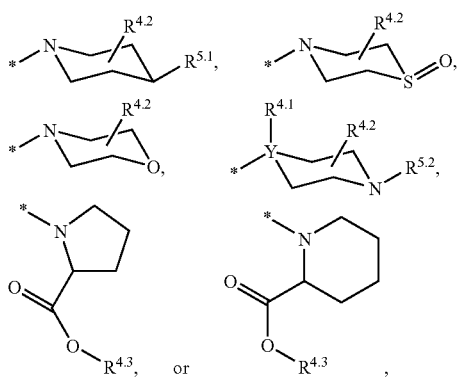

wherein
Y denotes C and
$R^{4.1}$ denotes H or $C_{1-3}$-alkyl, or
Y denotes N and
$R^{4.1}$ denotes a free pair of electrons,
with the proviso that X and Y do not simultaneously represent N,
$R^{4.2}$ denotes H or $C_{1-3}$-alkyl,
$R^{4.3}$ denotes H, $C_{1-6}$-alkyl, $H_2N\text{---}C_{2-4}$-alkylene, $(C_{1-3}$-alkyl)$\text{---}NH\text{---}C_{2-4}$-alkylene, $(C_{1-3}$-alkyl)$_2N\text{---}C_{2-4}$-alkylene, $H_2N\text{---}C(O)\text{---}C_{1-3}$-alkylene, $(C_{1-3}$-alkyl)$\text{---}NH\text{---}C(O)\text{---}C_{1-3}$-alkylene, $(C_{1-3}$-alkyl)$_2\text{-}N\text{---}C(O)\text{---}C_{1-3}$-alkylene, $C_{1-3}$-alkyl-$O\text{---}C(O)\text{---}C_{1-3}$-alkylene-O or $R^{4.3.1}\text{---}C_{2-4}$-alkylene, $R^{4.3.1}$ denotes a group selected from

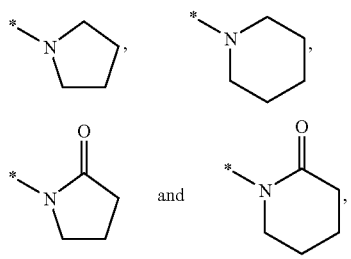

$R^{5.1}$ denotes $C_{1-6}$-alkyl, $C_{1-6}$-alkyl-O, $C_{1-6}$-alkyl-C(O)—O, $R^{5.1.1}$—O—C(O), $R^{5.1.1}$—O—C(O)—$C_{1-3}$-alkylene-NH, $R^{5.1.1}$—O—C(O)—$C_{1-3}$-alkylene-O, $R^{5.1.1}$—O—C(O)—$C_{1-3}$-alkylene, $R^{5.1.1}$—O—C(O)—C(O) or $R^{5.1.1}$—O—C(O)—$C_{1-3}$-alkylene-C(O), $R^{5.1.1}$ denotes H, $C_{1-8}$-alkyl, phenyl, indanyl, pyridyl-$C_{1-3}$-alkylene, HO—$C_{2-4}$-alkylene, $C_{1-6}$-alkyl-O—$C_{2-4}$-alkylene, $H_2N$—$C_{2-4}$-alkylene, $(C_{1-6}$-alkyl)—NH—$C_{2-4}$-alkylene, $(C_{1-6}$-alkyl)$_2$-N—$C_{2-4}$-alkylene, $H_2N$—C(O)—$C_{1-3}$-alkylene, $(C_{1-6}$-alkyl)—NH—C(O)—$C_{1-3}$-alkylene, $(C_{1-6}$-alkyl)$_2$-N—C(O)—$C_{1-3}$-alkylene, $C_{1-6}$-alkyl-C(O)—O—$C_{1-3}$-alkylene, $C_{1-6}$-alkyl-O—C(O)—O—$C_{1-3}$-alkylene, $R^{5.1.1.1}$—C(O)—$C_{1-3}$-alkylene or $R^{5.1.1.2}$—$C_{2-4}$-alkylene, $R^{5.1.1.1}$ denotes a group selected from

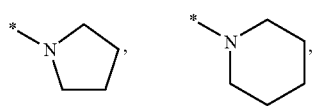

$R^{5.1.1.2}$ denotes a group selected from

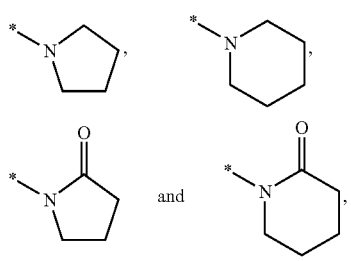

$R^{5.2.1}$ denotes $R^{5.2.1}$—O—C(O)—$C_{1-3}$-alkylene, $R^{5.2.1}$—O—C(O)—C(O), $R^{5.2.1}$—O—C(O)—$C_{1-3}$-alkylene-C(O) or $R^{5.2.1}$—C(O), $R^{5.2.1}$ denotes H, $C_{1-8}$-alkyl, phenyl, indanyl, pyridyl-$C_{1-3}$-alkylene, HO—$C_{2-4}$-alkylene, $C_{1-6}$-alkyl-O—$C_{2-4}$-alkylene, $H_2N$—$C_{2-4}$-alkylene, $(C_{1-6}$-alkyl)—NH—$C_{2-4}$-alkylene, $(C_{1-6}$-alkyl)$_2N$—$C_{2-4}$-alkylene, $H_2N$—C(O)—$C_{1-3}$-alkylene, $(C_{1-6}$-alkyl)—NH—C(O)—$C_{1-3}$-alkylene, $(C_{1-6}$-alkyl)$_2N$—C(O)—$C_{1-3}$-alkylene, $C_{1-6}$-alkyl-C(O)—O—$C_{1-3}$-alkylene, $C_{1-6}$-alkyl-O—C(O)—O—$C_{1-3}$-alkylene, $R^{5.2.1.1}$—C(O)—$C_{1-3}$-alkylene or $R^{5.2.1}$—$_{2-4}$-alkylene, $R^{5.2.1.1}$ denotes a group selected from

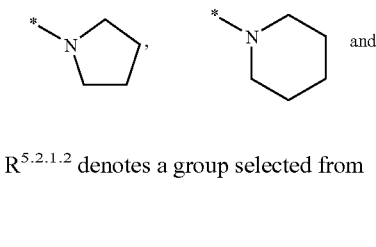

$R^{5.2.1.2}$ denotes a group selected from

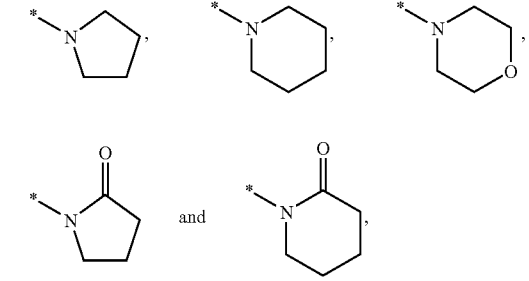

the tautomers, the diastereomers, the enantiomers, the hydrates thereof, the mixtures thereof and the salts thereof as well as the hydrates of the salts, particularly the physiologically acceptable salts thereof with inorganic or organic acids or bases.

A second embodiment of the present invention comprises those compounds of the above general formula I, wherein $R^1$ denotes a group selected from

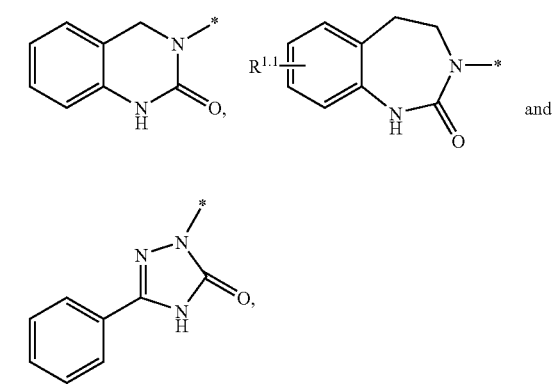

wherein $R^{1.1}$ denotes H or $H_3C$—O—, $R^2$ denotes a group selected from

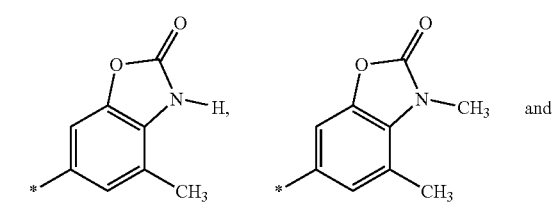

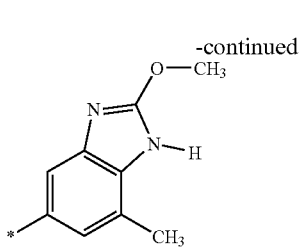

R³-R⁴ together denote a group of general formulae IV

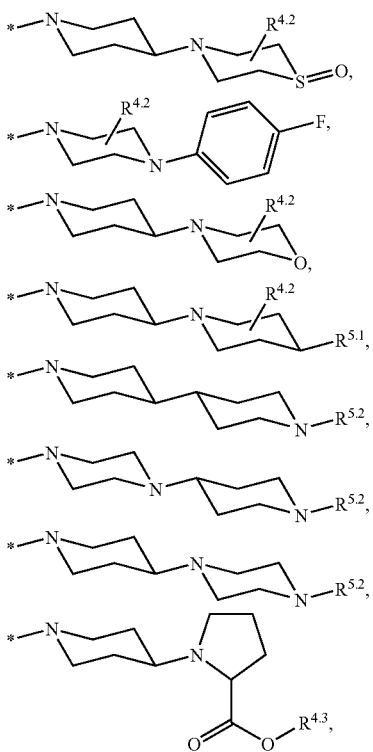

wherein

R$^{4.2}$ denotes H or H₃C,

R$^{4.3}$ denotes H, C$_{1-6}$-alkyl, H₂N—C$_{2-4}$-alkylene, (C$_{1-3}$-alkyl)—NH—C$_{2-4}$-alkylene, (C$_{1-3}$-alkyl)₂N—C$_{2-4}$-alkylene, H₂N—C(O)—C$_{1-3}$-alkylene, (C$_{1-3}$-alkyl)—NH—C(O)—C$_{1-3}$-alkylene, (C$_{1-3}$-alkyl)₂N—C(O)—C$_{1-3}$-alkylene or R$^{4.3.1}$—C$_{2-4}$-alkylene, R$^{4.3.1}$ denotes a group selected from

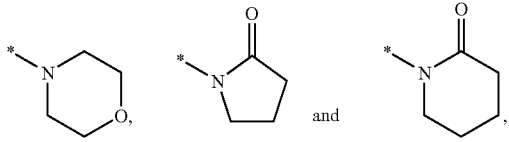

R$^{5.1}$ denotes C$_{1-3}$-alkyl, C$_{1-3}$-alkyl-O, C$_{1-3}$-alkyl-C(O)—O or R$^{5.1.1}$—O—C(O), R$^{5.1.1}$—O—C(O)—C$_{1-3}$-alkylene-NH, R$^{5.1.1}$—O—C(O)—C$_{1-3}$-alkylene-O or R$^{5.1.1}$—O—C(O)—C$_{1-3}$-alkylene, R$^{5.1.1}$ denotes H, C$_{1-8}$-alkyl, phenyl, indanyl, pyridyl-C$_{1-3}$-alkylene, HO—C$_{2-4}$-alkylene, C$_{1-3}$-alkyl-O—C$_{2-4}$-alkylene, (C$_{1-3}$-alkyl)₂N—C$_{2-4}$-alkylene, (C$_{1-3}$-alkyl)₂N—C(O)—C$_{1-3}$-alkylene, C$_{1-3}$-alkyl-C(O)—O—C$_{1-3}$-alkylene, C$_{1-3}$-alkyl-O—C(O)—O—C$_{1-3}$-alkylene, R$^{5.1.1.1}$—C(O)—C$_{1-3}$-alkylene or R$^{5.1.1.2}$—C$_{2-4}$-alkylene, R$^{5.1.1.1}$ denotes a group selected from

R$^{5.1.1.2}$ denotes a group selected from

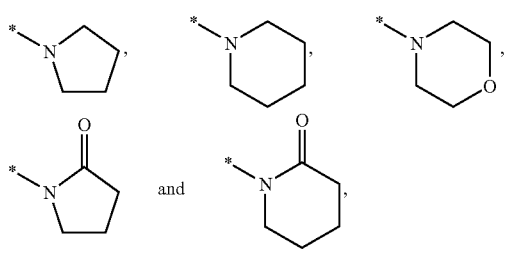

R$^{5.2}$ denotes C$_{1-3}$-alkyl-C(O), R$^{5.2.1}$—O—C(O)—C$_{1-3}$-alkylene, R$^{5.2.1}$—O—C(O)—C(O) or R$^{5.2.1}$—O—C(O)—C$_{1-3}$-alkylene-C(O), R$^{5.2.1}$ denotes H, C$_{1-8}$-alkyl, phenyl, indanyl, pyridyl-C$_{1-3}$-alkylene, HO—C$_{2-4}$-alkylene, C$_{1-3}$-alkyl-O—C$_{2-4}$-alkylene, (C$_{1-3}$-alkyl)₂N—C$_{2-4}$-alkylene, (C$_{1-3}$-alkyl)₂N—C(O)—C$_{1-3}$-alkylene, C$_{1-3}$-alkyl-C(O)—O—C$_{1-3}$-alkylene, C$_{1-3}$-alkyl-O—C(O)—O—C$_{1-3}$-alkylene, R$^{5.2.1.1}$—C(O)—C$_{1-3}$-alkylene or R$^{5.2.1.2}$—C$_{2-4}$-alkylene, R$^{5.2.1.1}$ denotes a group selected from

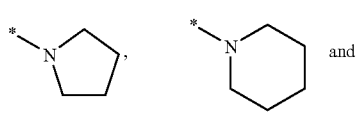

R$^{5.2.1.2}$ denotes a group selected from

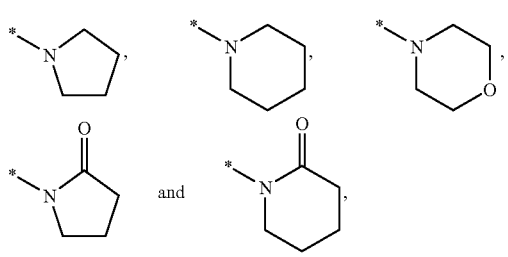

the tautomers, the diastereomers, the enantiomers, the hydrates thereof, the mixtures thereof and the salts thereof as well as the hydrates of the salts, particularly the physiologically acceptable salts thereof with inorganic or organic acids or bases.

A third embodiment of the present invention comprises those compounds of the above general formula I wherein R¹ denotes a group selected from

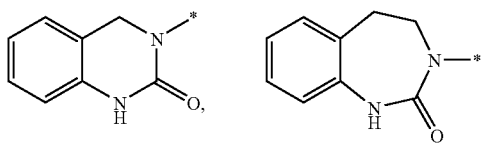

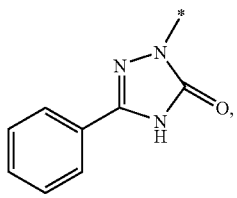

$R^2$ denotes a group selected from

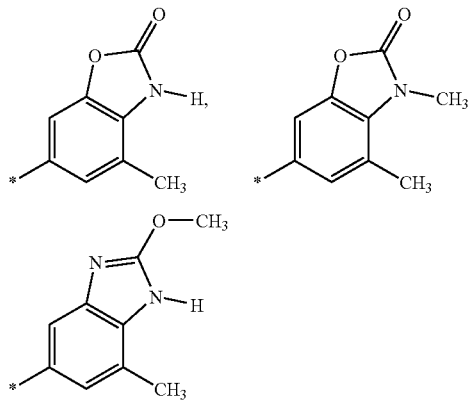

$R^3$-$R^4$ together denote a group of general formulae IV

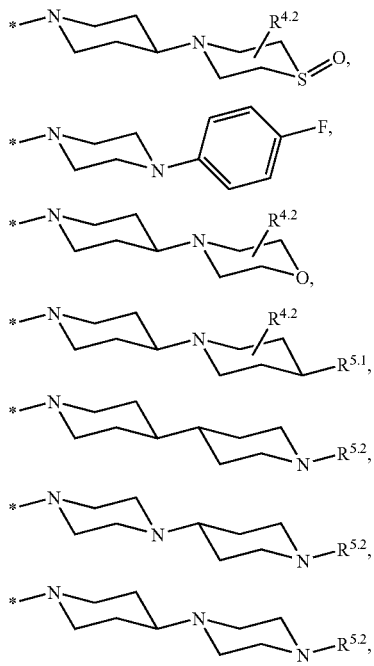

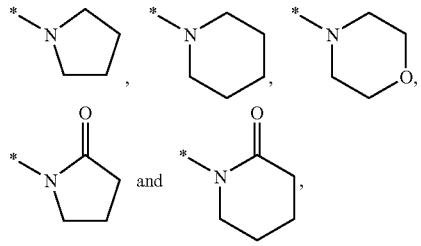

wherein
$R^{4.2}$ denotes H or $H_3C$,
$R^{4.3}$ denotes H, $C_{1-6}$-alkyl, $(C_{1-3}$-alkyl$)_2$N—$C_{2-4}$-alkylene, $(C_{1-3}$-alkyl$)_2$N—C(O)—$C_{1-3}$-alkylene or $R^{4.3.1}$—$C_{2-4}$-alkylene,
$R^{4.3.1}$ denotes a group selected from

[morpholine and pyrrolidinone structures]

$R^{5.1}$ denotes $R^{5.1.1}$—O—C(O) or $R^{5.1.1}$—O—C(O)—$C_{1-3}$-alkylene,
$R^{5.1.1}$ denotes H, $C_{1-8}$-alkyl, phenyl, indanyl, pyridyl-$C_{1-3}$-alkylene, HO—$C_{2-4}$-alkylene, $C_{1-6}$-alkyl-O—$C_{2-4}$-alkylene, $H_2N$—$C_{2-4}$-alkylene, $(C_{1-6}$-alkyl)—NH—$C_{2-4}$-alkylene, $(C_{1-6}$-alkyl$)_2$N—$C_{2-4}$-alkylene, $H_2N$—C(O)—$C_{1-3}$-alkylene, $(C_{1-6}$-alkyl)—NH—C(O)—$C_{1-3}$-alkylene, $(C_{1-6}$-alkyl$)_2$N—C(O)—$C_{1-3}$-alkylene, $C_{1-6}$-alkyl-C(O)—O—$C_{1-3}$-alkylene, $C_{1-6}$-alkyl-O—C(O)—O—$C_{1-3}$-alkylene, $R^{5.1.1.1}$—C(O)—$C_{1-3}$-alkylene or $R^{5.1.1.2}$—$C_{2-4}$-alkylene,
$R^{5.1.1.1}$ denotes a group selected from

[pyrrolidine and piperidine structures]

$R^{5.1.1.2}$ denotes a group selected from

[pyrrolidine, piperidine, morpholine, pyrrolidinone, piperidinone structures]

$R^{5.2.1}$ denotes $R^{5.2.1}$—O—C(O)—$C_{1-3}$-alkylene, $R^{5.2.1}$—O—C(O)—C(O) or $R^{5.2.1}$—O—C(O)—$C_{1-3}$-alkylene-C(O),
$R^{5.2.1}$ denotes H, $C_{1-8}$-alkyl, phenyl, indanyl, pyridyl-$C_{1-3}$-alkylene, HO—$C_{2-4}$-alkylene, $C_{1-6}$-alkyl-O—$C_{2-4}$-alkylene, $H_2N$—$C_{2-4}$-alkylene, $(C_{1-6}$-alkyl)—NH—$C_{2-4}$-alkylene, $(C_{1-6}$-alkyl$)_2$N—$C_{2-4}$-alkylene, $H_2N$—C(O)—$C_{1-3}$-alkylene, $(C_{1-6}$-alkyl)—NH—C(O)—$C_{1-3}$-alkylene, $(C_{1-6}$-alkyl$)_2$N—C(O)—$C_{1-3}$-alkylene, $C_{1-6}$-alkyl-C(O)—O—$C_{1-3}$-alkylene, $C_{1-6}$-alkyl-O—C (O)—O—$C_{1-3}$-alkylene, $R^{5.2.1.1}$—C(O)—$C_{1-3}$-alkylene or $R^{5.2.1.2}$—$C_{2-4}$-alkylene, $R^{5.2.1.1}$ denotes a group selected from

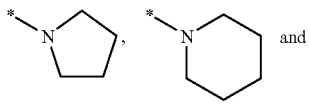

$R^{5.2.1.2}$ denotes a group selected from

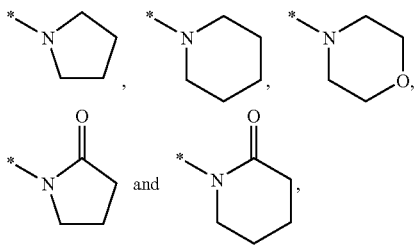

the tautomers, the diastereomers, the enantiomers, the hydrates thereof, the mixtures thereof and the salts thereof as well as the hydrates of the salts, particularly the physiologically acceptable salts thereof with inorganic or organic acids or bases.

A fourth embodiment of the present invention comprises those compounds of the above general formula I wherein $R^1$ denotes a group

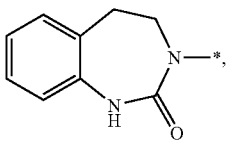

$R^2$ denotes a group selected from

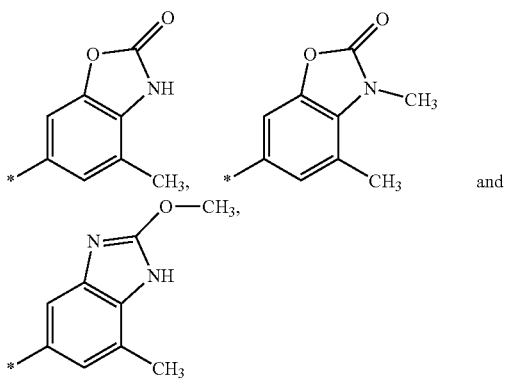

$R^3$-$R^4$ together denote a group selected from

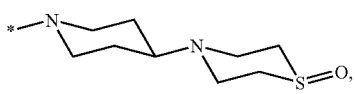

-continued

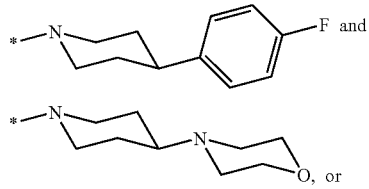

$R^3$-$R^4$ together denote a group of general formulae IV

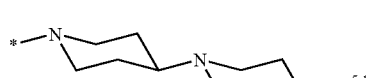

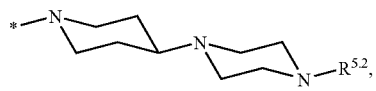

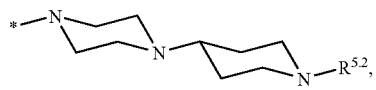

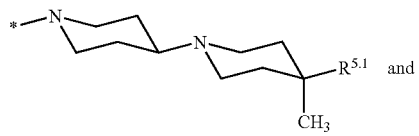

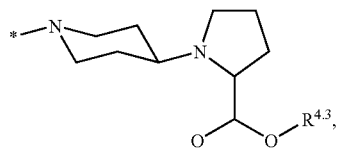

wherein
$R^{4.3}$ denotes H, $C_{1-6}$-alkyl, $(H_3C)_2N$—$C_{2-3}$-alkylene, $(H_3C)_2N$—C(O)—$C_{1-2}$-alkylene, $C_{1-2}$-alkyl-O—C(O)—O—$C_{2-3}$-alkylene or $R^{4.3.1}$—$C_{2-3}$-alkylene, $R^{4.3.1}$ denotes a group selected from

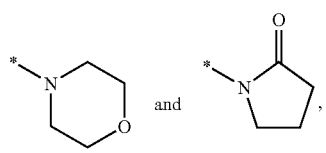

$R^{5.1}$ denotes $H_3C$, $H_3C$—O, $C_{1-2}$-alkyl-C(O)—O, $R^{5.1.1}$—O—C(O), $R^{5.1.1}$ denotes H, $C_{1-6}$-alkyl, $(H_3C)_2N$—$C_{2-3}$-alkylene, $(H_3C)_2N$—C(O)—$C_{1-2}$-alkylene, $C_{1-2}$-alkyl-O—C(O)—O—$C_{1-2}$-alkylene or $R^{5.1.1.1}$—$C_{2-3}$-alkylene, $R^{5.1.1.1}$ denotes a group selected from

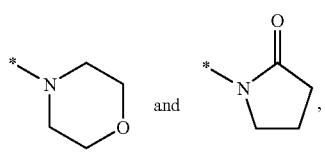

and

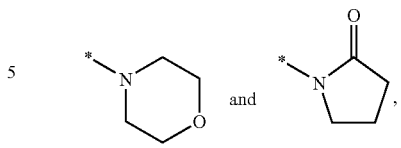

$R^{5.2}$ denotes $H_3C-C(O)$, $R^{5.2.1}-O-C(O)-C_{1-2}$-alkylene, $R^{5.2.1}-O-C(O)-C(O)$ or $R^{5.2.1}-O-C(O)-C_{1-2}$-alkylene-$C(O)$, $R^{5.2.1}$ denotes H, $C_{1-6}$-alkyl, $(H_3C)_2N-C_{2-3}$-alkylene, $(H_3C)_2N-C(O)-C_{1-2}$-alkylene, $C_{1-2}$-alkyl-$O-C(O)-O-C_{1-2}$-alkylene or $R^{5.2.1.1}-C_{2-3}$-alkylene, $R^{5.2.1.1}$ denotes a group selected from the tautomers, the diastereomers, the enantiomers, the hydrates thereof, the mixtures thereof and the salts thereof as well as the hydrates of the salts, particularly the physiologically acceptable salts thereof with inorganic or organic acids or bases.

The following compounds are also mentioned as examples of most particularly preferred compounds of the above general formula I:

| No. | Structure |
|---|---|
| (1) | 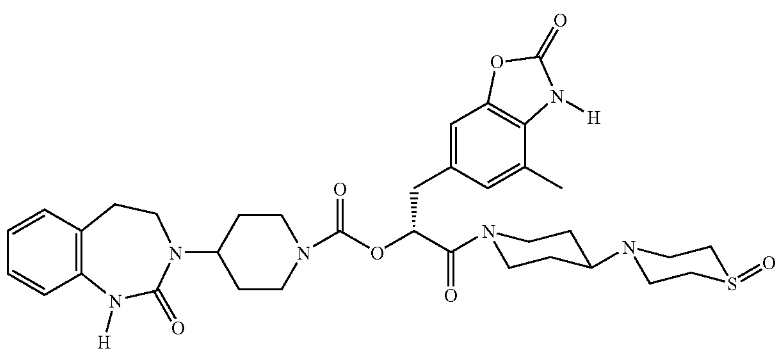 |
| (2) | 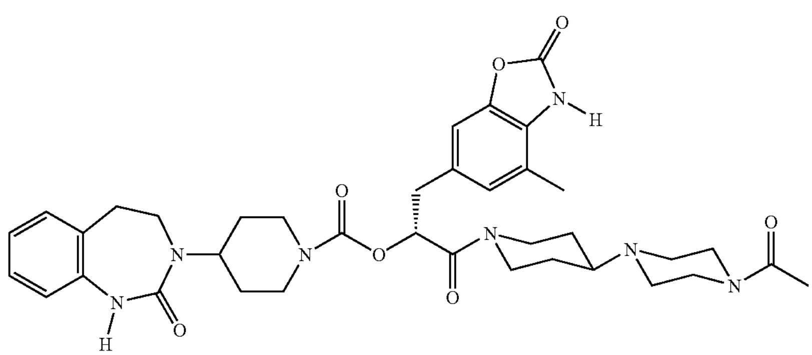 |
| (3) | 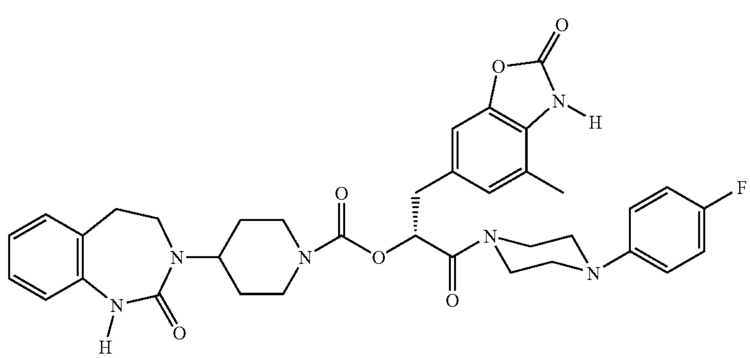 |

-continued
| No. | Structure |
|---|---|
| (4) | 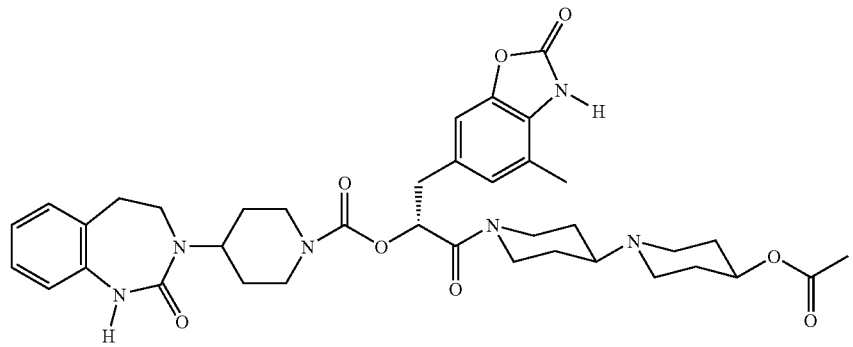 |
| (5) | 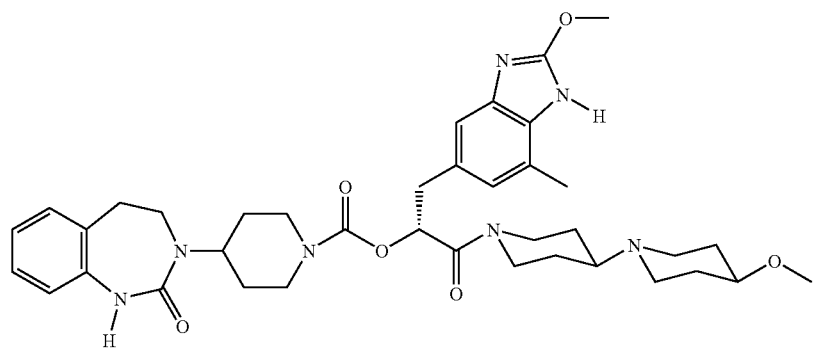 |
| (6) | 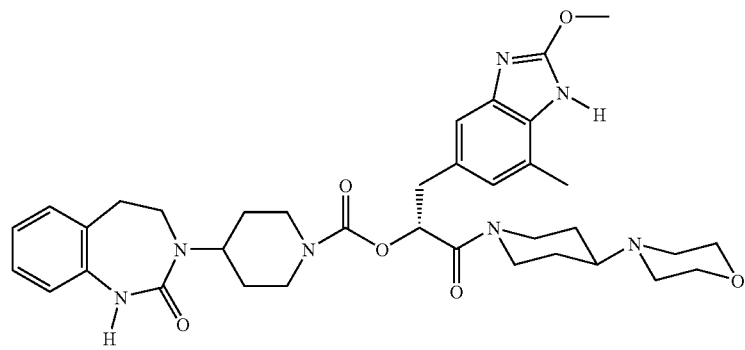 |
| (7) | 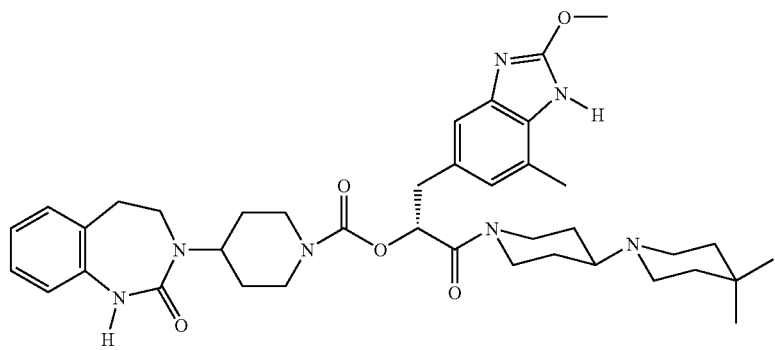 |

-continued
| No. | Structure |
|---|---|
| (8) | 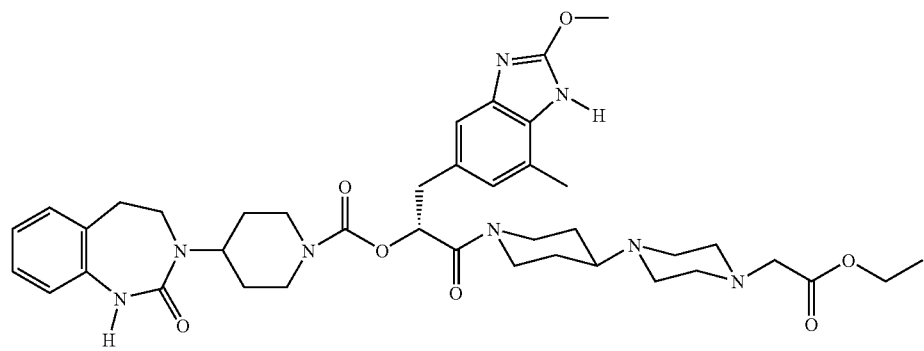 |
| (9) | 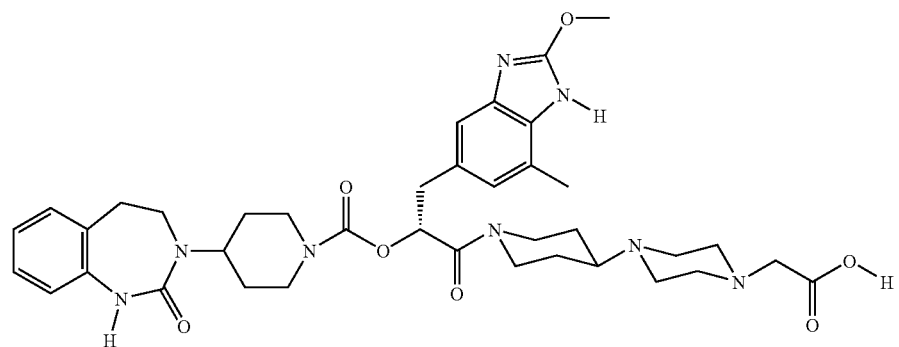 |
| (10) | 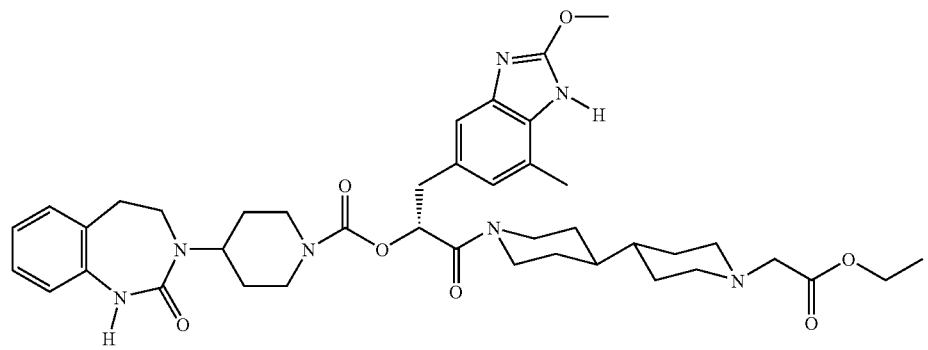 |
| (11) | 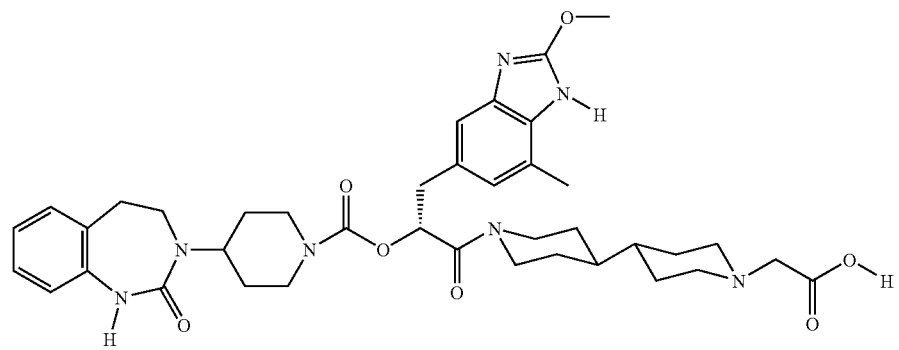 |

-continued
| No. | Structure |
|---|---|
| (12) | 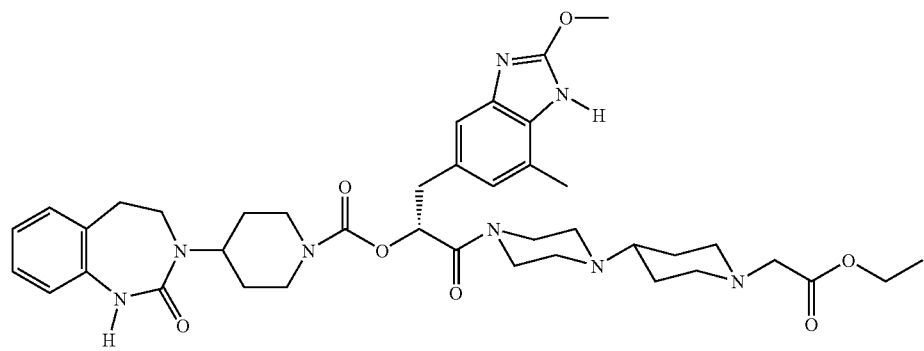 |
| (13) | 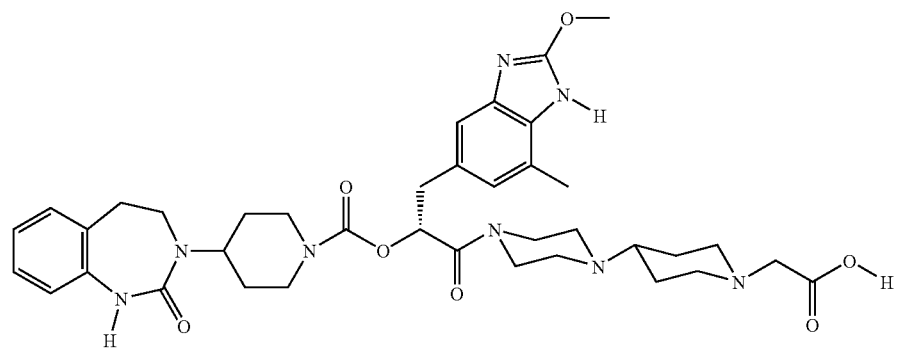 |
| (14) | 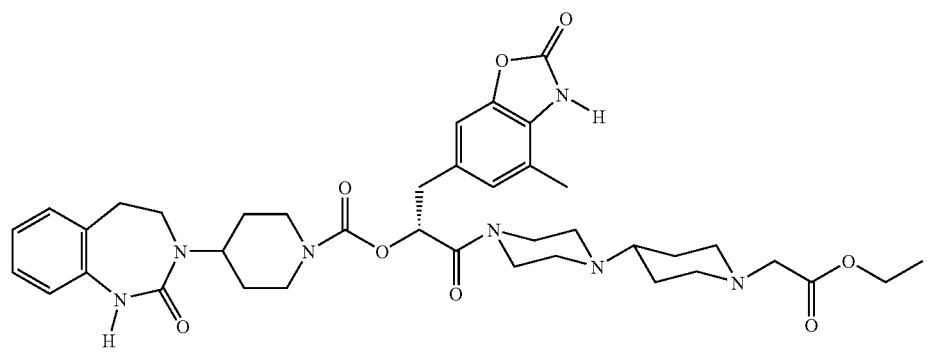 |
| (15) | 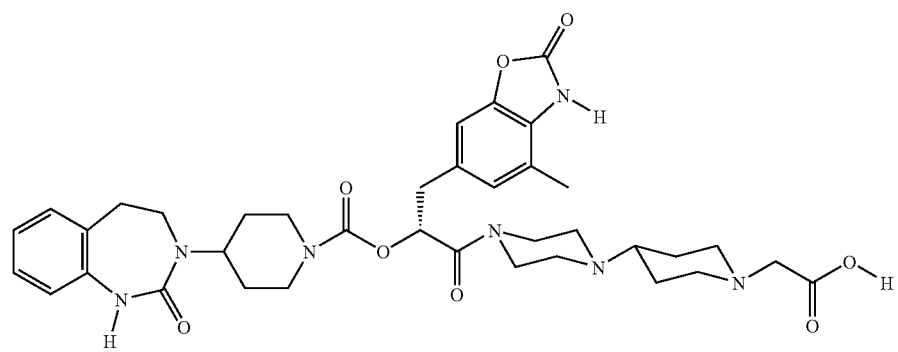 |

| No. | Structure |
|---|---|
| (16) | 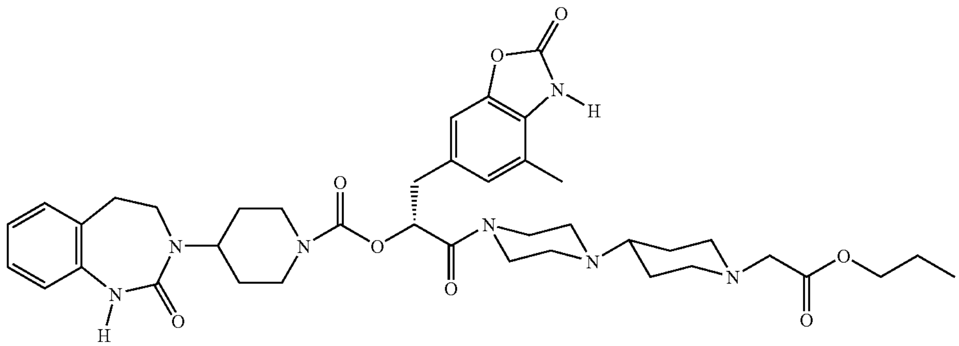 |
| (17) | 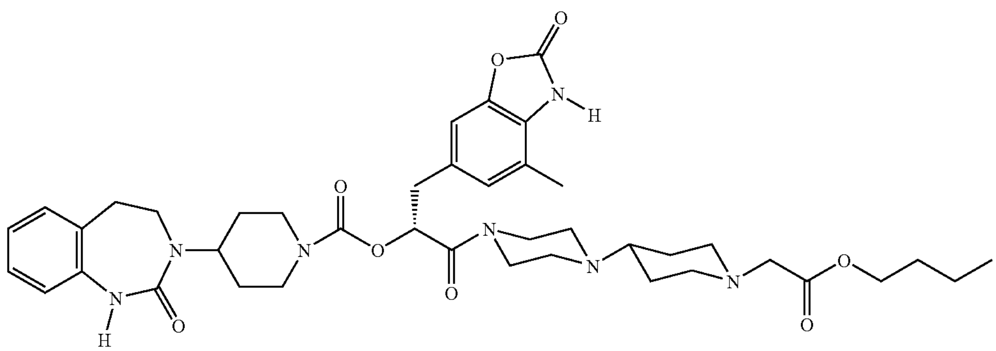 |
| (18) | 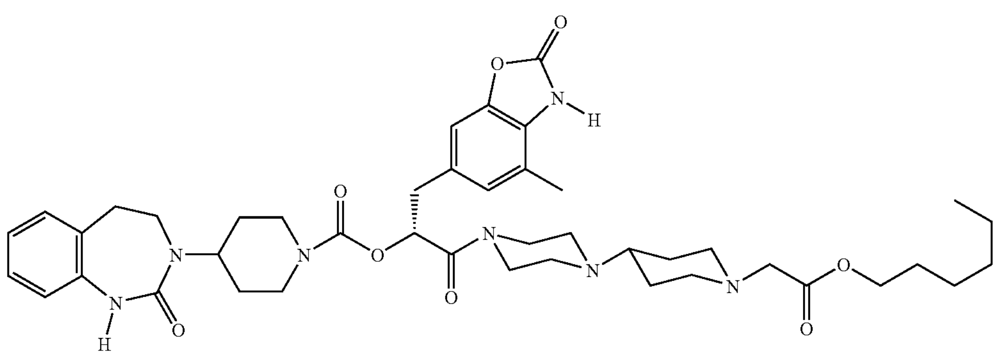 |
| (19) | 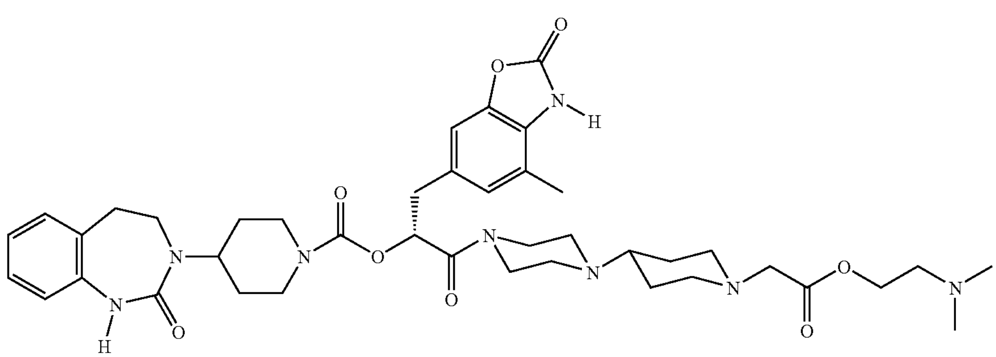 |

-continued

| No. | Structure |
| --- | --- |
| (20) | 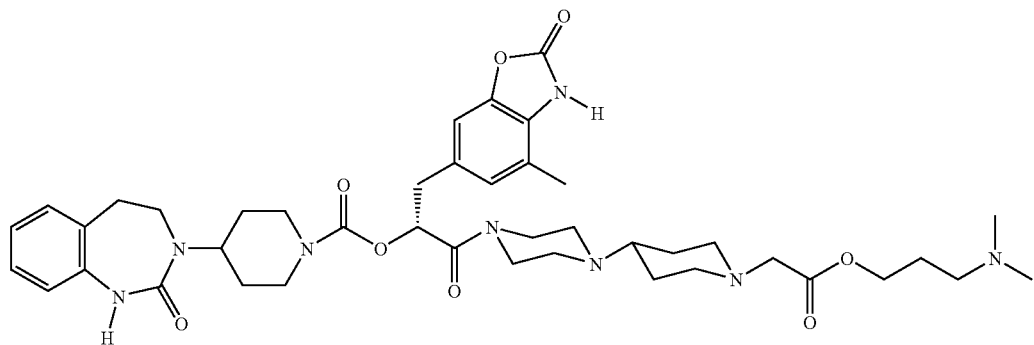 |
| (21) | 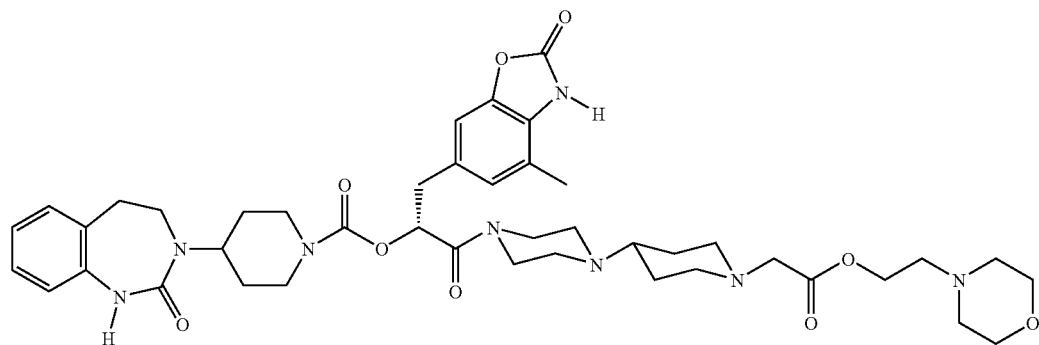 |
| (22) | 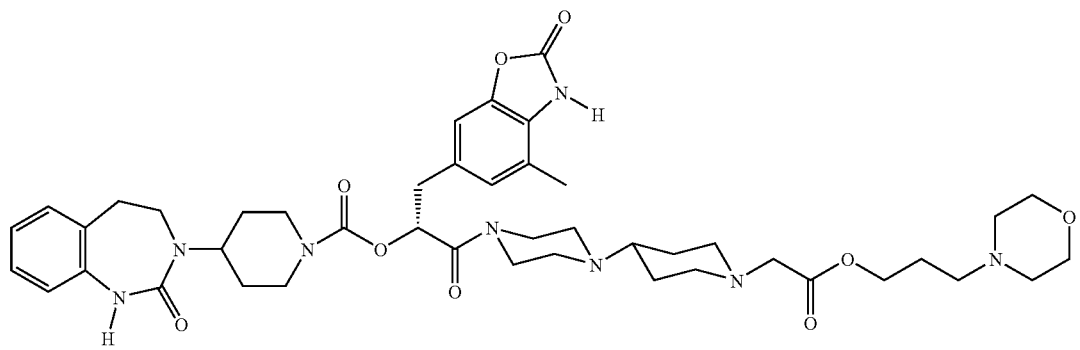 |
| (23) | 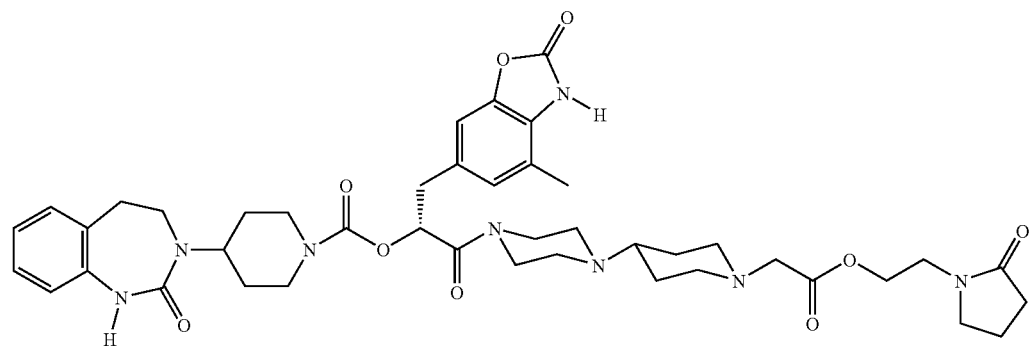 |

-continued
| No. | Structure |
|---|---|
| (24) | 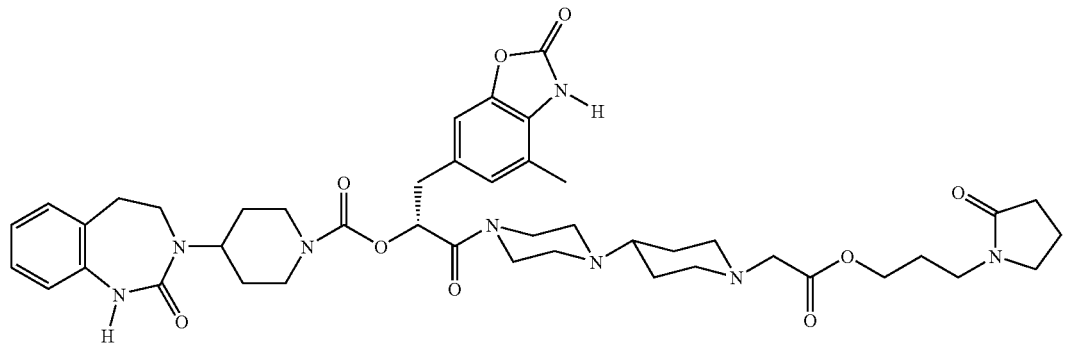 |
| (25) | 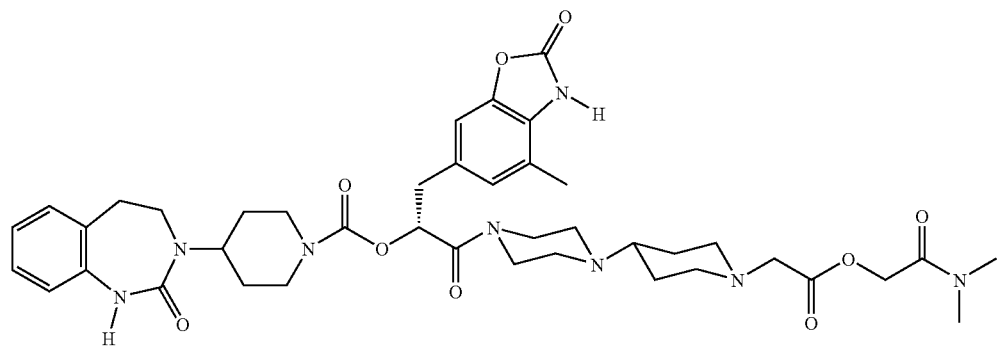 |
| (26) | 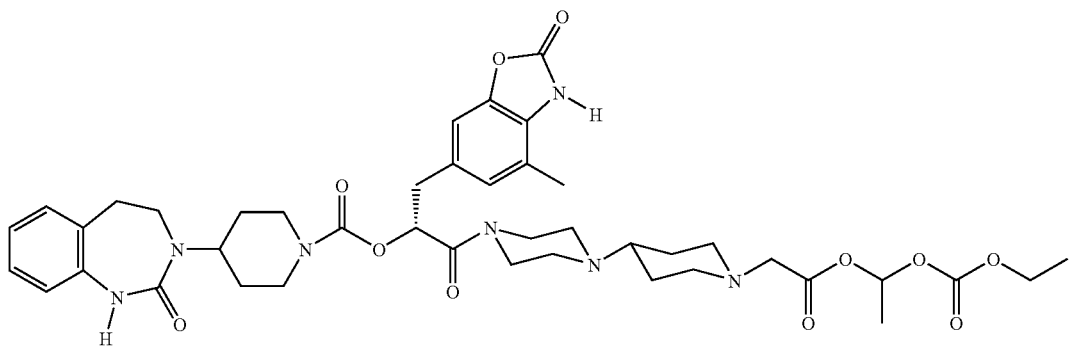 |
| (27) | 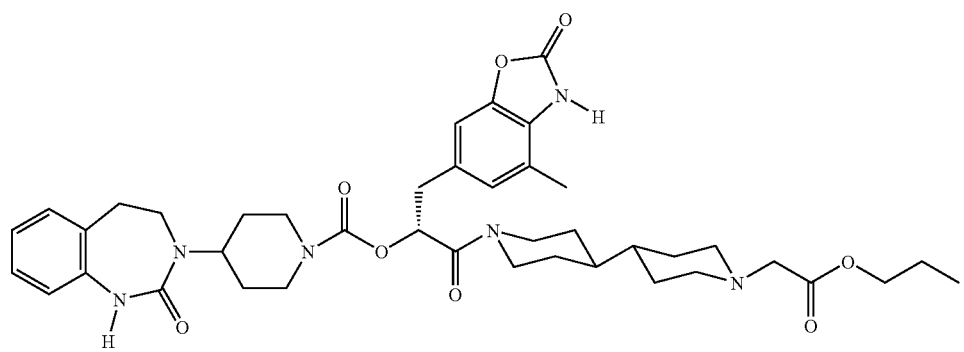 |

-continued
| No. | Structure |
|---|---|
| (28) | 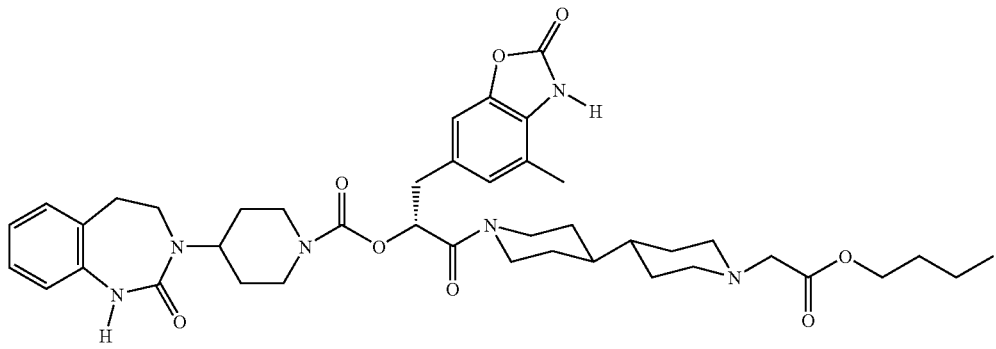 |
| (29) | 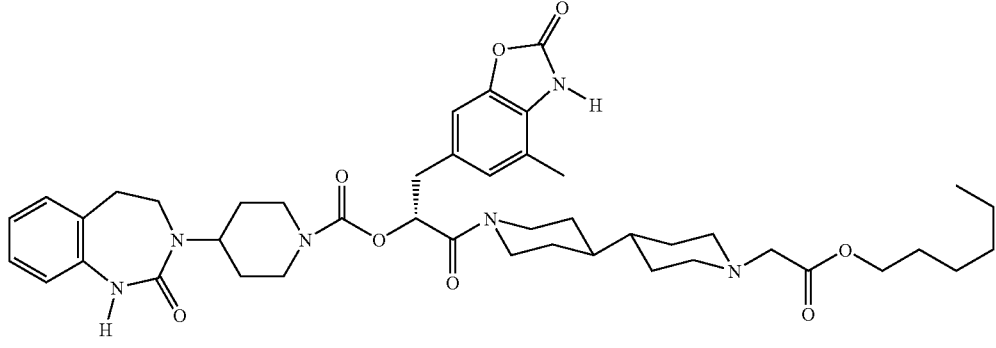 |
| (30) | 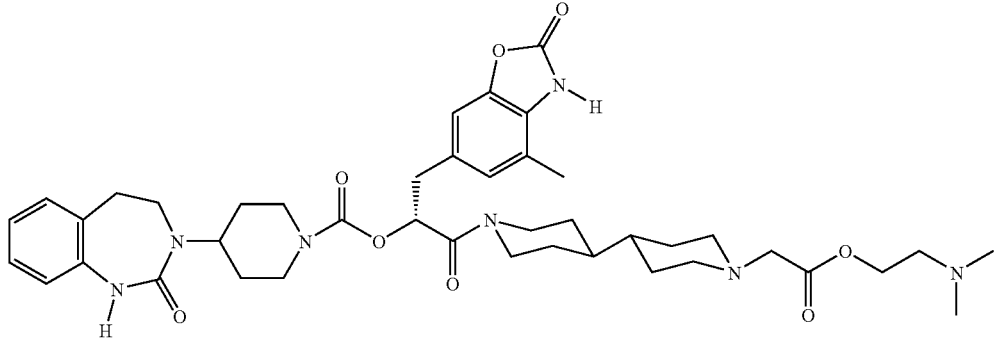 |
| (31) | 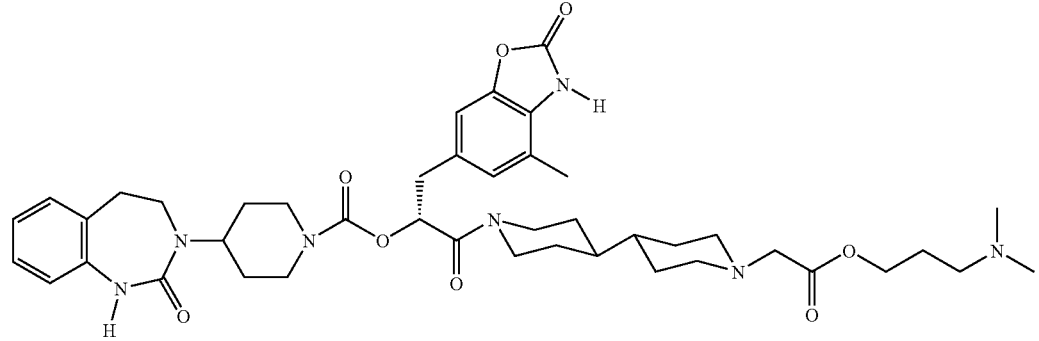 |

| No. | Structure |
|---|---|
| (32) | 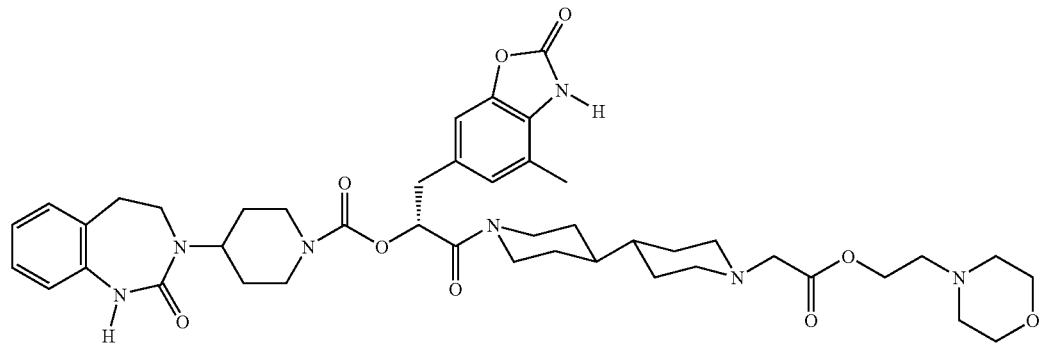 |
| (33) | 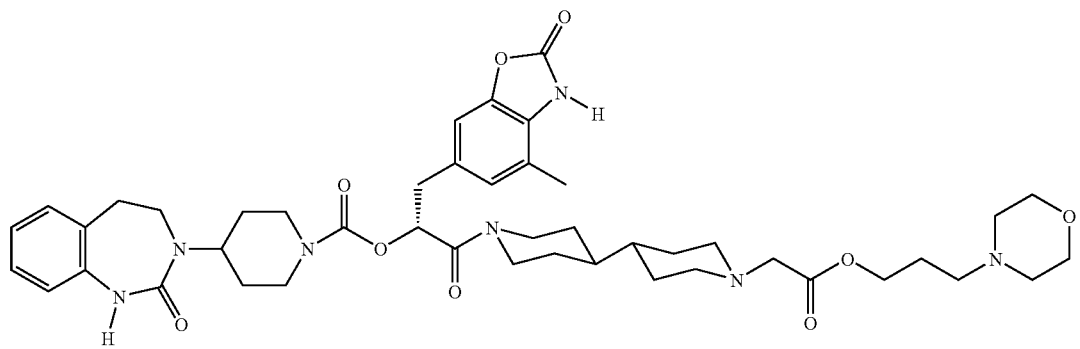 |
| (34) | 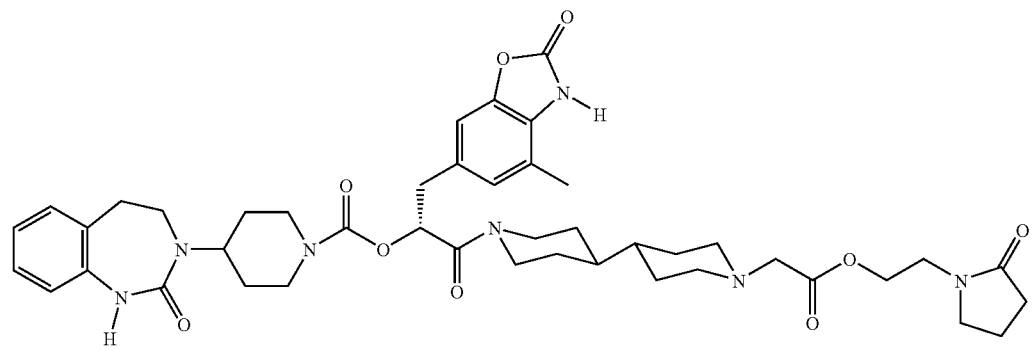 |
| (35) | 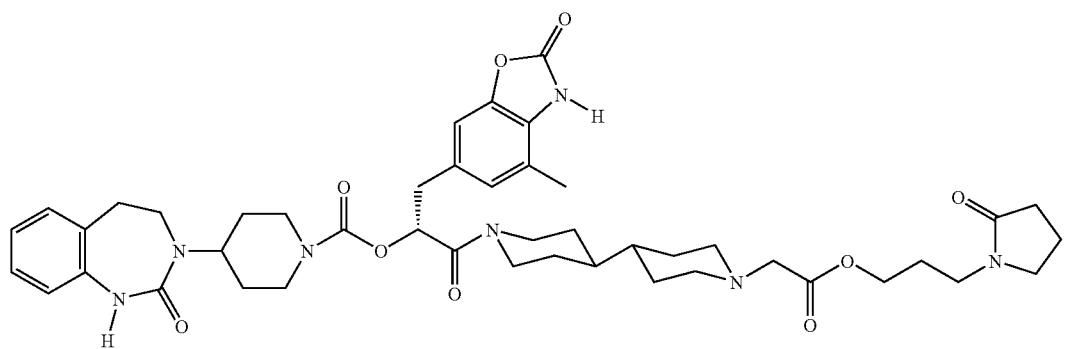 |

| No. | Structure |
|---|---|
| (36) | 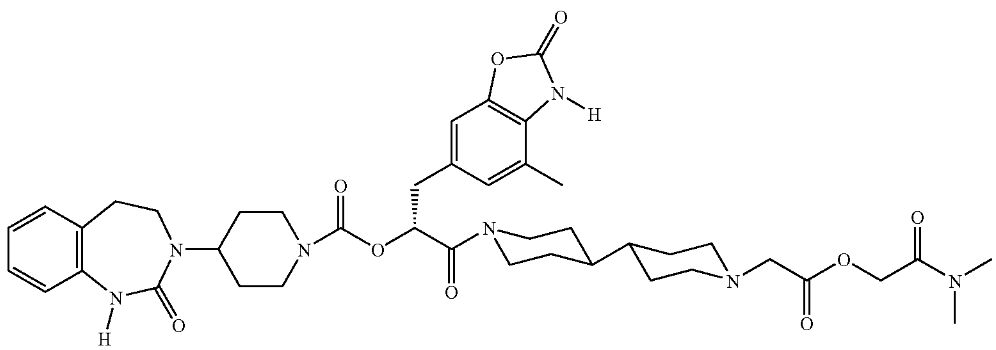 |
| (37) | 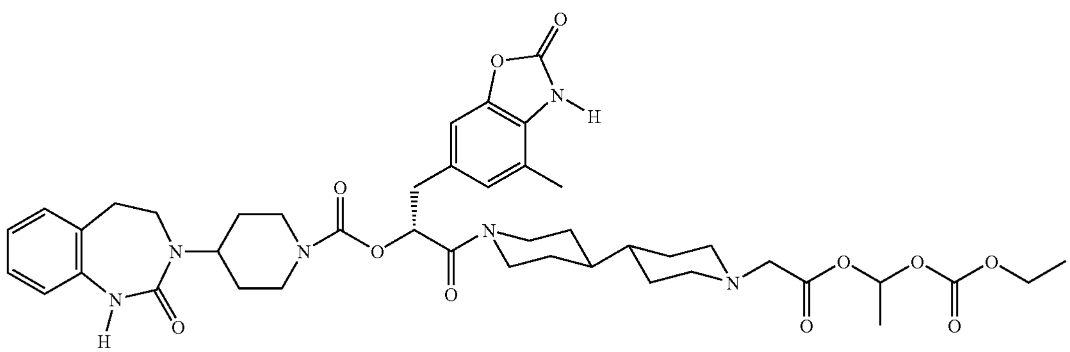 |
| (38) | 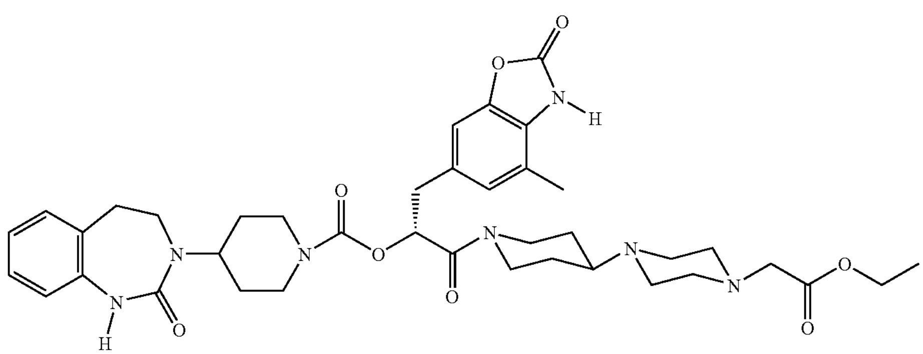 |
| (39) | 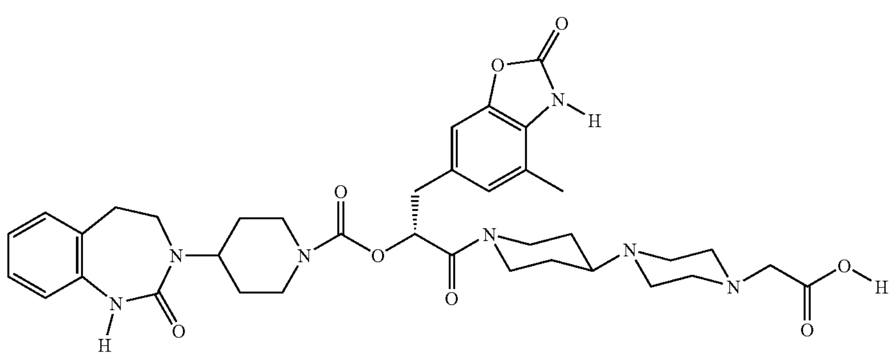 |

| No. | Structure |
|---|---|
| (40) | 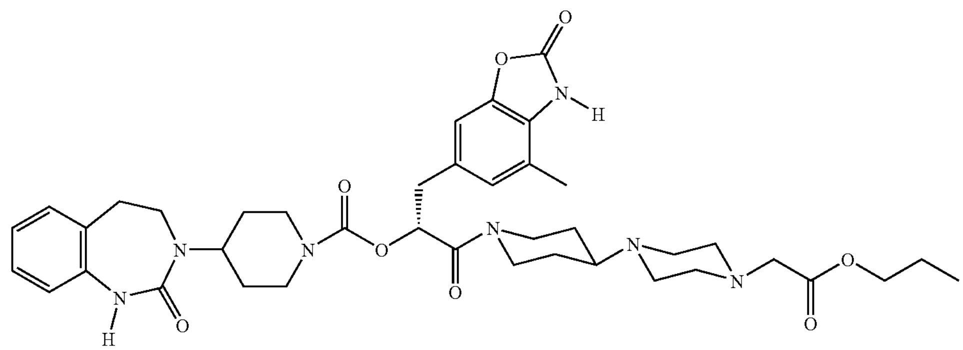 |
| (41) | 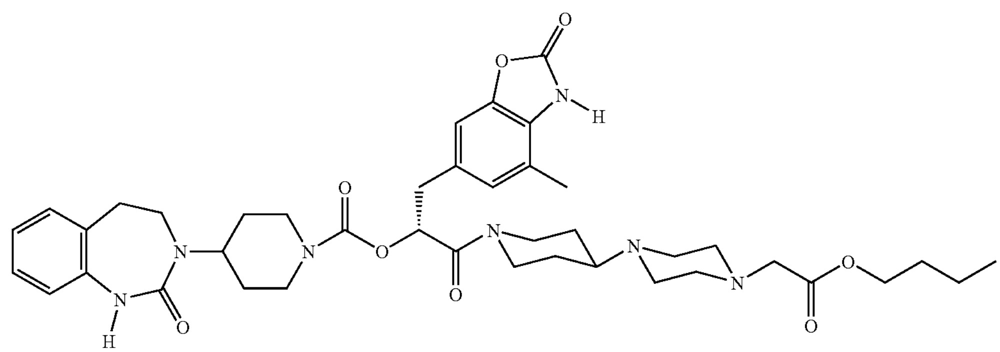 |
| (42) | 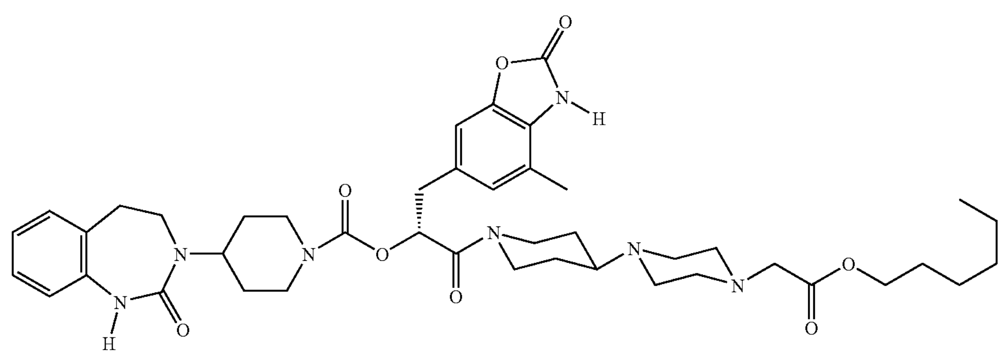 |
| (43) | 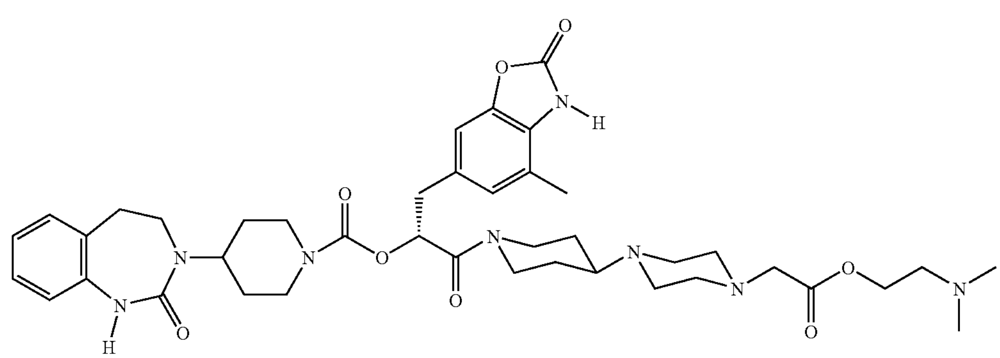 |

-continued
| No. | Structure |
|---|---|
| (44) | 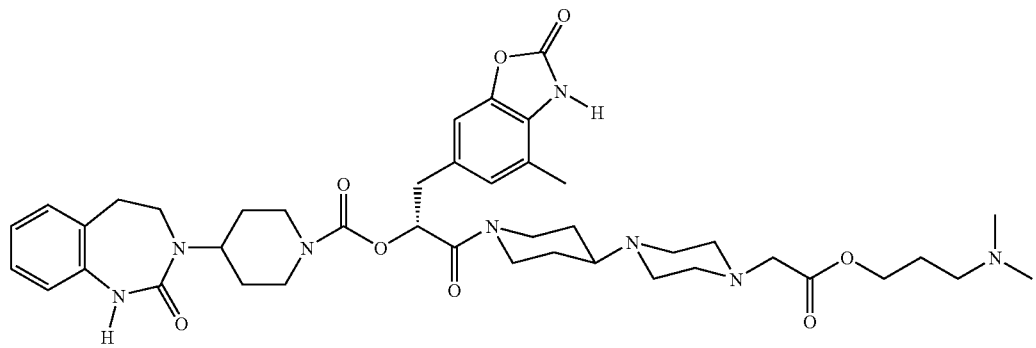 |
| (45) | 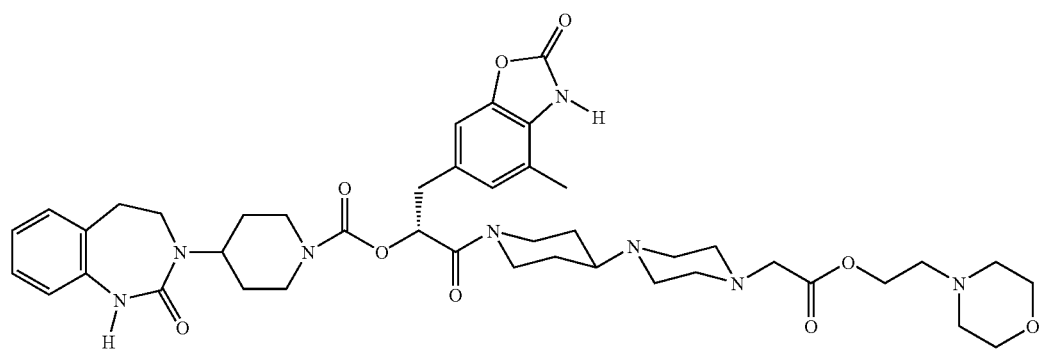 |
| (46) | 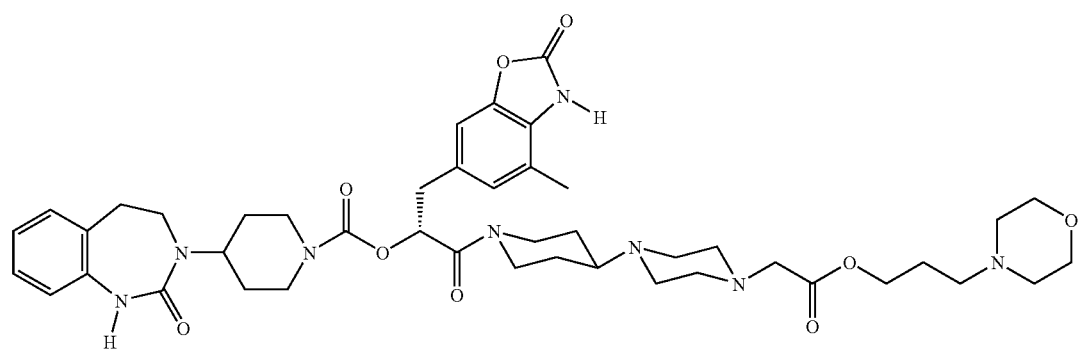 |
| (47) | 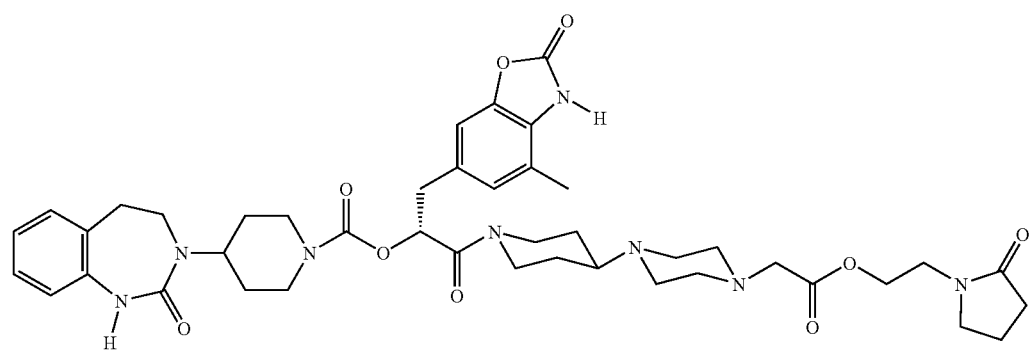 |

-continued
| No. | Structure |
|---|---|
| (48) | 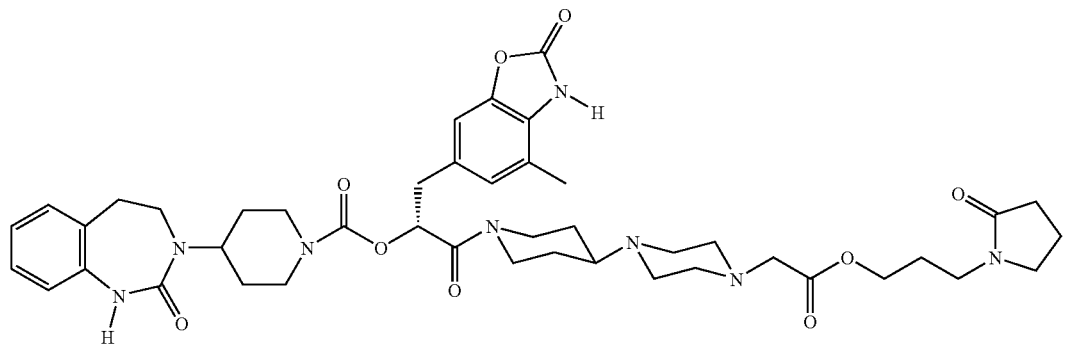 |
| (49) | 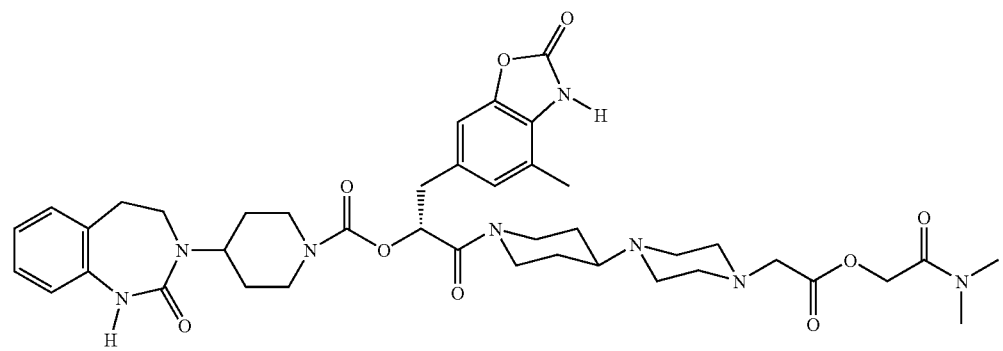 |
| (50) | 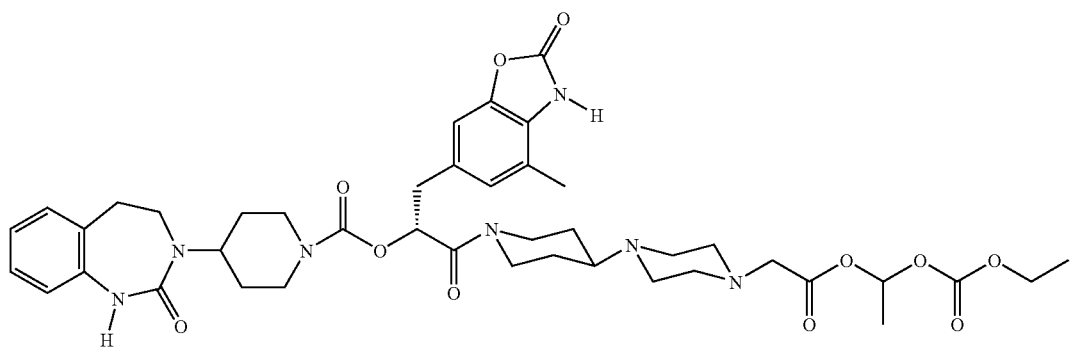 |
| (51) | 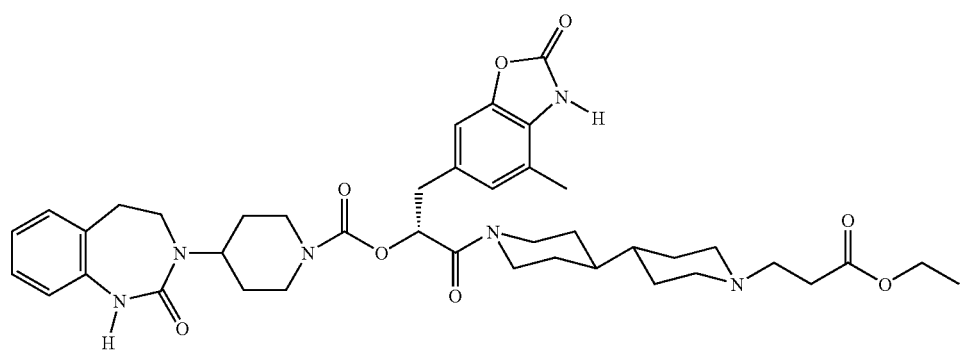 |

-continued
| No. | Structure |
|---|---|
| (52) | 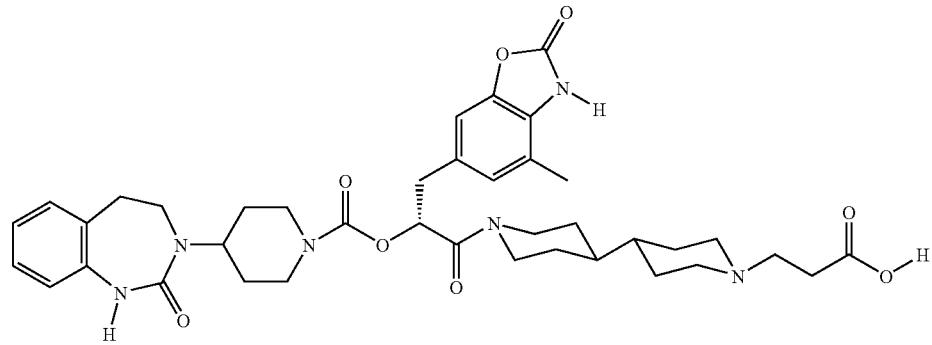 |
| (53) | 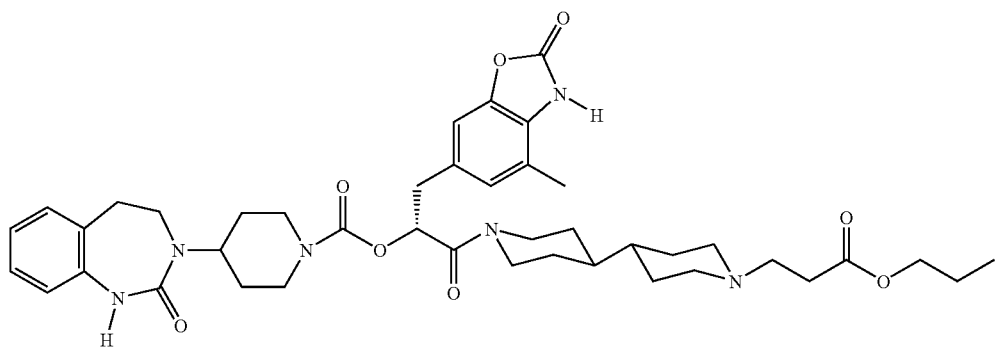 |
| (54) | 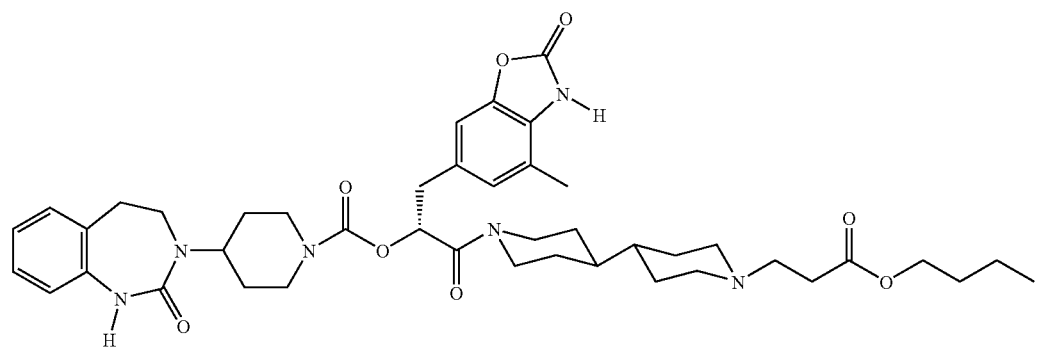 |
| (55) | 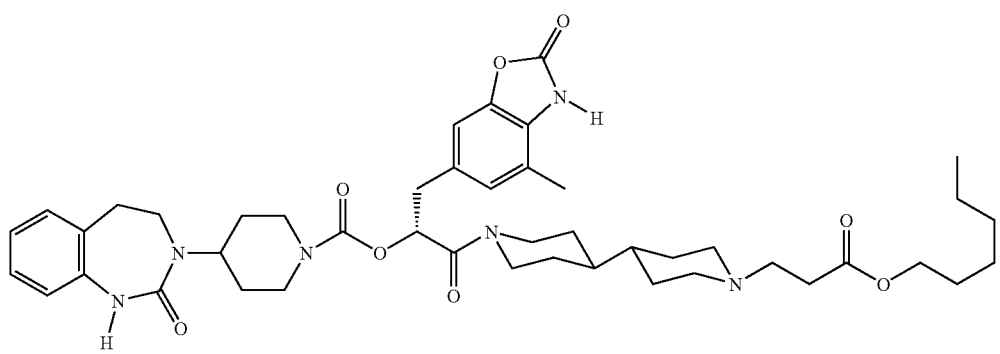 |

-continued
| No. | Structure |
|---|---|
| (56) | 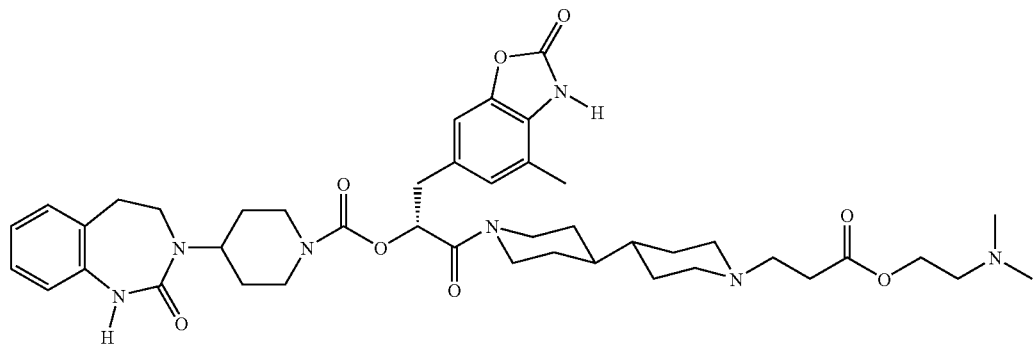 |
| (57) | 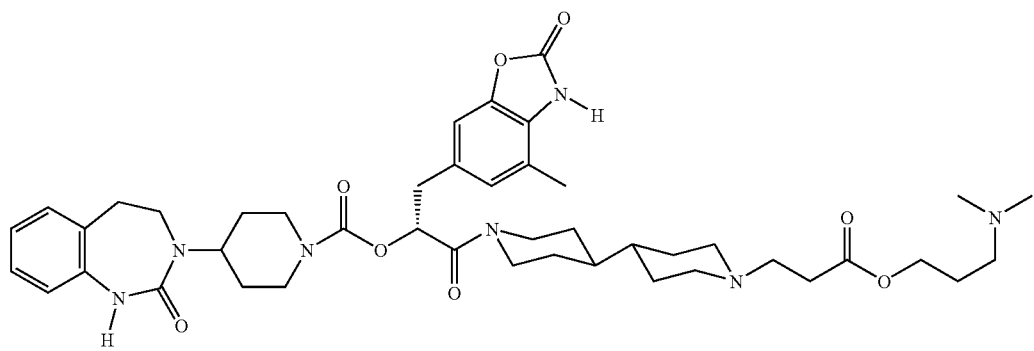 |
| (58) | 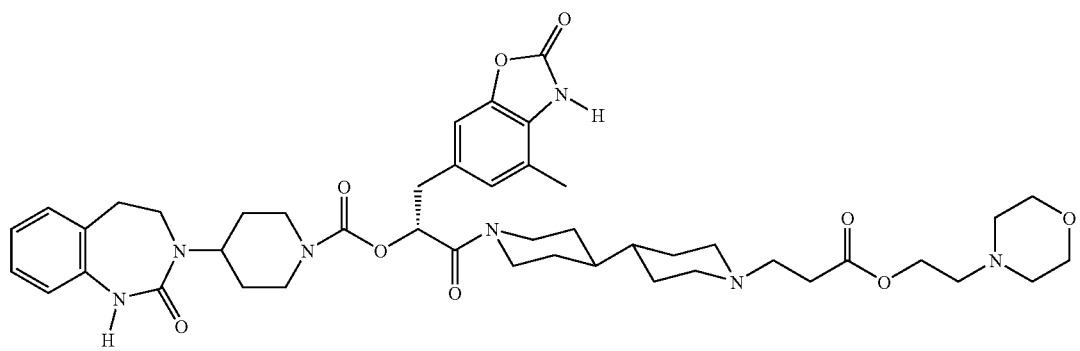 |
| (59) | 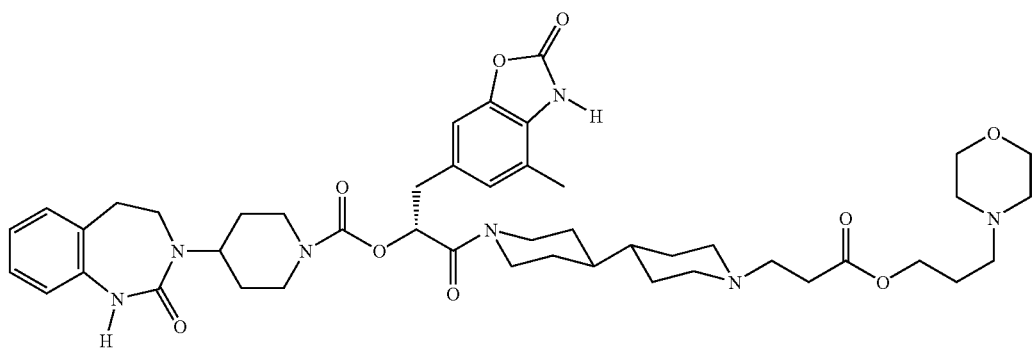 |

-continued
| No. | Structure |
|---|---|
| (60) | 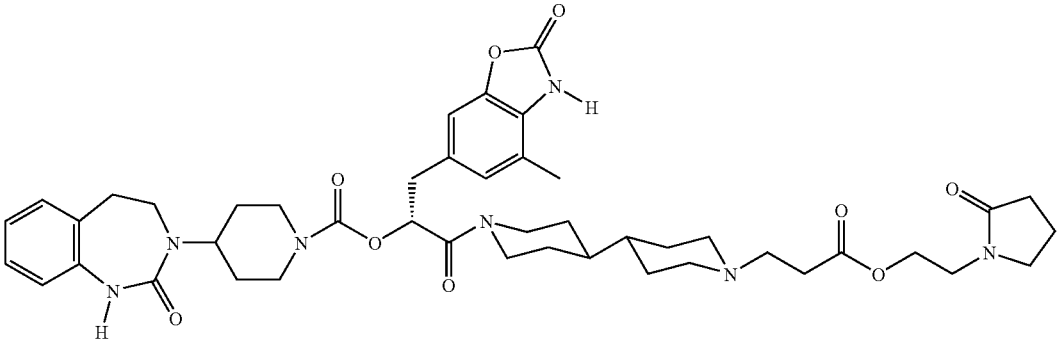 |
| (61) | 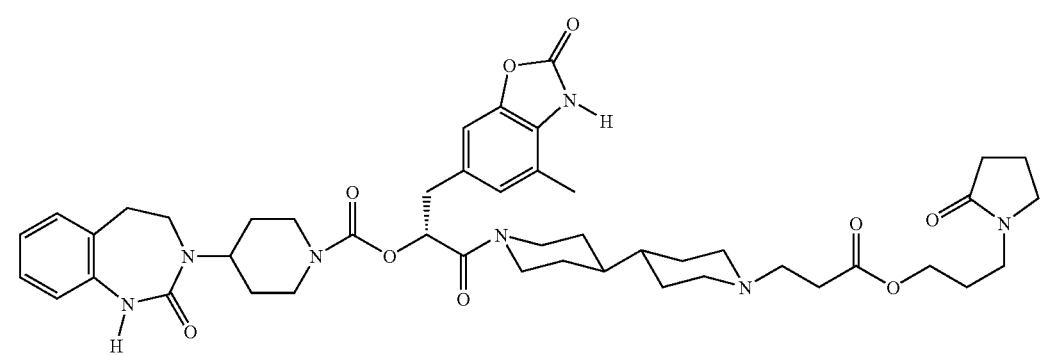 |
| (62) | 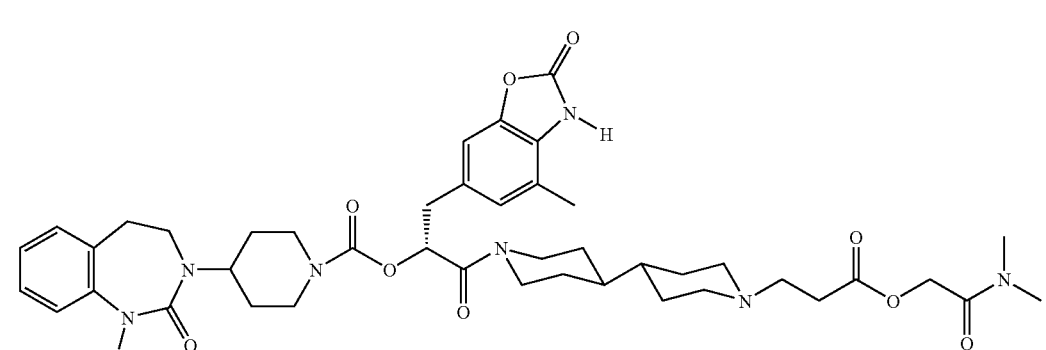 |
| (16) | 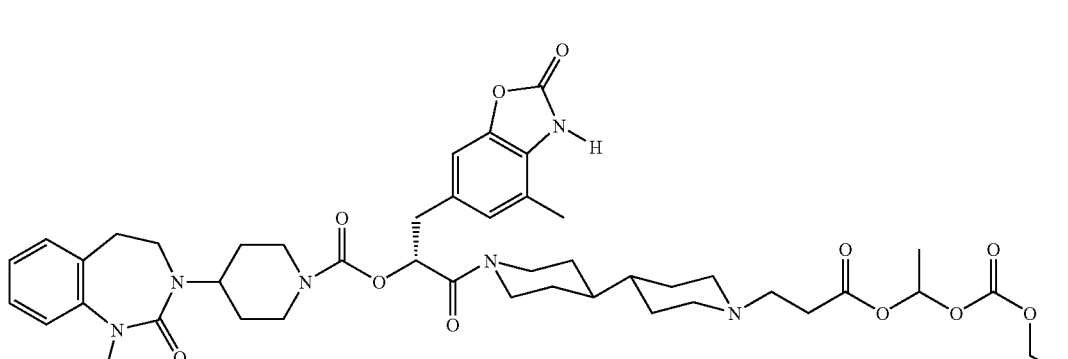 |

-continued

| No. | Structure |
|---|---|
| (63) | 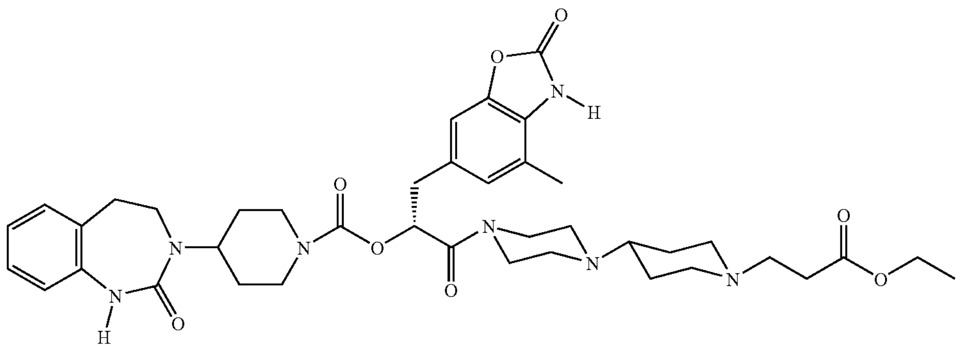 |
| (64) | 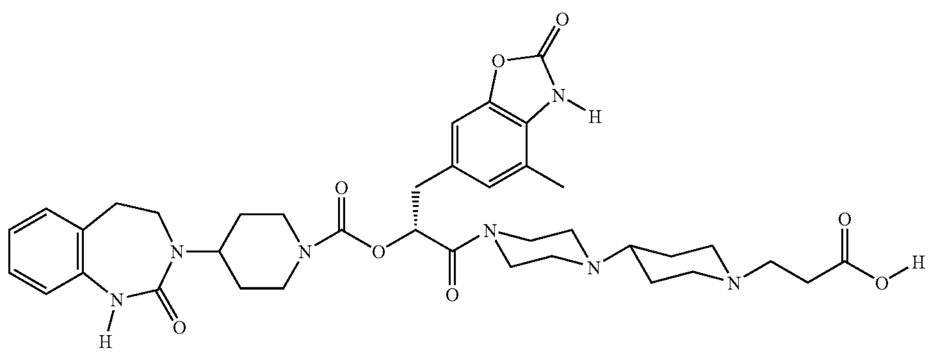 |
| (65) | 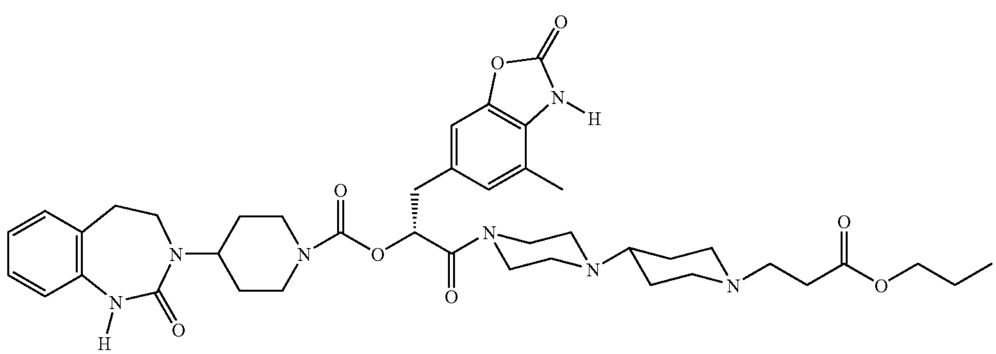 |
| (66) | 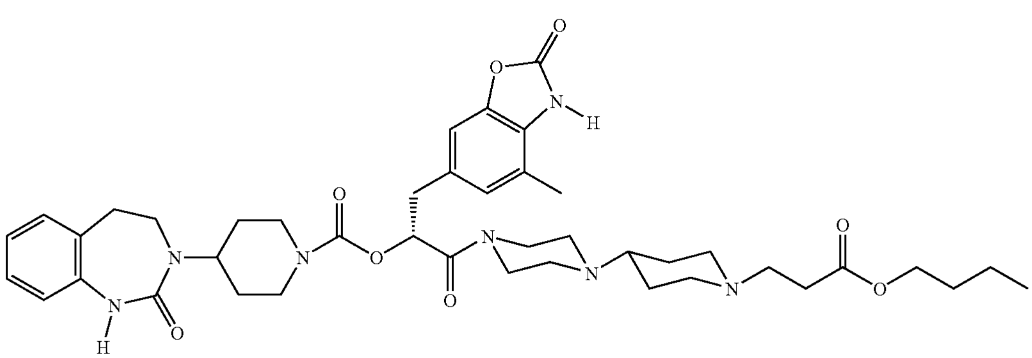 |

-continued
| No. | Structure |
|---|---|
| (67) | 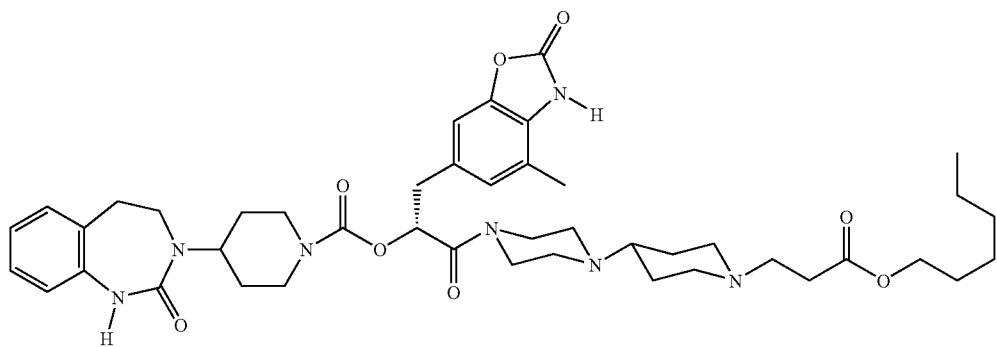 |
| (68) | 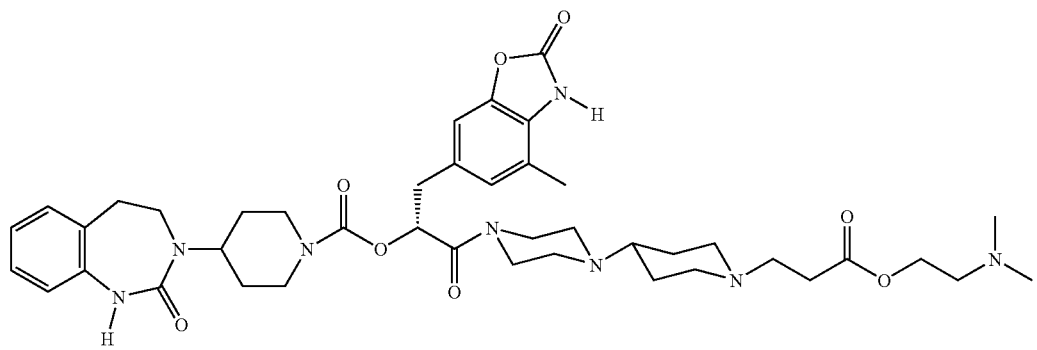 |
| (69) | 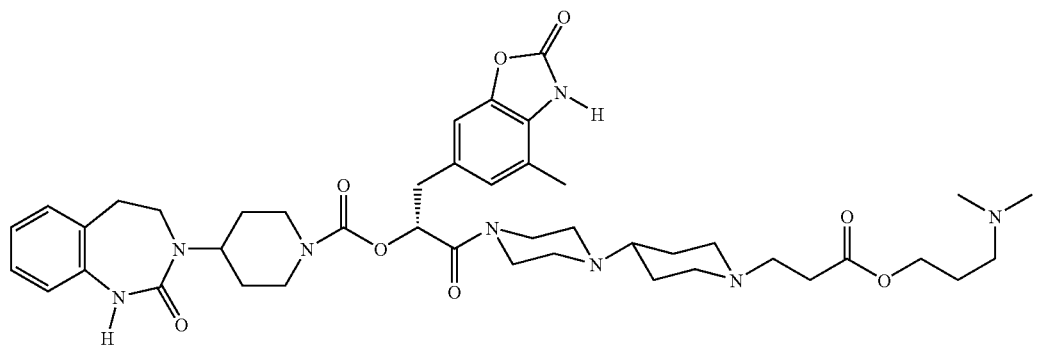 |
| (70) | 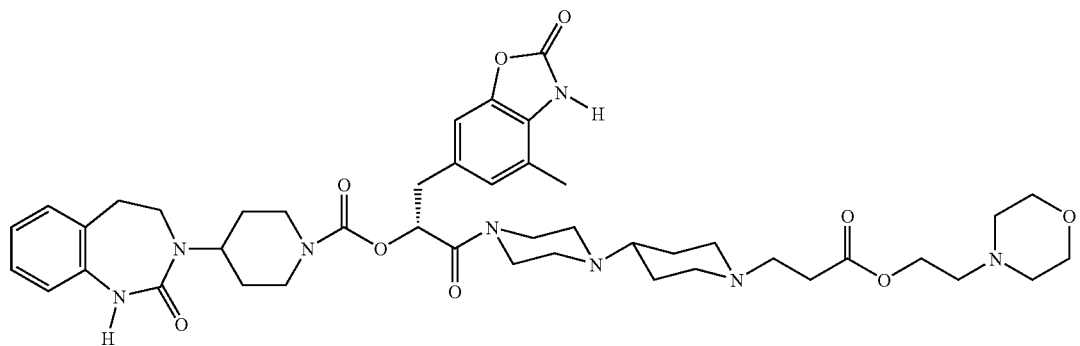 |

| No. | Structure |
|---|---|
| (71) | 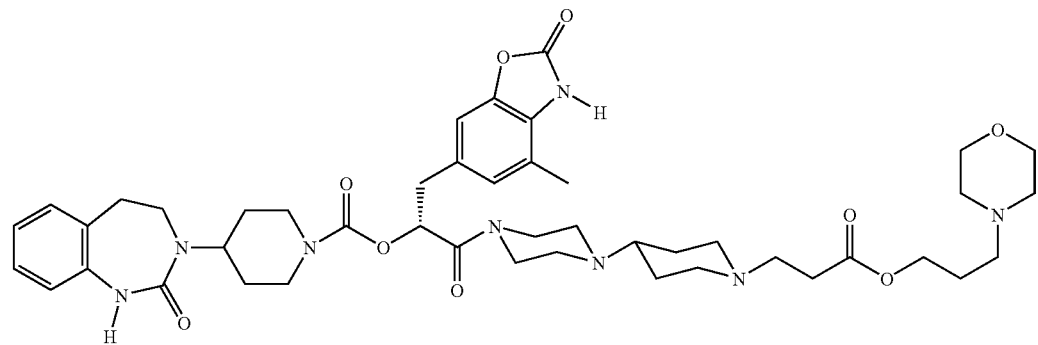 |
| (72) | 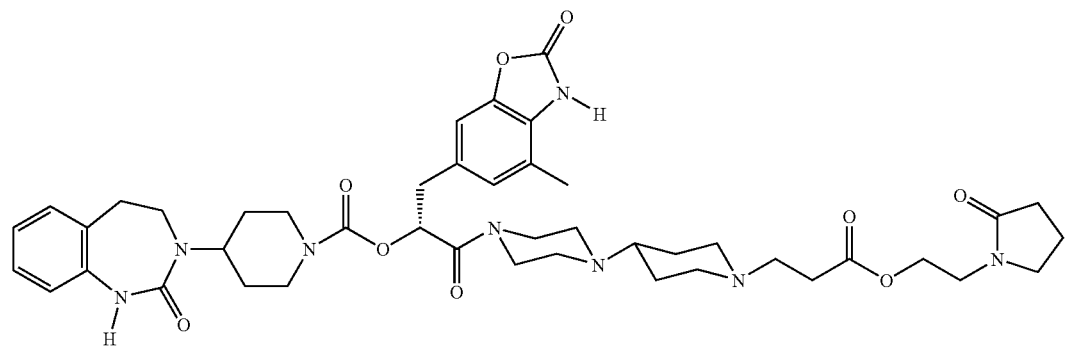 |
| (73) | 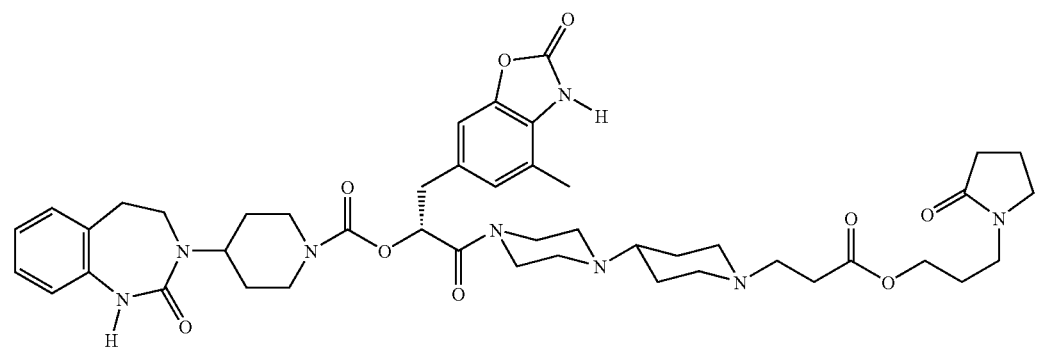 |
| (74) | 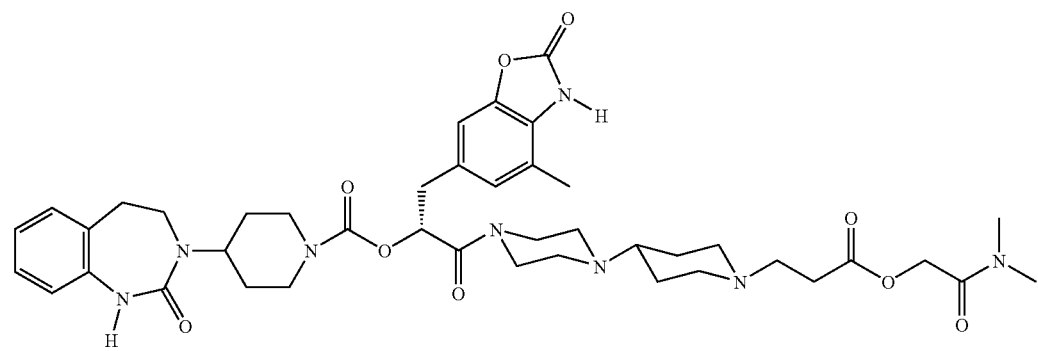 |

-continued
| No. | Structure |
|---|---|
| (75) | 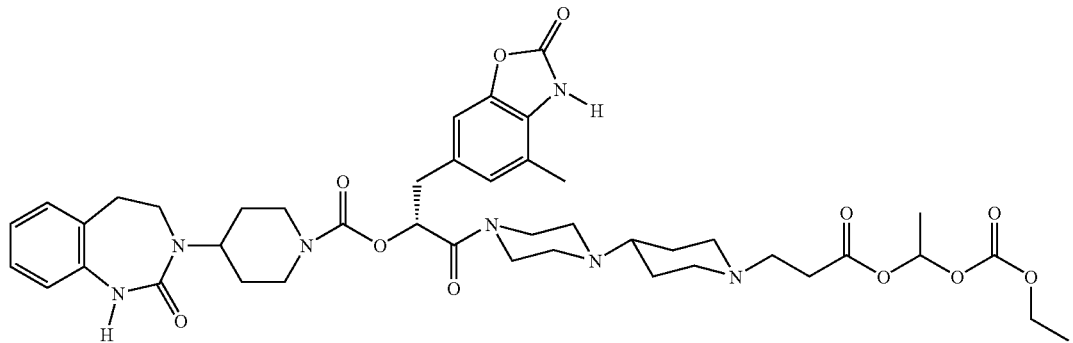 |
| (76) | 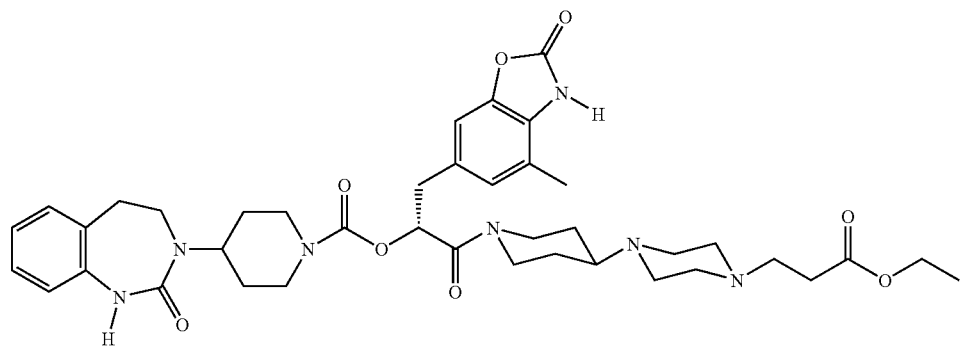 |
| (77) | 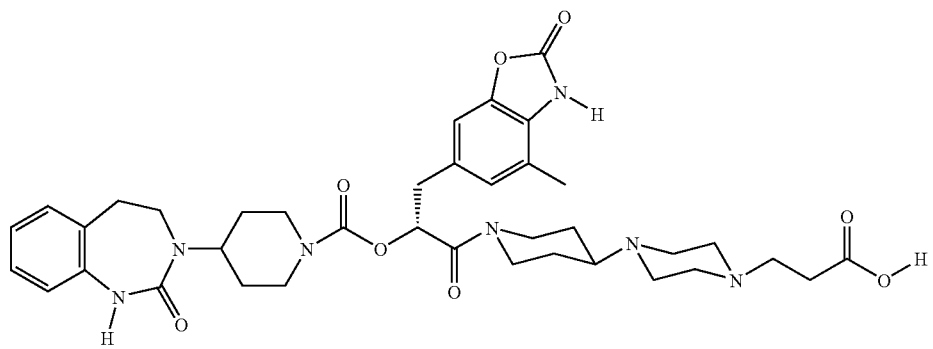 |
| (78) | 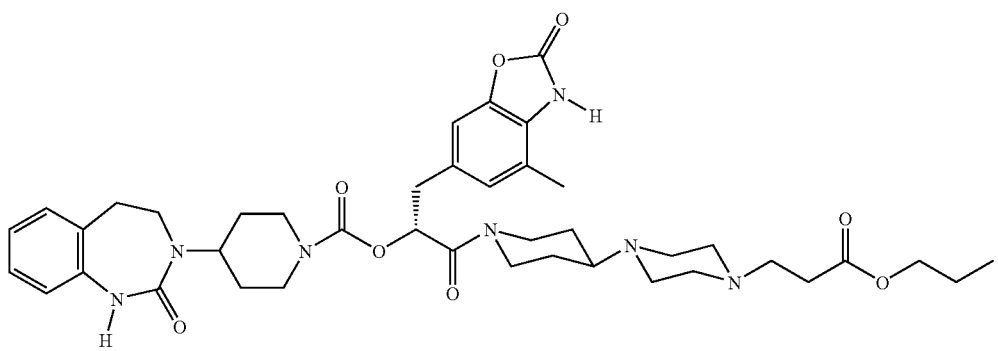 |

-continued
| No. | Structure |
|---|---|
| (79) | 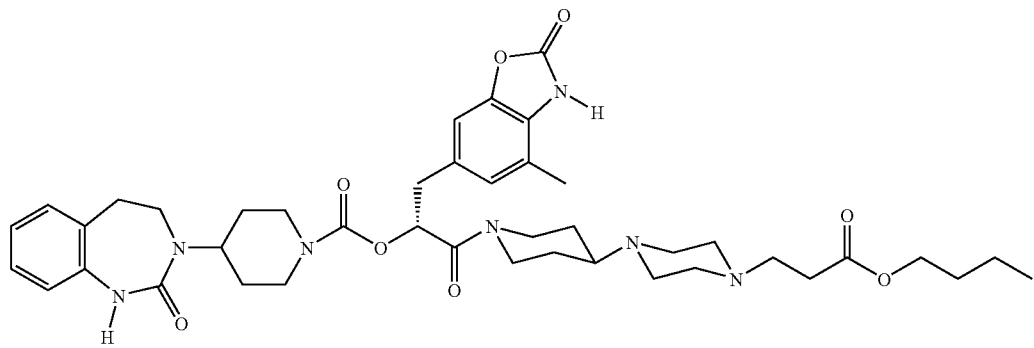 |
| (80) | 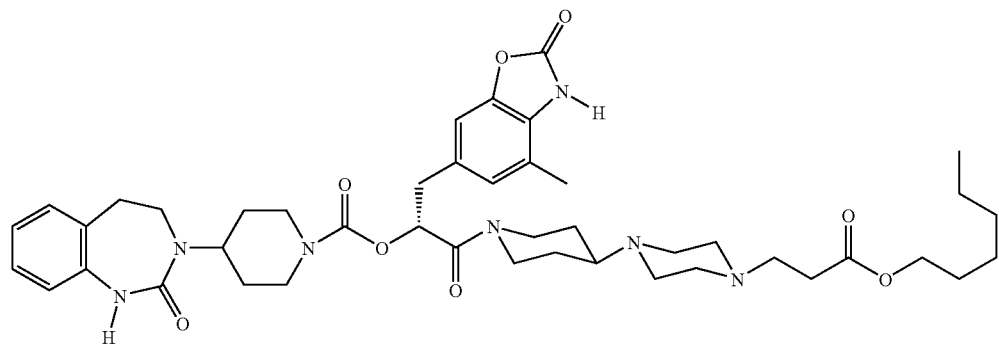 |
| (81) | 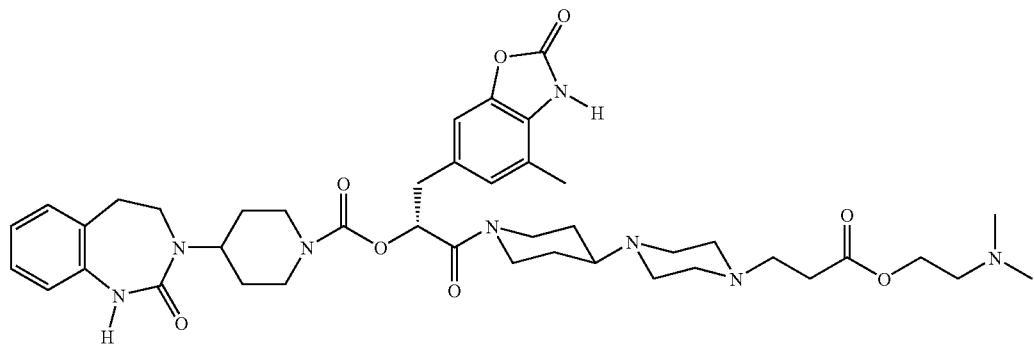 |
| (82) | 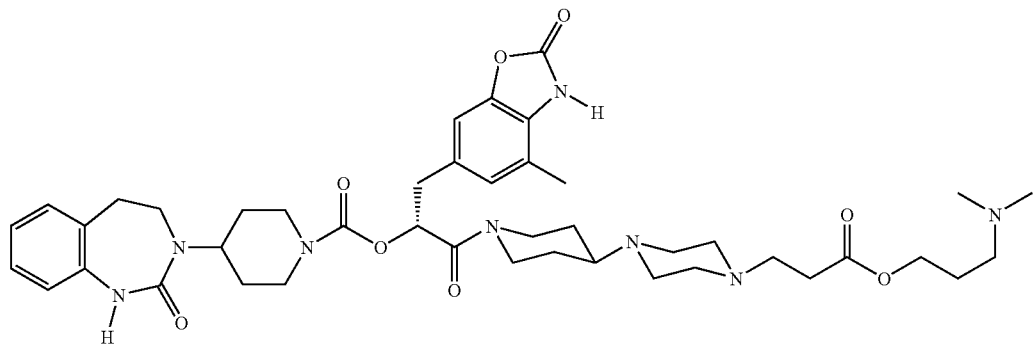 |

-continued
| No. | Structure |
|---|---|
| (83) | 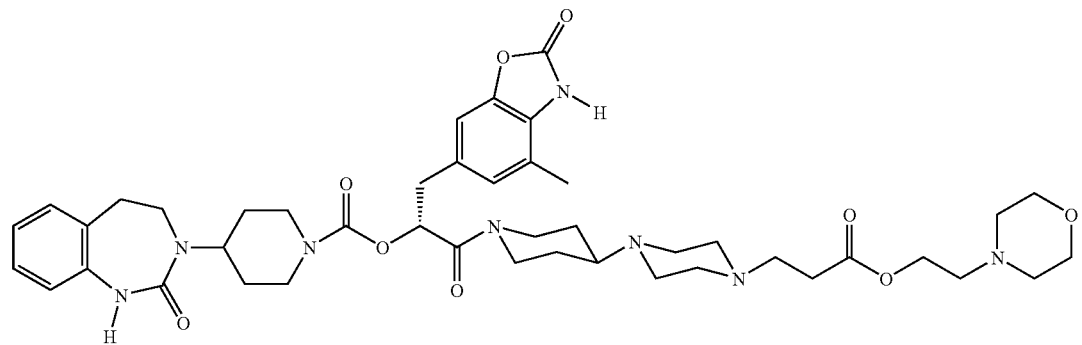 |
| (84) | 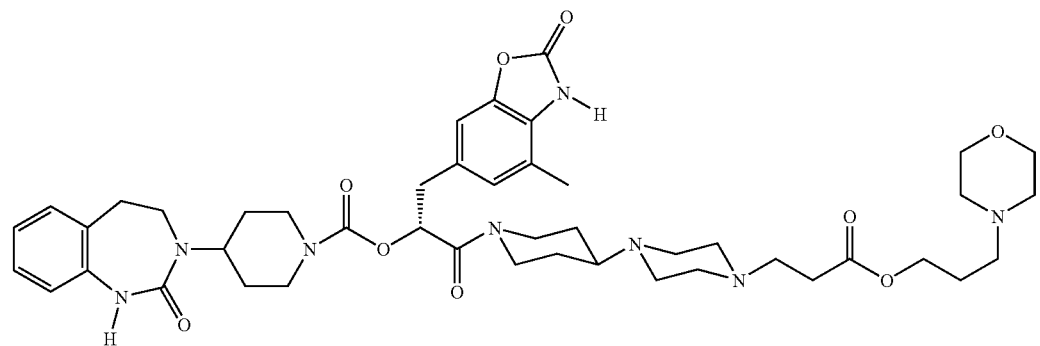 |
| (85) | 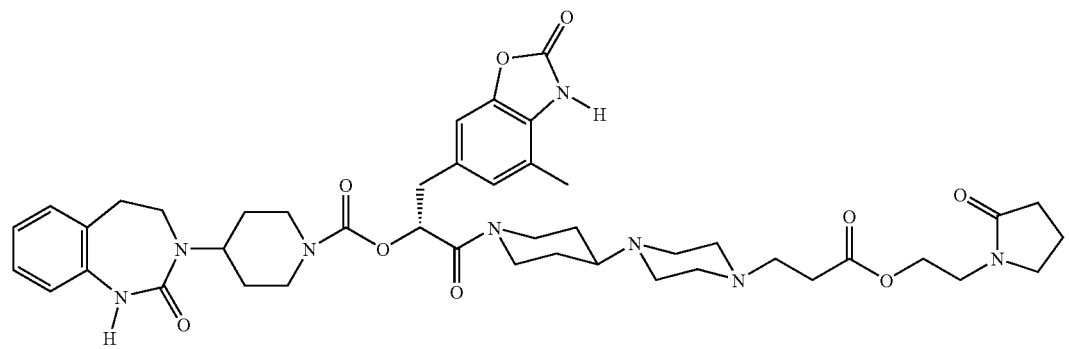 |
| (86) | 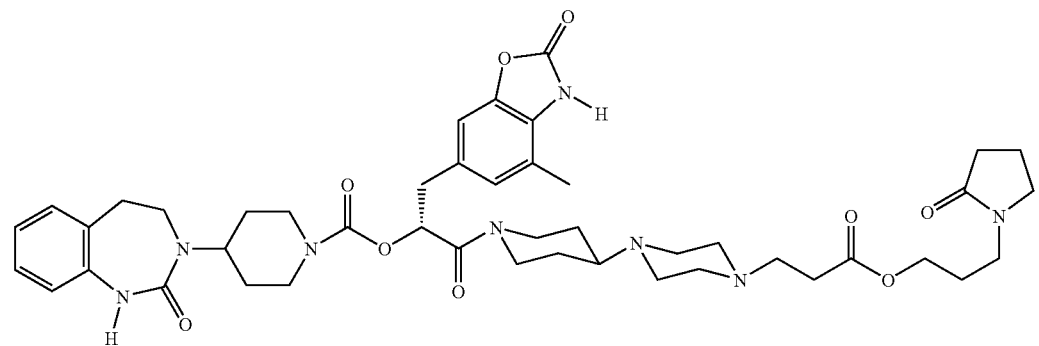 |

-continued
| No. | Structure |
|---|---|
| (87) | 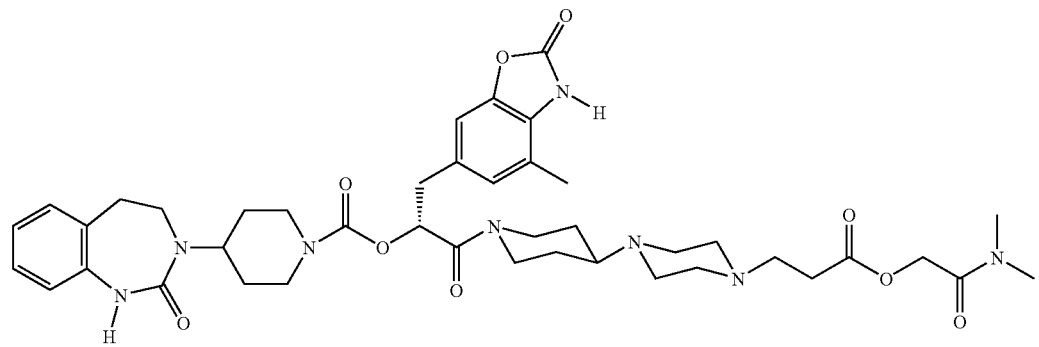 |
| (88) | 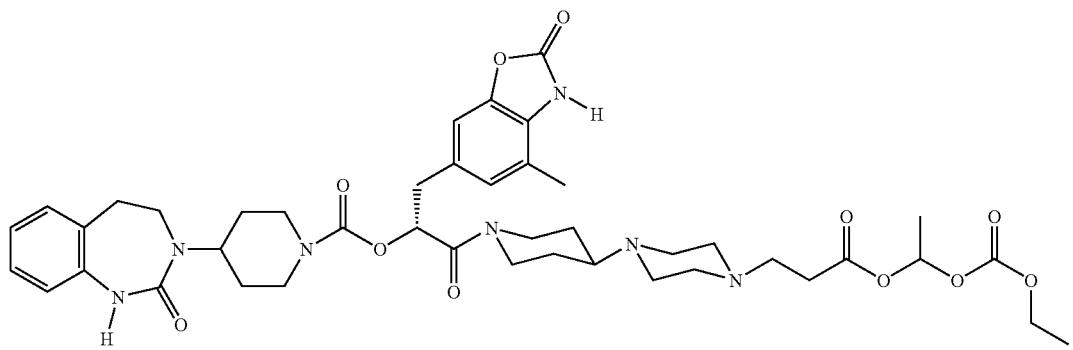 |
| (89) | 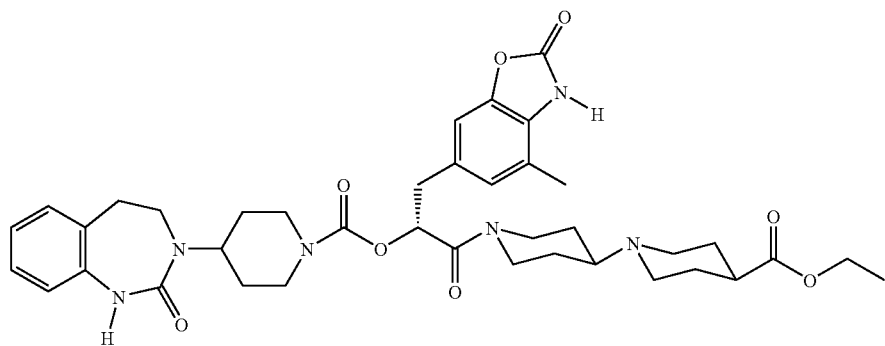 |
| (90) | 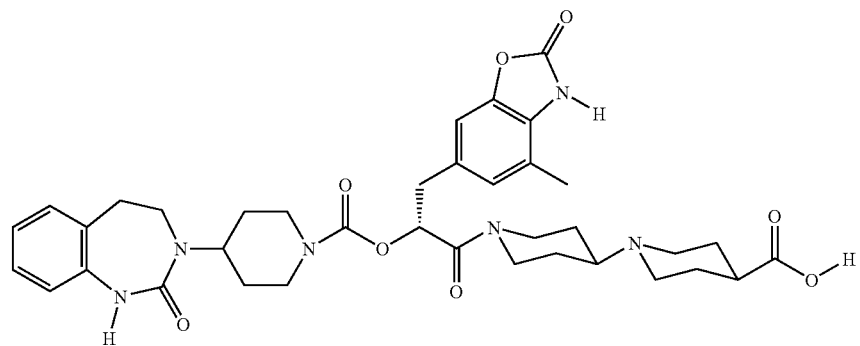 |

| No. | Structure |
|---|---|
| (91) | 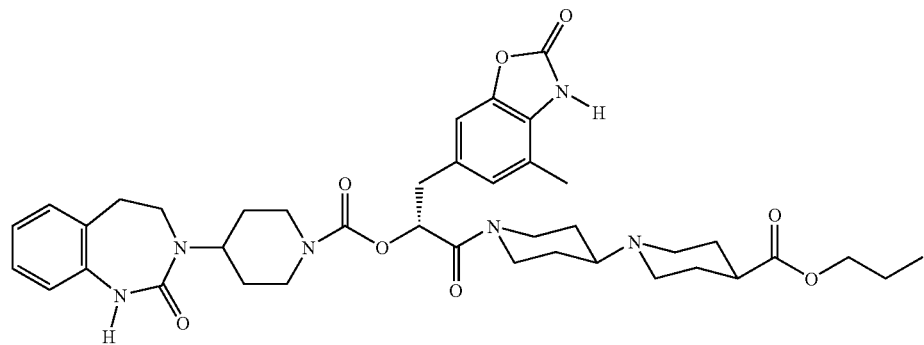 |
| (92) | 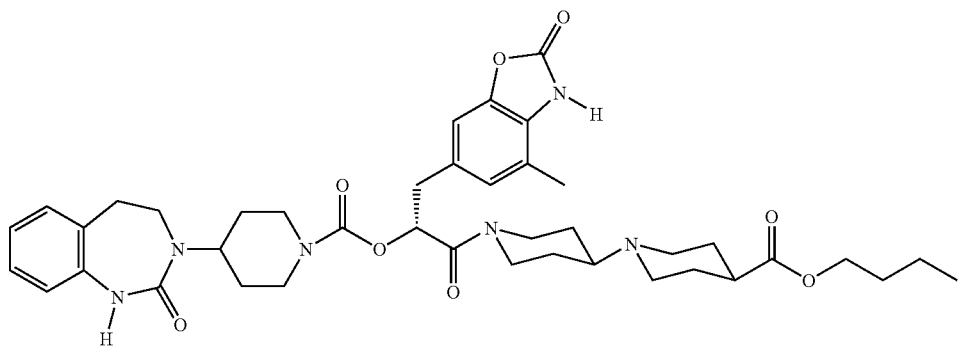 |
| (93) | 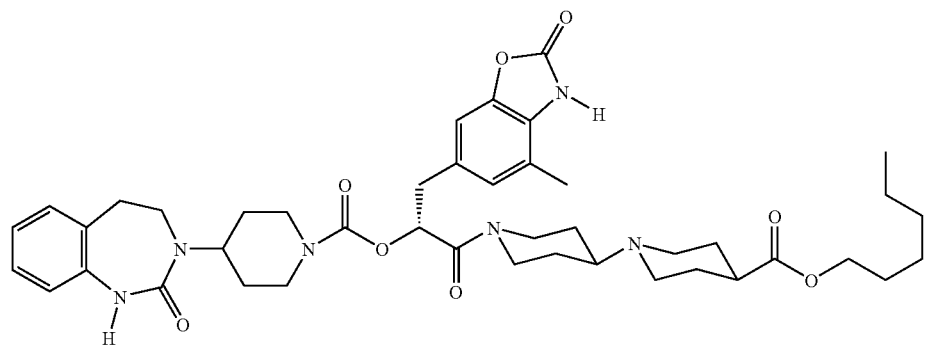 |
| (94) | 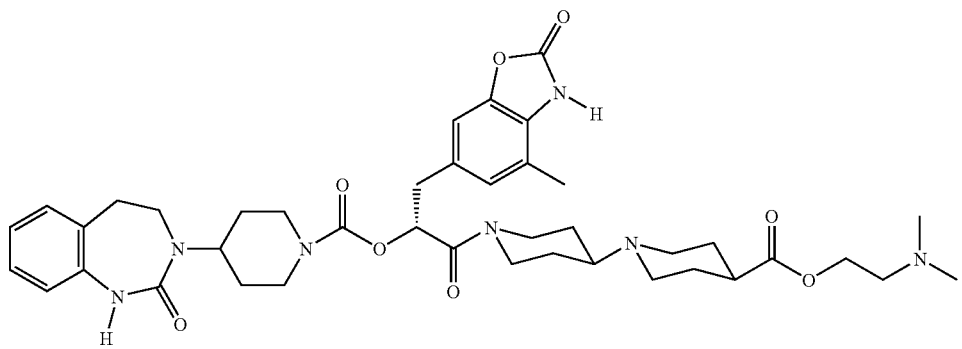 |

| No. | Structure |
|---|---|
| (95) | 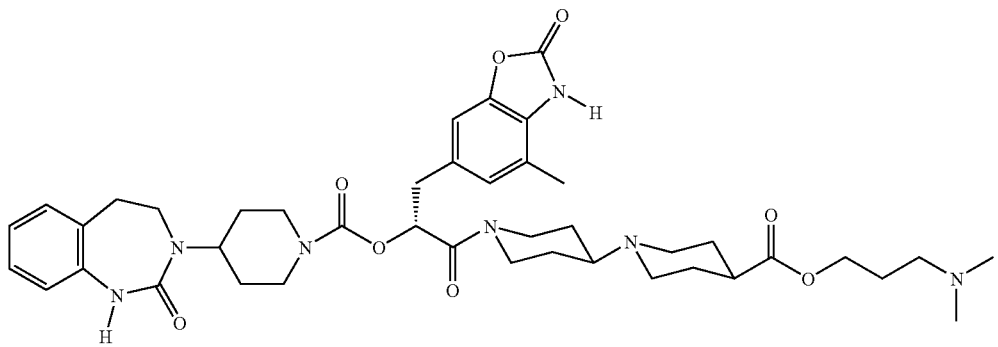 |
| (96) | 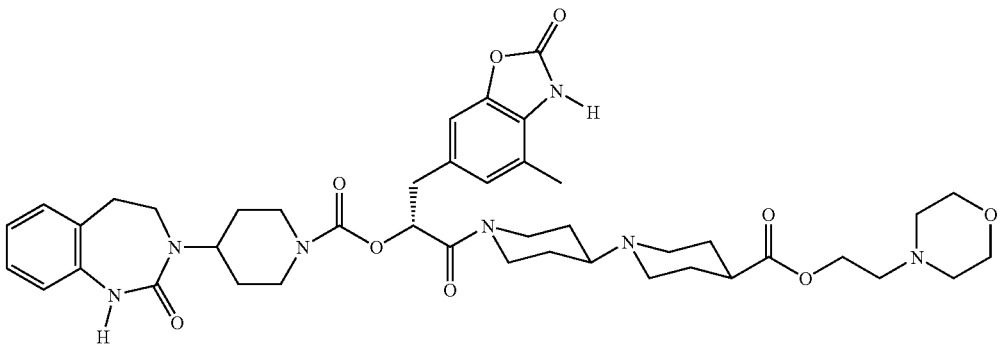 |
| (97) | 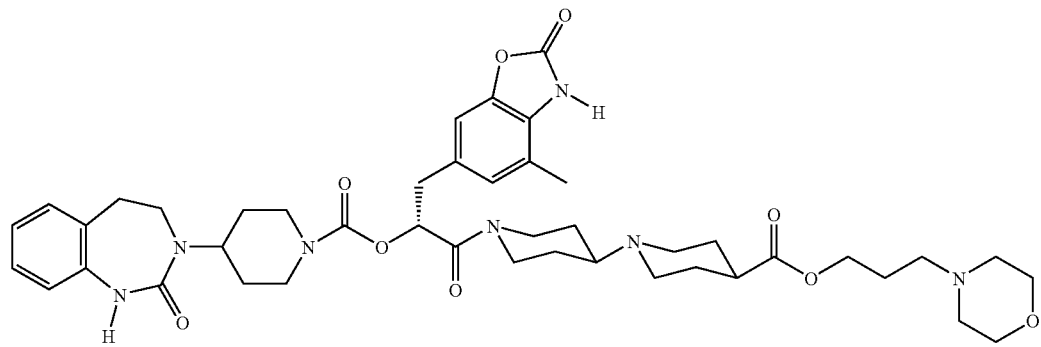 |
| (98) | 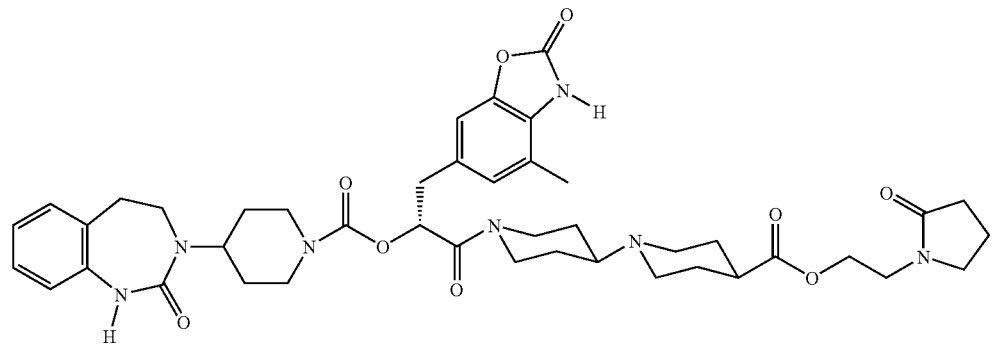 |

| No. | Structure |
|---|---|
| (99) | 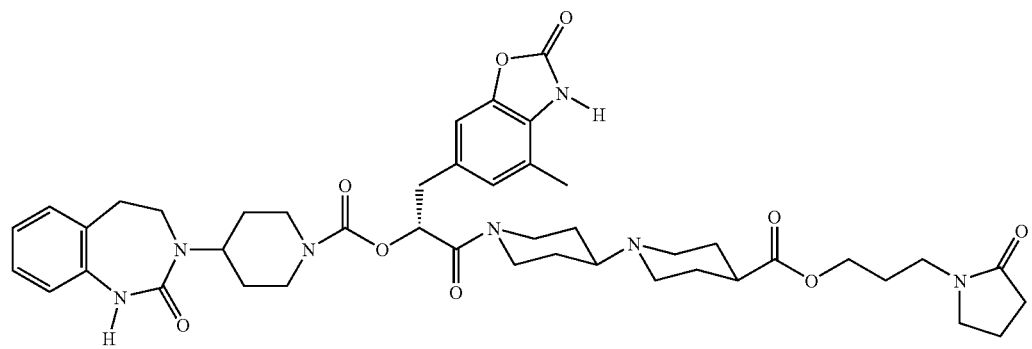 |
| (100) | 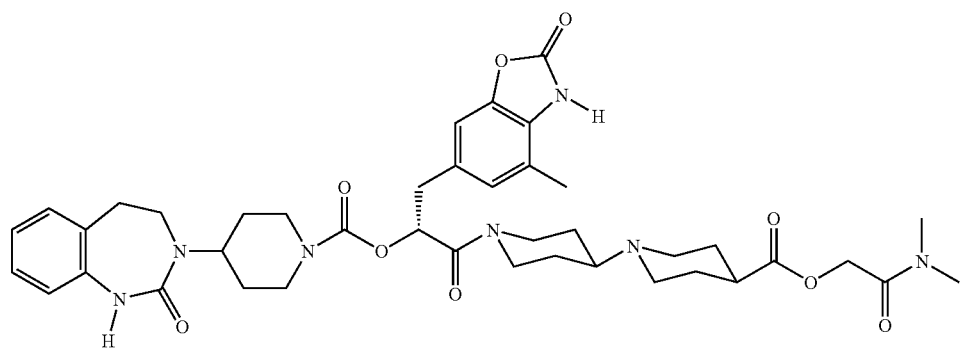 |
| (101) | 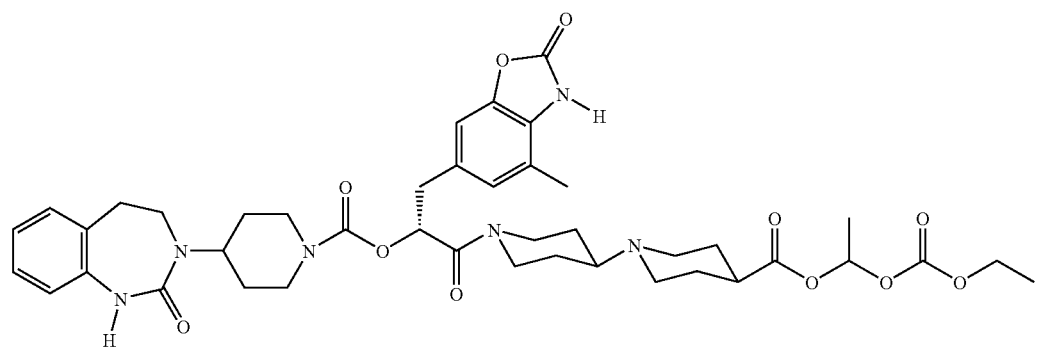 |
| (102) | 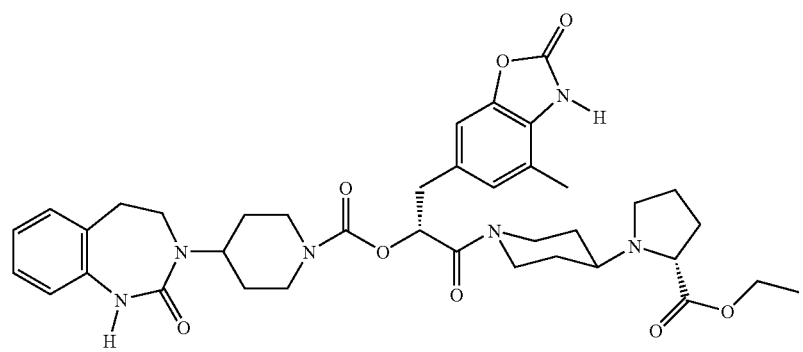 |

| No. | Structure |
|---|---|
| (103) | 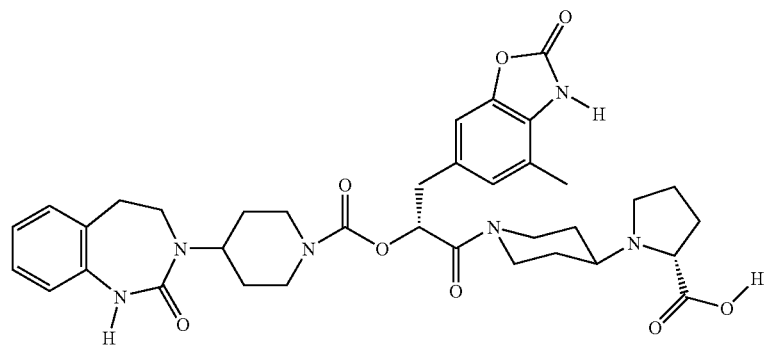 |
| (104) | 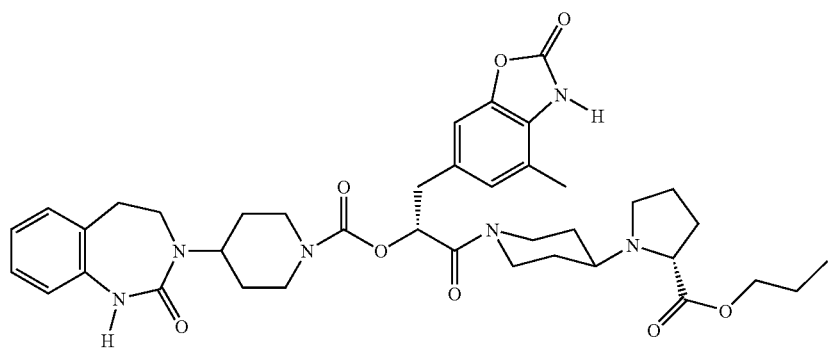 |
| (105) | 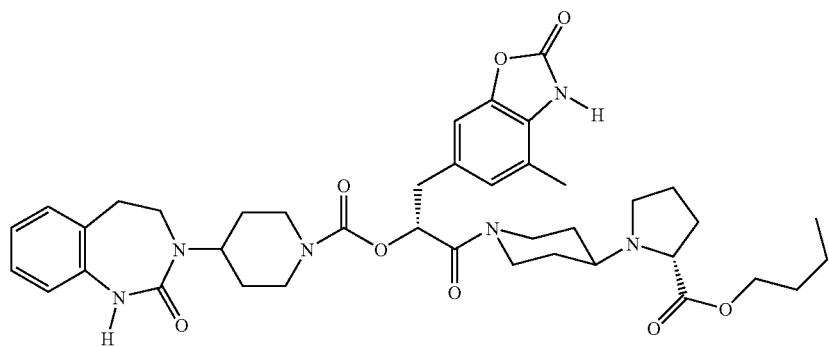 |
| (106) | 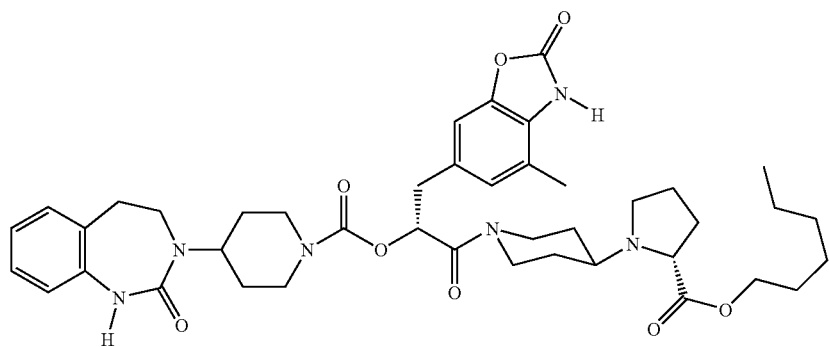 |

| No. | Structure |
|---|---|
| (107) | 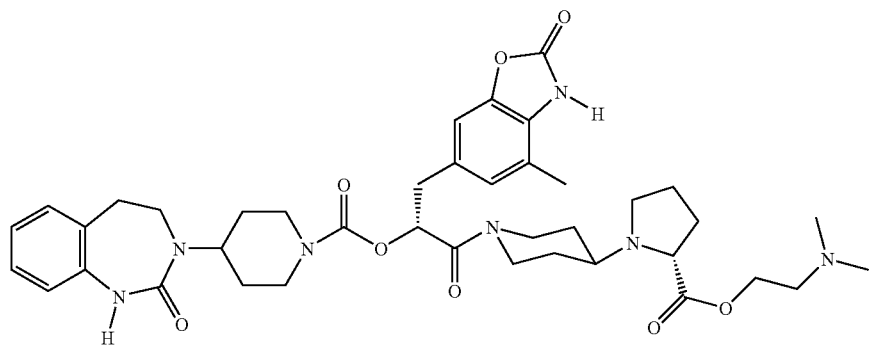 |
| (108) | 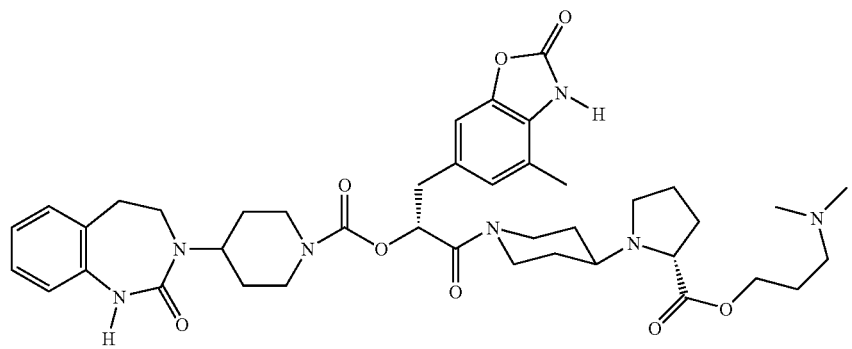 |
| (109) | 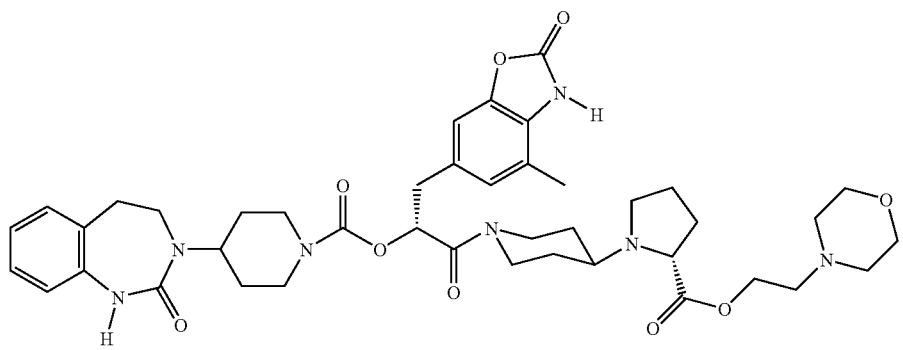 |
| (110) | 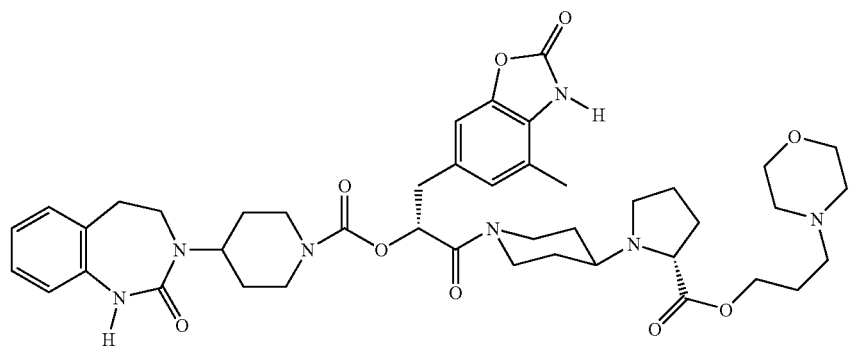 |

-continued
| No. | Structure |
|---|---|
| (111) | 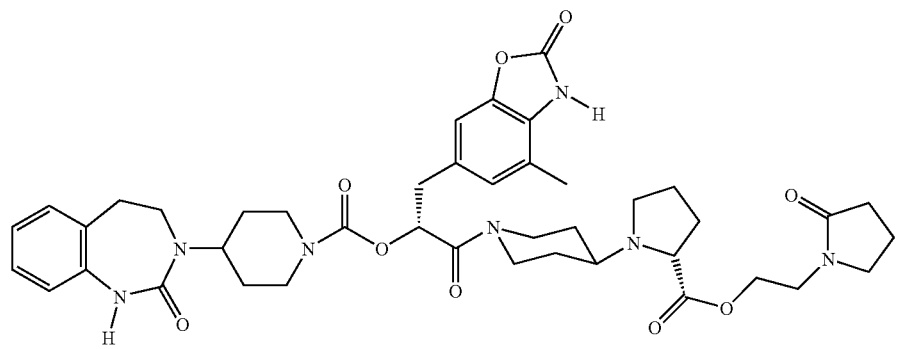 |
| (112) | 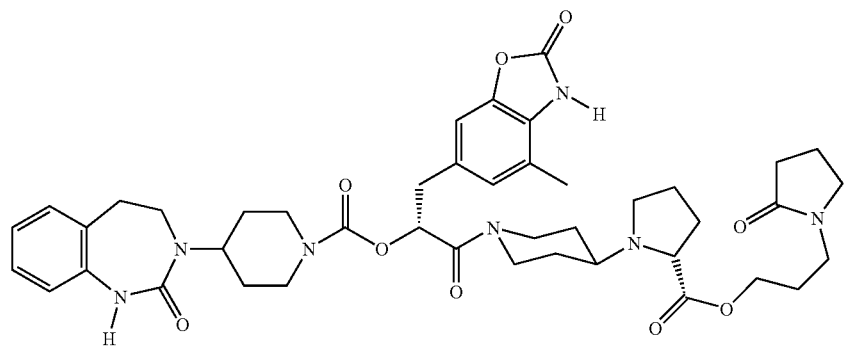 |
| (113) | 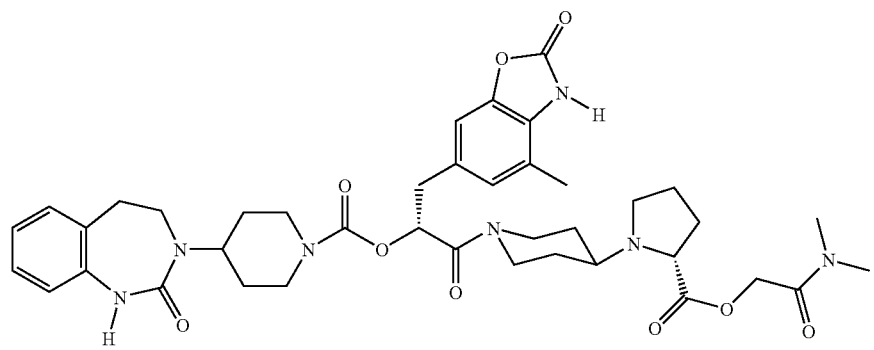 |
| (114) | 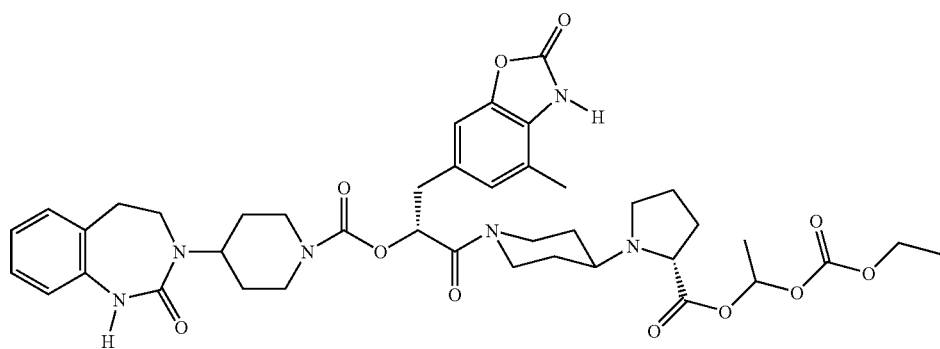 |

-continued
| No. | Structure |
|---|---|
| (115) | 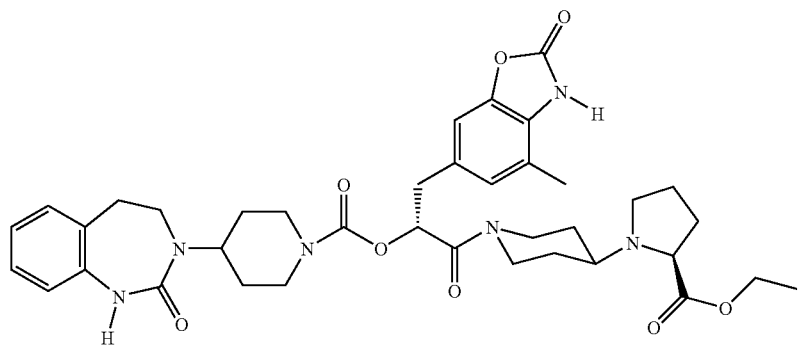 |
| (116) | 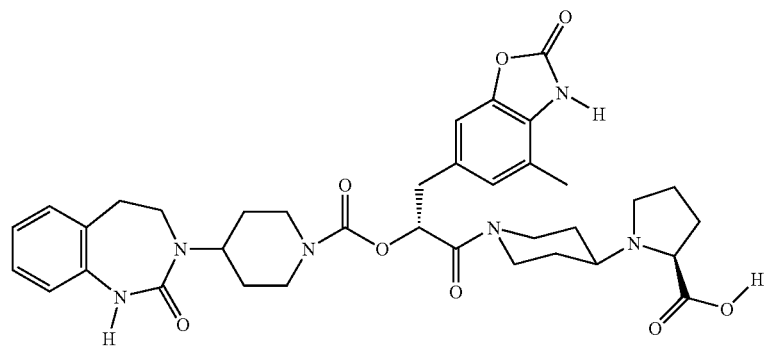 |
| (117) | 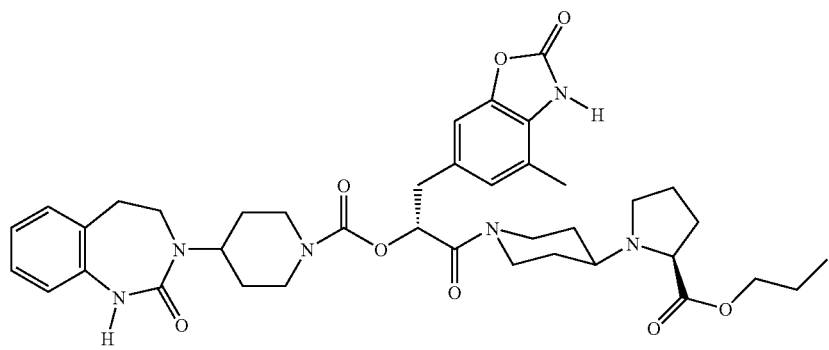 |
| (118) | 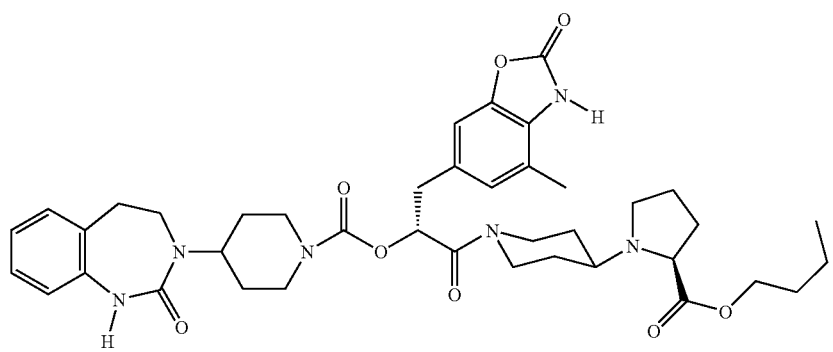 |

| No. | Structure |
|---|---|
| (119) | 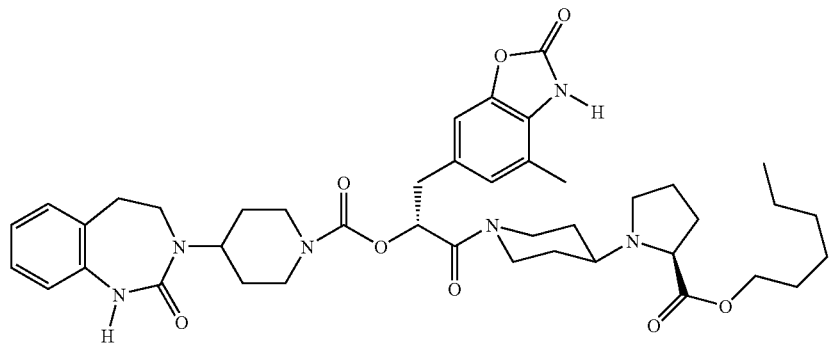 |
| (120) | 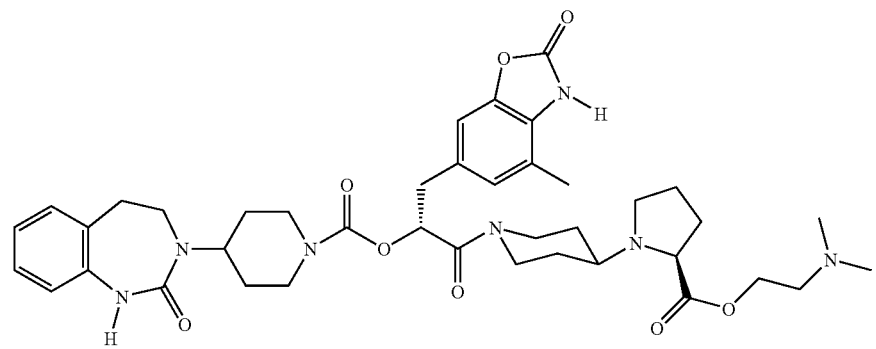 |
| (121) | 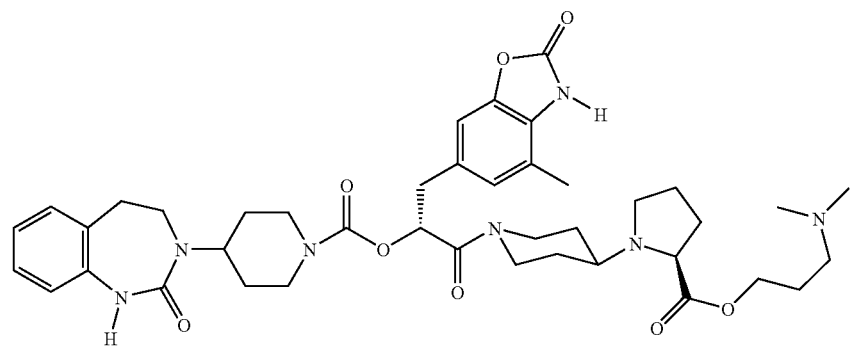 |
| (122) | 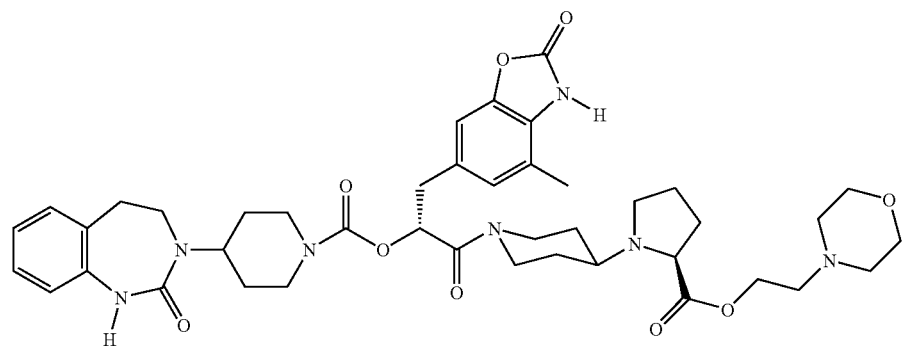 |

| No. | Structure |
|---|---|
| (123) | 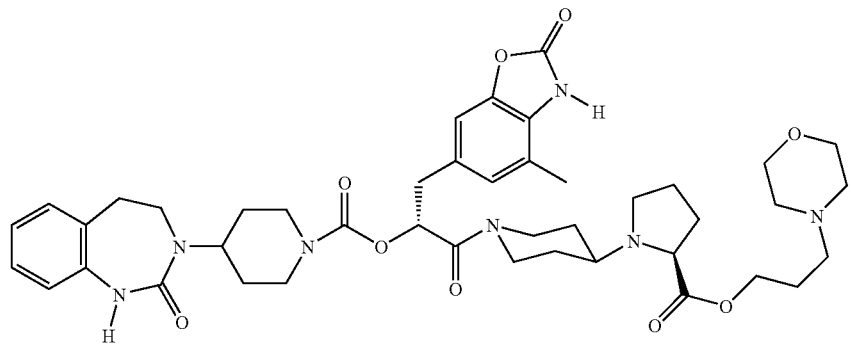 |
| (124) | 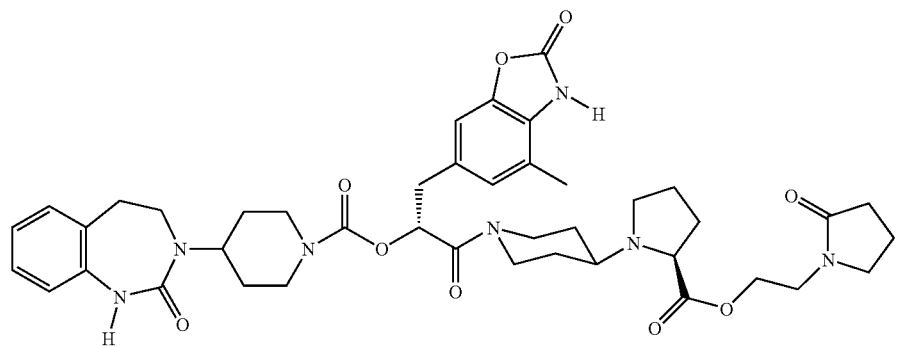 |
| (125) | 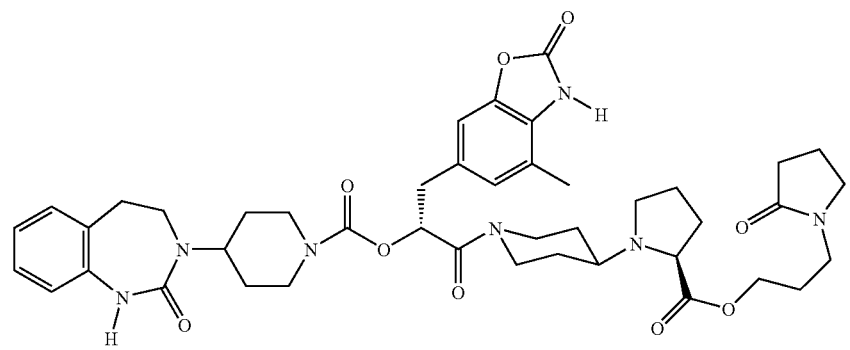 |
| (126) | 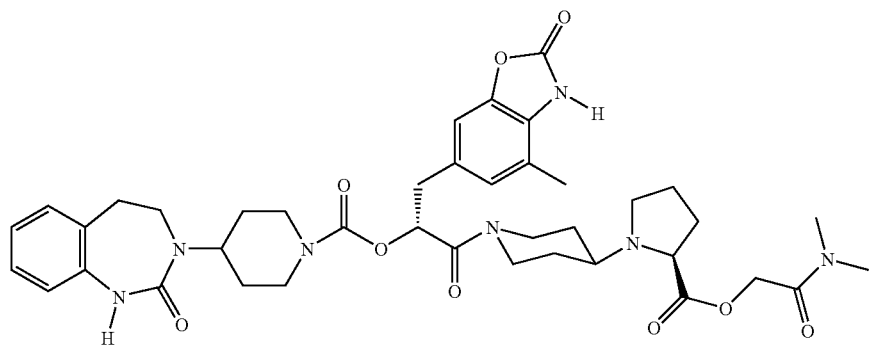 |

-continued
| No. | Structure |
|---|---|
| (127) | 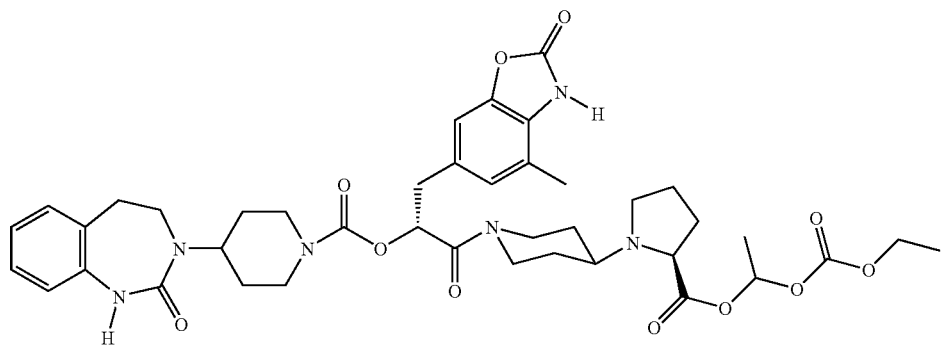 |
| (128) | 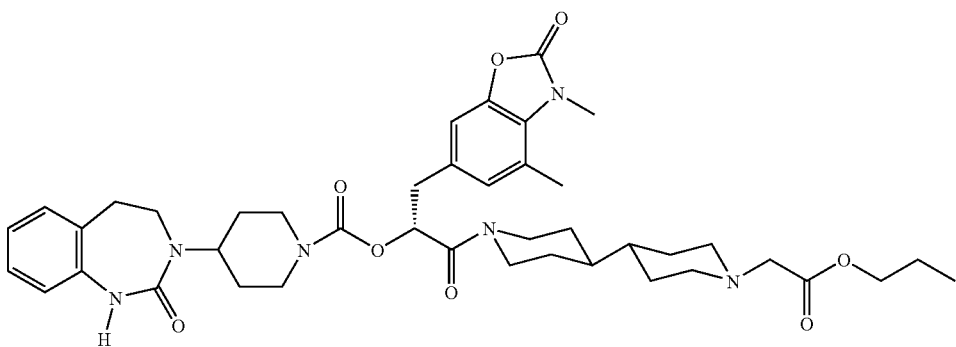 |
| (129) | 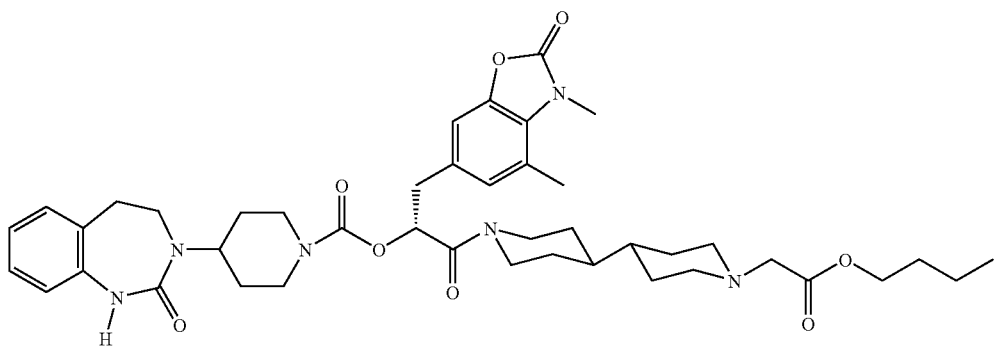 |
| (130) | 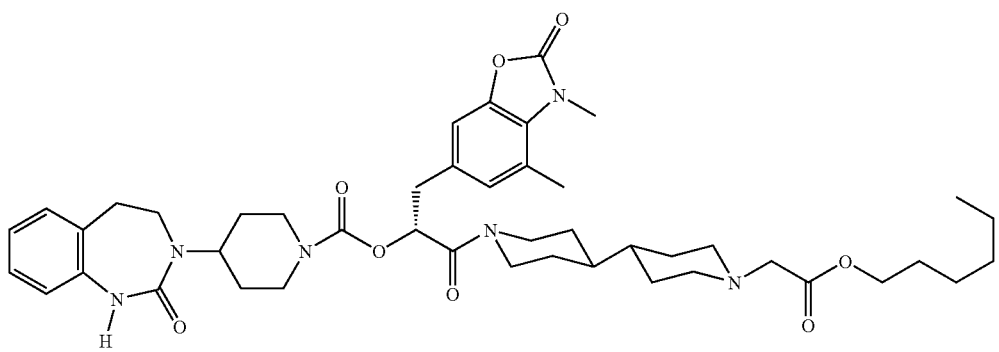 |

-continued
| No. | Structure |
|---|---|
| (131) | 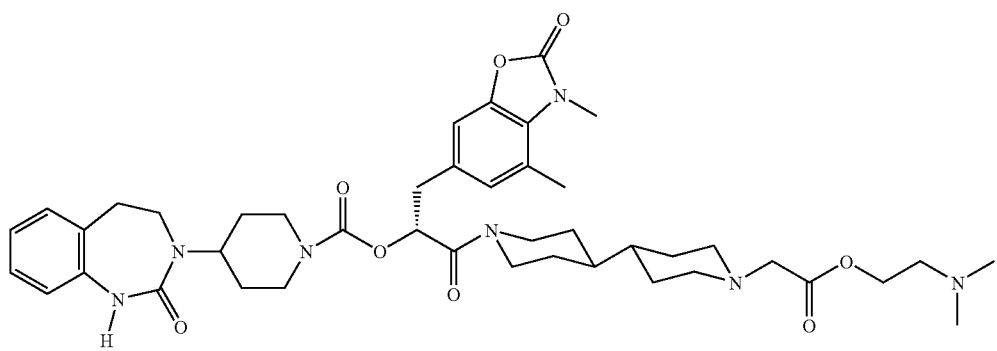 |
| (132) | 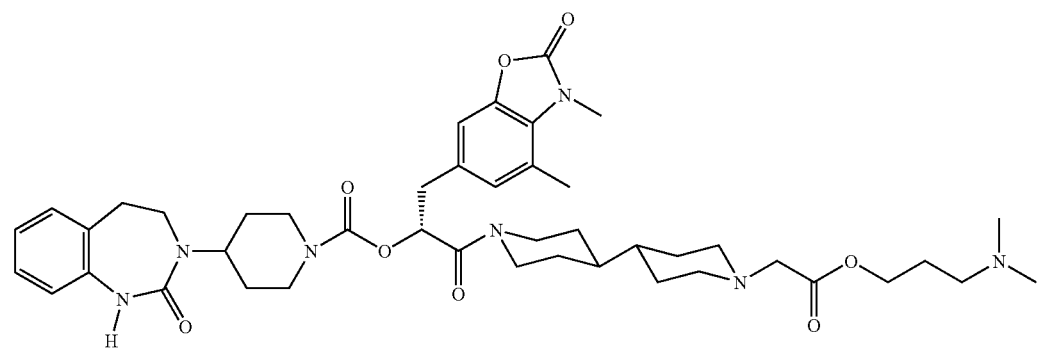 |
| (133) | 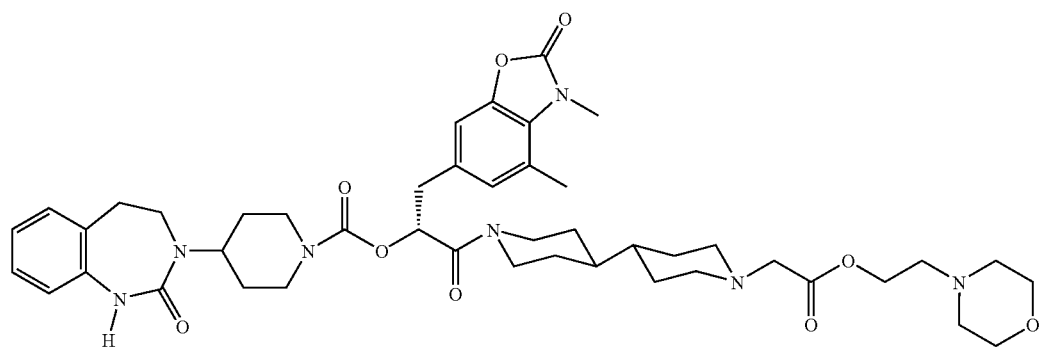 |
| (134) | 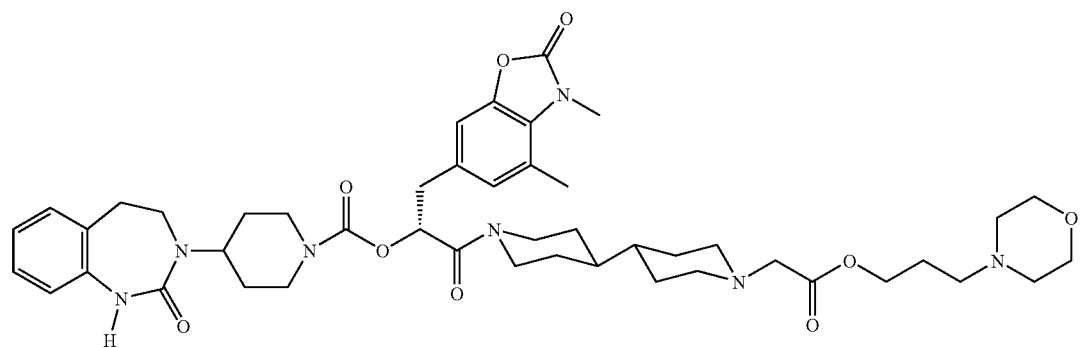 |

| No. | Structure |
|---|---|
| (135) | 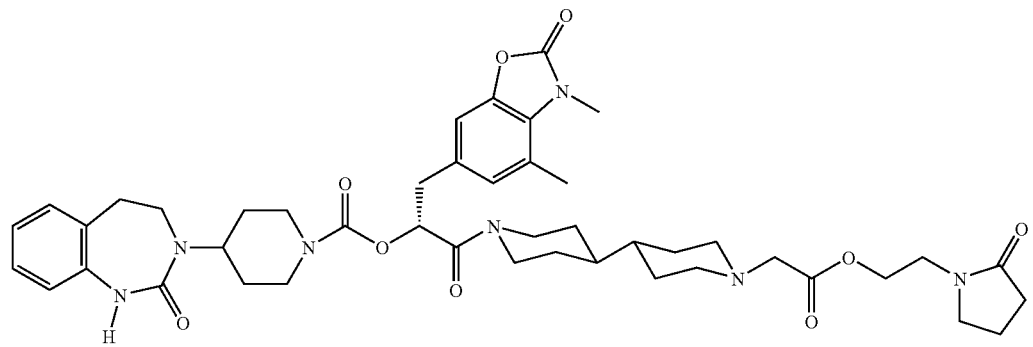 |
| (136) | 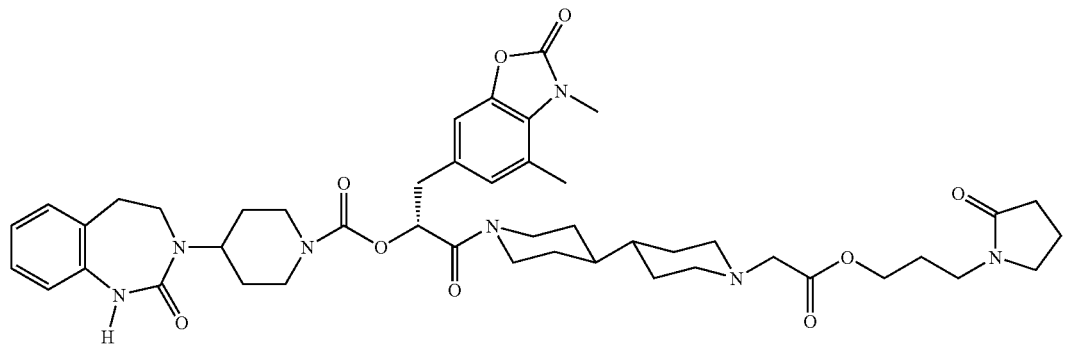 |
| (137) | 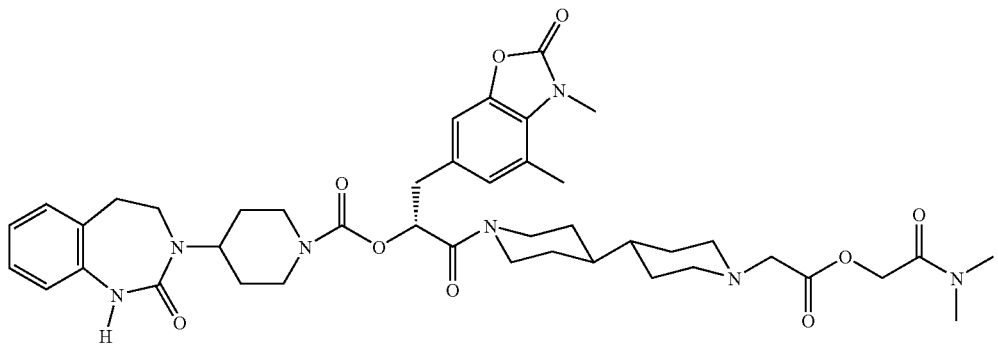 |
| (138) | 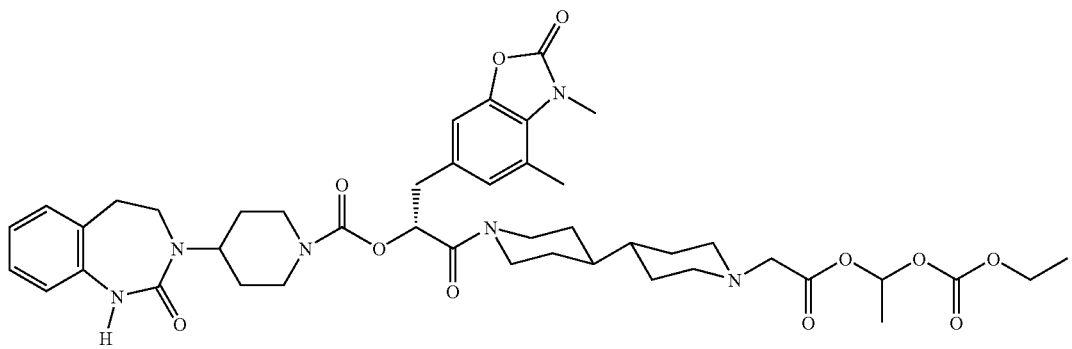 |

| No. | Structure |
|---|---|
| (139) | 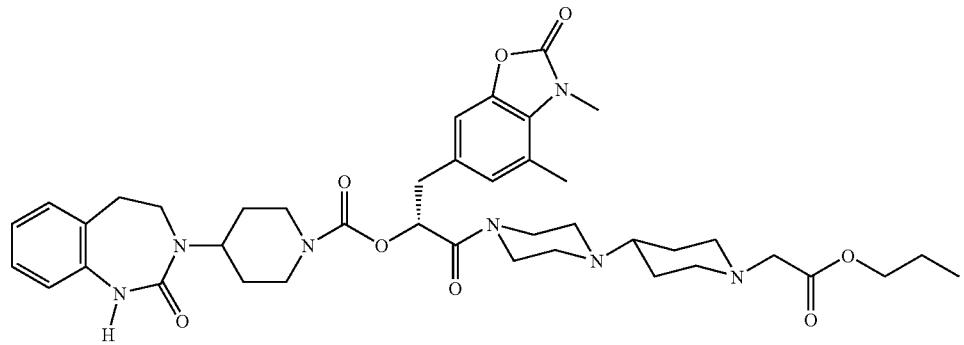 |
| (140) | 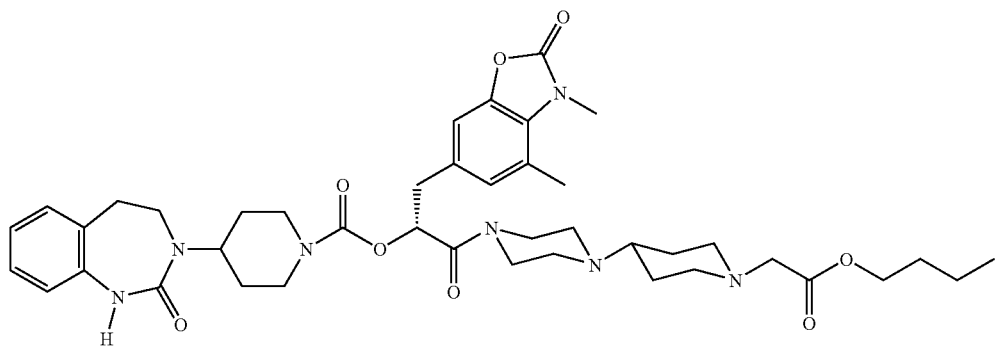 |
| (141) | 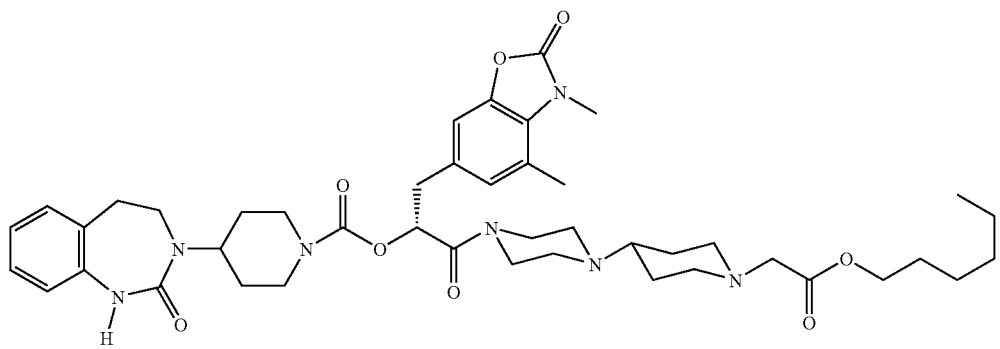 |
| (142) | 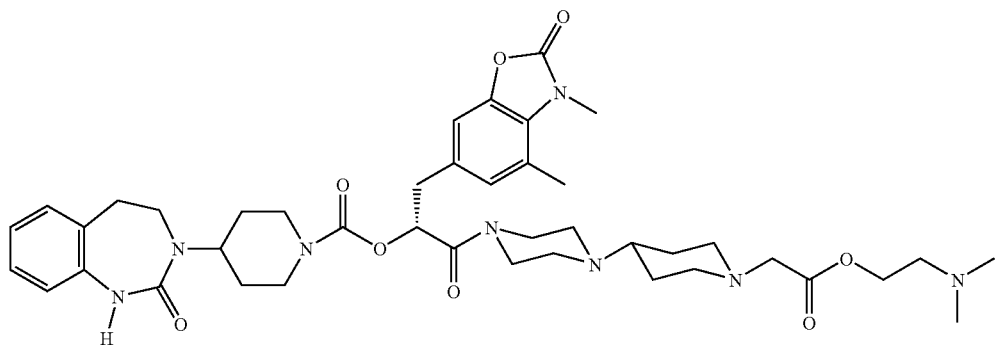 |

| No. | Structure |
|---|---|
| (143) | 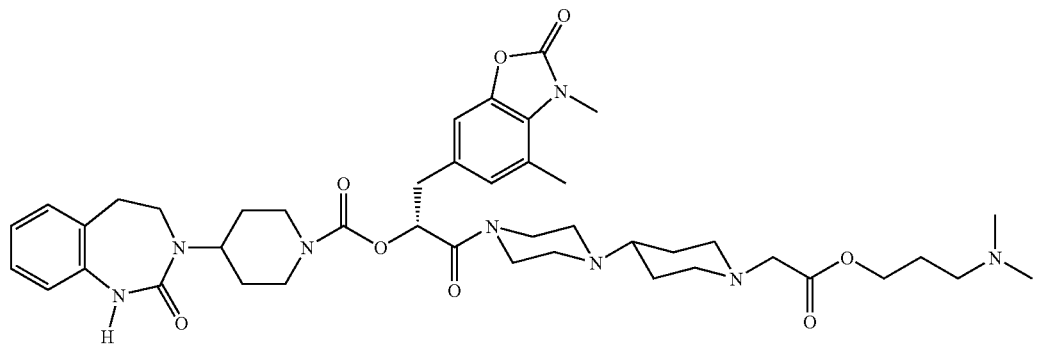 |
| (144) | 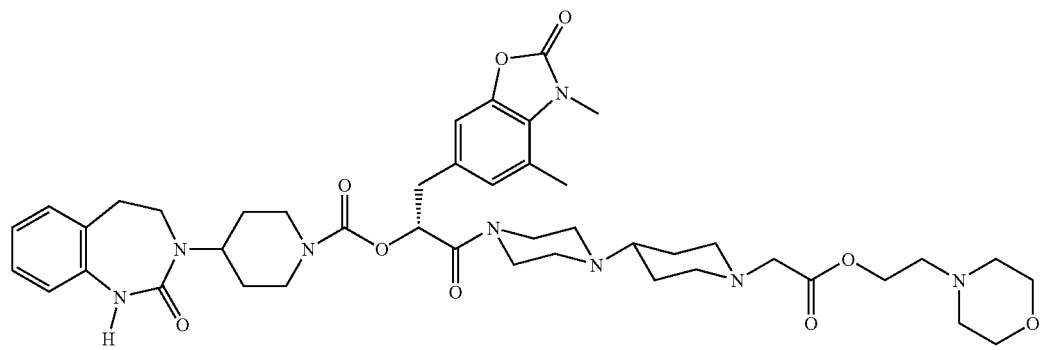 |
| (145) | 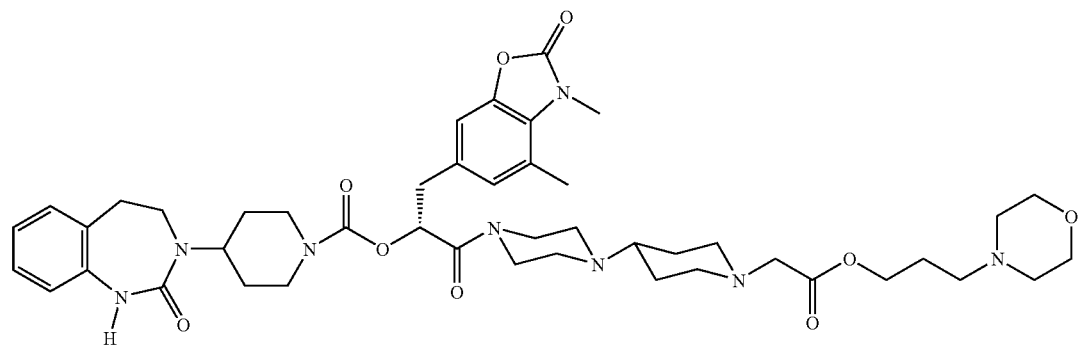 |
| (146) | 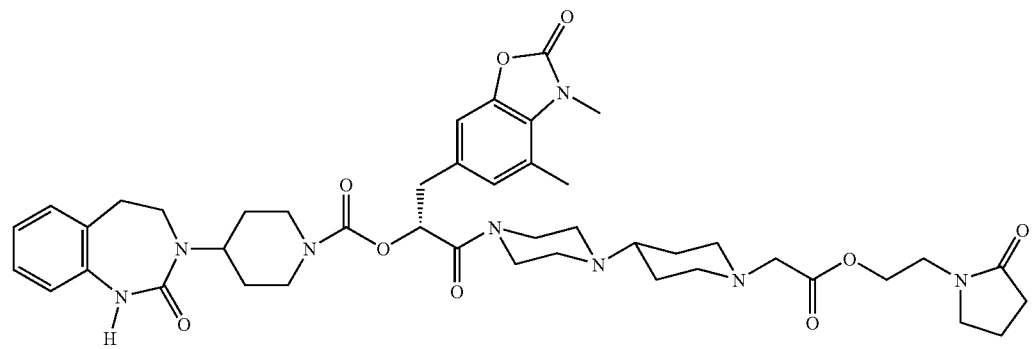 |

| No. | Structure |
|---|---|
| (147) | 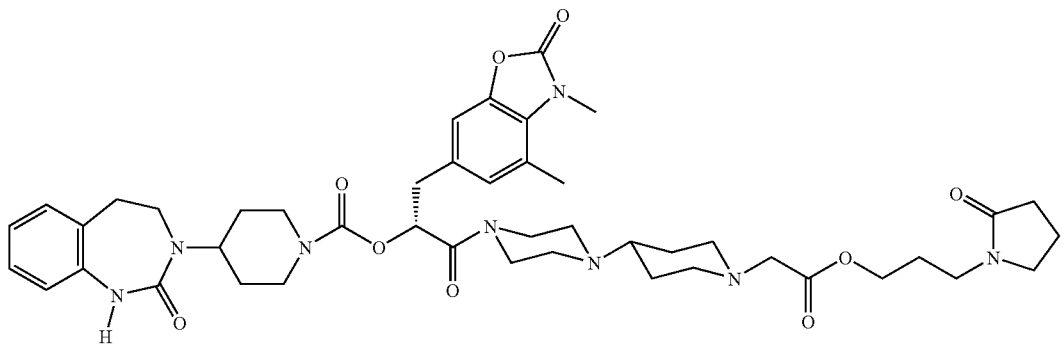 |
| (148) | 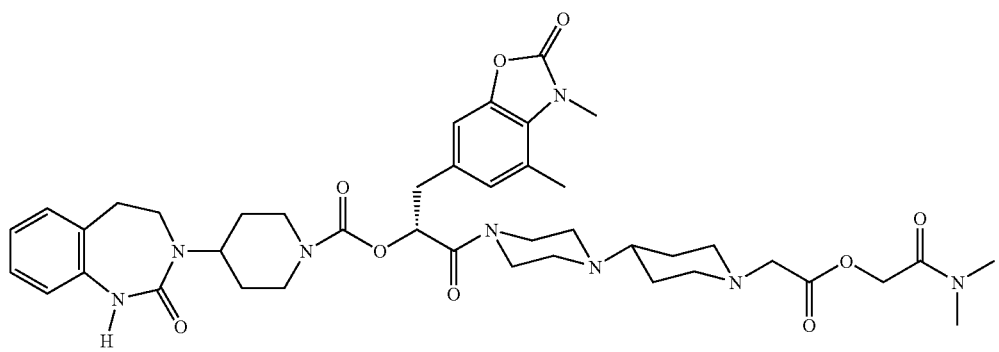 |
| (149) | 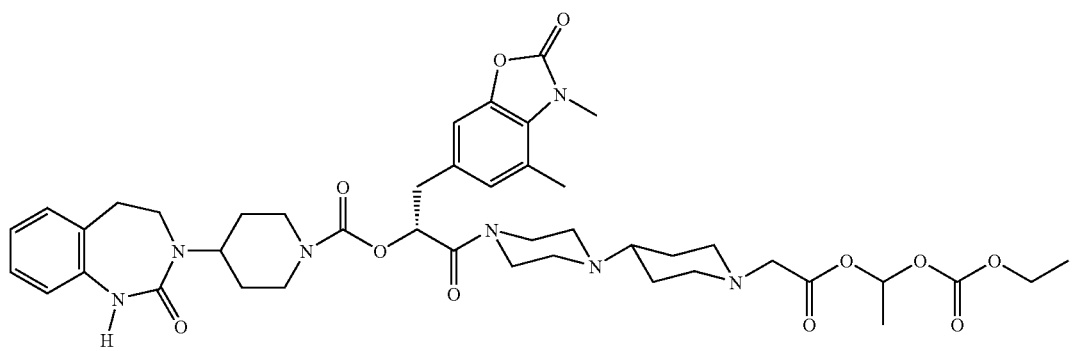 |
| (150) | 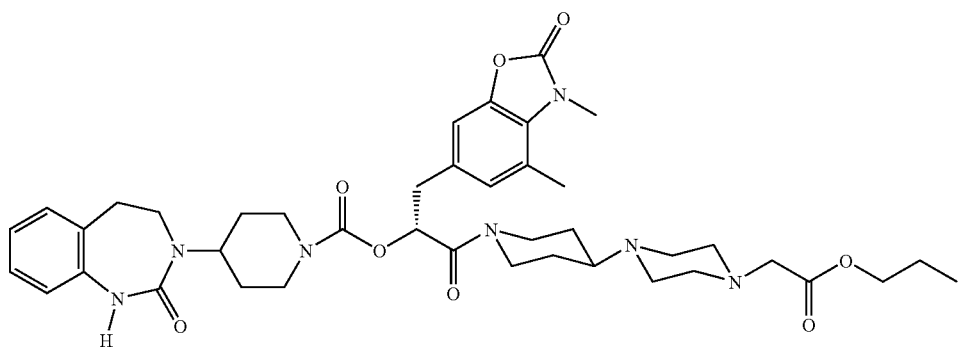 |

| No. | Structure |
|---|---|
| (151) | 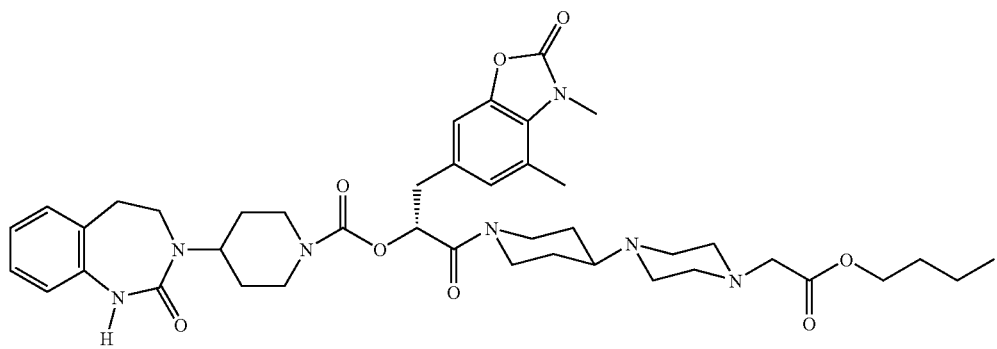 |
| (152) | 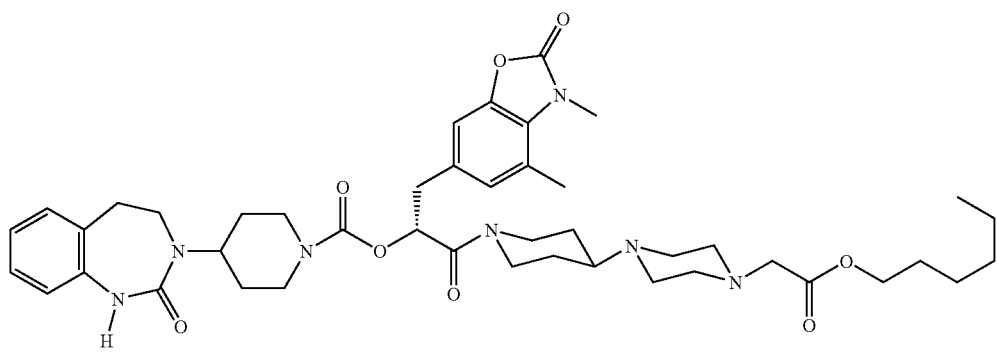 |
| (153) | 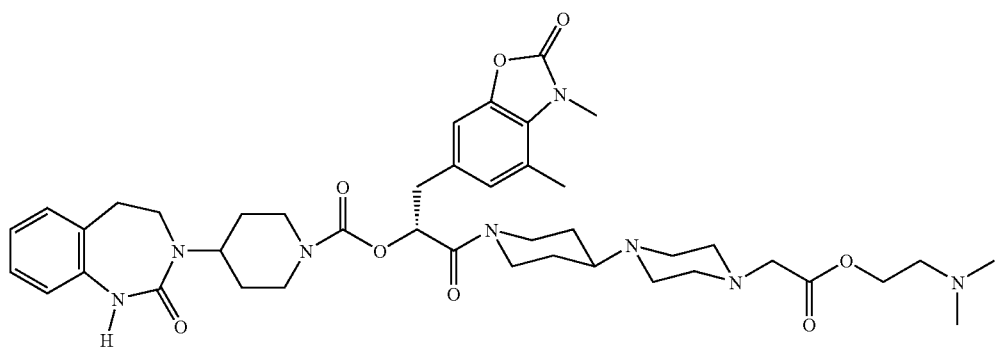 |
| (154) | 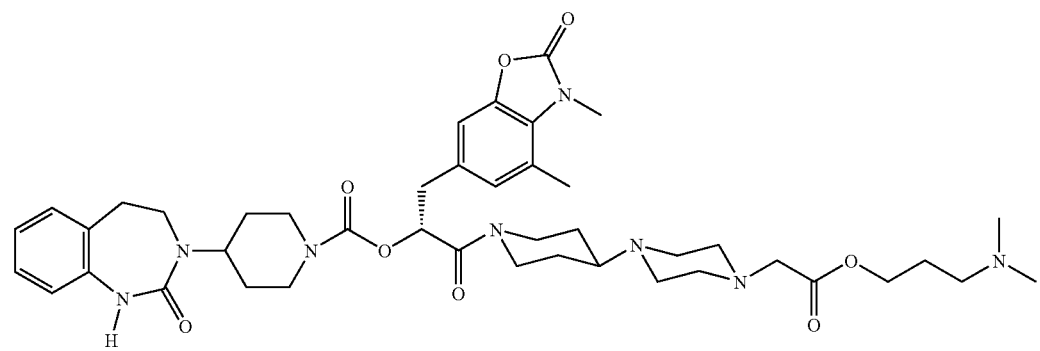 |

| No. | Structure |
|---|---|
| (155) | 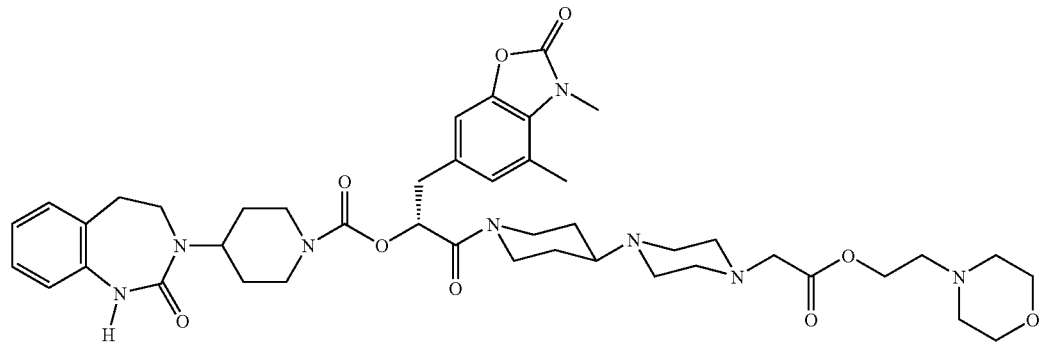 |
| (156) | 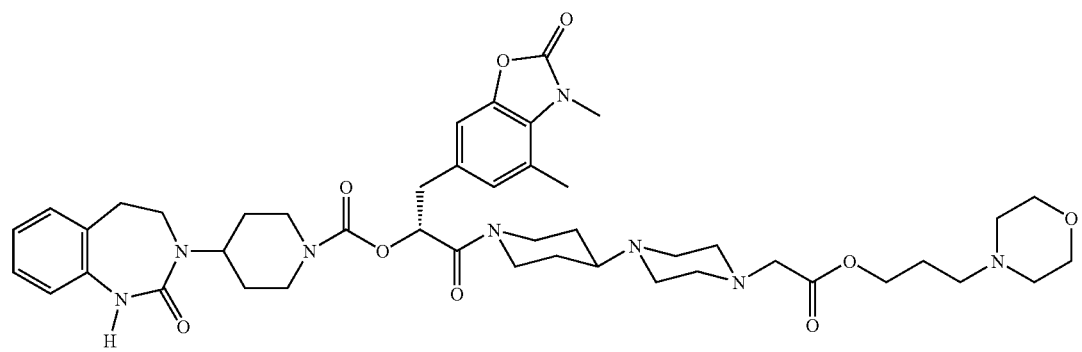 |
| (157) | 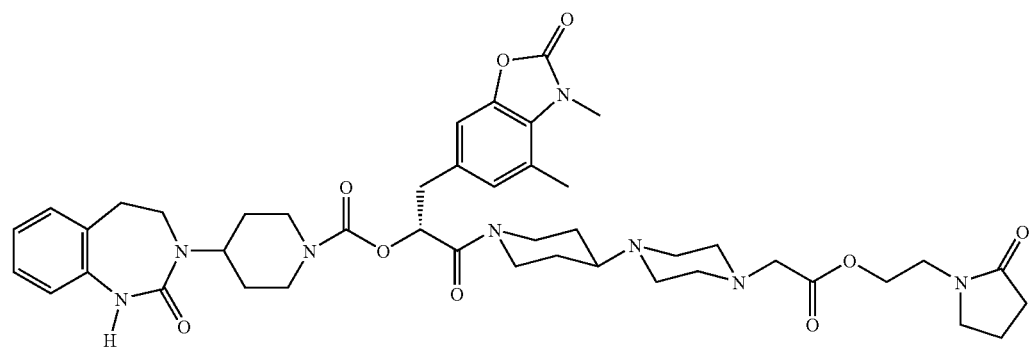 |
| (158) | 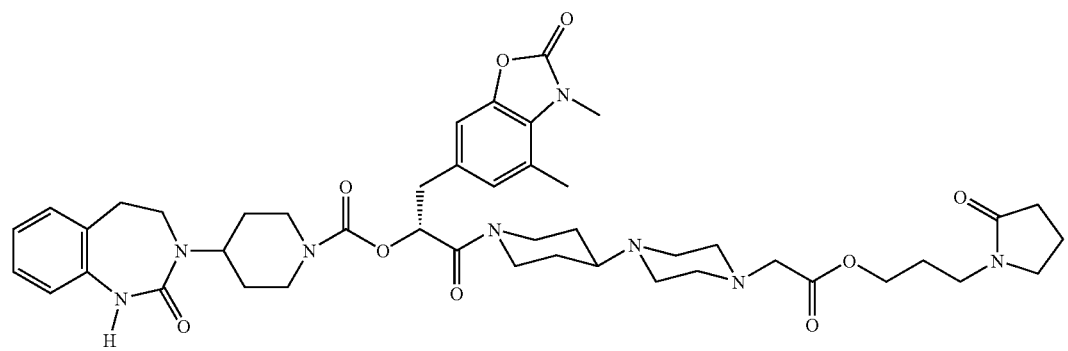 |

| No. | Structure |
|---|---|
| (159) | 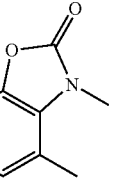 |
| (160) | 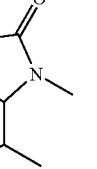 |
| (161) | 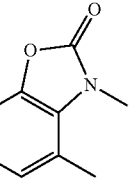 |
| (162) | 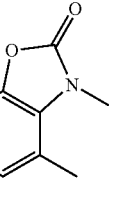 |

-continued
| No. | Structure |
|---|---|
| (163) | 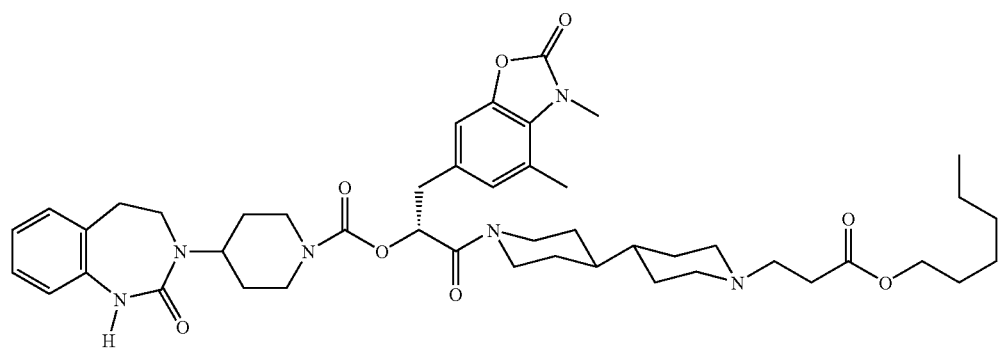 |
| (164) | 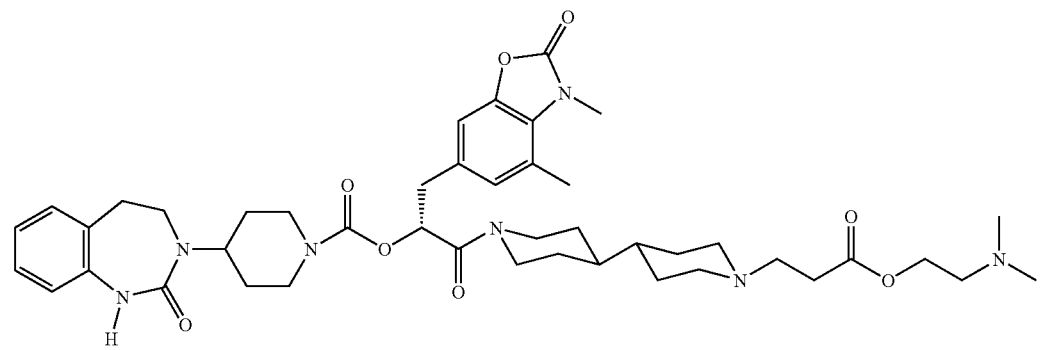 |
| (165) | 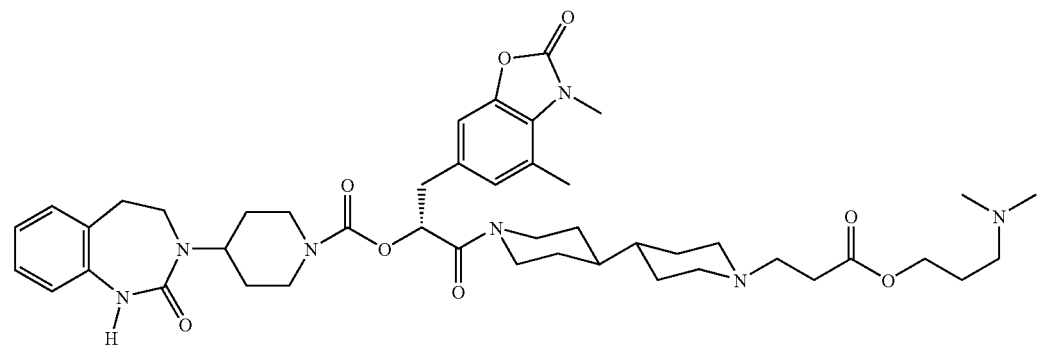 |
| (166) | 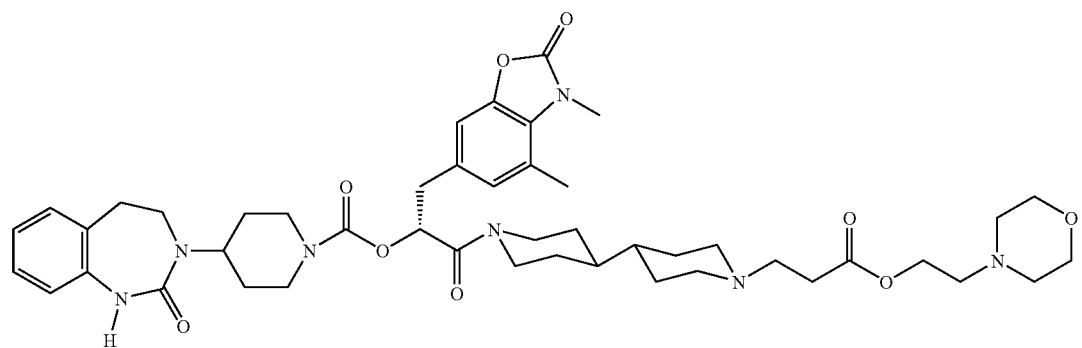 |

| No. | Structure |
|---|---|
| (167) | 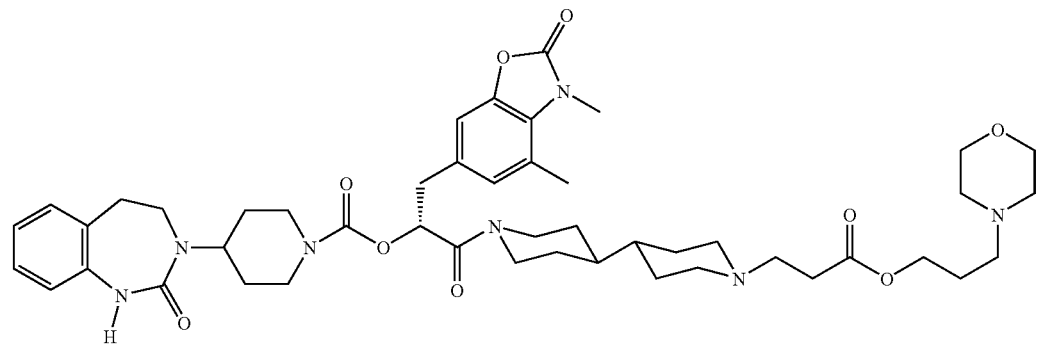 |
| (168) | 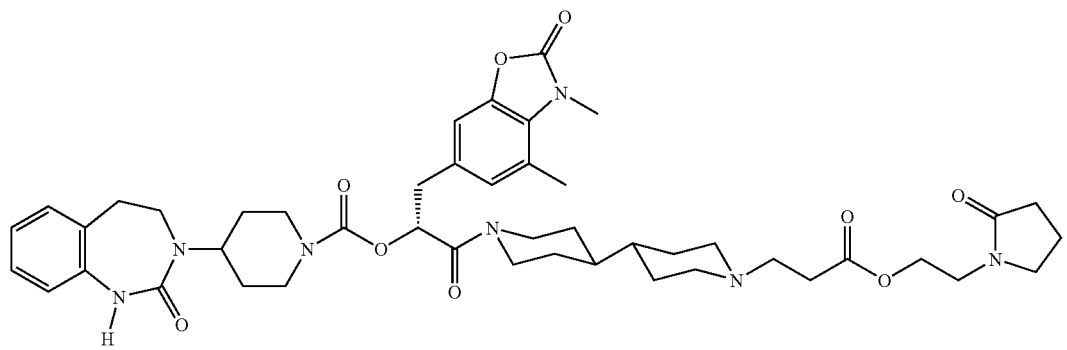 |
| (169) | 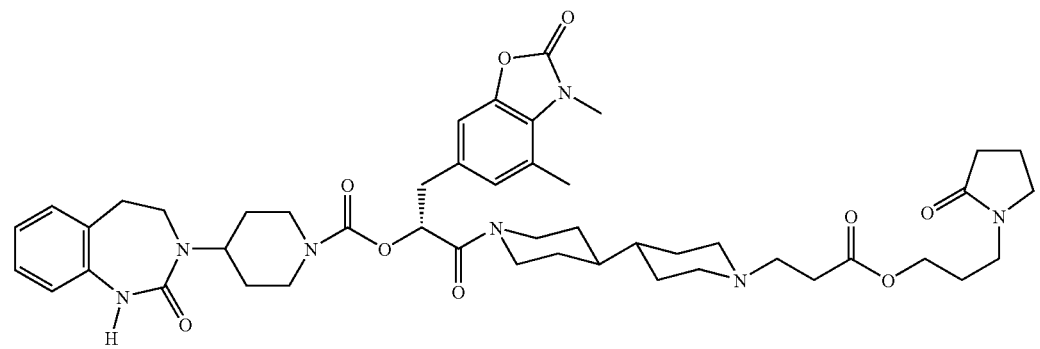 |
| (170) | 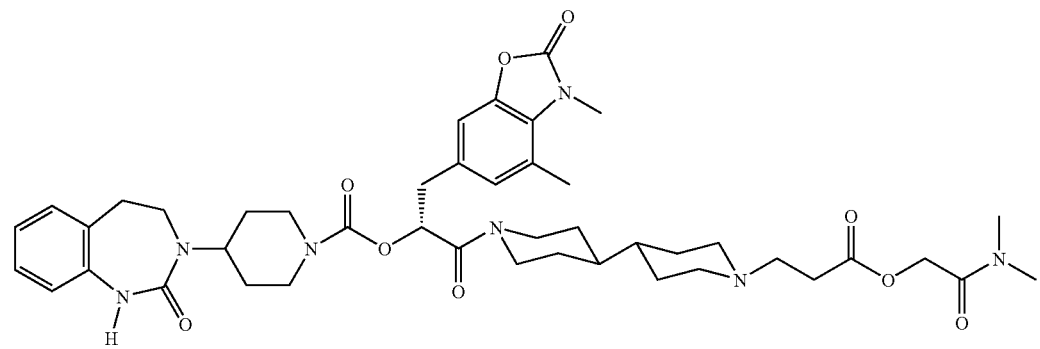 |

| No. | Structure |
|---|---|
| (171) | 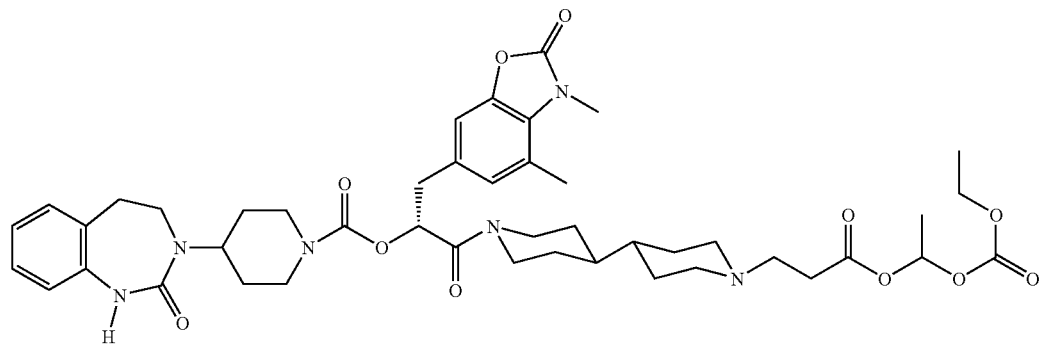 |
| (172) | 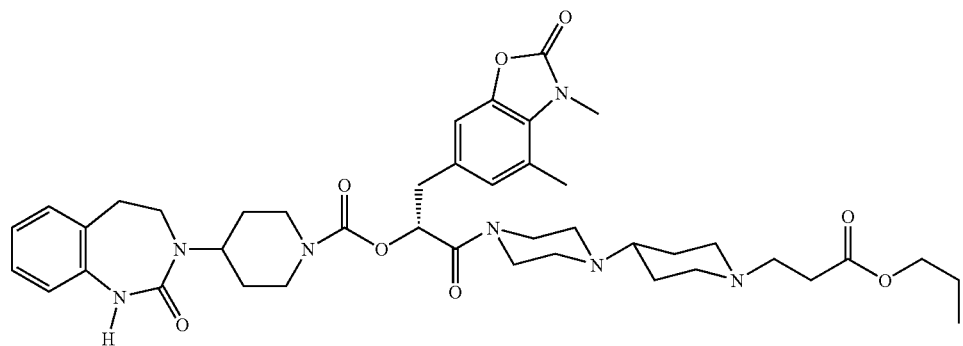 |
| (173) | 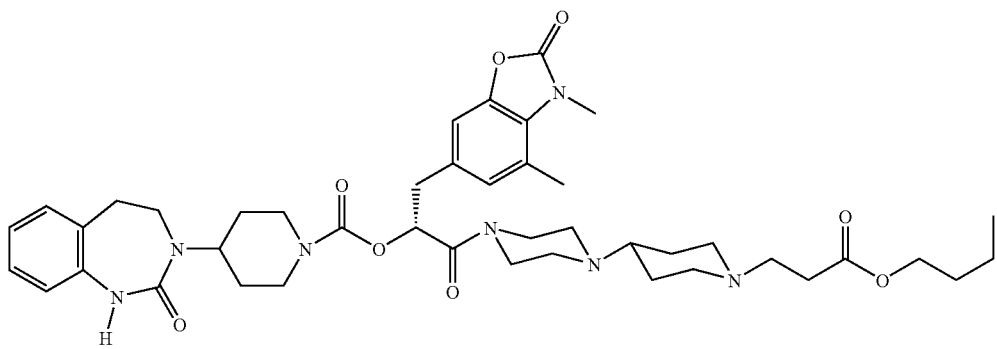 |
| (174) | 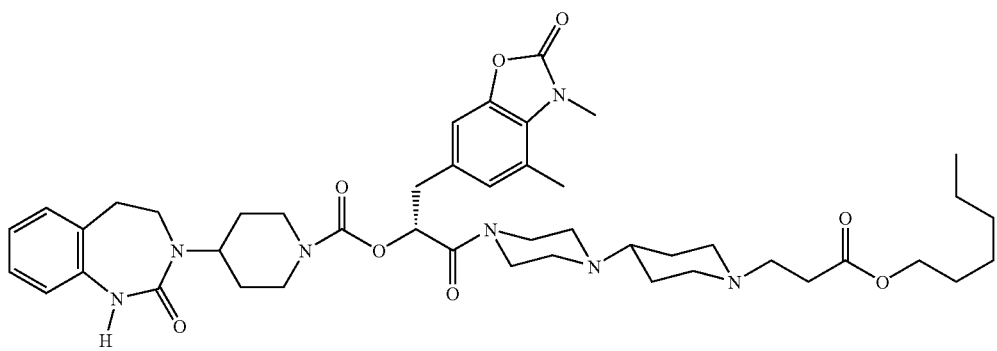 |

| No. | Structure |
|---|---|
| (175) | 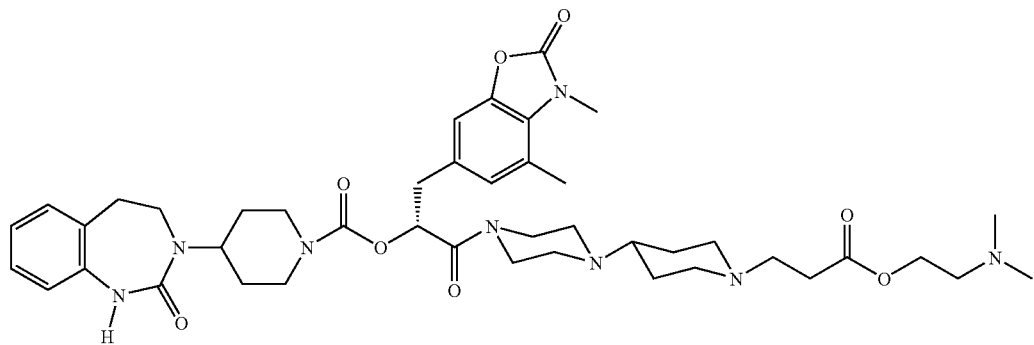 |
| (176) | 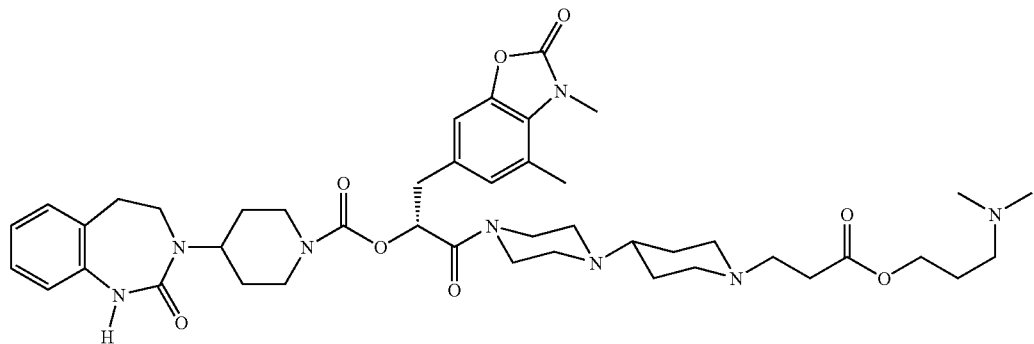 |
| (177) | 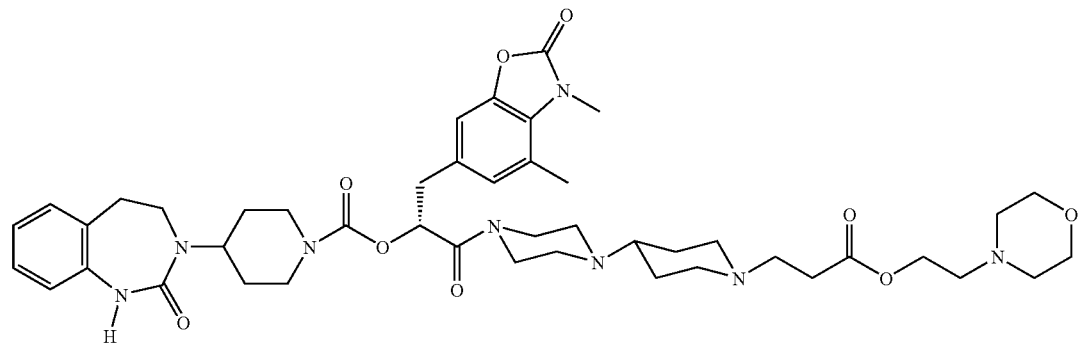 |
| (178) | 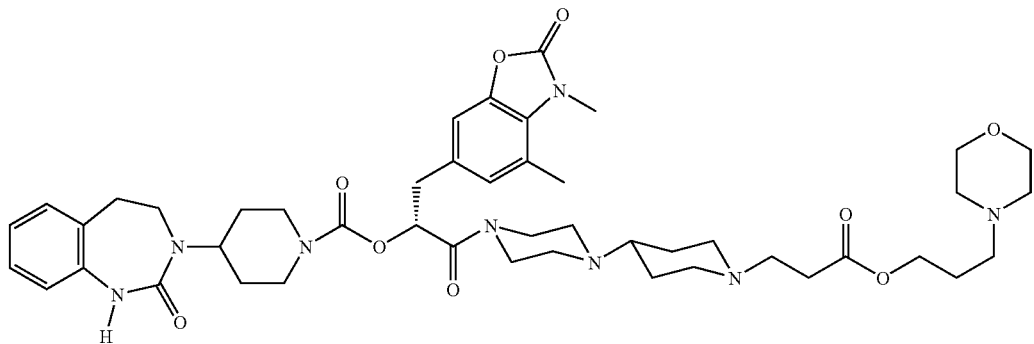 |

| No. | Structure |
|---|---|
| (179) | 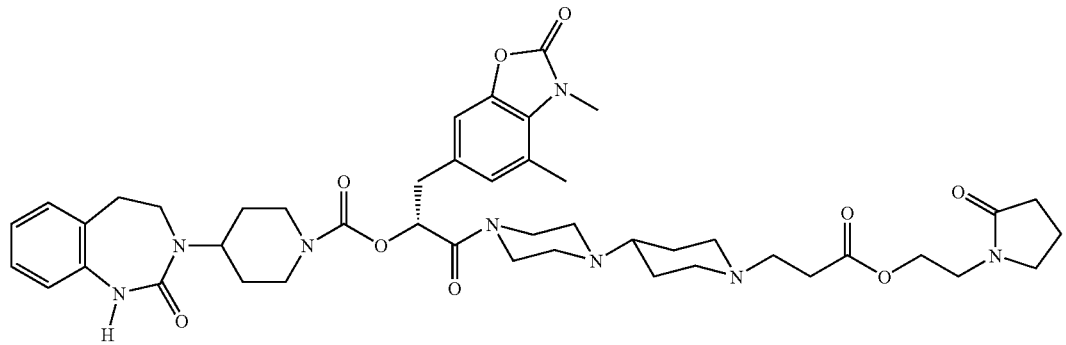 |
| (180) | 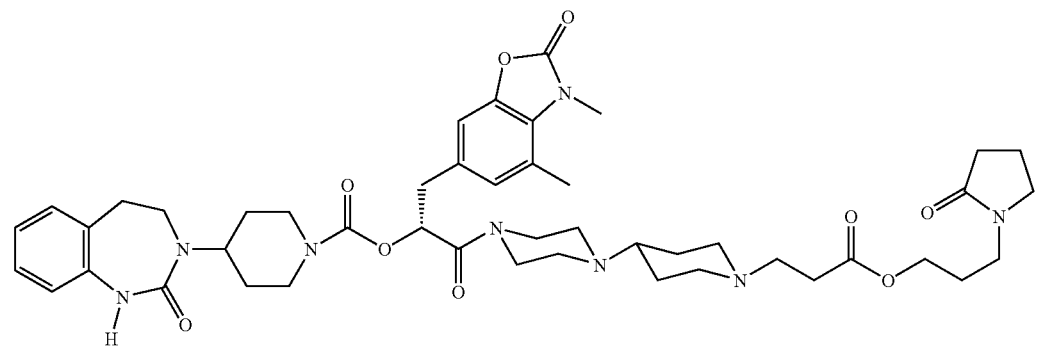 |
| (181) | 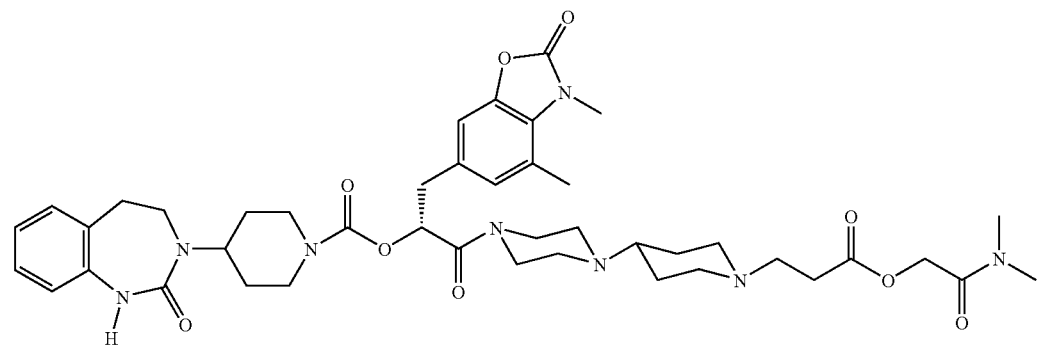 |
| (182) | 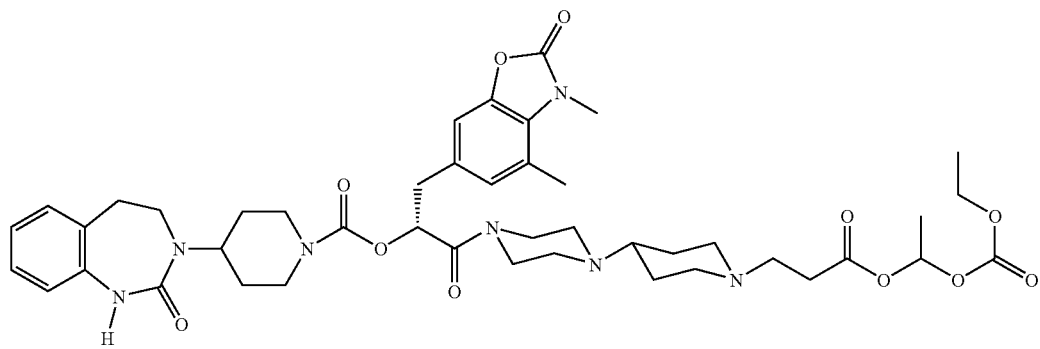 |

| No. | Structure |
|---|---|
| (183) | 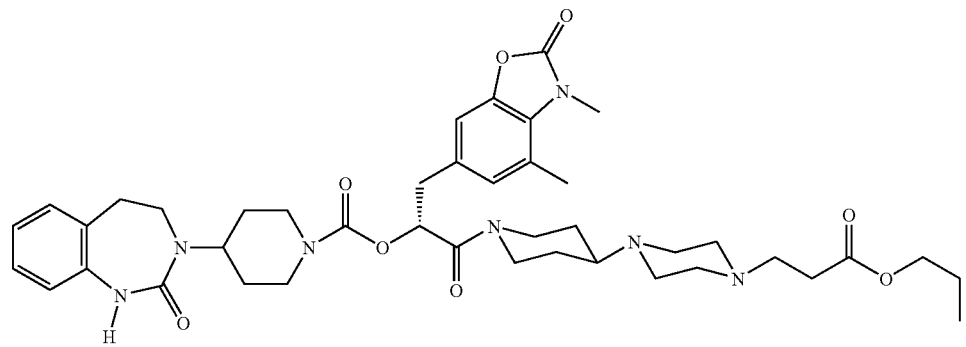 |
| (184) | 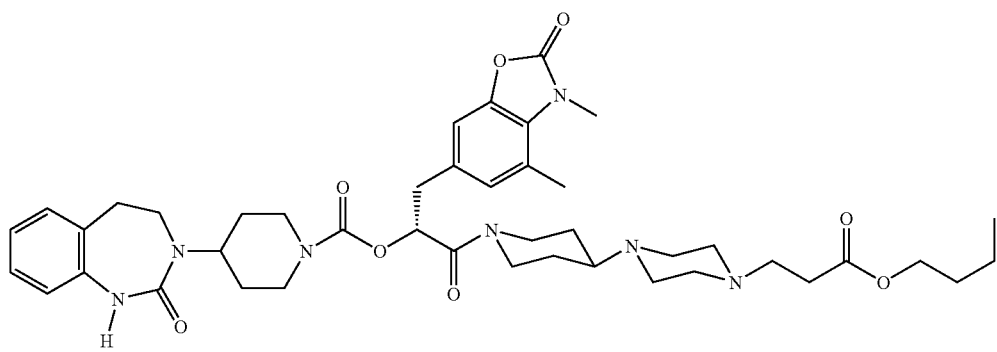 |
| (185) | 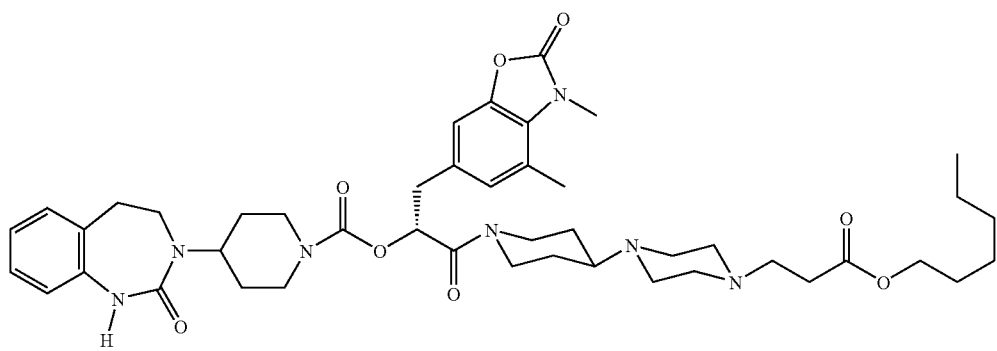 |
| (186) | 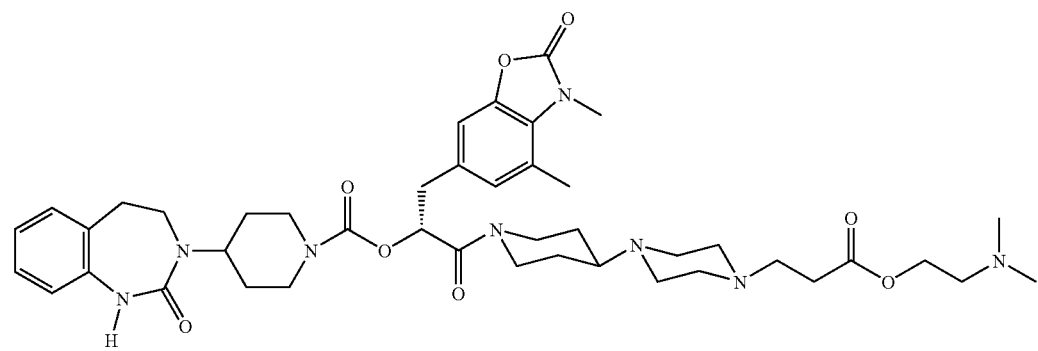 |

-continued
| No. | Structure |
|---|---|
| (187) | 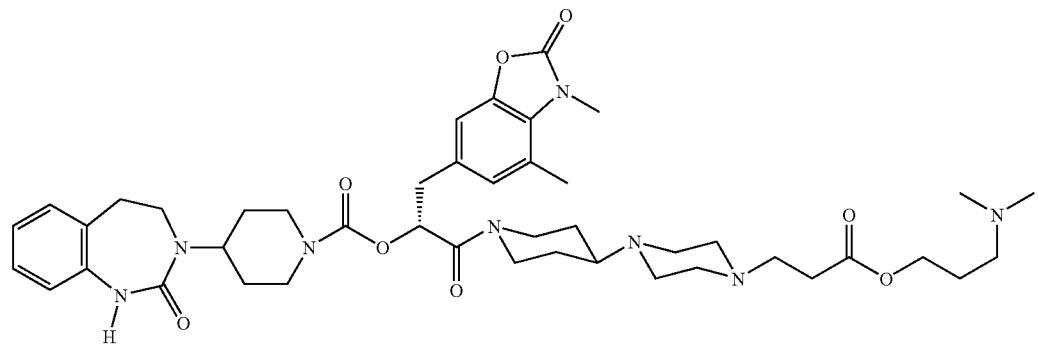 |
| (188) | 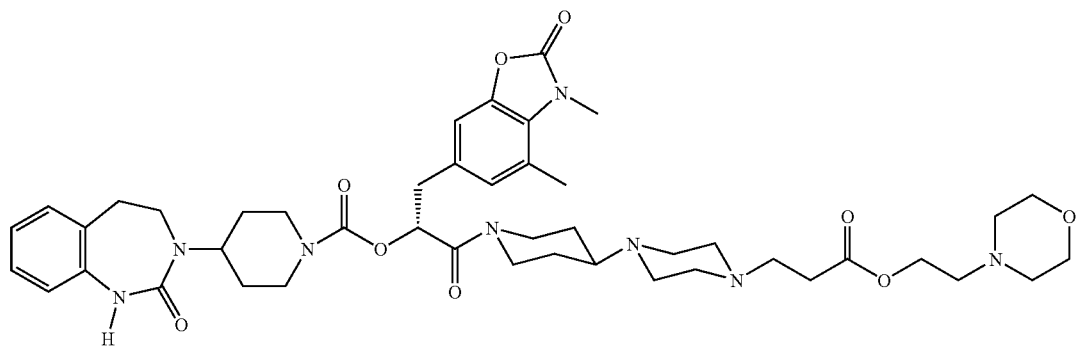 |
| (189) | 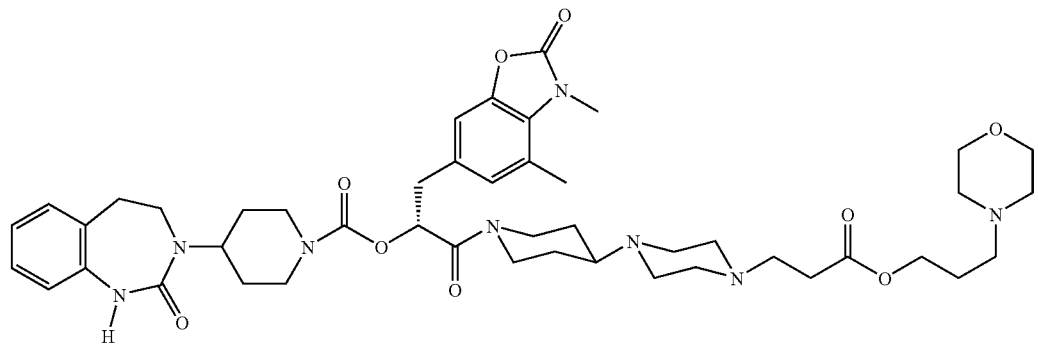 |
| (190) | 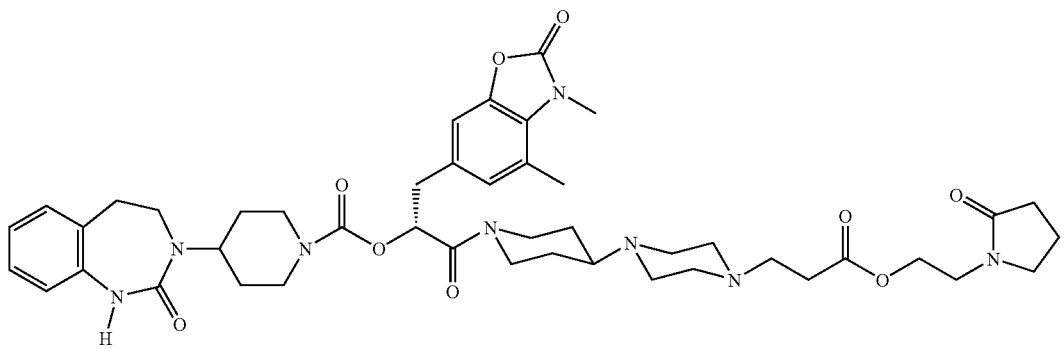 |

| No. | Structure |
|---|---|
| (191) | 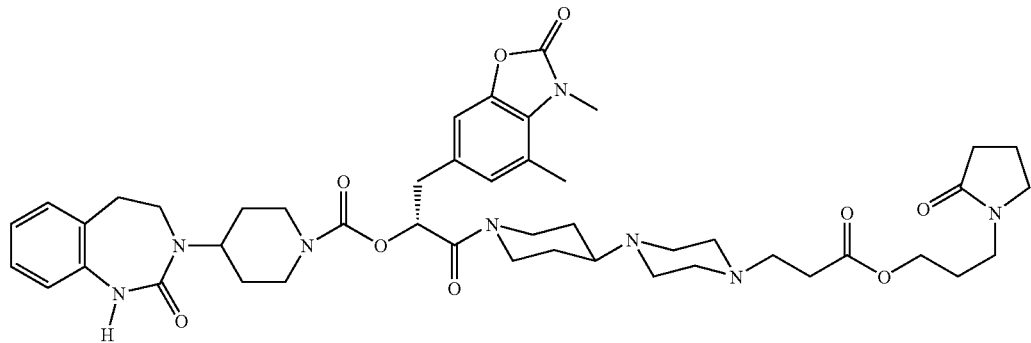 |
| (192) | 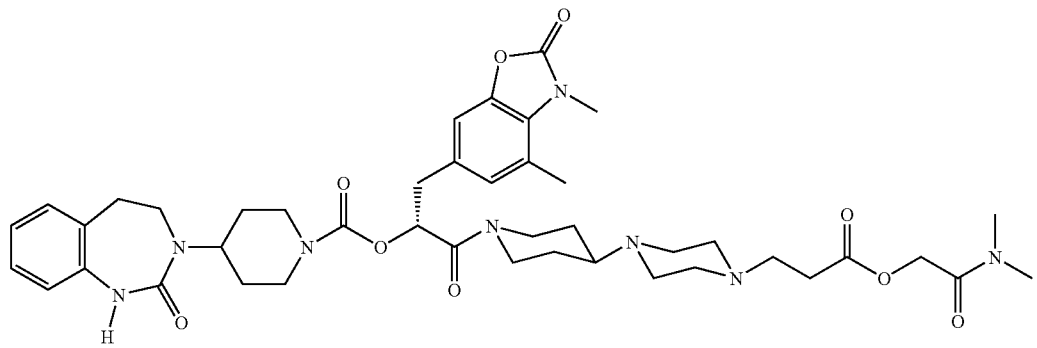 |
| (193) | 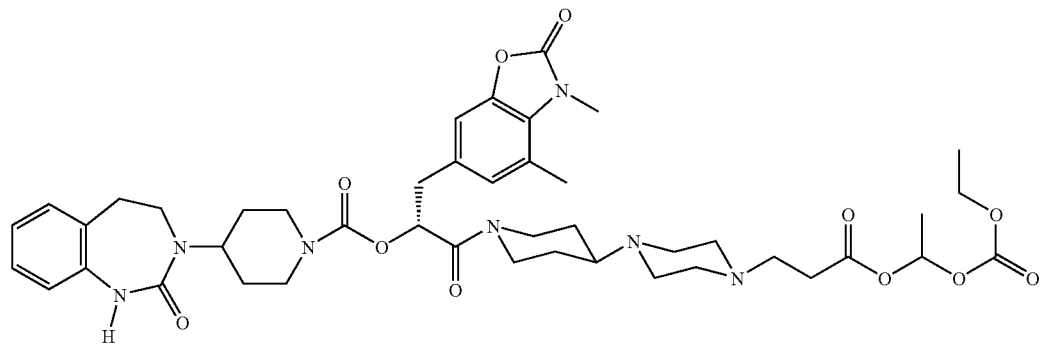 |
| (194) | 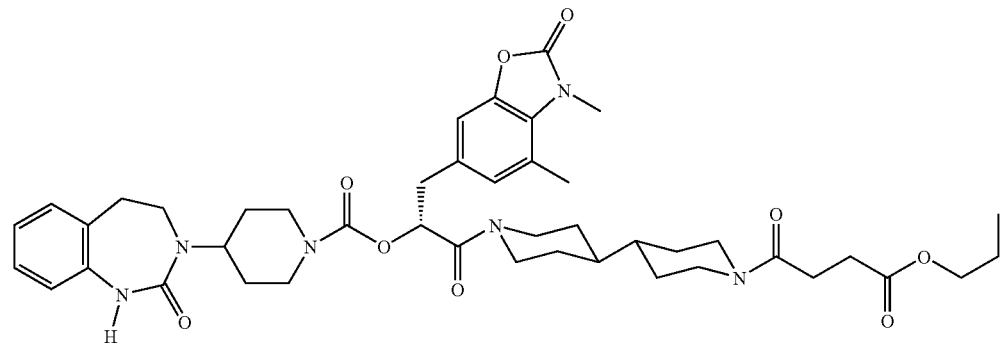 |

-continued
| No. | Structure |
|---|---|
| (195) | 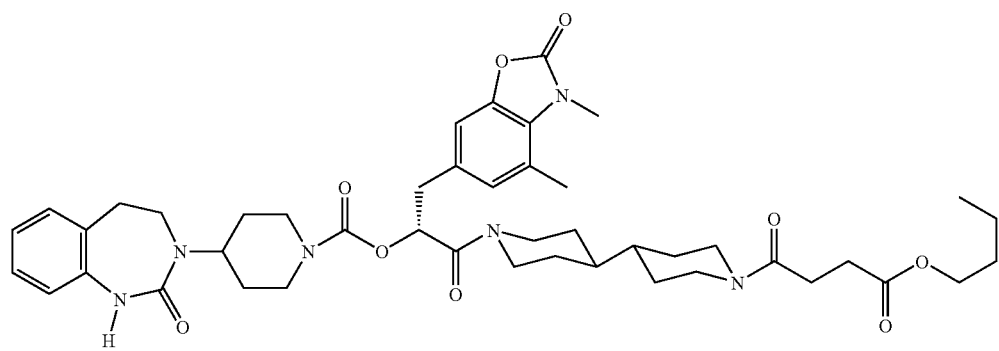 |
| (196) | 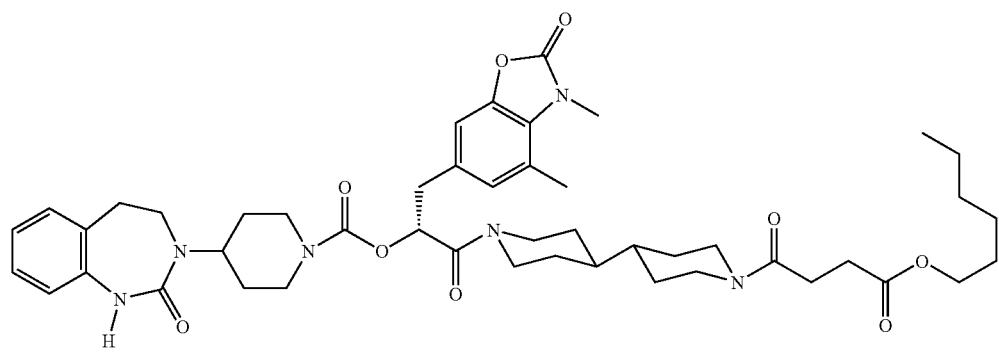 |
| (197) | 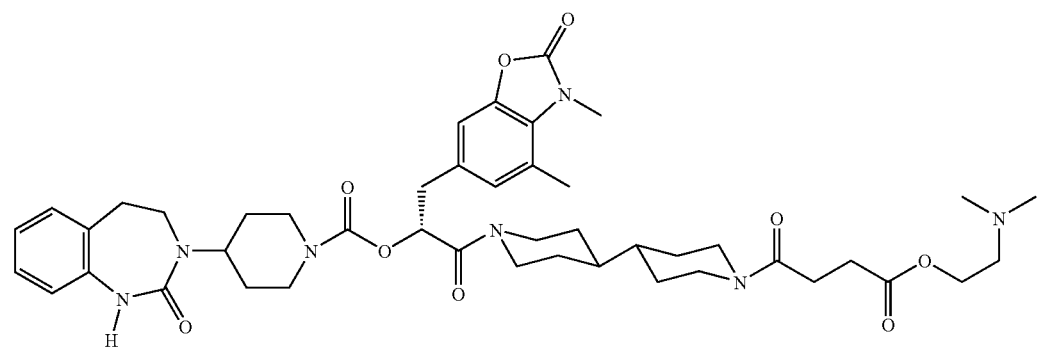 |
| (198) | 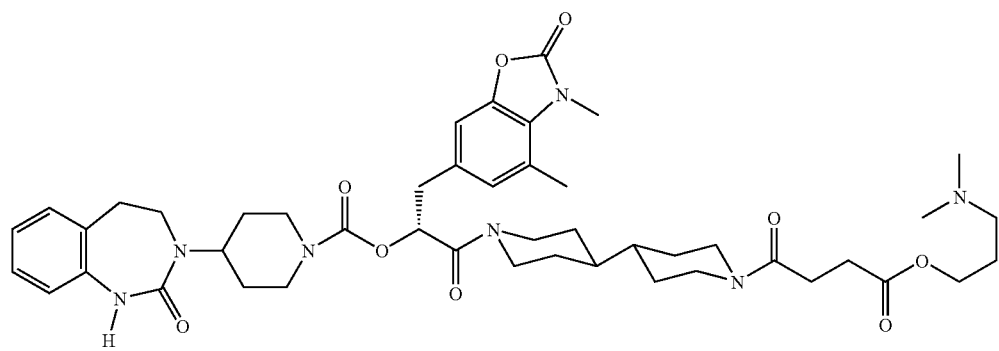 |

| No. | Structure |
|---|---|
| (199) | 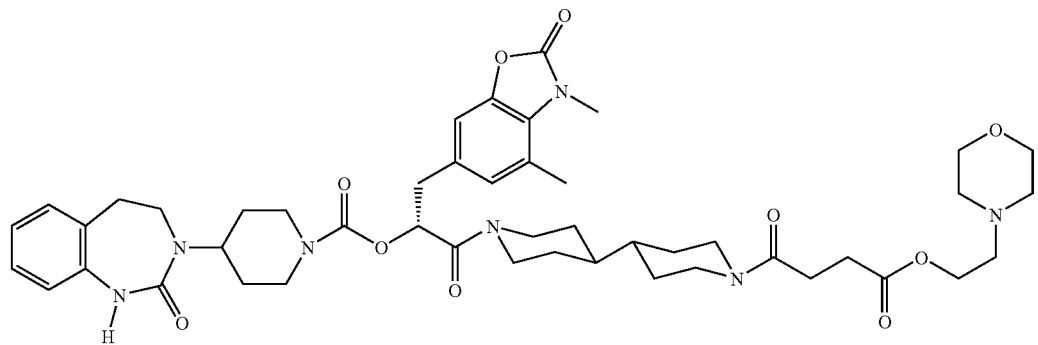 |
| (200) | 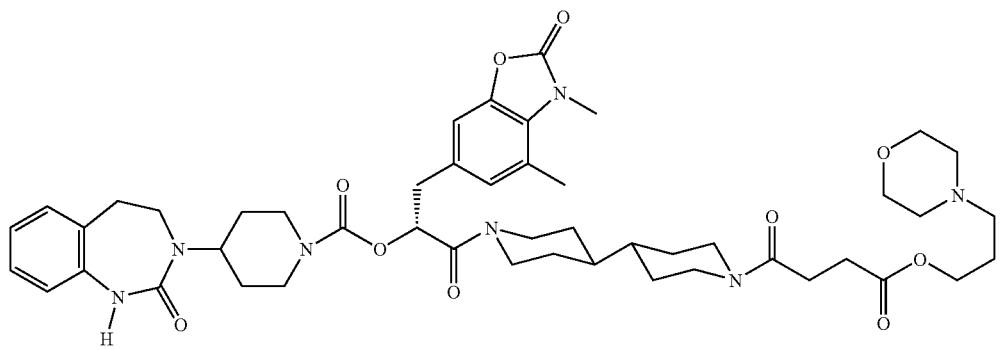 |
| (201) | 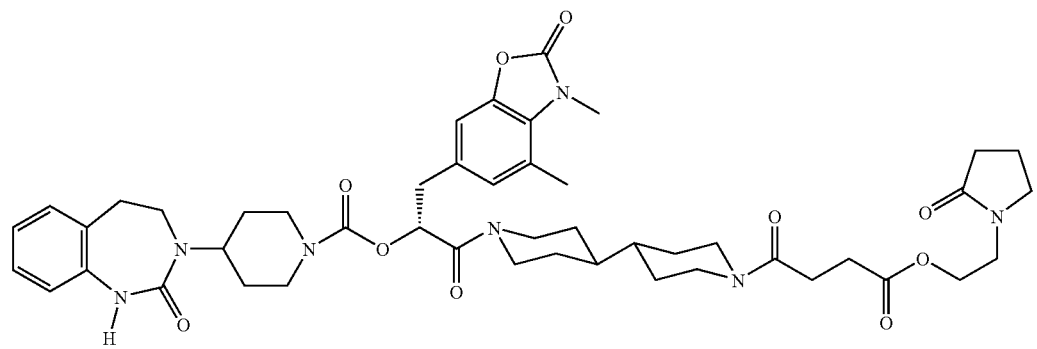 |
| (202) | 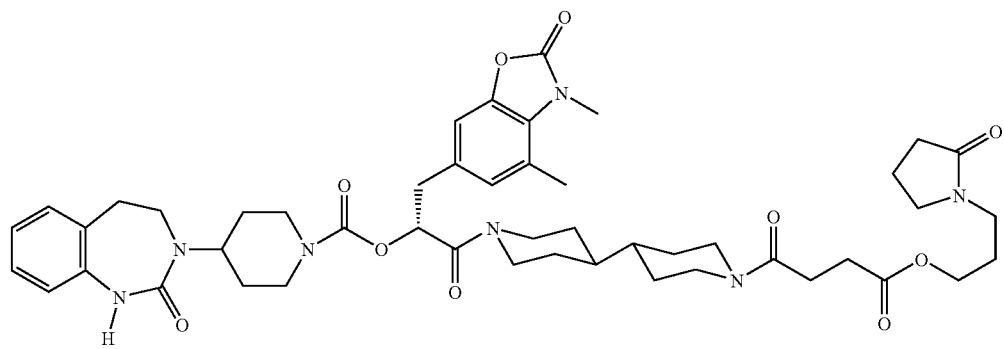 |

| No. | Structure |
|---|---|
| (203) | 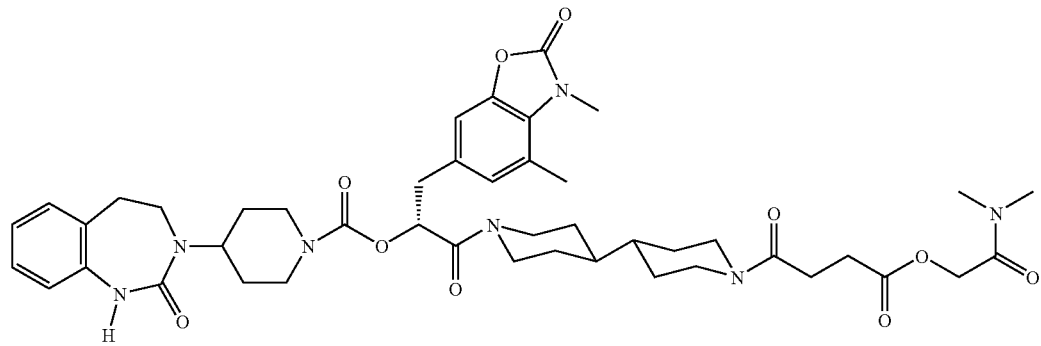 |
| (204) | 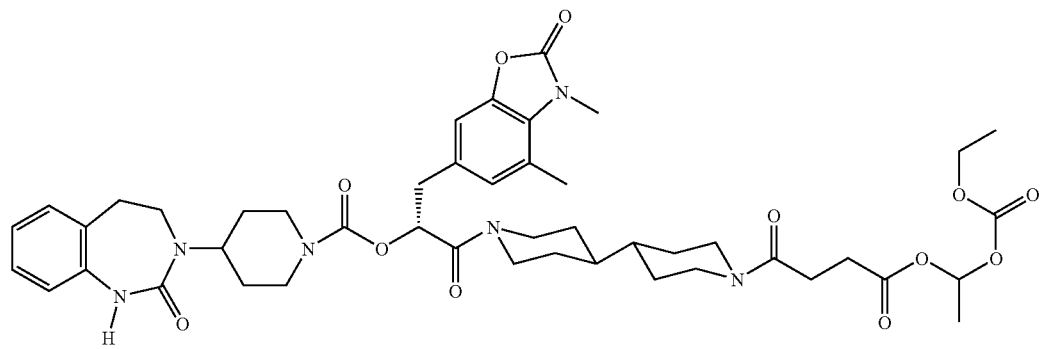 |
| (205) | 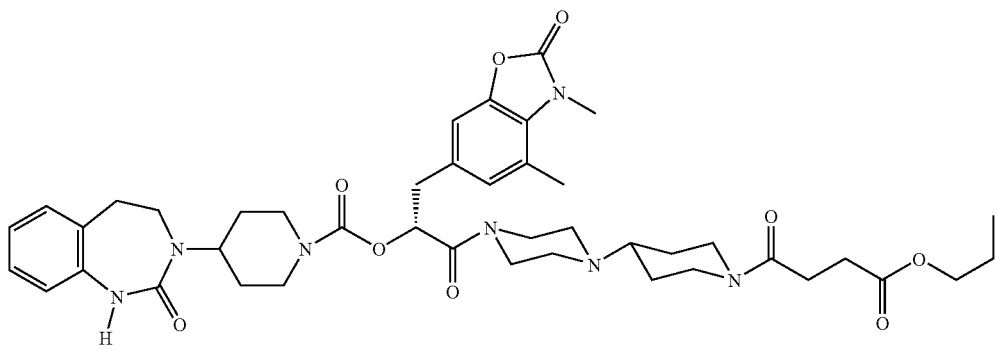 |
| (206) | 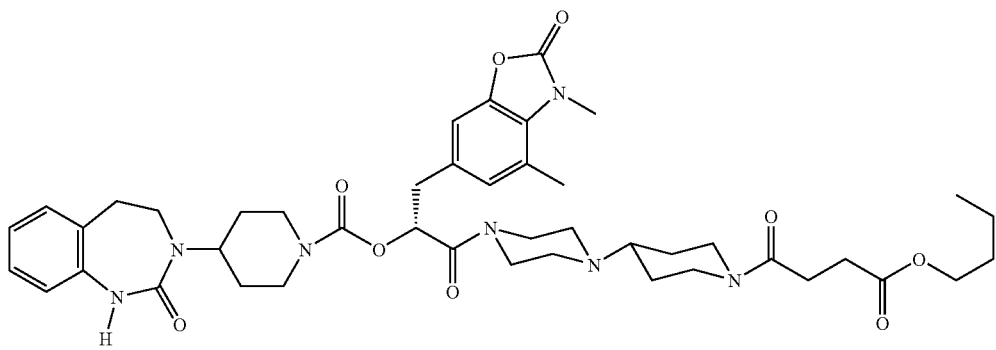 |

-continued
| No. | Structure |
|---|---|
| (207) | 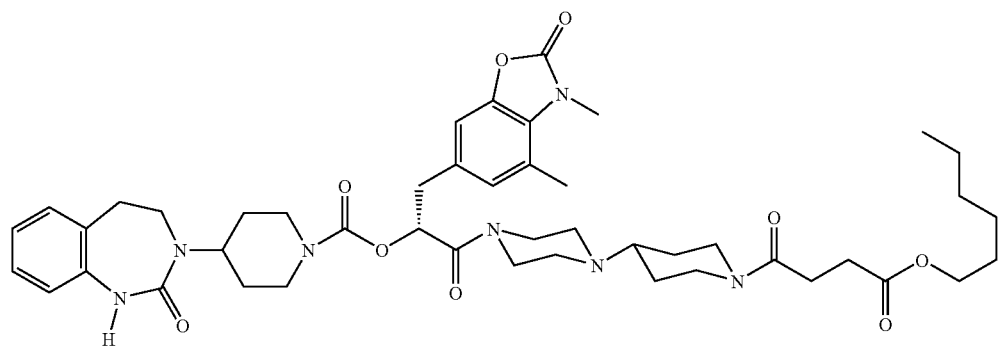 |
| (208) | 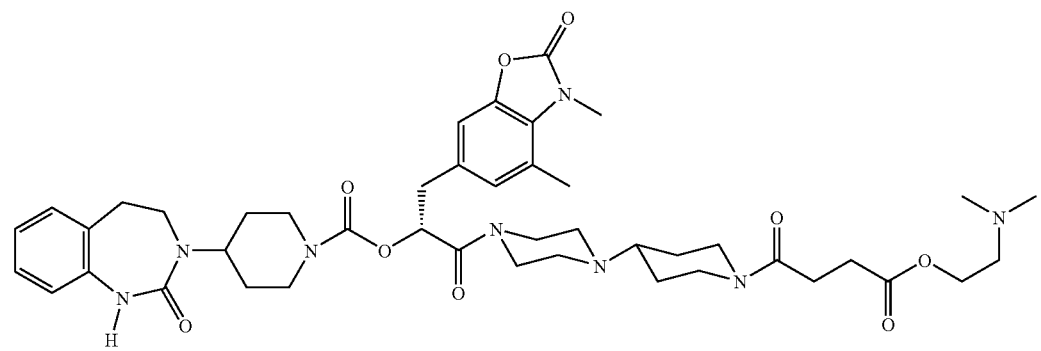 |
| (209) | 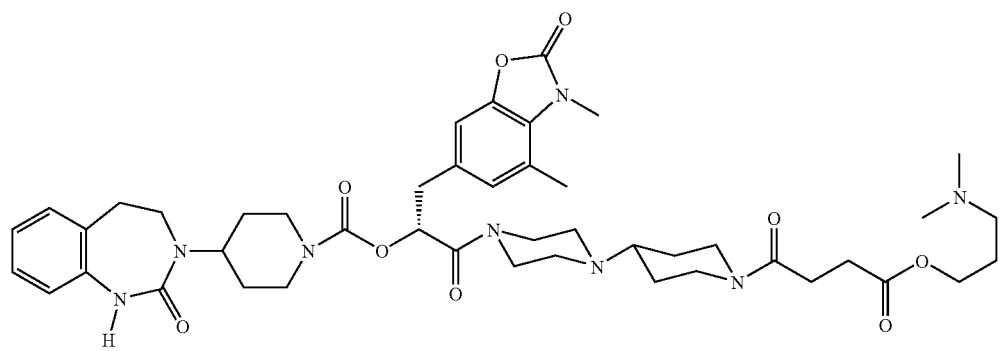 |
| (210) | 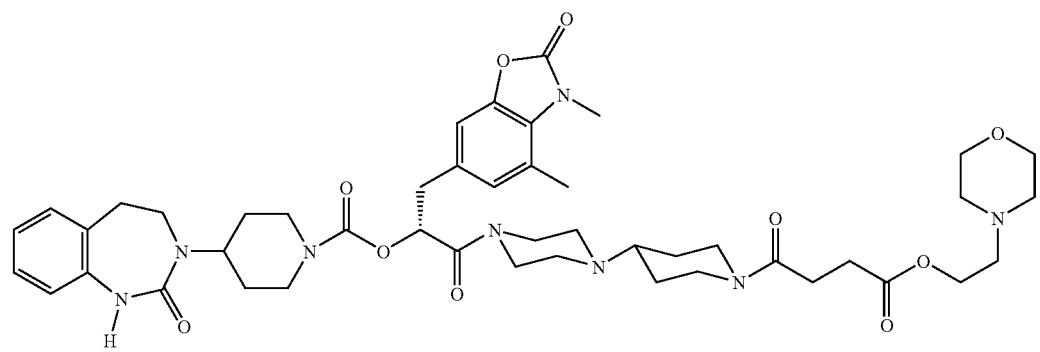 |

| No. | Structure |
|---|---|
| (211) | 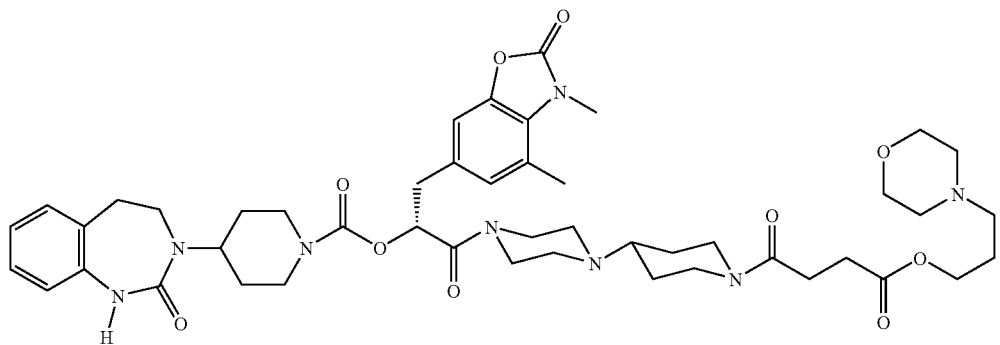 |
| (212) | 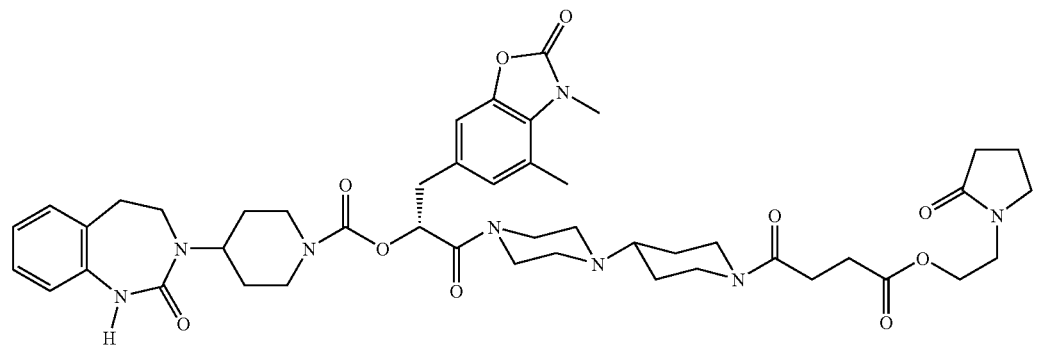 |
| (213) | 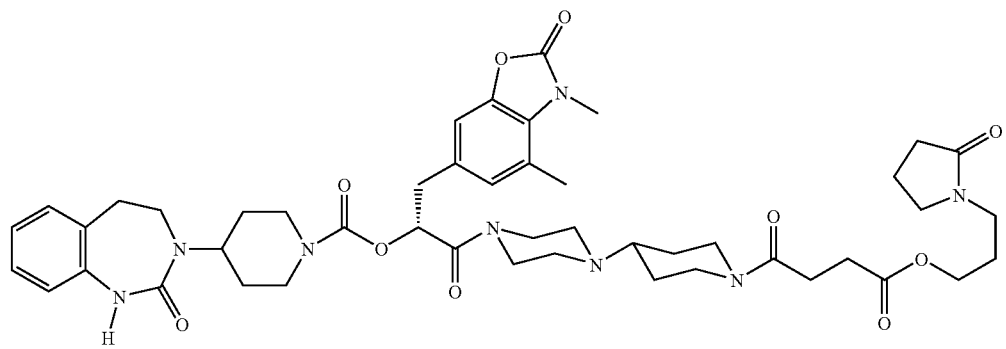 |
| (214) | 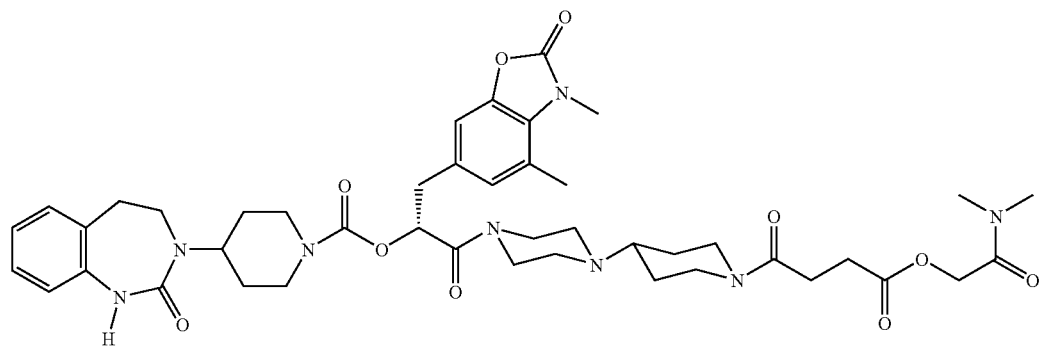 |

| No. | Structure |
|---|---|
| (215) | 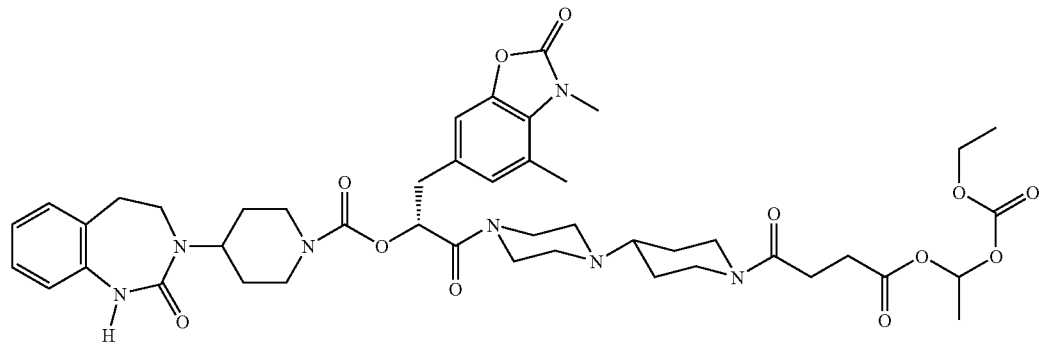 |
| (216) | 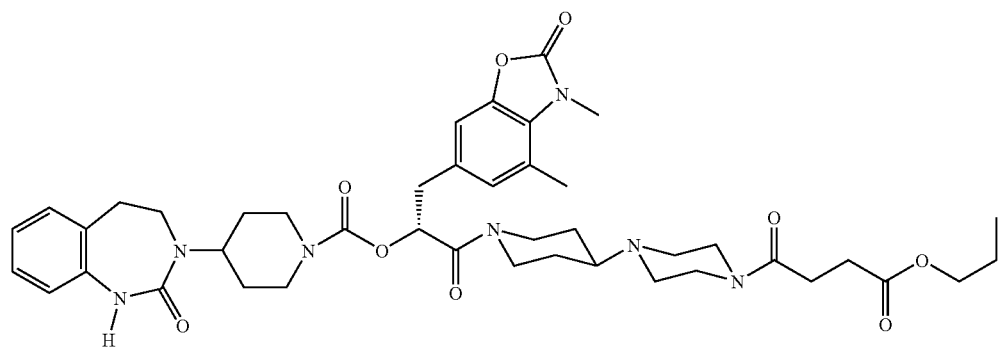 |
| (217) | 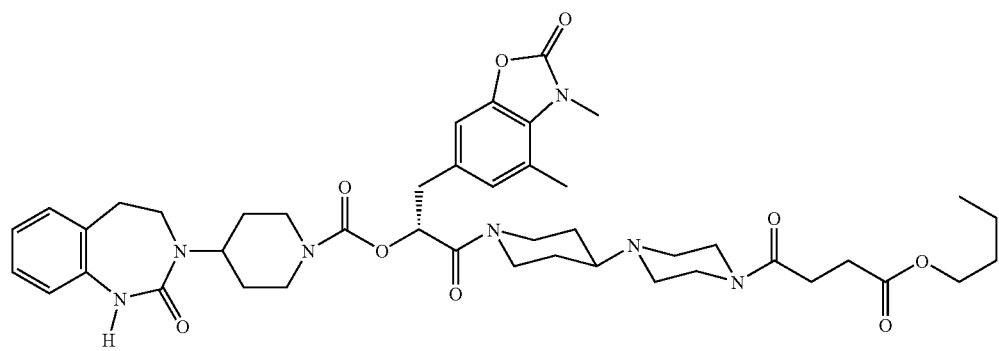 |
| (218) | 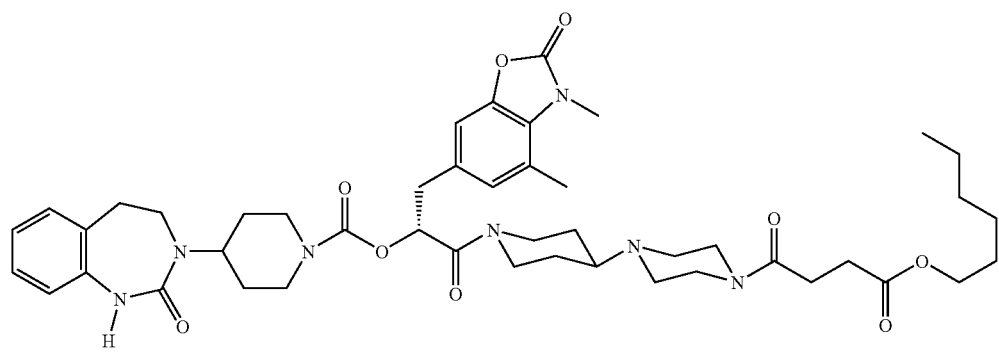 |

| No. | Structure |
|---|---|
| (219) | 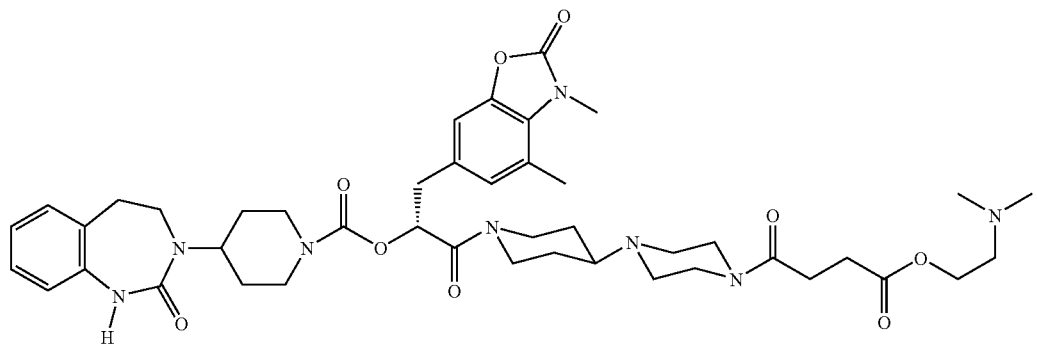 |
| (220) | 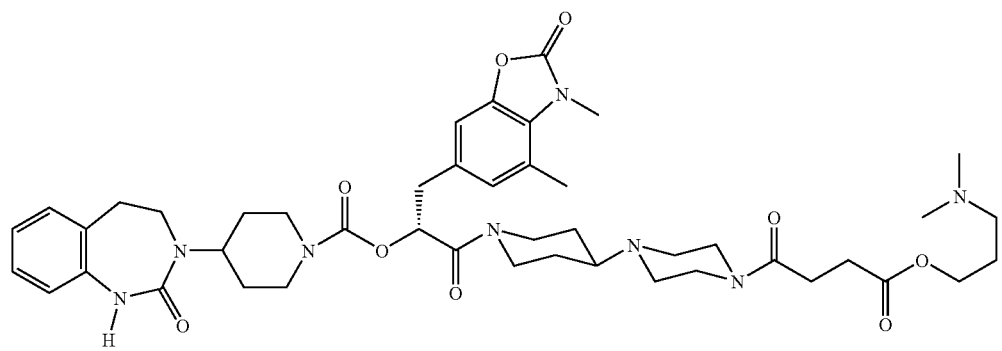 |
| (221) | 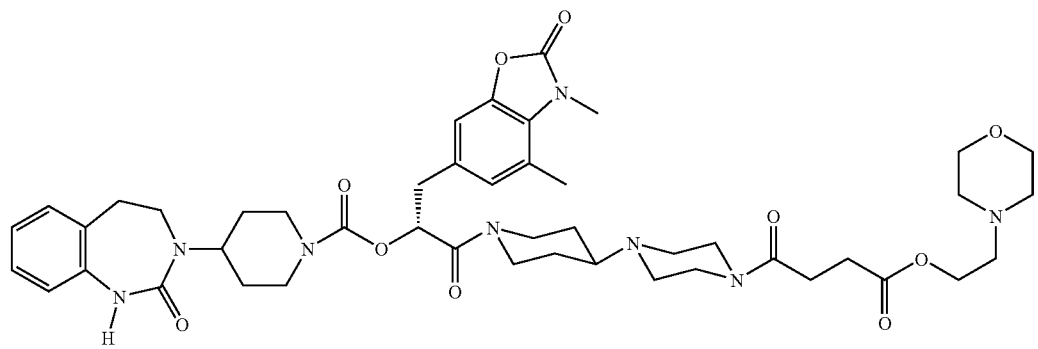 |
| (222) | 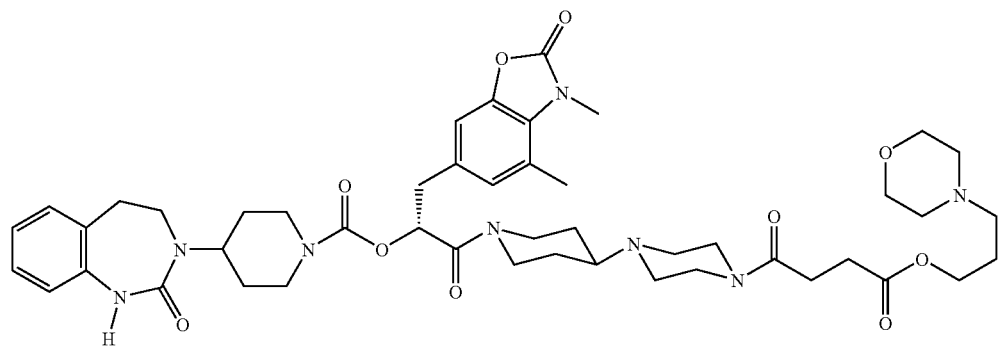 |

| No. | Structure |
|---|---|
| (223) | 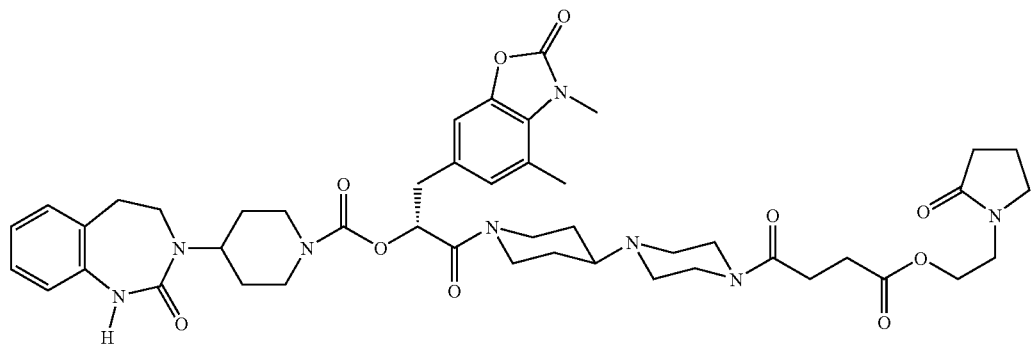 |
| (224) | 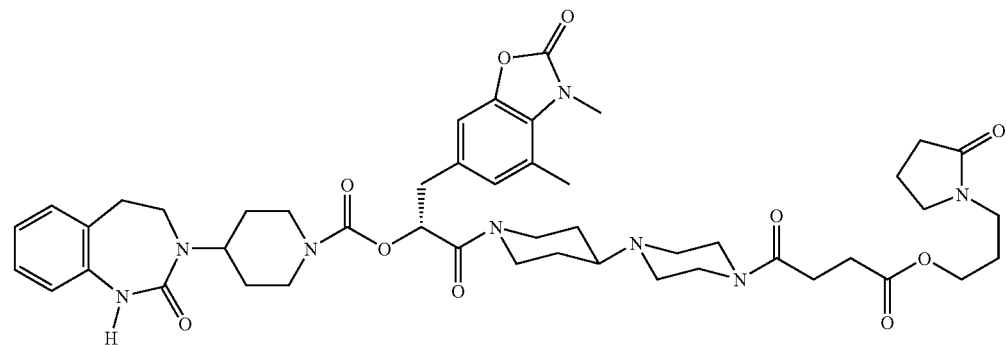 |
| (225) | 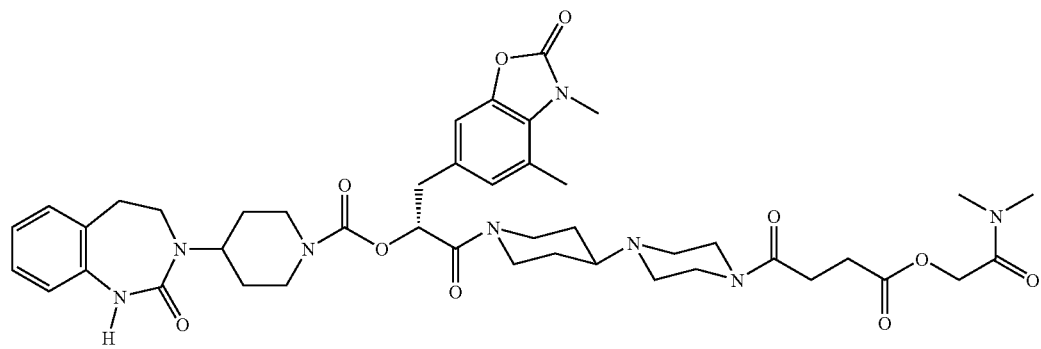 |
| (226) | 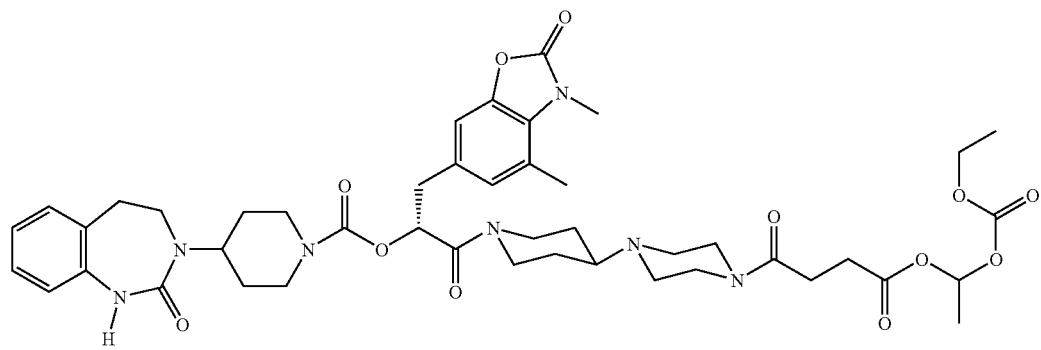 |

-continued
| No. | Structure |
|---|---|
| (227) | 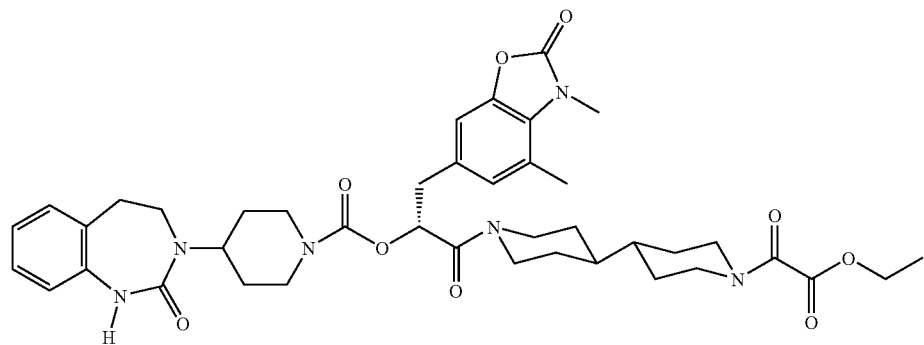 |
| (228) | 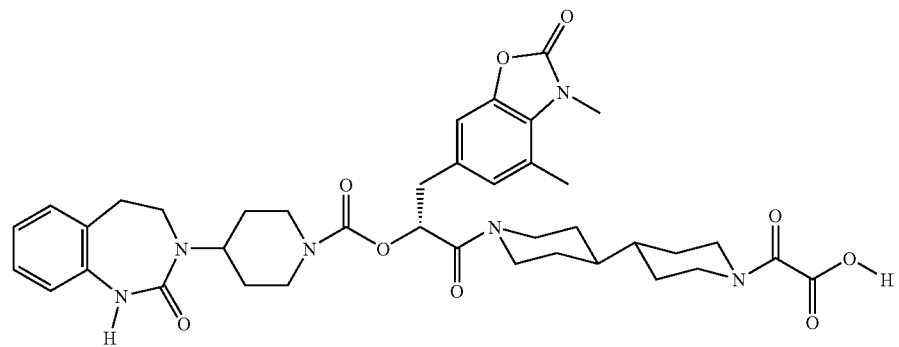 |
| (229) | 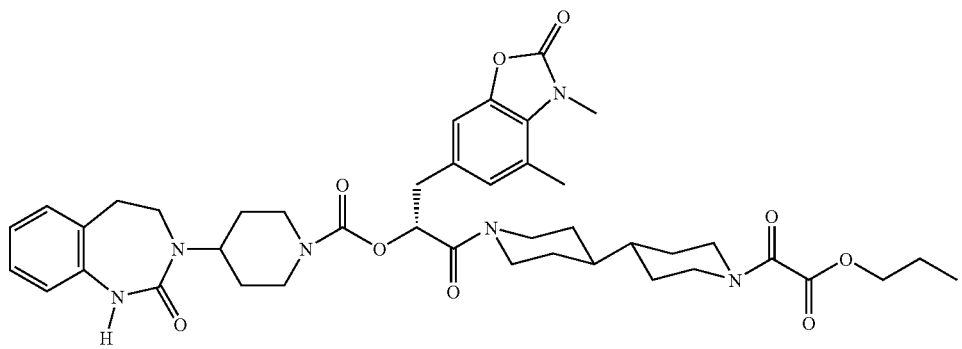 |
| (230) | 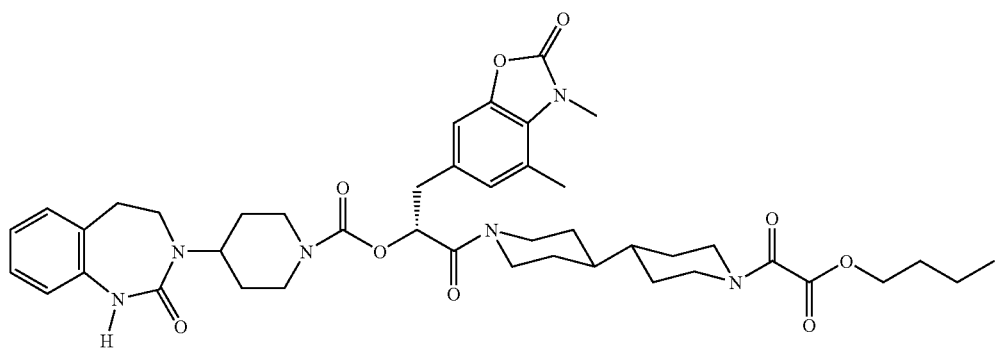 |

-continued
| No. | Structure |
|---|---|
| (231) | 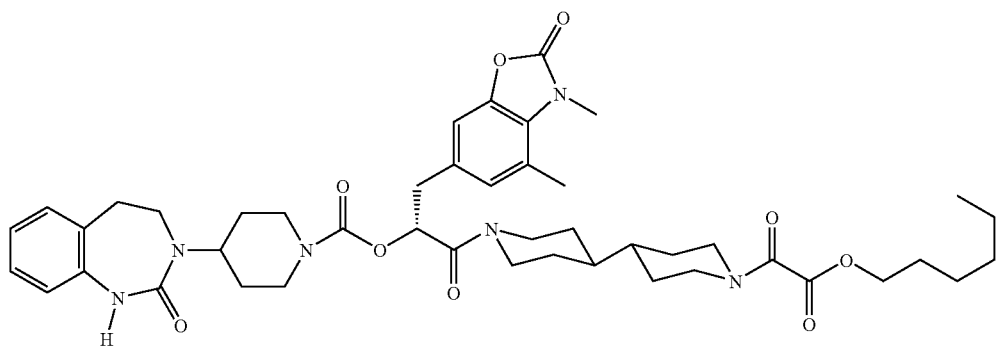 |
| (232) | 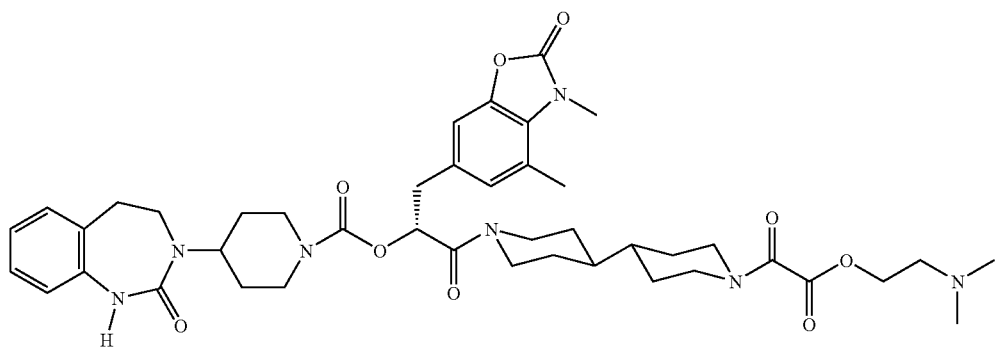 |
| (233) | 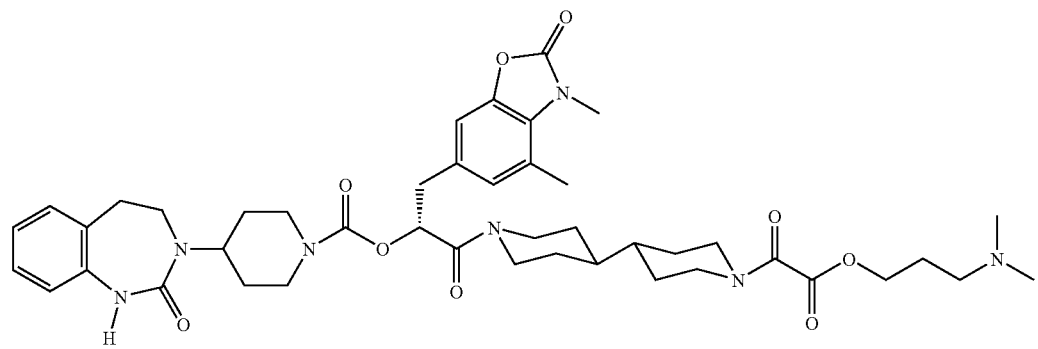 |
| (234) | 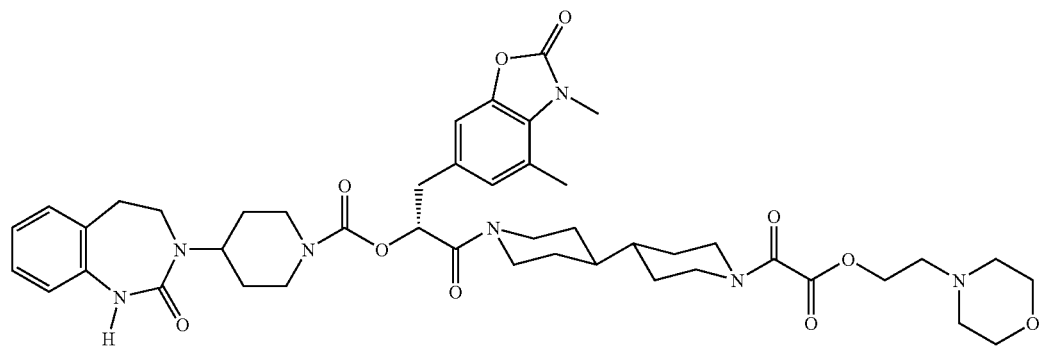 |

| No. | Structure |
|---|---|
| (235) | 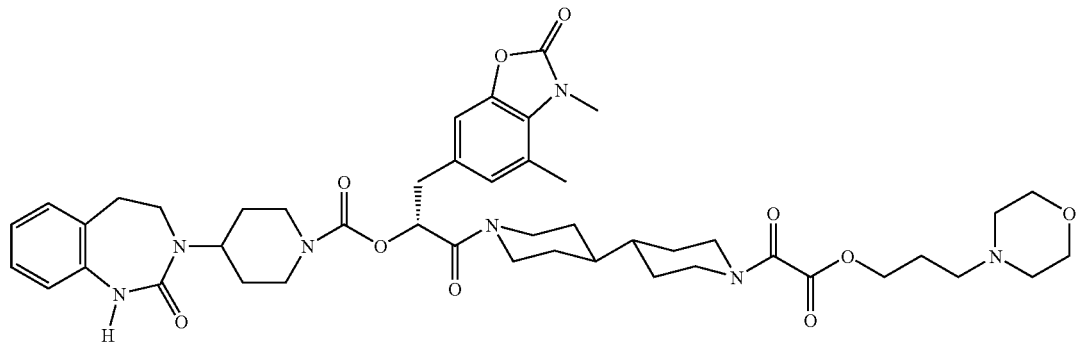 |
| (236) | 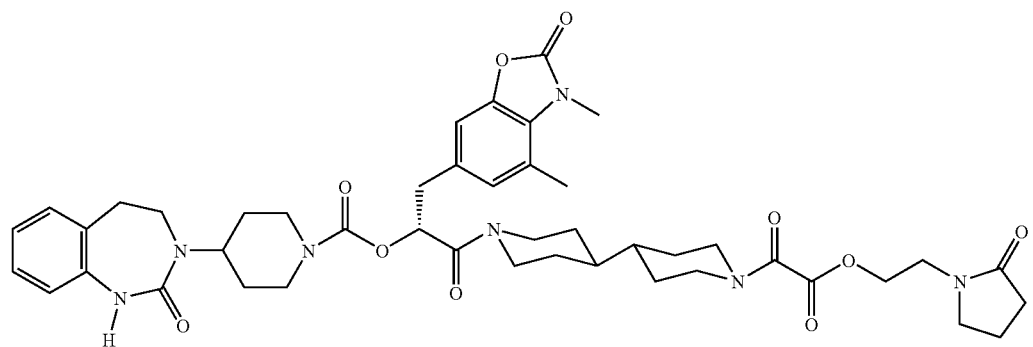 |
| (237) | 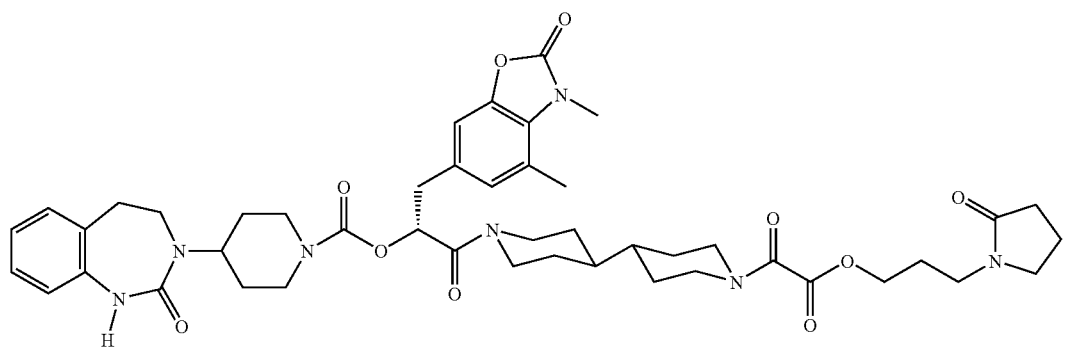 |
| (238) | 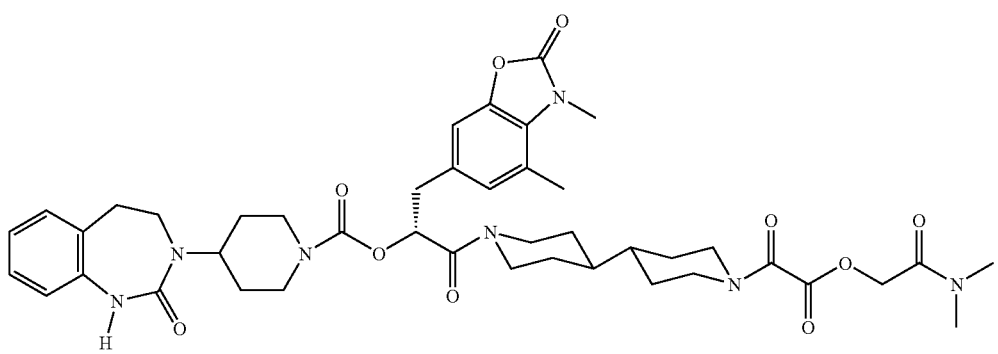 |

| No. | Structure |
|---|---|
| (239) | 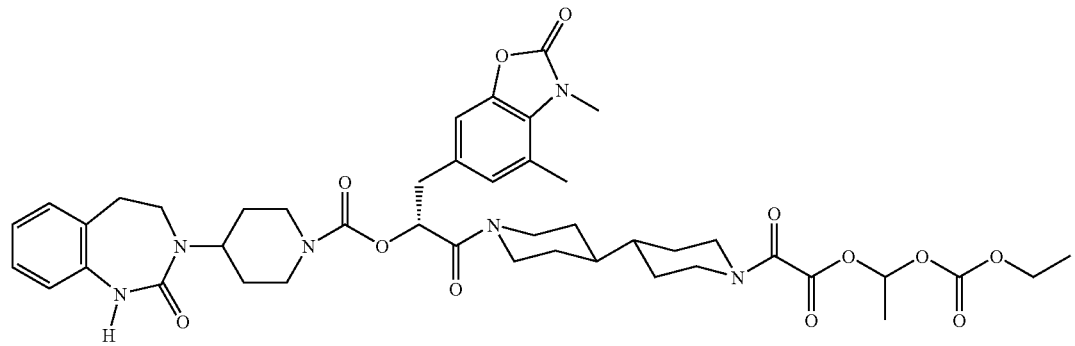 |
| (240) | 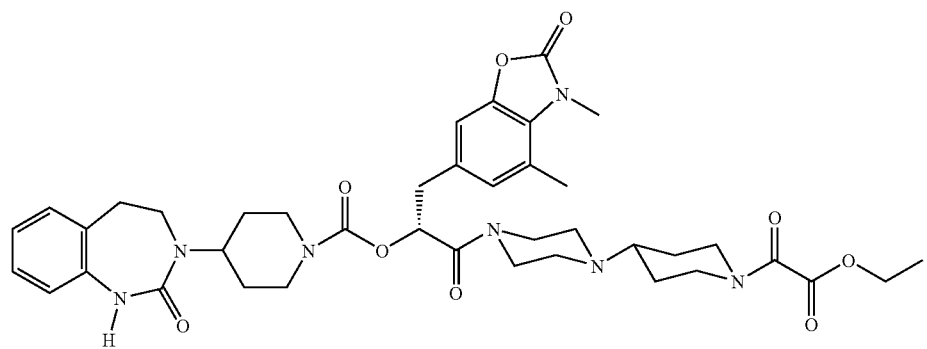 |
| (241) | 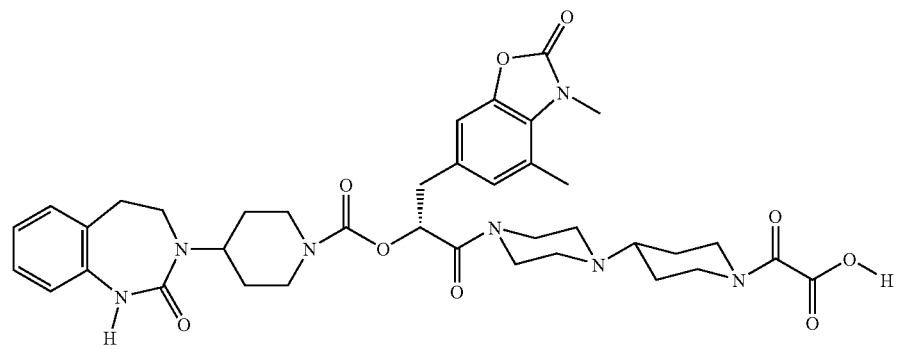 |
| (242) | 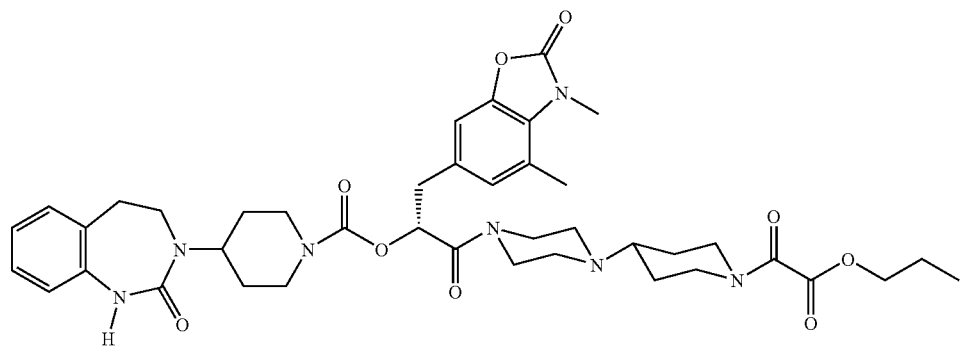 |

| No. | Structure |
|---|---|
| (243) | 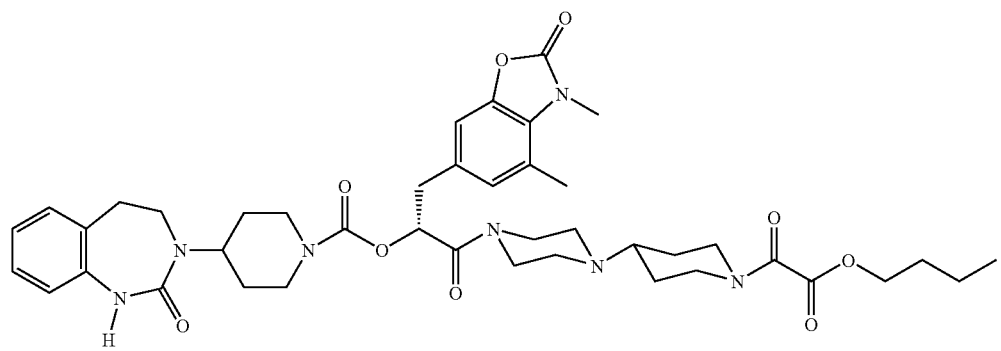 |
| (244) | 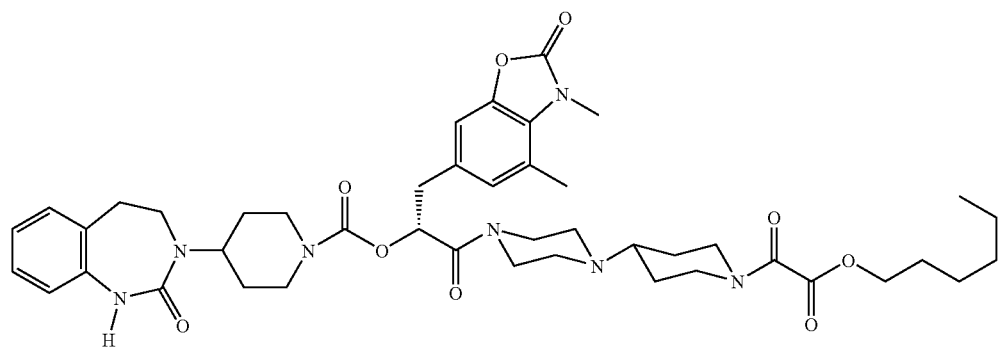 |
| (245) | 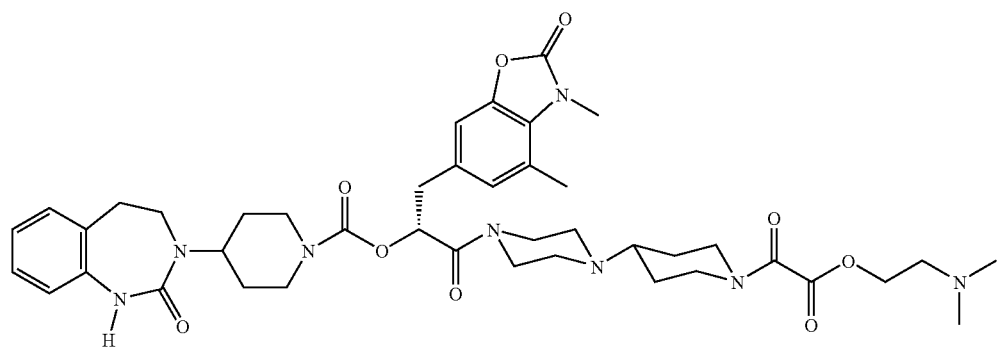 |
| (246) | 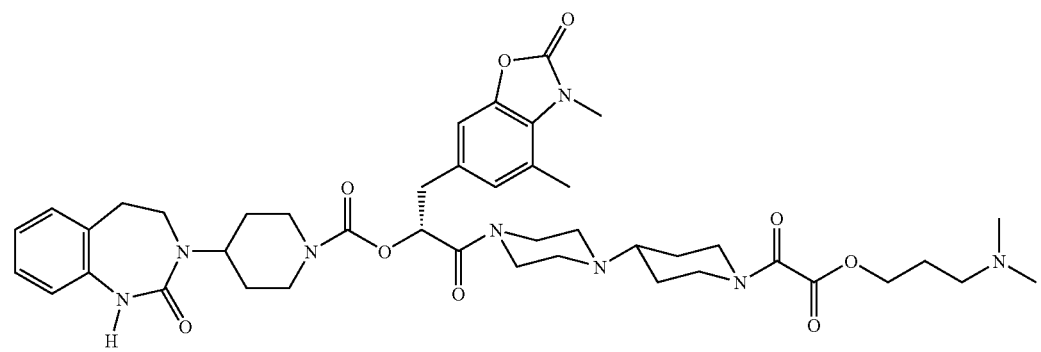 |

| No. | Structure |
|---|---|
| (247) | 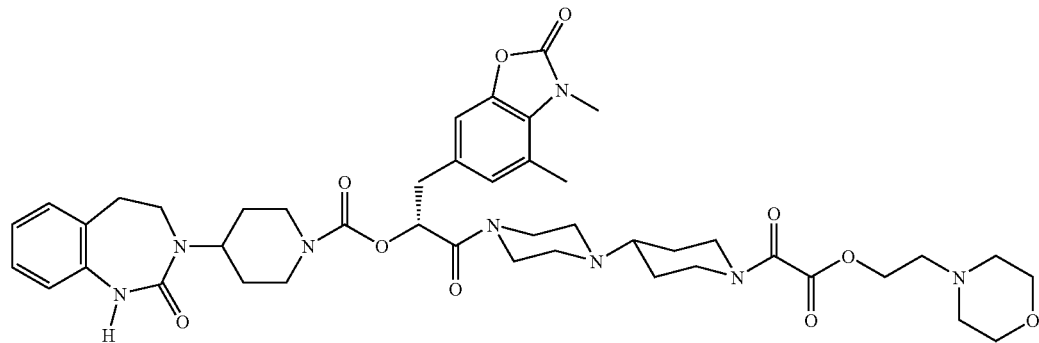 |
| (248) | 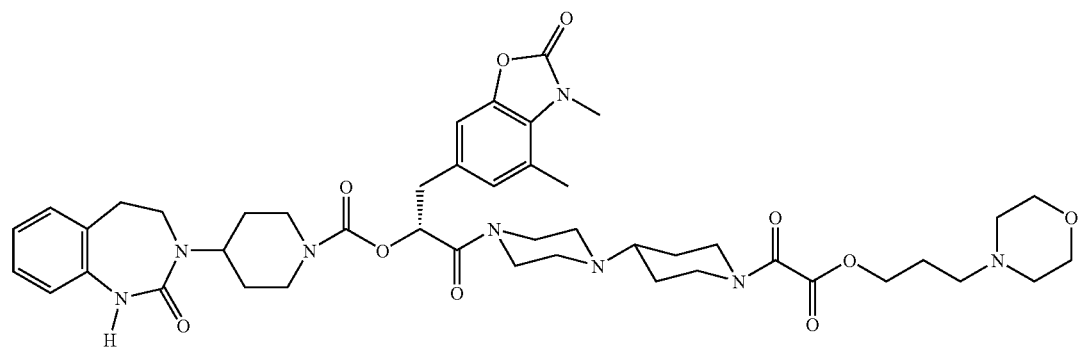 |
| (249) | 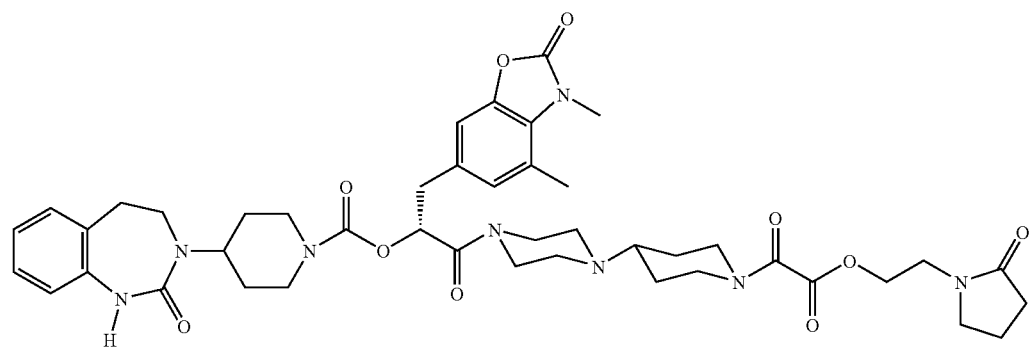 |
| (250) | 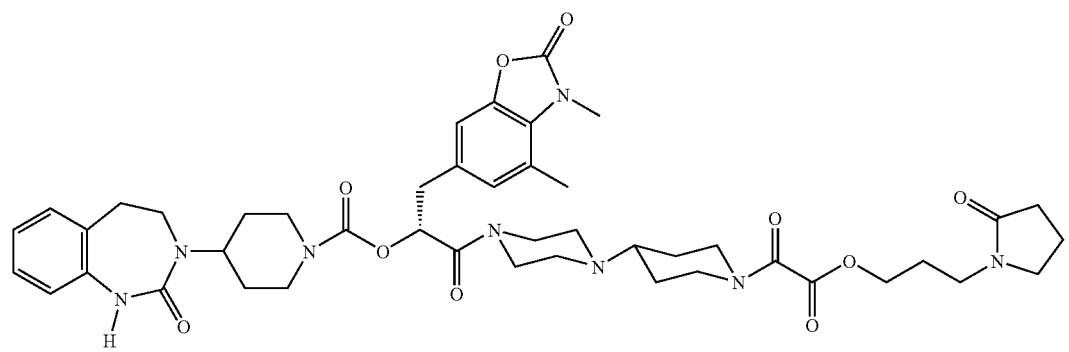 |

-continued
| No. | Structure |
|---|---|
| (251) | 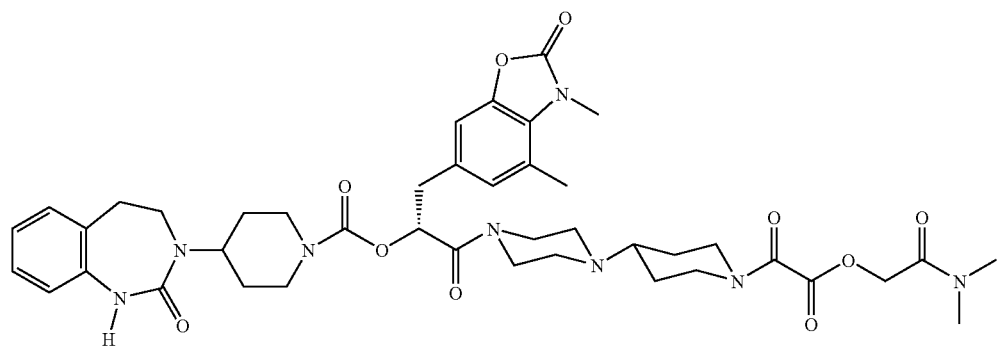 |
| (252) | 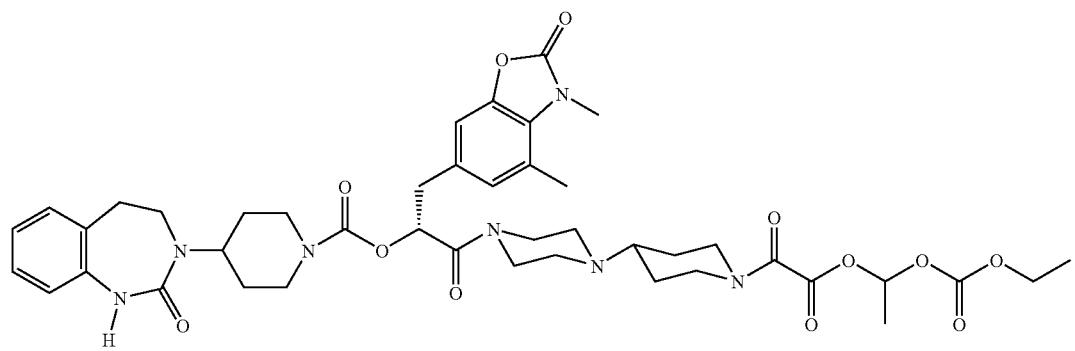 |
| (253) | 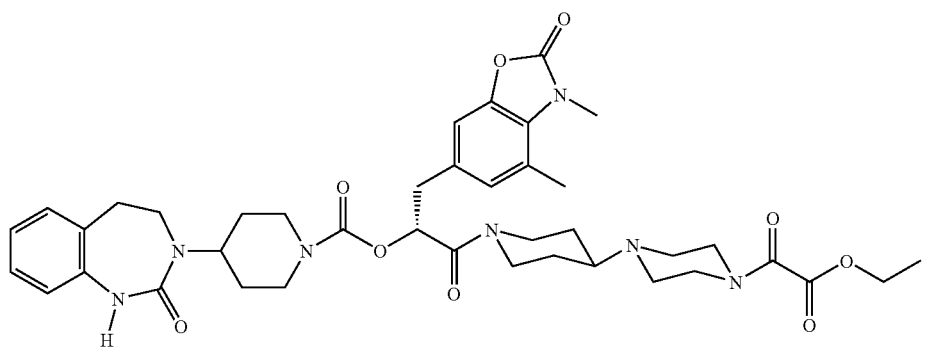 |
| (254) | 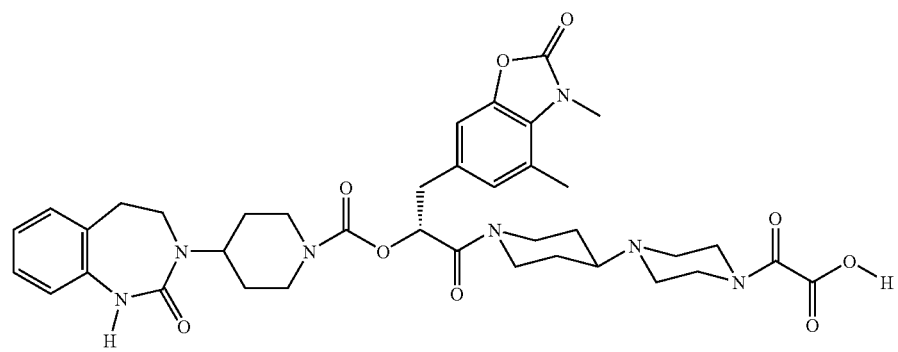 |

-continued
| No. | Structure |
|-----|-----------|
| (255) | 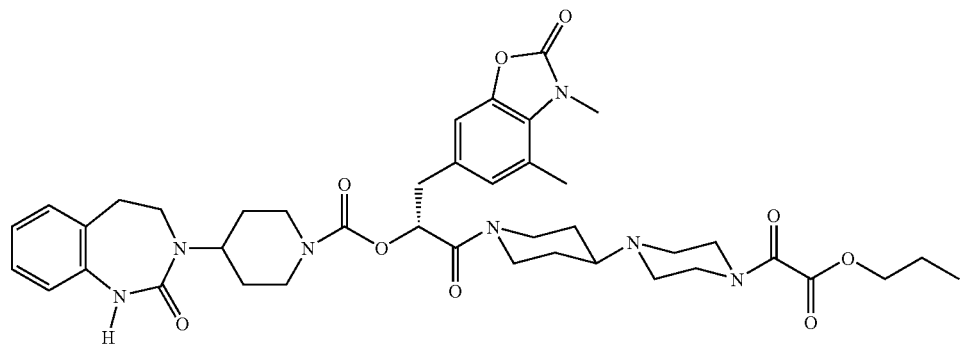 |
| (256) | 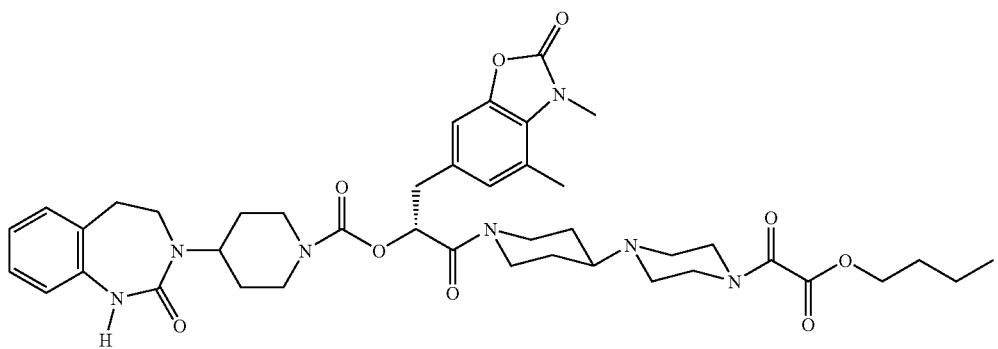 |
| (257) | 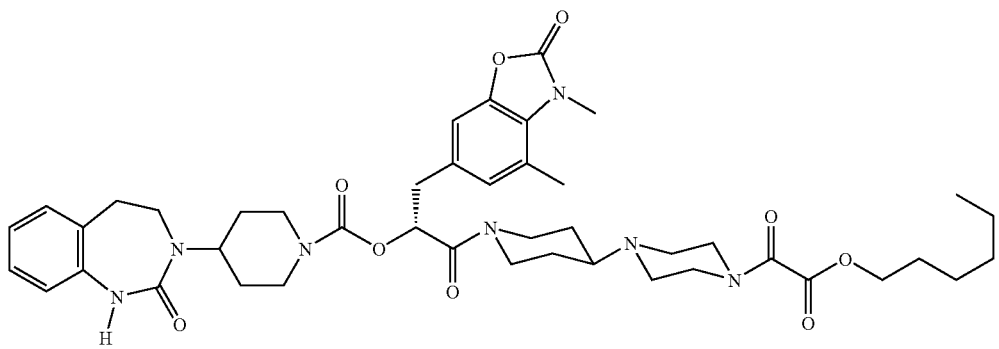 |
| (258) | 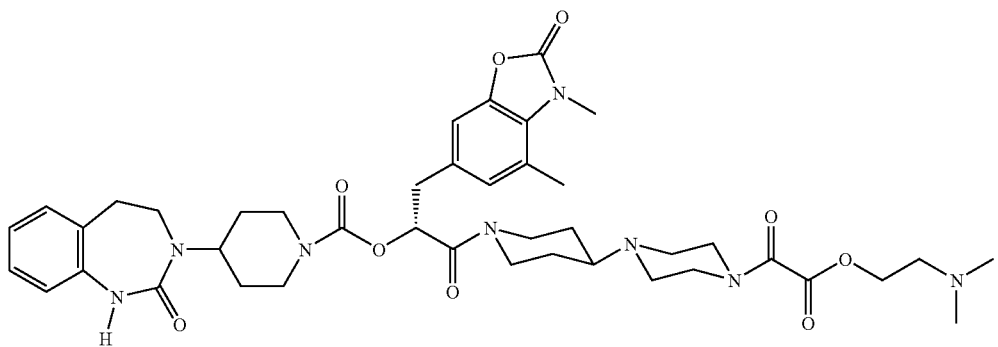 |

| No. | Structure |
|---|---|
| (259) | 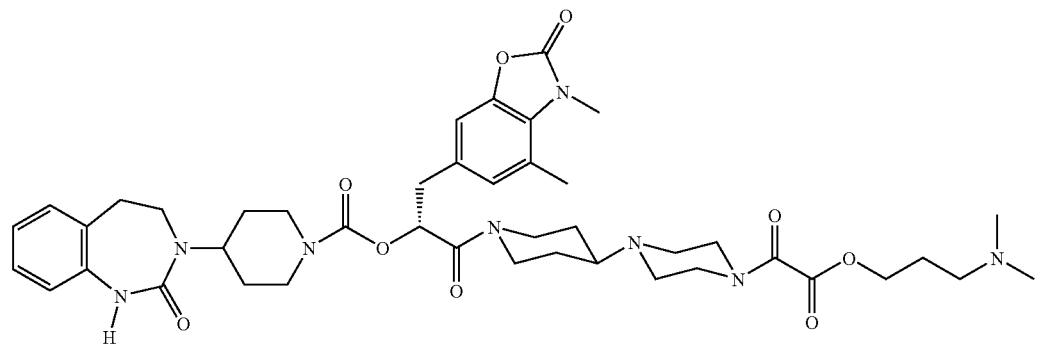 |
| (260) | 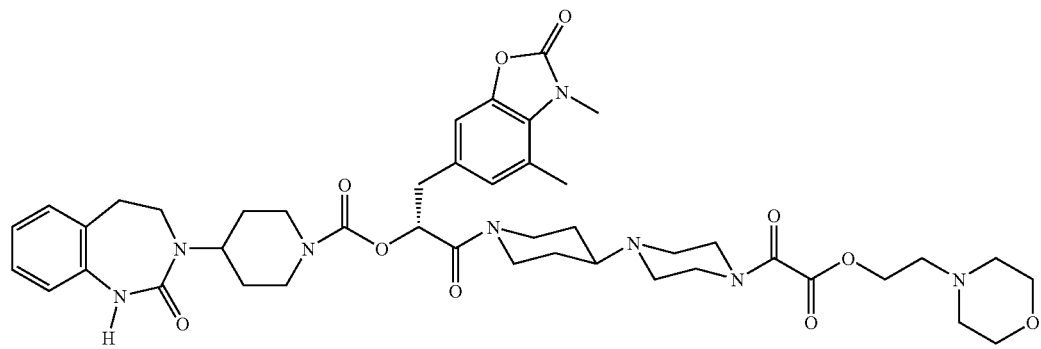 |
| (261) | 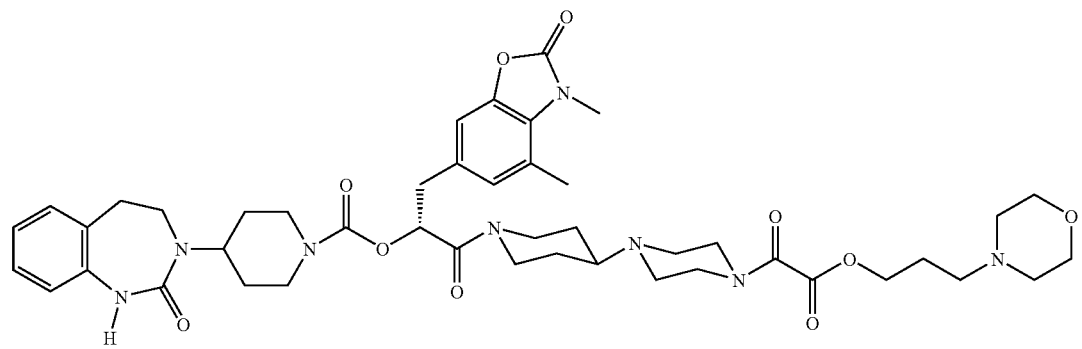 |
| (262) | 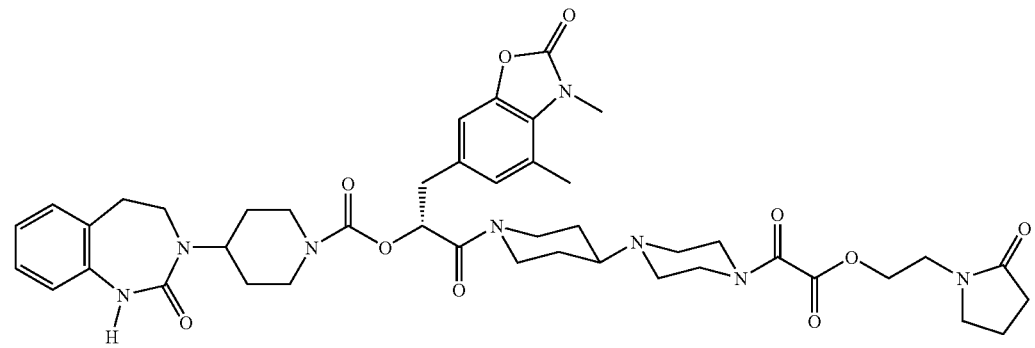 |

| No. | Structure |
|---|---|
| (263) | 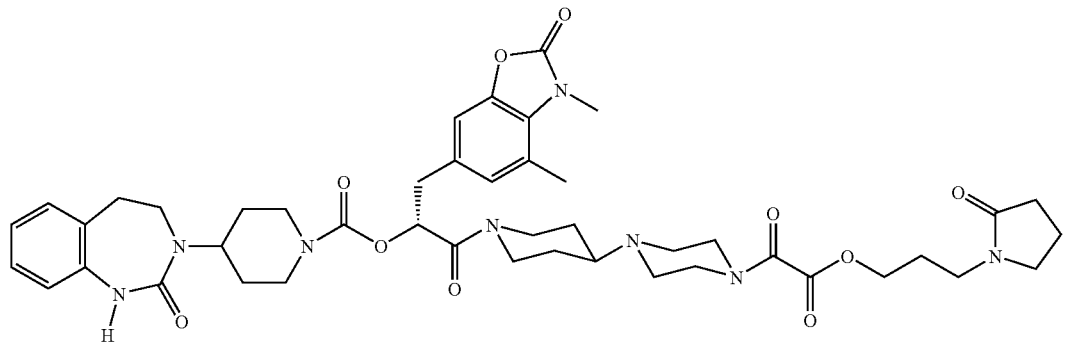 |
| (264) | 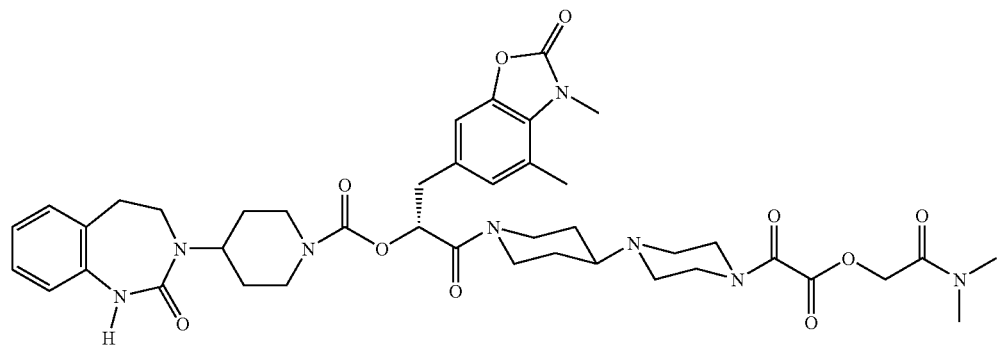 |
| (265) | 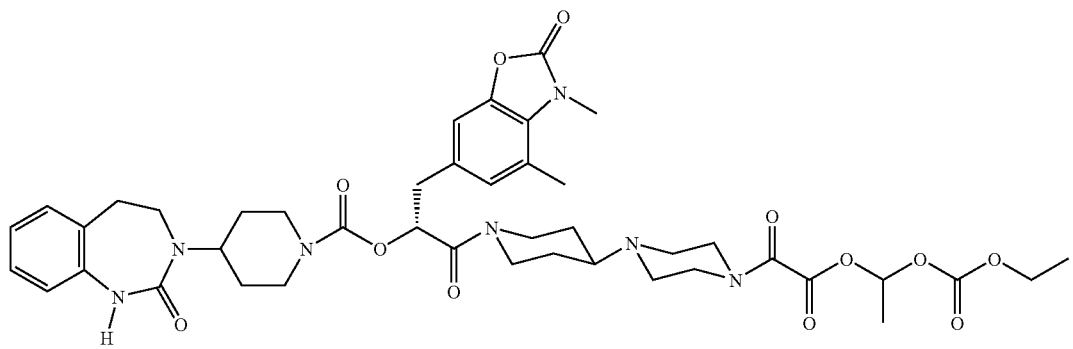 |
| (266) | 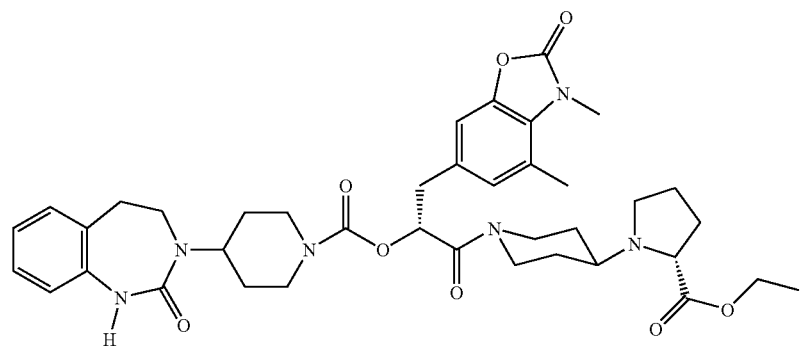 |

| No. | Structure |
|---|---|
| (267) | 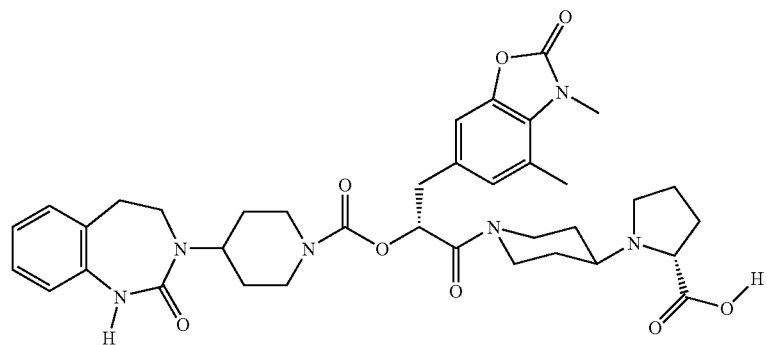 |
| (268) | 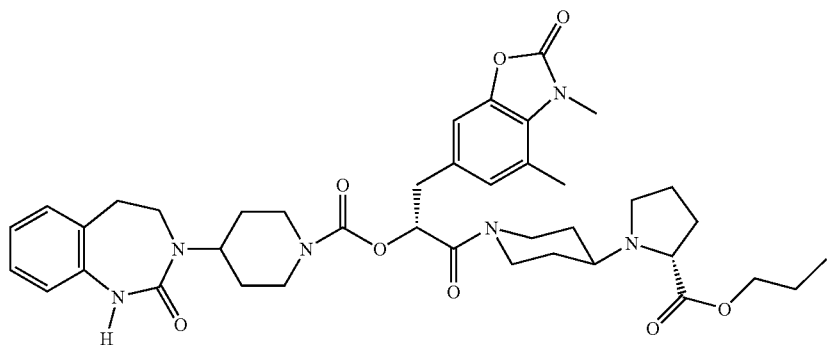 |
| (269) | 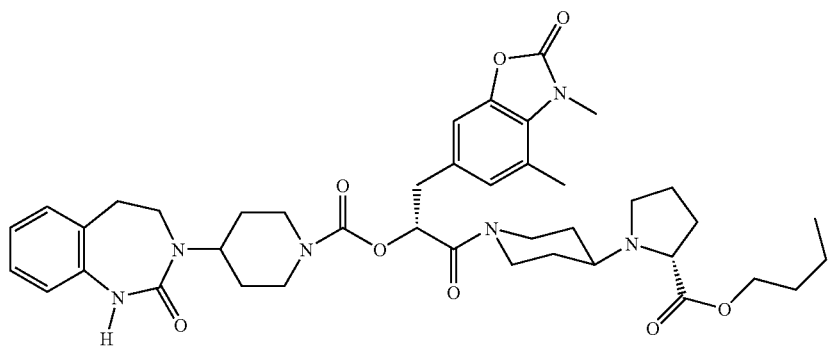 |
| (270) | 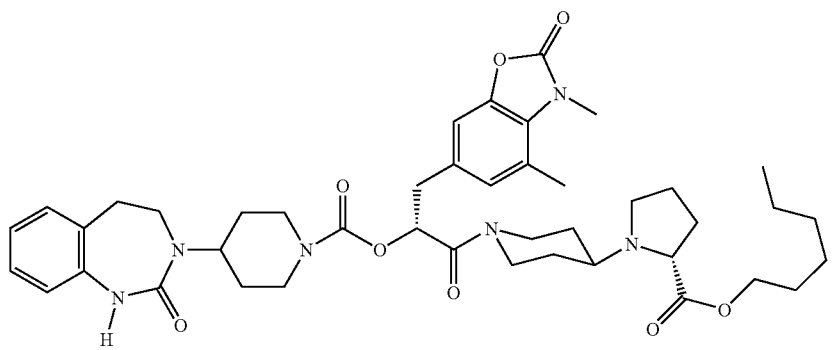 |

-continued
| No. | Structure |
|---|---|
| (271) | 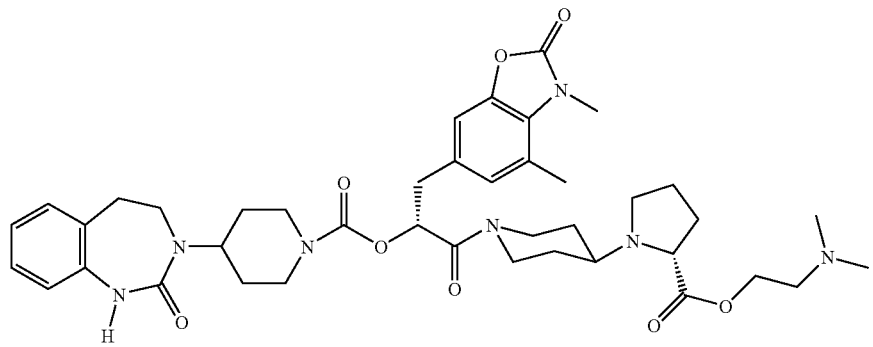 |
| (272) | 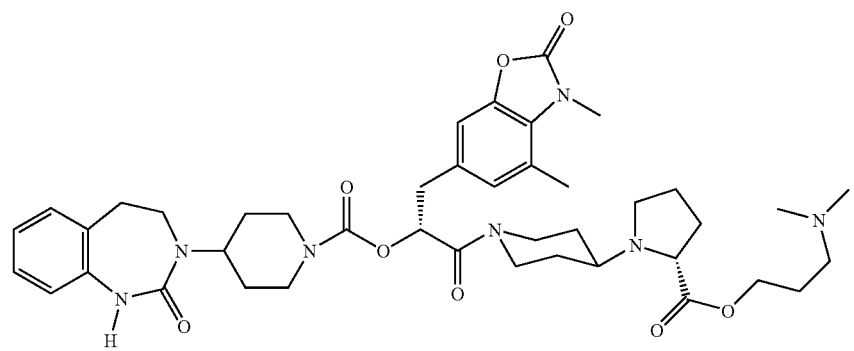 |
| (273) | 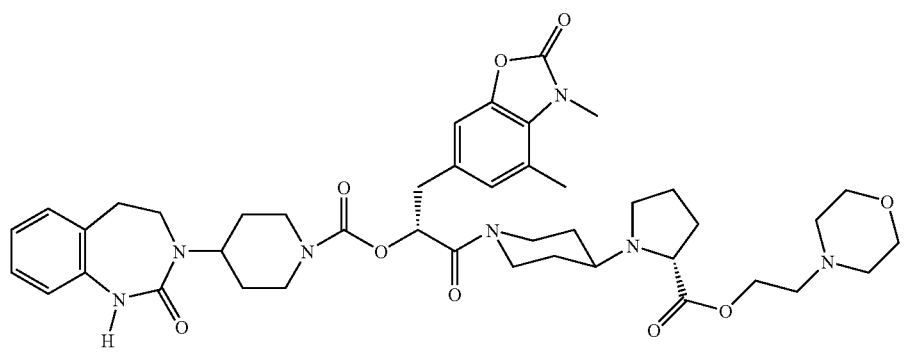 |
| (274) | 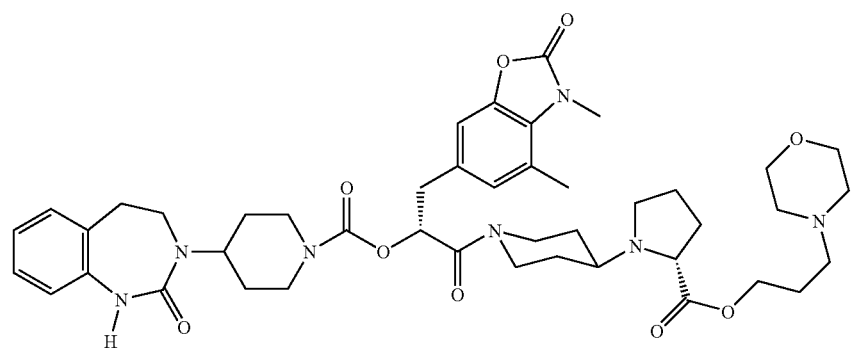 |

-continued
| No. | Structure |
|---|---|
| (275) | 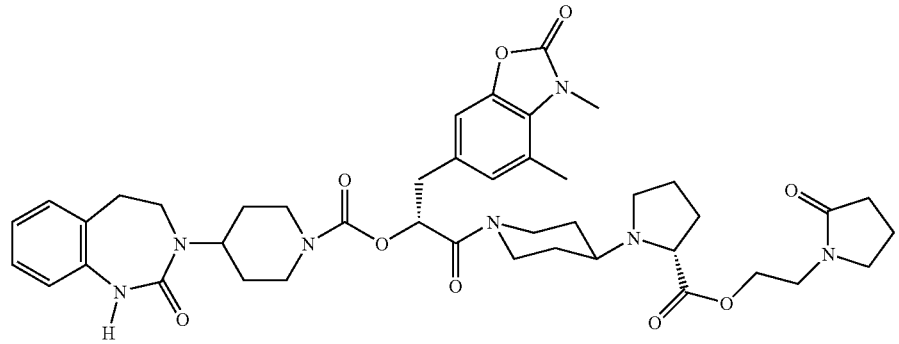 |
| (276) | 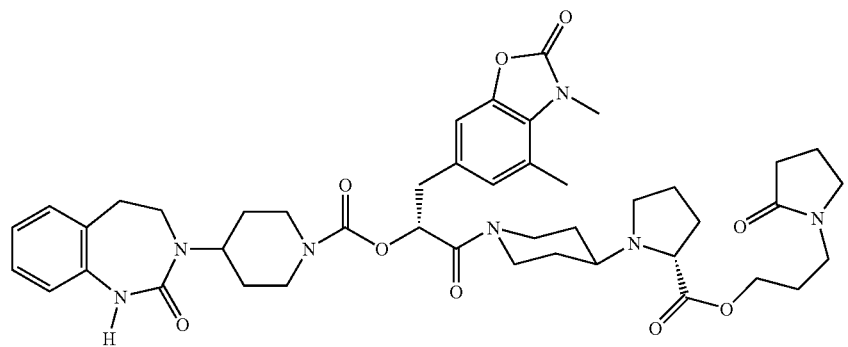 |
| (277) | 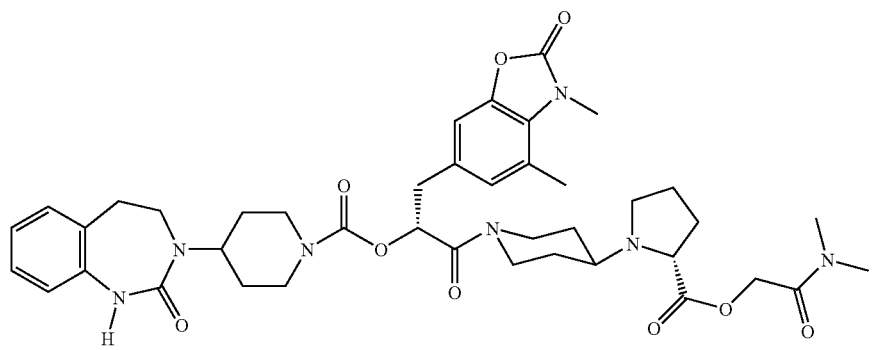 |
| (278) | 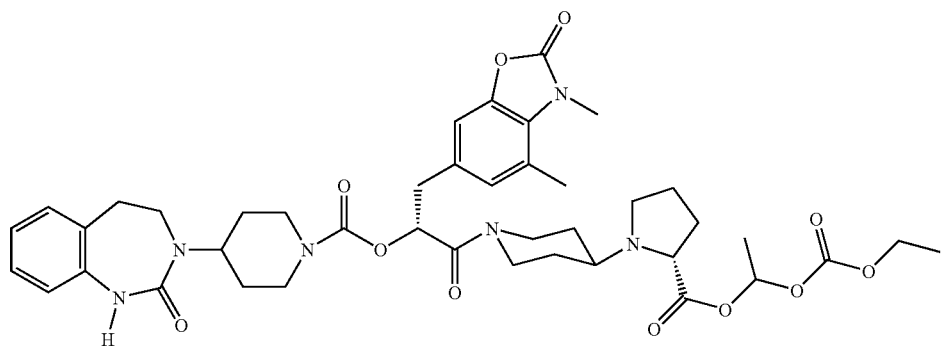 |

-continued
| No. | Structure |
|---|---|
| (279) | 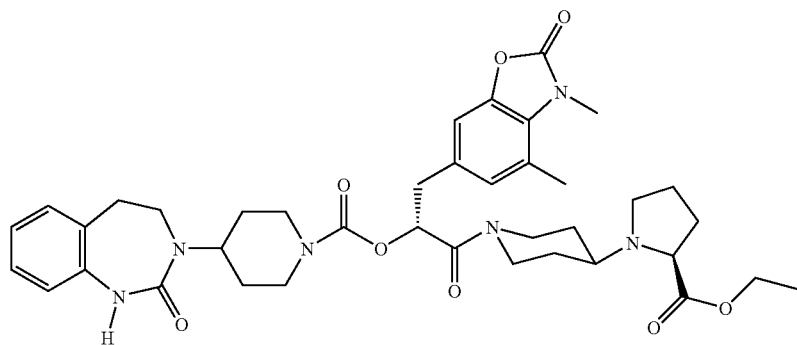 |
| (280) | 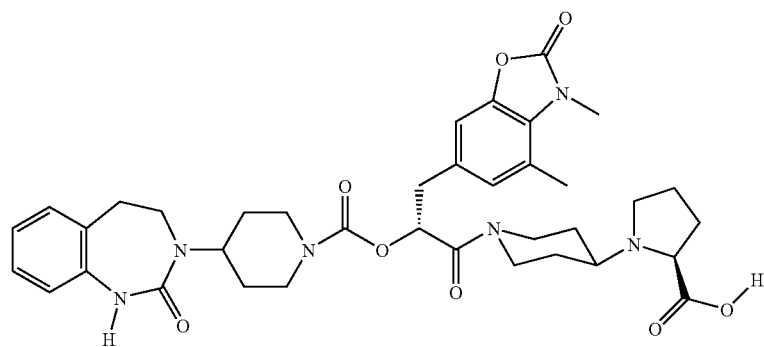 |
| (281) | 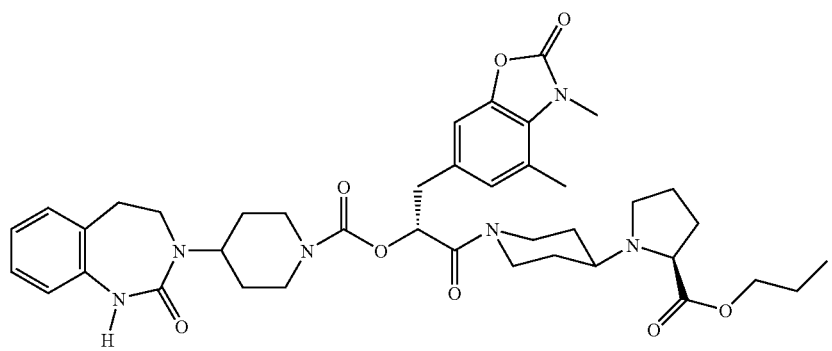 |
| (282) | 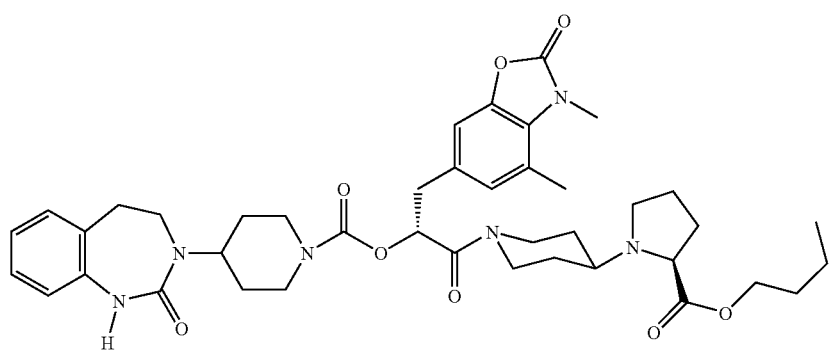 |

| No. | Structure |
|---|---|
| (283) | 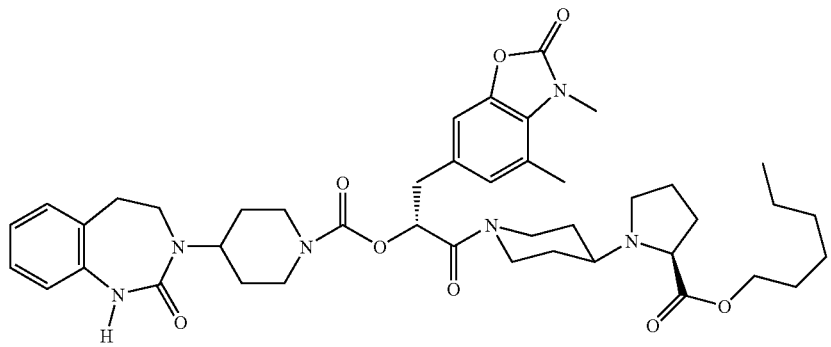 |
| (284) | 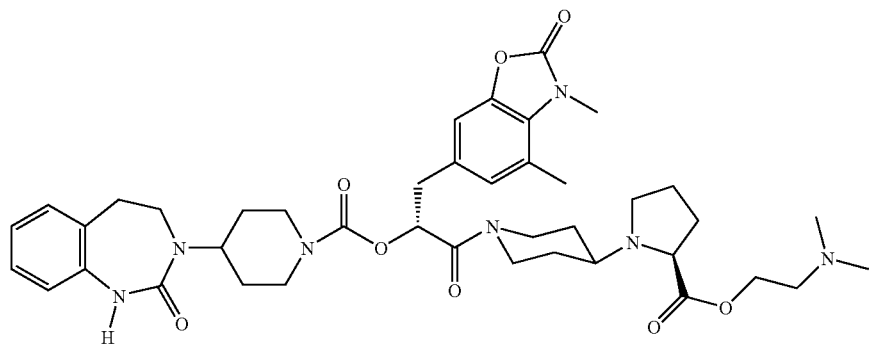 |
| (285) | 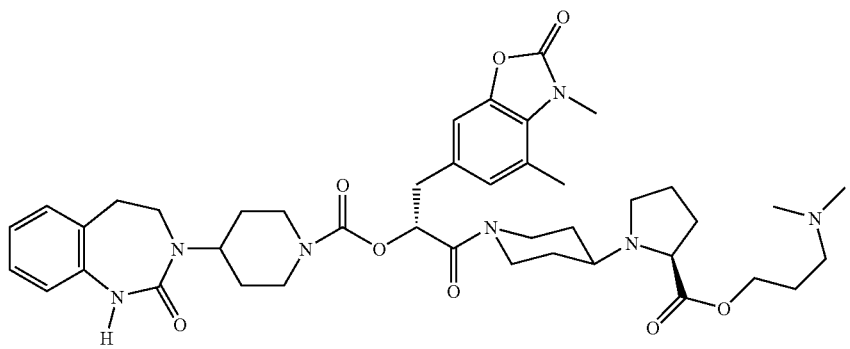 |
| (286) | 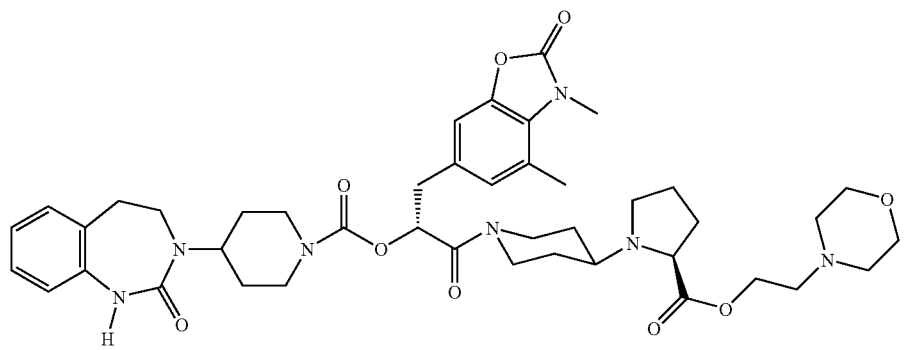 |

-continued
| No. | Structure |
|---|---|
| (287) | 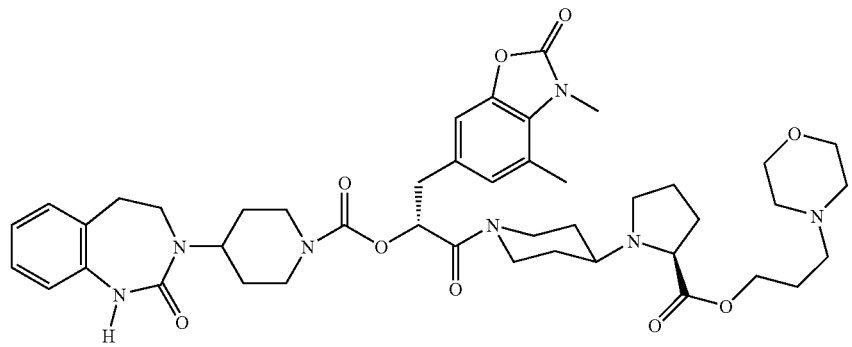 |
| (288) | 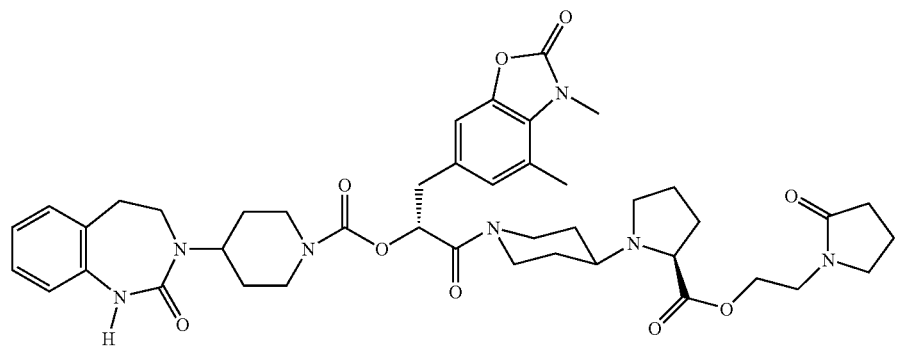 |
| (289) | 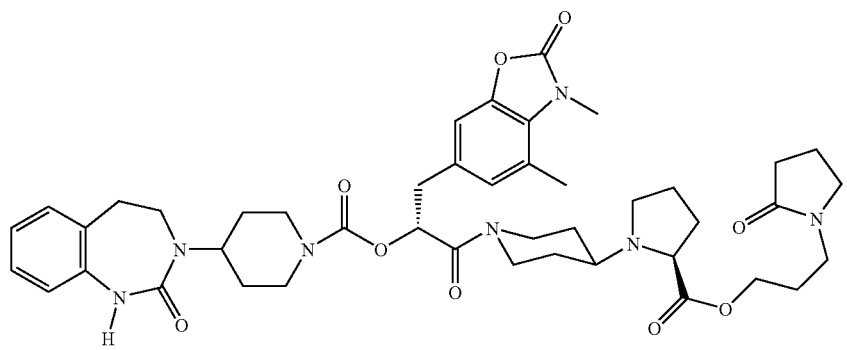 |
| (290) | 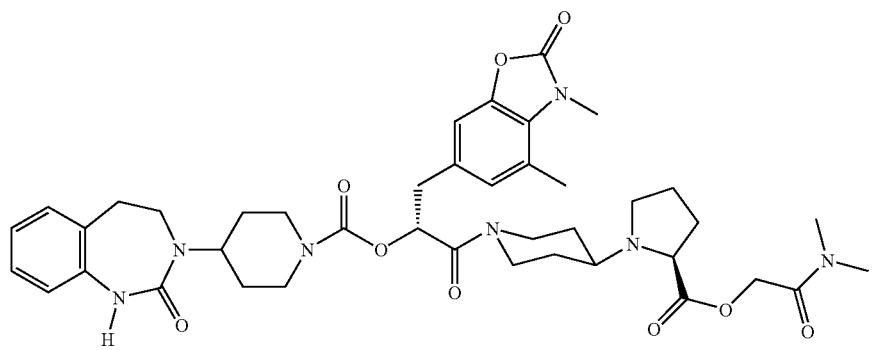 |

| No. | Structure |
|---|---|
| (291) | 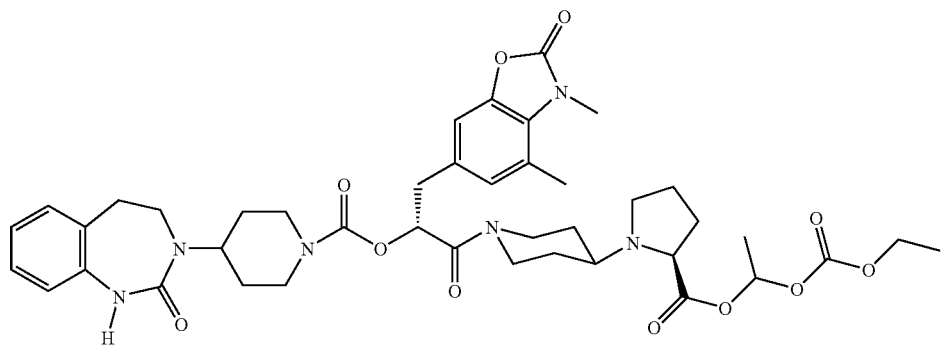 |
| (292) | 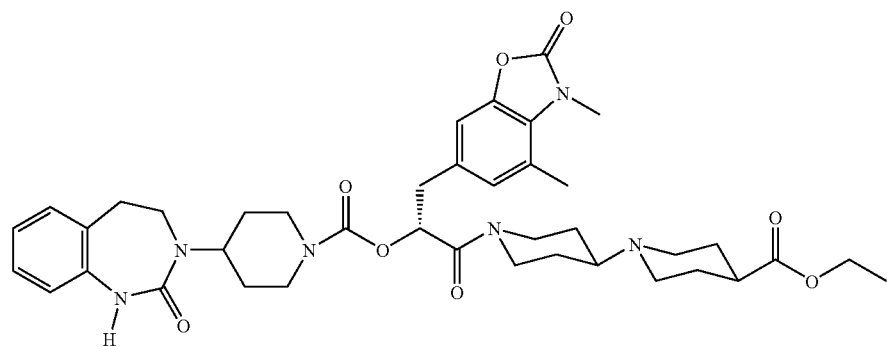 |
| (293) | 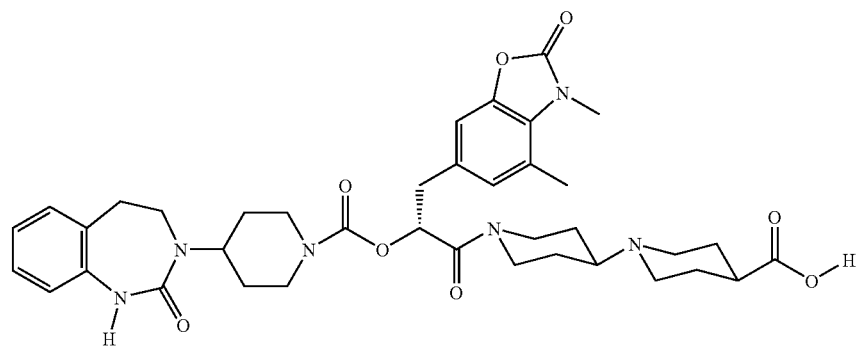 |
| (294) | 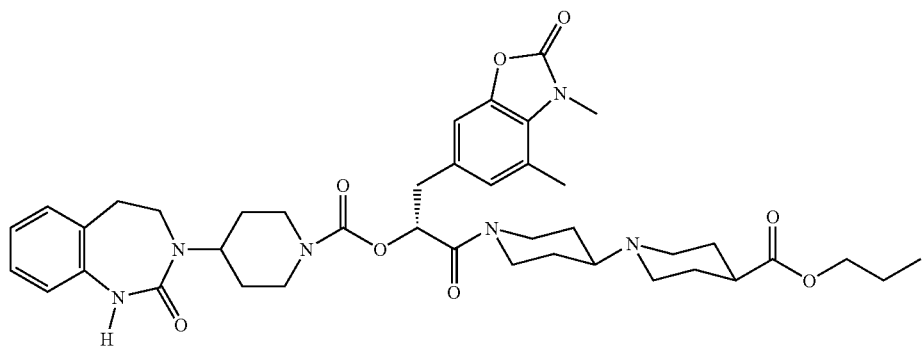 |

-continued
| No. | Structure |
|---|---|
| (295) | 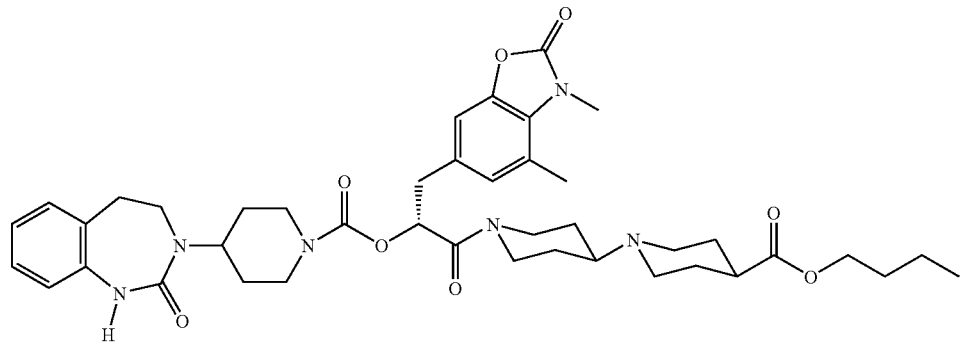 |
| (296) | 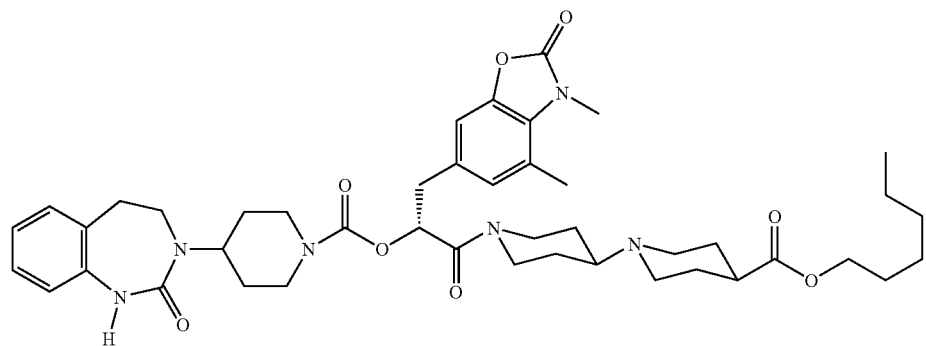 |
| (297) | 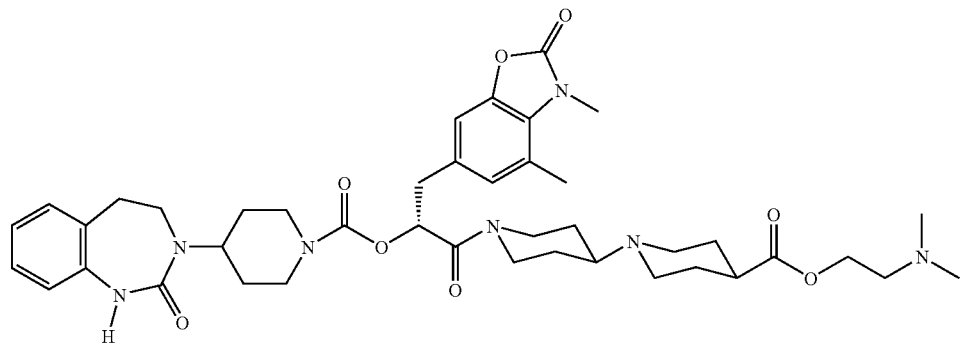 |
| (298) | 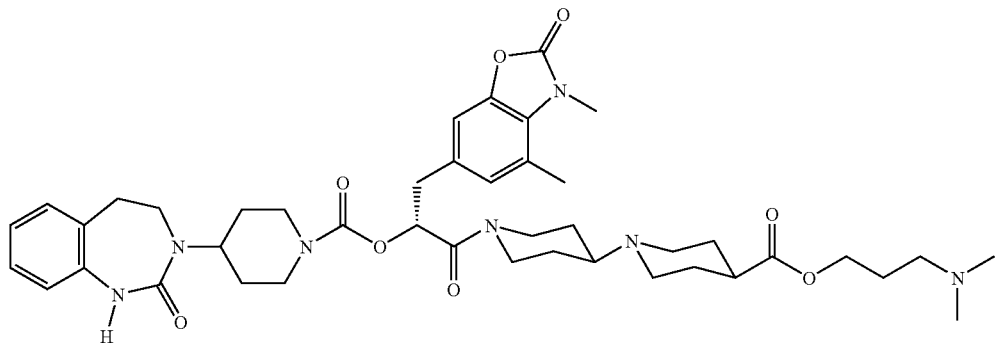 |

-continued
| No. | Structure |
|---|---|
| (299) | 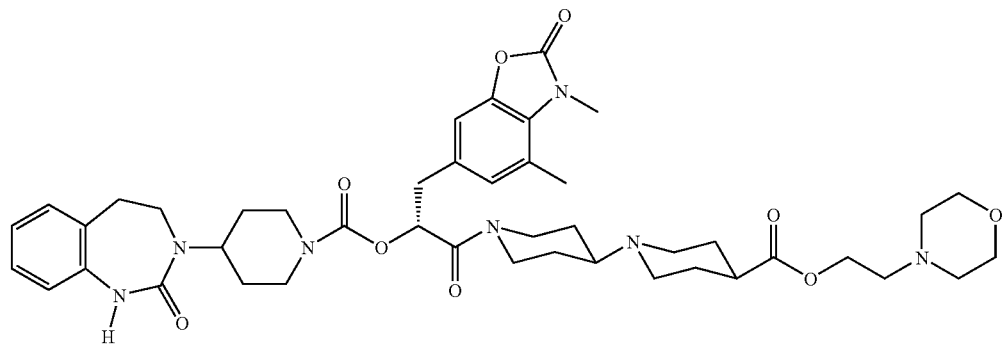 |
| (300) | 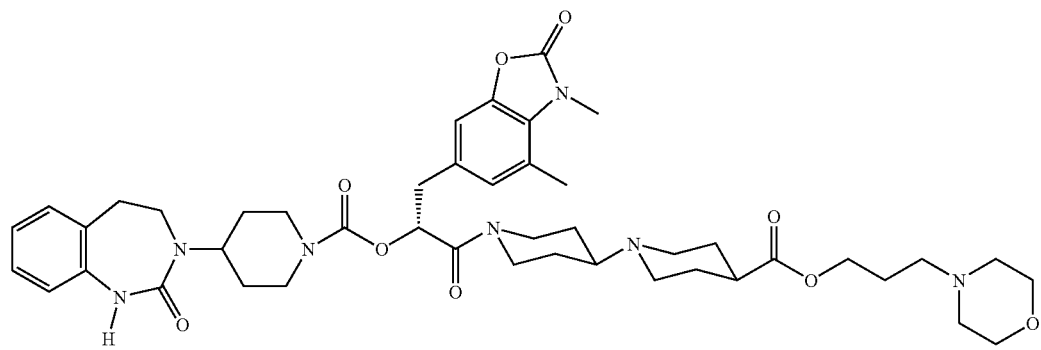 |
| (301) | 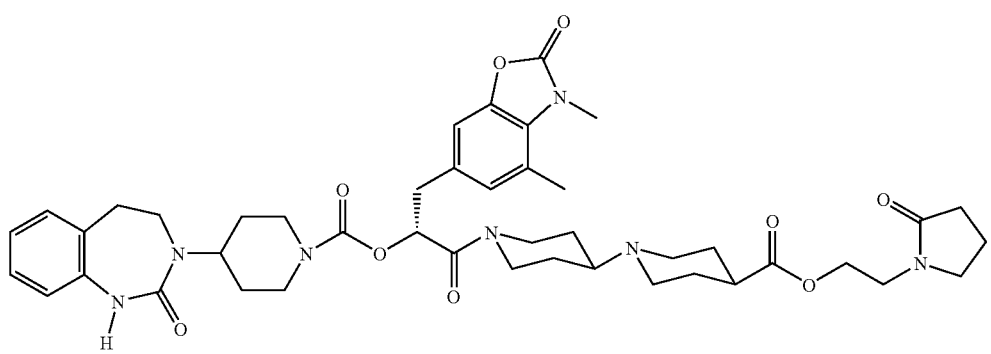 |
| (302) | 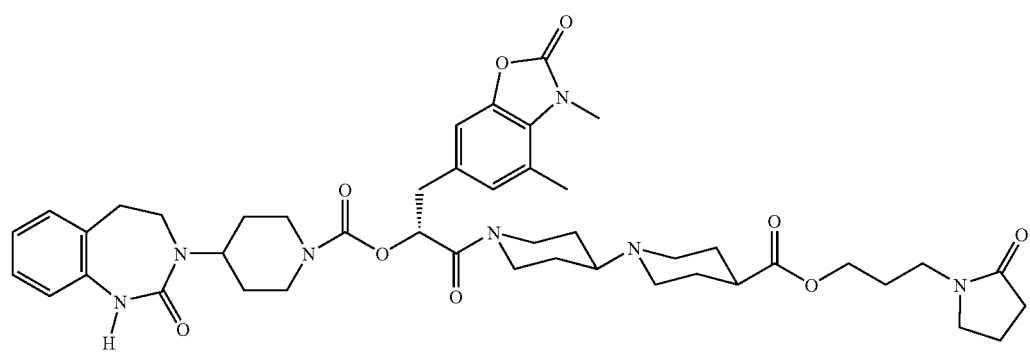 |

| No. | Structure |
|---|---|
| (303) | 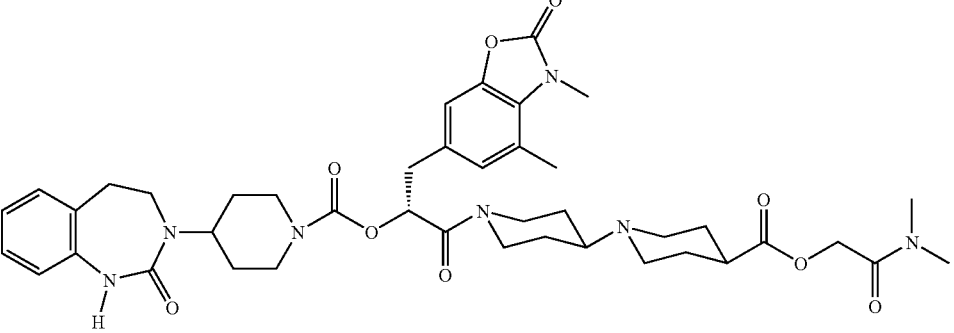 |
| (304) | 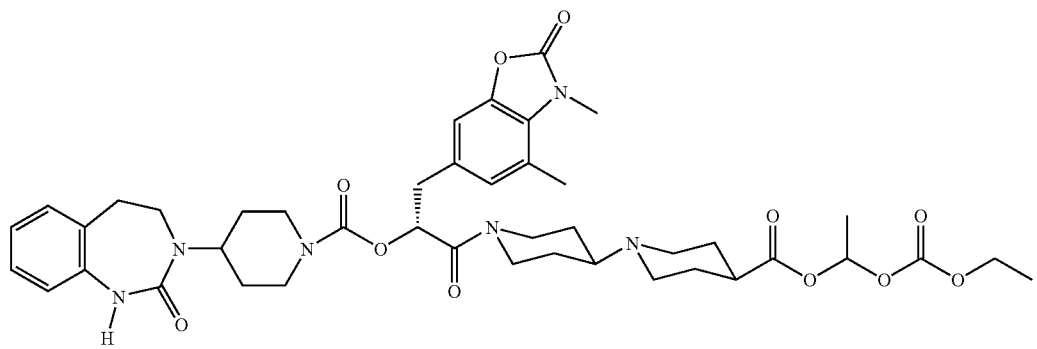 |
| (305) | 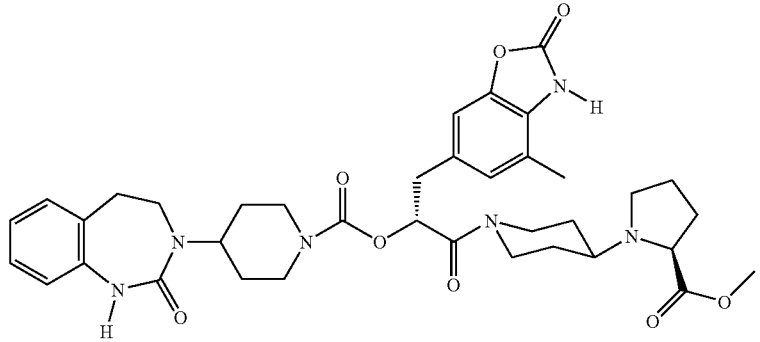 | the tautomers, the diastereomers, the enantiomers, the hydrates thereof, the mixtures thereof and the salts thereof as well as the hydrates of the salts, particularly the physiologically acceptable salts thereof with inorganic or organic acids or bases.

TERMS AND DEFINITIONS USED

Unless otherwise stated, all the substituents are independent of one another. If for example there are a plurality of $C_{1-6}$-alkyl groups as substituents in one group, in the case of three $C_{1-6}$-alkyl substituents, independently of one another, one may represent methyl, one n-propyl and one tert-butyl.

Within the scope of this application, in the definition of possible substituents, these may also be represented in the form of a structural formula. If present, an asterisk (*) in the structural formula of the substituent is to be understood as being the linking point to the rest of the molecule.

The subject-matter of this invention also includes the compounds according to the invention, including the salts thereof, wherein one or more hydrogen atoms, for example one, two, three, four or five hydrogen atoms, are replaced by deuterium.

By the term "phenyl" are meant both unsubstituted and mono- or disubstituted phenyl groups. Examples of substituents, which may be identical or different, include fluorine, chlorine or bromine atoms, $C_{1-3}$-alkyl, $F_3C$, $C_{1-3}$-alkyl-O or $F_3C$—O groups.

By the term "$C_{1-2}$-alkyl" (including those which are part of other groups) are meant branched and unbranched alkyl groups with 1 or 2 carbon atoms, by the term "$C_{1-3}$-alkyl" are meant branched and unbranched alkyl groups with 1 to 3 carbon atoms, by the term "$C_{1-6}$-alkyl" are meant branched and unbranched alkyl groups with 1 to 6 carbon atoms and by the term "$C_{1-8}$-alkyl" are meant branched and unbranched alkyl groups with 1 to 8 carbon atoms. Examples include: methyl, ethyl, n-propyl, iso-propyl, n-butyl, iso-butyl, sec-butyl, tert-butyl, n-pentyl, iso-pentyl, neo-pentyl or hexyl. The following abbreviations may optionally also be used for the above-mentioned groups: Me, Et, n-Pr, i-Pr, n-Bu, i-Bu, tert-Bu, etc. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-2}$-alkylene" (including those which are part of other groups) are meant branched and unbranched alkylene groups with 1 or 2 carbon atoms, by the term "$C_{1-3}$-alkylene" are meant branched and unbranched alkylene groups with 1 to 3 carbon atoms, by the term "$C_{2-3}$-alkylene" are meant branched and unbranched alkylene groups with 2 or 3 carbon atoms and by the term "$C_{2-4}$-alkylene" are meant branched and unbranched alkylene groups with 2 to 4 carbon atoms. Examples include: methylene, ethylene, propylene, 1-methylethylene, butylene, 1-methylpropylene, 1,1-dimethylethylene, 1,2-dimethylethylene. Unless stated otherwise, the definitions propylene and butylene include all the possible isomeric forms with the same number of carbons. Thus, for example, propyl also includes 1-methylethylene and butylene includes 1-methylpropylene, 1,1-dimethylethylene, 1,2-dimethylethylene.

It should also be mentioned that within the scope of the present invention the terms "alkylene" and "alkylenyl" are used synonymously.

Compounds of general formula I may have acid groups, mainly carboxyl groups, and/or basic groups such as e.g. amino functions. Compounds of general formula I may therefore be present as internal salts, as salts with pharmaceutically useable inorganic acids such as for example hydrobromic acid, phosphoric acid, nitric acid, hydrochloric acid, sulphuric acid, methanesulphonic acid, ethanesulphonic acid, benzenesulphonic acid, p-toluenesulphonic acid or organic acids such as for example malic acid, succinic acid, acetic acid, fumaric acid, maleic acid, mandelic acid, lactic acid, tartaric acid, citric acid or as salts with pharmaceutically useable bases such as alkali or alkaline earth metal hydroxides, e.g. sodium hydroxide or potassium hydroxide, or carbonates, ammonia, zinc or ammonium hydroxides or organic amines such as e.g. diethylamine, triethylamine, ethanolamine, diethanolamine, triethanolamine, cyclohexylamine, dicyclohexylamine, inter alia.

The compounds according to the invention may be present as racemates, provided that they have only one chiral element, but may also be obtained as pure enantiomers, i.e. in the (R) or (S) form. Compounds which are present as racemates or in the (R) form are preferred.

However, the application also includes the individual diastereomeric pairs of antipodes or mixtures thereof, which are obtained if there is more than one chiral element in the compounds of general formula I, as well as the individual optically active enantiomers of which the above-mentioned racemates are made up.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

Methods of Preparation

The compounds of general formula I are prepared by methods known in principle. The following methods have proved particularly useful for preparing the compounds of general formula I according to the invention:

(a) For preparing compounds of general formula I wherein all the groups are as hereinbefore defined:

coupling a carboxylic acid of general formula V

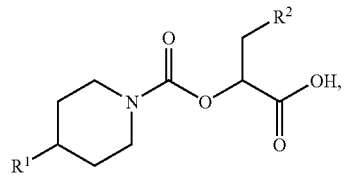

wherein $R^1$ and $R^2$ are as hereinbefore defined, with an amine of general formula VI

H—$R^3$-$R^4$, wherein $R^3$ and $R^4$ are as hereinbefore defined, the linking taking place via the nitrogen atom of $R^3$.

Before the reaction is carried out any carboxylic acid functions, primary or secondary amino functions or hydroxy functions present in the groups of the amine of formula H—$R^3$-$R^4$ may be protected by conventional protective groups and after the reaction has taken place any protective groups used may be cleaved again using methods familiar to those skilled in the art.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N—N', N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30° C. and +30° C., preferably −20° C. and +25° C. If necessary, N-ethyl-diisopropylamine (Hünig base) is preferably used as an additional auxiliary base.

The so-called "anhydride process" is used as a further coupling method for synthesising compounds of general formula I (cf. also: M. Bodanszky, "Peptide Chemistry", Springer-Verlag 1988, p. 58-59; M. Bodanszky, "Principles of Peptide Synthesis", Springer-Verlag 1984, p. 21-27). The Vaughan variant of the "mixed anhydride process" is preferred (J. R. Vaughan Jr., J. Amer. Chem. Soc. 73, 3547 (1951)), in which the mixed anhydride of the carboxylic acid of general formula V which is to be coupled and monoisobutyl carbonate is obtained, using isobutyl chlorocarbonate in the presence of bases such as 4-methylmorpholine or 4-ethylmorpholine. The preparation of this mixed anhydride and the coupling with the amines of general formula VI are carried out in a one-pot process, using the above-mentioned solvents and at temperatures between −20° C. and +25° C., preferably 0° C. and +25° C.

(b) For preparing compounds of general formula I wherein all the groups are as hereinbefore defined:

coupling a compound of general formula VII

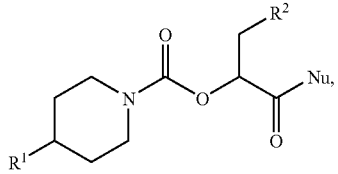

wherein $R^1$ and $R^2$ are as hereinbefore defined and Nu denotes a leaving group, for example a halogen atom, such as the chlorine, bromine or iodine atom, an alkylsulphonyloxy group with 1 to 10 carbon atoms in the alkyl moiety, a phenylsulphonyloxy or naphthylsulphonyloxy group optionally mono-, di- or trisubstituted by chlorine or bromine atoms, by methyl or nitro groups, wherein the substituents may be identical or different, a 1H-imidazol-1-yl, a 1H-pyrazol-1-yl optionally substituted by one or two methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yl-oxy, 2,5-dioxo-pyrrolidin-1-yloxy, phthalimidyloxy, 1H-benzotriazol-1-yloxy or azide group, with an amine of general formula V

wherein all the groups are as hereinbefore defined and the link is effected via the nitrogen atom of the amine $R^3$.

Before the reaction is carried out any carboxylic acid functions, primary or secondary amino functions or hydroxy functions present in the groups of the amine of general formula VI may be protected by conventional protective groups and after the reaction has taken place any protective groups used may be cleaved again using methods familiar to those skilled in the art.

The reaction is carried out under Schotten-Baumann or Einhorn conditions, i.e. the components are reacted in the presence of at least one equivalent of an auxiliary base at temperatures between −50° C. and +120° C., preferably −10° C. and +30° C., and optionally in the presence of solvents. The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof; if alkali metal or alkaline earth metal hydroxides, alkali metal carbonates or acetates are used as the auxiliary bases, water may also be added to the reaction mixture as cosolvent.

The new compounds of general formula I according to the invention contain one or more chiral centres. If for example there are two chiral centres present, the compounds may occur in the form of two diastereomeric pairs of antipodes. The invention includes the individual isomers as well as the mixtures thereof.

The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula I may be separated for example by HPLC on suitable chiral stationary phases (e.g. Chiral AGP, Chiralpak AD). Racemates which contain a basic or acidic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+) or (−)-camphorsulphonic acid, or an optically active base, for example with (R)-(+)-1-phenylethylamine, (S)-(−)-1-phenylethylamine or (S)-brucine.

According to a conventional method of separating isomers, the racemate of a compound of general formula I is reacted with one of the abovementioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. with dilute hydrochloric acid or aqueous methanesulphonic acid, and in this way the corresponding free compound is obtained in the (+) or (−) form.

The (R) or (S) enantiomer alone or a mixture of two optically active diastereomeric compounds covered by general formula I may also be obtained by performing the syntheses described above with a suitable reaction component in the (R) or (S) configuration.

The hydroxycarboxylic acids of general formula V needed as starting compounds may be obtained by reacting piperidines of general formula VIII

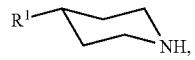

wherein $R^1$ is as hereinbefore defined, with carbonic acid derivatives of general formula IX

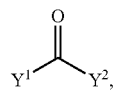

wherein $Y^1$ and $Y^2$ represent nucleofugic groups, which may be identical or different, preferably the chlorine atom or the p-nitrophenoxy or trichloromethoxy group, and with compounds of general formula X

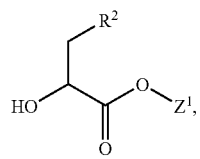

wherein $R^2$ is as hereinbefore defined and $Z^1$ denotes a protective group for a carboxy group, for example a $C_{1-6}$-alkyl or an optionally substituted benzyl group, while the alkyl groups may be straight-chain or branched and the benzyl group may be substituted by one or two methoxy groups.

Preferably $Z^1$ denotes the methyl, ethyl, tert-butyl or benzyl group. Before the reaction is carried out any hydroxy functions present in the group $R^2$ of a compound of formula (VI) may be protected by conventional protective groups and after the reaction is complete any protective groups used may be cleaved again using methods familiar to the skilled man.

In a first step the compounds of general formula VIII are reacted in a solvent, for example in dichloromethane, THF, pyridine or mixtures thereof, at a temperature between −20° C. and 50° C. in the presence of a base, for example triethylamine, pyridine or ethyldiisopropylamine, with the carbonic acid derivatives of general formula IX. The intermediate thus formed may be purified or reacted further without purification. The reaction of these intermediates with compounds of general formula X also takes place in one of the above-mentioned solvents and at the temperatures specified above, in the presence of a base, such as triethylamine or pyridine, with or without the addition of an activating reagent, such as e.g. 4-dimethylaminopyridine. To activate them the compounds of general formula X may also be deprotonated using a metal hydride, such as e.g. NaH or KH, while in this case there is no need for the base or the activating reagent to be present.

The starting compounds of formula VIII and IX are either commercially obtainable, known from the literature or may be prepared using methods known from the literature.

One way of obtaining compounds of general formula X comprises reacting aldehydes of general formula XI

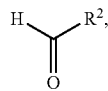

wherein $R^2$ is as hereinbefore defined, with N-acetylglycine in acetic anhydride as solvent in the presence of alkali metal acetate, preferably sodium or potassium acetate, at suitable temperatures, preferably at 80 to 130° C.

The azlactones obtained as primary product are hydrolysed without being isolated to form the compounds of general formula XII

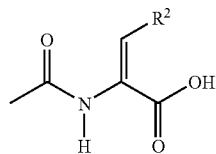

wherein $R^2$ is as hereinbefore defined. By further reaction in the presence of aqueous inorganic acids, such as sulphuric, phosphoric or hydrochloric acid, but preferably hydrochloric acid, compounds of general formula XIII are obtained

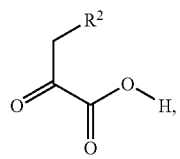

wherein $R^2$ is as hereinbefore defined.

These are then converted with suitable reducing agents into the compounds of general formula XIV

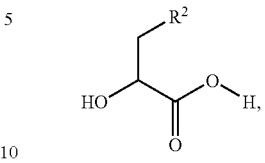

wherein $R^2$ is as hereinbefore defined.

Suitable reducing agents are alkali metal borohydrides, such as sodium or potassium borohydride. Other suitable reducing agents are chlorodialkylboranes, such as chlorodicyclohexylborane. If chiral chlorodialkylboranes, such as e.g. B-chlorodiisopinocampheylborane, are used, the compounds of general formula XIV may be isolated in enantiomerically pure form. The further reaction of compounds of general formula XIV to form compounds of general formula X is carried out in an alcoholic medium, preferably in methanol or ethanol, in the presence of a suitable acid, such as hydrochloric acid. Alternatively, the reaction may be carried out by reacting with thionyl chloride in alcoholic solvents, preferably methanol.

All the compounds of general formula I which contain primary or secondary amino, hydroxy or hydroxycarbonyl functions are preferably obtained from precursors with protective groups. Examples of protective groups for amino functions include a benzyloxycarbonyl, 2-nitrobenzyloxycarbonyl, 4-nitro-benzyloxycarbonyl, 4-methoxy-benzyloxycarbonyl, 2-chloro-benzyloxycarbonyl, 3-chloro-benzyloxycarbonyl, 4-chloro-benzyloxycarbonyl, 4-biphenylyl-α, α-dimethyl-benzyl-oxycarbonyl or 3,5-dimethoxy-α,α-dimethyl-benzyloxycarbonyl group, an alkoxycarbonyl group with a total of 1 to 5 carbon atoms in the alkyl moiety, for example the methoxycarbonyl, ethoxycarbonyl, n-propoxycarbonyl, iso-propoxycarbonyl, n-butoxycarbonyl, 1-methylpropoxycarbonyl, 2-methylpropoxy-carbonyl or tert-butyloxycarbonyl group, the allyloxycarbonyl, 2,2,2-trichloro-(1,1-dimethylethoxy)carbonyl or 9-fluorenylmethoxycarbonyl group or a formyl, acetyl or trifluoracetyl group.

Examples of protective groups for hydroxy functions include a trimethylsilyl, triethylsilyl, triisopropyl, tert-butyldimethylsilyl or tert-butyldiphenylsilyl group, a tert-butyl, benzyl, 4-methoxybenzyl or 3,4-dimethoxybenzyl group. Examples of protective groups for hydroxycarbonyl functions include an alkyl group with a total of 1 to 5 carbon atoms, for example the methyl, ethyl, n-propyl, isopropyl, n-butyl, tert-butyl, allyl, 2,2,2-trichloroethyl, benzyl or 4-methoxybenzyl group.

The compounds of general formula I obtained may, if they contain suitable basic functions, be converted, particularly for pharmaceutical use, into their physiologically acceptable salts with inorganic or organic acids. Suitable acids include for example hydrochloric acid, hydrobromic acid, phosphoric acid, nitric acid, sulphuric acid, methanesulphonic acid, ethanesulphonic acid, benzenesulphonic acid, p-toluenesulphonic acid, acetic acid, fumaric acid, succinic acid, lactic acid, mandelic acid, malic acid, citric acid, tartaric acid or maleic acid.

Moreover, if they contain a carboxylic acid function, the new compounds of formula I may be converted into the addition salts thereof with inorganic or organic bases, particularly, for pharmaceutical use, into their physiologically acceptable addition salts. Suitable bases for this include for example sodium hydroxide, potassium hydroxide, ammonia, cyclohexylamine, dicyclohexylamine, ethanolamine, diethanolamine and triethanolamine.

The present invention relates to racemates if the compounds of general formula I have only one chiral element. However, the application also includes the individual diastereomeric pairs of antipodes or mixtures thereof which are obtained if there is more than one chiral element in the compounds of general formula I, as well as the individual optically active enantiomers of which the above-mentioned racemates are made up.

Also included in the subject matter of this invention are the compounds according to the invention, including the salts thereof, in which one or more hydrogen atoms, for example one, two, three, four or five hydrogen atoms, are replaced by deuterium.

The new compounds of general formula I and the physiologically acceptable salts thereof have valuable pharmacological properties, based on their selective CGRP-antagonistic properties. The invention further relates to pharmaceutical compositions containing these compounds, their use and the preparation thereof. The new compounds mentioned above and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of the above-mentioned compounds for human CGRP-receptors and their antagonistic properties:

A. Binding Studies with SK-N-MC Cells (Expressing the Human CGRP Receptor)

SK-N-MC cells are cultivated in "Dulbecco's modified Eagle medium". The medium is removed from confluent cultures. The cells are washed twice with PBS buffer (Gibco 041-04190 M), detached by the addition of PBS buffer mixed with 0.02% EDTA, and isolated by centrifuging. After resuspension in 20 ml of "Balanced Salts Solution" [BSS (in mM): NaCl 120, KCl 5.4, NaHCO$_3$ 16.2, MgSO$_4$ 0.8, NaHPO$_4$ 1.0, CaCl$_2$ 1.8, D-glucose 5.5, HEPES 30, pH 7.40] the cells are centrifuged twice at 100×g and resuspended in BSS. After the number of cells has been determined, the cells are homogenised using an Ultra-Turrax and centrifuged for 10 minutes at 3000×g. The supernatant is discarded and the pellet is recentrifuged in Tris buffer (10 mM Tris, 50 mM NaCl, 5 mM MgCl$_2$, 1 mM EDTA, pH 7.40) enriched with 1% bovine serum albumin and 0.1% bacitracin, and resuspended (1 ml/1000000 cells). The homogenised product is frozen at −80° C. The membrane preparations are stable for more than 6 weeks under these conditions.

After thawing, the homogenised product is diluted 1:10 with assay buffer (50 mM Tris, 150 mM NaCl, 5 mM MgCl$_2$, 1 mM EDTA, pH 7.40) and homogenised for 30 seconds with an Ultra-Turrax. 230 µl of the homogenised product are incubated for 180 minutes at ambient temperature with 50 pM $^{125}$I-iodotyrosyl-Calcitonin-Gene-Related Peptide (Amersham) and increasing concentrations of the test substances in a total volume of 250 µl. The incubation is ended by rapid filtration through GF/B glass fibre filters treated with polyethyleneimine (0.1%) using a cell harvester. The protein-bound radioactivity is measured using a gamma counter. Non-specific binding is defined as the bound radioactivity after the presence of 1 µM human CGRP-alpha during incubation.

The concentration binding curves are analysed using computer-aided non-linear curve fitting.

The compounds mentioned hereinbefore show IC$_{50}$ values ≦10000 nM in the test described.

B. CGRP Antagonism in SK-N-MC Cells

SK-N-MC cells (1 million cells) are washed twice with 250 µl incubation buffer (Hanks' HEPES, 1 mM 3-isobutyl-1-methylxanthine, 1% BSA, pH 7.4) and pre-incubated at 37° C. for 15 minutes. After the addition of CGRP (10 µl) as agonist in increasing concentrations ($10^{31\ 11}$ to $10^{-6}$ M), or additionally the substance in 3 to 4 different concentrations, the mixture is incubated for another 15 minutes.

Intracellular cAMP is then extracted by the addition of 20 µl of 1 M HCl and centrifugation (2000×g, 4° C., for 15 minutes). The supernatants are frozen in liquid nitrogen and stored at −20° C.

The cAMP contents of the samples are determined by radioimmunoassay (Messrs. Amersham) and the pA$_2$ values of antagonistically acting substances are determined graphically.

The compounds according to the invention exhibit CGRP-antagonistic properties in the in vitro test model described, in a dosage range between $10^{-12}$ and $10^{-5}$ M.

Indications

In view of their pharmacological properties the compounds according to the invention and the salts thereof with physiologically acceptable acids are thus suitable for the acute and prophylactic treatment of headaches, particularly migraine or cluster headaches and tension headaches. Moreover, the compounds according to the invention also have a positive effect on the following diseases: non-insulin-dependent diabetes mellitus ("NIDDM"), cardiovascular diseases, morphine tolerance, diarrhoea caused by clostridium toxin, skin diseases, particularly thermal and radiation-induced skin damage including sunburn, lichen, pruritis, pruritic toxidermies and severe itching, inflammatory diseases, e.g. inflammatory diseases of the joints (osteoarthritis, rheumatoid arthritis, neurogenic arthritis), generalised soft-tissue rheumatism (fibromyalgia), neurogenic inflammation of the oral mucosa, inflammatory lung diseases, allergic rhinitis, asthma, COPD, diseases accompanied by excessive vasodilatation and resultant reduced blood supply to the tissues, e.g. shock and sepsis, chronic pain, e.g. diabetic neuropathies, neuropathies induced by chemotherapy, HIV-induced neuropathies, postherpetic neuropathies, neuropathies induced by tissue trauma, trigeminal neuralgias, temporomandibular dysfunctions, CRPS (complex regional pain syndrome), back pain, and visceral complaints, such as e.g. irritable bowel syndrome (IBS) and inflammatory bowel syndrome. In addition, the compounds according to the invention have a general pain-relieving effect. The symptoms of menopausal hot flushes caused by vasodilatation and increased blood flow in oestrogen-deficient women and hormone-treated patients with prostate carcinoma and castrated men are favourably affected by the CGRP antagonists of the present application in a preventive and acute-therapeutic capacity, this therapeutic approach being distinguished from hormone replacement by the absence of side effects.

Preferably, the compounds according to the invention are suitable for the acute and prophylactic treatment of migraine and cluster headaches, for treating irritable bowel syndrome (IBS) and for the preventive and acute-therapeutic treatment of hot flushes in oestrogen-deficient women.

The dosage required to achieve a corresponding effect is conveniently 0.0001 to 3 mg/kg of body weight, preferably 0.01 to 1 mg/kg of body weight, when administered intravenously or subcutaneously, and 0.01 to 10 mg/kg of body weight, preferably 0.1 to 10 mg/kg of body weight when administered orally, nasally or by inhalation, 1 to 3× a day in each case.

If the treatment with CGRP antagonists and/or CGRP release inhibitors is given as a supplement to conventional hormone replacement, it is advisable to reduce the doses specified above, in which case the dosage may be from 1/5 of the lower limits mentioned above up to 1/1 of the upper limits specified.

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

Combinations

Categories of active substance which may be used in combination include e.g. antiemetics, prokinetics, neuroleptics, antidepressants, neurokinin antagonists, anticonvulsants, histamine-H1-receptor antagonists, β-blockers, α-agonists and α-antagonists, ergot alkaloids, mild analgesics, non-steroidal antiphlogistics, corticosteroids, calcium antagonists, $5\text{-HT}_{1B/1D}$-agonists or other anti-migraine agents which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal antiinflammatories aceclofenac, acemetacin, acetylsalicylic acid, acetaminophen (paracetamol), azathioprine, diclofenac, diflunisal, fenbufen, fenoprofen, flurbiprofen, ibuprofen, indometacin, ketoprofen, leflunomide, lornoxicam, mefenamic acid, naproxen, phenylbutazone, piroxicam, sulphasalazine, zomepirac or the pharmaceutically acceptable salts thereof as well as meloxicam and other selective COX2-inhibitors, such as for example rofecoxib, valdecoxib, parecoxib, etoricoxib and celecoxib, as well as substances that inhibit earlier or later stages of prostaglandin synthesis or prostaglandin receptor antagonists such as e.g. EP2-receptor antagonists and IP-receptor antagonists.

It is also possible to use ergotamine, dihydroergotamine, metoclopramide, domperidone, diphenhydramine, cyclizine, promethazine, chlorpromazine, vigabatrin, timolol, isometheptene, pizotifen, botox, gabapentin, pregabalin, duloxetine, topiramate, riboflavin, montelukast, lisinopril, micardis, prochloroperazine, dexamethasone, flunarizine, dextropropoxyphene, meperidine, metoprolol, propranolol, nadolol, atenolol, clonidine, indoramin, carbamazepine, phenytoin, valproate, amitryptiline, imipramine, venlafaxine, lidocaine or diltiazem and other $5\text{-HT}_{1B/1D}$-agonists such as, for example, almotriptan, avitriptan, eletriptan, frovatriptan, naratriptan, rizatriptan, sumatriptan and zolmitriptan.

Furthermore, CGRP antagonists with vanilloid receptor antagonists, such as e.g. VR-1 antagonists, glutamate receptor antagonists, such as e.g. mGlu5 receptor antagonists, mGlu1 receptor antagonists, iGlu5 receptor antagonists, AMPA receptor antagonists, purine receptor blockers, such as e.g. P2X3 antagonists, NO-synthase inhibitors, such as e.g. iNOS inhibitors, calcium channel blockers, such as e.g. PQ-type blockers, N-type blockers, potassium channel openers, such as e.g. KCNQ channel openers, sodium channel blockers, such as e.g. PN3 channel blockers, NMDA receptor antagonists, acid-sensing ion channel antagonists, such as e.g. ASIC3 antagonists, bradykinin receptor antagonists such as e.g. B1 receptor antagonists, cannabinoid receptor agonists, such as e.g. CB2 agonists, CB1 agonists, somatostatin receptor agonists, such as e.g. sst2 receptor agonists may be added.

The dosage of these active substances is expediently 1/5 of the lowest usually recommended dose to 1/1 of the normally recommended dose, i.e. for example 20 to 100 mg of sumatriptan.

Formulations

The compounds prepared according to the invention may be administered either on their own or optionally in combination with other active substances for the treatment of migraine by intravenous, subcutaneous, intramuscular, intraarticular, intrarectal, intranasal route, by inhalation, topically, transdermally or orally, while aerosol formulations are particularly suitable for inhalation. The combinations may be administered either simultaneously or sequentially.

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula I according to the preferred embodiments above.

It is particularly preferable if the compounds of formula I are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula I are administered by inhalation, particularly preferably if they are administered once or twice a day. For this purpose, the compounds of formula I have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the compounds of formula I are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain I dissolved in the propellant gas or in dispersed form. The propellant gases which may be used to prepare the inhalation aerosols are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula I are preferably used according to the invention to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as, for example, sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

Experimental Section

As a rule IR, $^1$H-NMR and/or mass spectra have been obtained for the compounds prepared. Unless stated otherwise, the acid, base and salt solutions used in working up the reaction solutions are aqueous systems of the specified concentrations.

Unless stated otherwise, $R_f$ values are determined using ready-made TLC silica gel plates 60 F254 (E. Merck, Darmstadt, Item no. 1.05714) without chamber saturation.

The $R_f$ values determined under the heading Polygram are obtained using Polygram SIL G/$_{UV254}$ ready-made TLC films (coated with 0.2 mm silica gel) made by Messrs Macherey-Nagel (Düren, Item no. 805 021).

The ratios given for the eluants relate to units by volume of the particular solvents. The units by volume given for $NH_3$ relate to a concentrated solution of $NH_3$ in water.

Silica gel made by Millipore (MATREX™, 35-70 μm) is used for chromatographic purifications.

Aluminium oxide (Alox) made by ICN Biomedicals (Eschwege, Item no. 02090) is used for chromatographic purifications. The required activity grade is produced before use, in accordance with the manufacturer's instructions.

The HPLC data provided are measured under the parameters listed below:

Method A:

Analytical column: Merck Chromolith Speed ROD, RP18e; 4.6×50 mm; column temperature: 30° C.; flow: 1.5 mL/min; injection volume: 5 μl; detection at 254 nm

| time (min) | percent by volume of water (with 0.1% formic acid) | percent by volume of acetonitrile (with 0.1% formic acid) |
|---|---|---|
| 0 | 90 | 10 |
| 4.5 | 10 | 90 |
| 5 | 10 | 90 |
| 5.5 | 90 | 10 |

Method B:

Analytical column: Zorbax column (Agilent Technologies), SB (Stable Bond) C18; 3.5 μm; 4.6×75 mm; column temperature: 30° C.; flow: 1.6 mL/min; injection volume: 5 μL; detection at 254 nm

| time (min) | percent by volume of water (with 0.1% formic acid) | percent by volume of acetonitrile (with 0.1% formic acid) |
|---|---|---|
| 0 | 95 | 5 |
| 4.5 | 10 | 90 |
| 5 | 10 | 90 |
| 5.5 | 90 | 10 |

Method C:

Analytical column: Zorbax column (Agilent Technologies), SB (Stable Bond) C18; 3.5 μm; 4.6×75 mm; column temperature: 30° C.; flow: 0.8 mL/min; injection volume: 5 μL; detection at 254 nm

| time (min) | percent by volume of water (with 0.1% formic acid) | percent by volume of acetonitrile (with 0.1% formic acid) |
|---|---|---|
| 0 | 95 | 5 |
| 9 | 10 | 90 |
| 10 | 10 | 90 |
| 11 | 95 | 5 |

In preparative HPLC purifications as a rule the same gradients are used as were used to obtain the analytical HPLC data.

The products are collected under mass control, the fractions containing product are combined and freeze-dried.

In the absence of any more information regarding the configuration, it is unclear whether there are pure enantiomers involved or whether partial or even total racemisation has taken place.

The following abbreviations are used in the test descriptions:

| | |
|---|---|
| AcOH | acetic acid |
| CDI | N,N'-carbonyldiimidazole |
| Cyc | cyclohexane |
| DCM | dichloromethane |
| DIPE | diisopropylether |
| DMF | N,N-dimethylformamide |
| EtOAc | ethyl acetate |
| EtOH | ethanol |
| HCl | hydrochloric acid |
| HOAc | acetic acid |
| i.vac. | in vacuo (under vacuum) |
| MeOH | methanol |
| PE | petroleum ether |
| RT | room temperature |
| TBME | tert-butylmethylether |
| TBTU | O-(benzotriazol-1-yl)-N,N,N',N'-tetra-methyluronium-tetrafluoroborate |
| THF | tetrahydrofuran |

Example 1

(R)-2-[4-(4-fluoro-phenyl)-piperazin-1-yl]-1-(4-methyl-2-oxo-2.3-dihydro-benzoxazol-6-ylmethyl)-2-oxo-ethyl 4-(2-oxo-1,2,4,5-tetrahydro-1,3-benzodiazepin-3-yl)-piperidine-1-carboxylate

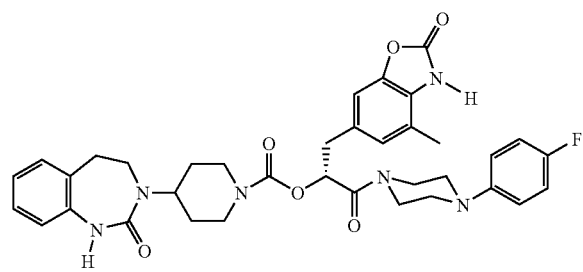

1a) 4-methyl-3H-benzoxazol-2-one 76.0 g (0.45 mol) CDI in 1 L DCM were added dropwise at 0° C. to a solution of 50.0 g (0.39 mol) 5-amino-m-cresol and 210 mL (1.2 mol) in 1 L DCM. After the reaction had ended the reaction mixture was combined with 250 mL water, the organic phase was separated off and washed twice with 250 mL 1 M $KHSO_4$ solution and 250 mL water and dried on $MgSO_4$. After the desiccant and solvent had been eliminated the residue obtained was dissolved in 200 mL EtOAc, refluxed, combined with 100 mL PE, slowly cooled to RT, the precipitate formed was suction filtered and dried.

Yield: 39.2 g (67% of theory)
ESI-MS: $(M+H)^+$=150
$R_f$=0.65 (silica gel, DCM/Cyc/MeOH/$NH_3$ 70:15:15:2)

1b) 6-bromo-4-methyl-3H-benzoxazol-2-one 35.8 g (199.1 mmol) N-bromosuccinimide were added to a solution of 29.5 g (197.8 mmol) 4-methyl-3H-benzoxazol-2-one in 200 mL AcOH and stirred overnight at RT. The reaction solution was combined with 800 mL water, stirred for 15 min at RT, the precipitate was suction filtered, washed with water and dried at 60° C. in the vacuum dryer.

Yield: 43.0 g (95% of theory)
ESI-MS: $(M+H)^+$=226/228 (Br)
$R_f$=0.35 (silica gel, DCM/Cyc/MeOH/$NH_3$ 70:15:15:2)

1c) methyl (Z,E)-2-acetylamino-3-(4-methyl-2-oxo-2,3-dihydro-benzoxazol-6-yl)-acrylate Under a nitrogen atmosphere 5.4 g (23.9 mmol) $Pd(OAc)_2$ and 7.5 g (24.0 mmol) tri-o-tolyl-phosphane were added to a solution of 38.3 g (168.0 mmol) 6-bromo-4-methyl-3H-benzoxazol-2-one and 28.0 g (191.7 mmol) methyl 2-acetylamino-acrylate in 800 mL acetonitrile and 480 mL triethylamine, the reaction mixture was stirred for 18 h at 80° C. and then evaporated down i.vac. The residue was combined with 100 mL water and 50 mL EtOAc and the precipitate was filtered off. The crystals were dissolved by refluxing in MeOH/DCM 1:1, combined with activated charcoal, filtered off and the filtrate was evaporated to dryness.

Yield: 31.2 g (64% of theory)
ESI-MS: $(M+H)^+$=291
$R_f$=0.38 (silica gel, DCM/Cyc/MeOH/$NH_3$ 70:15:15:2)

1d) 3-(4-methyl-2-oxo-2,3-dihydro-benzoxazol-6-yl)-2-oxo-propionic acid 160 mL of 4 M HCl were added to a solution of 31.2 g (107.5 mmol) methyl (Z,E)-2-acetylamino-3-(4-methyl-2-oxo-2,3-dihydro-benzoxazol-6-yl)-acrylate in 320 mL 1,4-dioxane and the reaction solution was refluxed for 5 h. The mixture was evaporated down i.vac., the precipitate was filtered off, washed with water and dried at 60° C. in the vacuum dryer.

Yield: 24.9 g (98% of theory)
ESI-MS: $(M+H)^+$=236
$R_f$=0.38 (silica gel, DCM/Cyc/MeOH/$NH_3$ 70:15:15:2)

1e) (R)-2-hydroxy-3-(4-methyl-2-oxo-2,3-dihydro-benzoxazol-6-yl)-propionic acid

Under a nitrogen atmosphere a solution of 60.0 g (187.1 mmol) of (1R)-B-chlorodiisopinocampheylboran in 200 mL THF was added dropwise within 15 min to a solution, cooled to −35° C., of 24.9 g (105.9 mmol) 3-(4-methyl-2-oxo-2,3-dihydro-benzoxazol-6-yl)-2-oxo-propionic acid and 20.0 mL (143.9 mmol) triethylamine in 400 mL THF and the reaction solution was stirred overnight at RT. Then the reaction solution was carefully made alkaline with 1 M NaOH at 5° C., combined with 400 mL EtOAc and stirred for 15 min. The organic phase was separated off and extracted twice with 100 mL of 1 M NaOH and with 100 mL of water. The combined aqueous phases were acidified with semiconcentrated HCl and extracted twice with in each case 150 mL of EtOAc. The combined organic phases were dried on $MgSO_4$ and evaporated down i.vac.

Yield: 20.8 g (83% of theory)
ESI-MS: $(M+H)^+$=238
$R_f$=0.10 (silica gel, DCM/Cyc/MeOH/$NH_3$ 70:15:15:2)

1f) methyl (R)-2-hydroxy-3-(4-methyl-2-oxo-2,3-dihydro-benzoxazol-6-yl)-propionate 23.0 g (97.0 mmol) (R)-2-hydroxy-3-(4-methyl-2-oxo-2,3-dihydro-benzoxazol-6-yl)-propionic acid were dissolved in 200 mL methanolic HCl (1.3 M), stirred overnight at RT and then evaporated down i. vac. The residue was combined with 200 mL EtOAc, washed with 15% $K_2CO_3$ solution and the organic phase was dried on $Na_2SO_4$. After the desiccant and solvent had been eliminated the residue was combined with DIPE, the crystals were filtered off and dried at 50° C. in the vacuum dryer.
Yield: 14.6 g (60% of theory)
ESI-MS: $(M+H)^+$=252
$R_f$=0.44 (silica gel, DCM/Cyc/MeOH/$NH_3$ 70:15:15:2)

1g) (R)-1-carboxy-2-(4-methyl-2-oxo-2,3-dihydro-benzoxazol-6-yl)-ethyl 4-(2-oxo-1,2,4,5,-tetrahydro-1,3-benzodiazepin-3-yl)-piperidine-1-carboxylate Under a nitrogen atmosphere 4.1 g (20.1 mmol) 4-nitrophenyl chloroformate in 20 mL THF was metered in to 40 mL pyridine within 10 min at a bath temperature of 60° C., the mixture was stirred for 5 min, then 5.0 g (19.9 mmol) methyl (R)-2-hydroxy-3-(4-methyl-2-oxo-2,3-dihydro-benzoxazol-6-yl)-propionate and 20 mL pyridine were added and the reaction mixture was stirred for 1.5 h at 60° C. The reaction solution was combined with 4.9 g (20.0 mmol) 3-piperidin-4-yl-1,3,4,5-tetrahydro-1,3-benzodiazepin-2-one and stirred for 2 h at 100° C. After the reaction had ended the mixture was combined with 150 mL EtOAc, washed three times with 70 mL 1 M $KHSO_4$ solution and 12 times with 50 mL of 15% $K_2CO_3$ solution and the organic phase was dried on $MgSO_4$. After the desiccant and solvent had been eliminated the residue was dissolved in 60 mL THF, combined with 250 mg LiOH in 10 mL water and the reaction mixture was stirred for 3 h at RT. The THF was eliminated i.vac., the aqueous residue was combined with 60 mL TBME, insoluble ingredients were filtered off, the organic phase was separated off and the aqueous phase was acidified with 1 M HCl. After 1 h at RT the precipitate formed was suction filtered, washed with water and dried at 60° C. in the vacuum dryer.
Yield: 2.5 g (25% of theory)
ESI-MS: $(M-H)^-$=507
$R_f$=0.10 (silica gel, DCM/Cyc/MeOH/$NH_3$ 70:15:15:2)

1h) (R)-2-[4-(4-fluoro-phenyl)-piperazin-1-yl]-1-(4-methyl-2-oxo-2,3-dihydro-b enzoxazol-6-ylmethyl)-2-oxo-ethyl 4-(2-oxo-1,2,4,5-tetrahydro-1,3-benzodiazepin-3-yl)-piperidine-1-carboxylate 234 mg (1.30 mmol) 1-(4-fluoro-phenyl)-piperazine were added to a solution of 600 mg (1.18 mmol) (R)-1-carboxy-2-(4-methyl-2-oxo-2,3-dihydrobenz-oxazol-6-yl)-ethyl 4-(2-oxo-1,2,4,5,-tetrahydro-1,3-benzodiazepin-3-yl)-piperidine-1-carboxylate, 417 mg (1.30 mmol) TBTU, 183 µL (1.30 mmol) triethylamine in 10 mL DMF and the reaction mixture was shaken at RT. The reaction solution was purified by HPLC without any further working up, the fractions containing the product were combined and lyophilised.
Yield: 490 mg (62% of theory)
ESI-MS: $(M+H)^+$=671
retention time (HPLC): 4.0 min (methode B)

Example 1.1

(R)-2-[4-(4-acetyl-piperazin-1-yl)-piperidin-1-yl]-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate

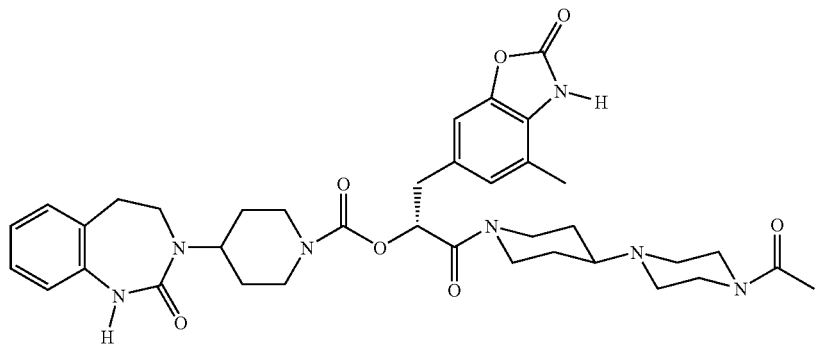

Prepared analogously to Example 1 h from 600 mg (1.18 mmol) (R)-1-carboxy-2-(4-methyl-2-oxo-2,3-dihydrobenzoxazol-6-yl)-ethyl 4-(2-oxo-1,2,4,5-tetrahydro-1,3-benzodiazepin-3-yl)-piperidine-1-carboxylate and 275 mg (1.30 mmol) 1-(4-piperidin-4-yl-piperazin-1-yl)-ethanone.
Yield: 420 mg (51% of theory)
ESI-MS: $(M+H)^+$=702
retention time (HPLC): 2.7 min (method B)

Example 1.2

(R)-1-(4-methyl-2-oxo-2,3-dihydro-benzoxazol-6-yl methyl)-2-oxo-2-[4-(1-oxo-1$\lambda^4$-thiomorpho-lin-4-yl)-piperidin-1-yl]-ethyl 4-(2-oxo-1,2,4,5-tetrahydro-1,3-benzodiazepin-3-yl)-piperidine-1-carboxylate

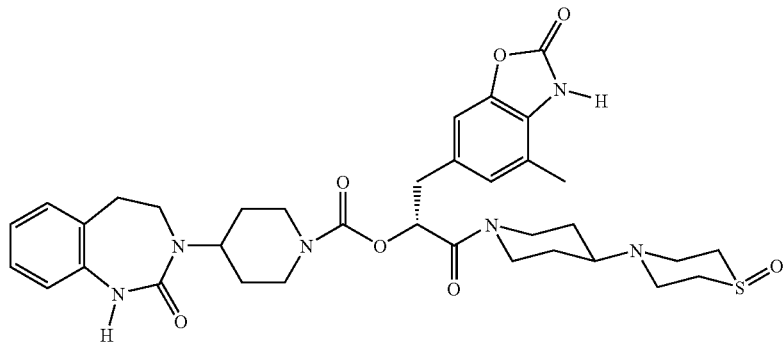

1.2a) (R)-1-(4-methyl-2-oxo-2,3-dihydro-benzoxazol-6-ylmethyl)-2-oxo-2-(4-oxo-piperid-1-yl)-ethyl 4-(2-oxo-1,2,4,5-tetrahydro-1,3-benzodiazepin-3-yl)-piperidine-1-carboxylate 200 mg (1.30 mmol) piperidin-4-one (used as the hydrate of the hydrochloride salt) were added to a solution of 500 mg (0.98 mmol) (R)-1-carboxy-2-(4-methyl-2-oxo-2,3-dihydrobenz-oxazol-6-yl)-ethyl 4-(2-oxo-1,2,4,5,-tetrahydro-1,3-benzodiazepin-3-yl)-piperidine-1-carboxylate, 350 mg (1.09 mmol) TBTU, 300 µL (2.15 mmol) triethylamine in 10 mL DMF and the reaction mixture was stirred for 4 h at RT. The reaction solution was evaporated down i. vac., the residue was taken up in DCM, the organic phase was washed with saturated NaHCO$_3$ solution and dried on Na$_2$SO$_4$. After the desiccant and solvent had been eliminated the residue was purified by chromatography (silica gel, gradient DCM/MeOH 20:1 to DCM/MeOH 10:1). The fractions containing the product were concentrated by evaporation, the residue was stirred with DIPE, suction filtered and dried.

Yield: 480 mg (83% of theory)
ESI-MS: (M−H)$^-$=588
retention time (HPLC): 3.2 min (method B)

1.2b) (R)-1-(4-methyl-2-oxo-2,3-dihydro-benzoxazol-6-ylmethyl)-2-oxo-2-[4-(1-oxo-1$\lambda^4$-thiomorpho-lin-4-yl)-piperidin-1-yl]-ethyl 4-(2-oxo-1,2,4,5-tetrahydro-1,3-benzodiazepin-3-yl)-piperidine-1-carboxylate A solution of 80 mg (0.14 mmol) (R)-1-(4-methyl-2-oxo-2,3-dihydro-benzoxazol-6-ylmethyl)-2-oxo-2-(4-oxo-piperidin-1-yl)-ethyl 4-(2-oxo-1,2,4,5-tetrahydro-1,3-benzodiazepin-3-yl)-piperidine-1-carboxylate and 32 mg (0.27 mmol) thiomorpholin-1-oxide in 5 mL DCM was stirred overnight at RT. After the solution had been cooled to 0° C., 15 µL (0.27 mmol) of AcOH and 50 mg (0.33 mmol) of sodium triacetoxyborohydride were added and the reaction mixture was stirred for 4 h at this temperature. It was evaporated down i.vac., the residue was taken up in 1 mL MeOH, filtered to remove any insoluble constituents and the crude product was purified by HPLC. The fractions containing the product were combined and lyophilised.

Yield: 24 mg (26% of theory)
ESI-MS: (M+H)$^+$=693
retention time (HPLC): 2.7 min (method B)

Example 1.3

(R)-2-(4-acetoxy-1,4'-bipiperidinyl-1'-yl)-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate

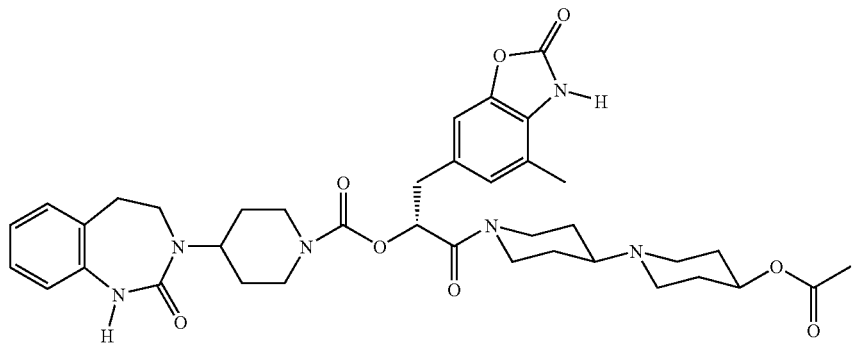

50 mg (0.22 mmol) [1,4']bipiperidinyl-4-yl acetate were added to a solution of 100 mg (0.20 m mol) (R)-1-carboxy-2-(4-methyl-2-oxo-2,3-dihydrobenz-oxazol-6-yl)-ethyl 4-(2-oxo-1,2,4,5,-tetrahydro-1,3-benzodiazepin-3-yl)-piperidine-1-carboxylate, 70 mg (0.22 mmol) TBTU and 35 μL (0.25 mmol) triethylamine in 1.5 mL DMF and the reaction mixture was stirred overnight at RT. The reaction solution was combined with 100 mL water and 100 mL of saturated NaHCO₃ solution, extracted three times with 70 mL EtOAc and the combined organic phases were dried on MgSO₄. After the desiccant and solvent had been eliminated the residue was purified by chromatography (silica gel, gradient DCM to DCM/MeOH/NH₃ 50:47:3). The fractions containing the product were combined, evaporated down i. vac., the residue was triturated with DIPE, suction filtered and dried.

Yield: 20 mg (14% of theory)
ESI-MS: (M+H)⁺=717
R$_f$=0.49 (silica gel, DCM/Cyc/MeOH/NH₃ 70:15:15:2)

Example 2

(R)-2-[4-(4-ethoxycarbonylmethyl-piperazin-1-yl)-piperidin-1-yl]-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate

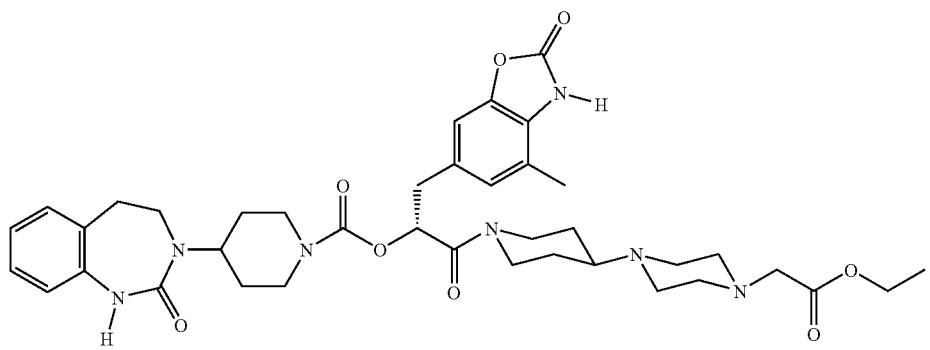

56 mg (0.22 mmol) ethyl (4-piperidin-4-yl-piperazin-1-yl)-acetate were added to a solution of 100 mg (0.20 mmol) (R)-1-carboxy-2-(4-methyl-2-oxo-2,3-dihydrobenz-oxazol-6-yl)-ethyl 4-(2-oxo-1,2,4,5,-tetrahydro-1,3-benzodiazepin-3-yl)-piperidine-1-carboxylate, 71 mg (0.22 mmol) TBTU and 31 μL (0.22 mmol) triethylamine in 1 mL DMF and the reaction mixture was shaken overnight at RT. The reaction solution was purified by HPLC without working up; the fractions containing the product were concentrated by evaporation and lyophilised.

Yield: 60 mg (41% of theory)
ESI-MS: (M+H)⁺=746
retention time (HPLC): 2.5 min (method B)

Example 2.1

(R)-2-[4-(4-carboxymethyl-piperazin-1-yl)-piperidin-1-yl]-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate

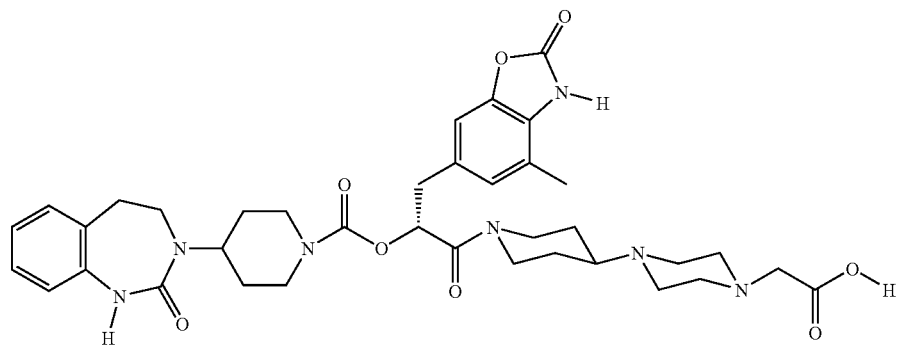

A solution of 1 mg (0.04 mmol) LiOH in 0.5 mL water was added to a solution of 20 mg (0.03 mmol) (R)-2-[4-(4-ethoxy-carbonylmethyl-piperazin-1-yl)-piperidin-1-yl]-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate in 1 mL THF and the reaction mixture was stirred overnight at RT. To complete the reaction a further 1 mg of LiOH was added and the mixture was stirred for 3 h at RT. The solvents were eliminated in a nitrogen current and the residue was lyophilised. The product was obtained as the lithium salt.

Yield: 15 mg (80% of theory)
ESI-MS: (M+H)$^+$=718
retention time (HPLC): 2.5 min (method B)

Example 3

(R)-2-[4-((S)-2-methoxycarbonyl-pyrrolidin-1-yl)-piperid in-1-yl]-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate

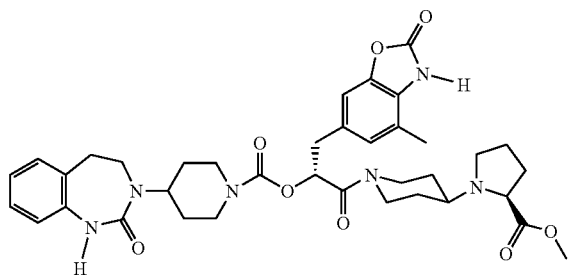

93 mg (0.44 mmol) methyl (S)-1-piperidin-4-yl-pyrrolidine-2-carboxylate were added to a solution of 200 mg (0.39 mmol) (R)-1-carboxy-2-(4-methyl-2-oxo-2,3-dihydrobenzoxazol-6-yl)-ethyl 4-(2-oxo-1,2,4,5,-tetrahydro-1,3-benzodiazepin-3-yl)-piperidine-1-carboxylate, 140 mg (0.44 mmol) TBTU and 61 µL (0.44 mmol) triethylamine in 2 mL DMF and the reaction mixture was shaken overnight at RT. The reaction solution was purified by HPLC without working up; the fractions containing the product were concentrated by evaporation and lyophilised.

Yield: 218 mg (79% of theory)
ESI-MS: (M+H)$^+$=703
retention time (HPLC): 2.5 min (method A)

Example 3.1

(R)-2-[4-((S)-2-carboxy-pyrrolidin-1-yl)-piperid in-1-yl]-1-(4-methyl-2-oxo-2,3-dihydro-benzoxazol-6-yl methyl)-2-oxo-ethyl 4-(2-oxo-1,2,4,5-tetrahydro-1,3-benzodiazepin-3-yl)-piperidine-1-carboxylate

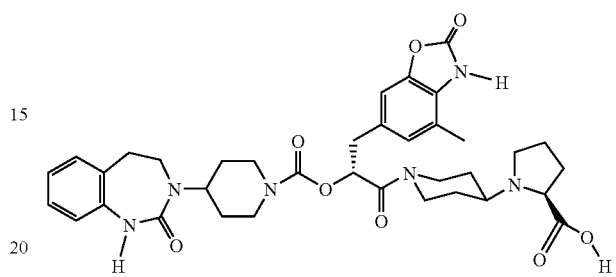

A solution of 17 mg (0.71 mmol) LiOH in 3 mL water was added to a solution of 200 mg (0.29 mmol) (R)-2-[4-((S)-2-methoxycarbonyl-pyrrolidin-1-yl)-piperidin-1-yl]-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate in 9 mL THF and the reaction mixture was stirred for 66 h at RT. The solvents were eliminated in a nitrogen current and the residue was purified by HPLC. The fractions containing the product were combined and lyophilised.

Yield: 49 mg (25% of theory)
ESI-MS: (M+H)$^+$=689
retention time (HPLC): 2.5 min (method A)

Example 3.2

(R)-2-[4-((S)-2-dimethylcarbamoylmethoxycarbonyl-pyrrolidin-1-yl)-piperidin-1-yl]-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate

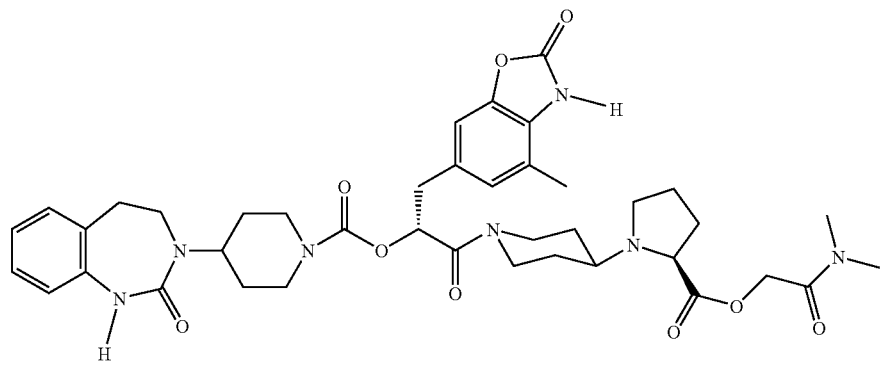

6 mg (0.06 mmol) 2-hydroxy-N,N-dimethyl-acetamide were added to a solution of 34 mg (0.05 mmol) (R)-2-[4-((S)-2-carboxy-pyrrolidin-1-yl)-piperidin-1-yl]-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate, 18 mg (0.06 mmol) TBTU and 8 μL triethylamine in 2 mL DMF and the reaction mixture was shaken overnight at RT. The reaction solution was purified by HPLC without working up; the fractions containing the product were combined and lyophilised.

Yield: 22 mg (58% of theory)
ESI-MS: (M+H)$^+$=774
retention time (HPLC): 2.5 min (method A)

Example 4

(R)-2-[4-((R)-2-ethoxycarbonyl-pyrrolidin-1-yl)-piperidin-1-yl]-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate

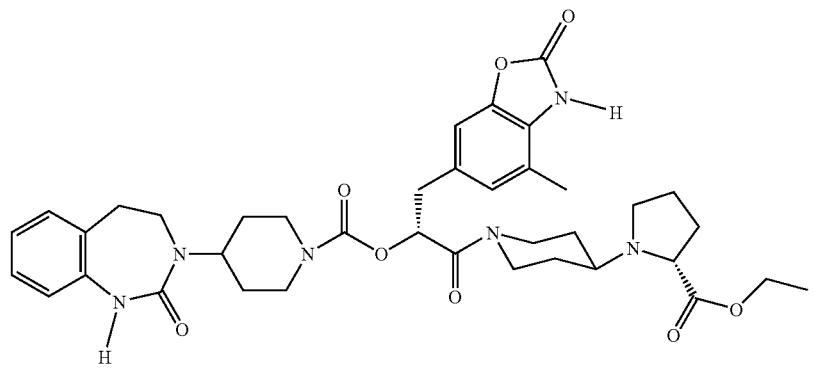

Prepared analogously to Example 3 from 200 mg (0.39 mmol) (R)-1-carboxy-2-(4-methyl-2-oxo-2,3-dihydrobenzoxazol-6-yl)-ethyl 4-(2-oxo-1,2,4,5-tetrahydro-1,3-benzodiazepin-3-yl)-piperidine-1-carboxylate and 99 mg (0.44 mmol) ethyl (R)-1-piperidin-4-yl-pyrrolidine-2-carboxylate. After purification by HPLC (solvent mixture contains 0.1% trifluoroacetic acid) the product was obtained as the trifluoroacetate salt.

Yield: 275 mg (84% of theory)
ESI-MS: (M+H)$^+$=717
retention time (HPLC): 2.6 min (method A)

Example 4.1

(R)-2-[4-((R)-2-carboxy-pyrrolidin-1-yl)-piperidin-1-yl]-1-(4-methyl-2-oxo-2,3-dihydro-benzoxazol-6-yl methyl)-2-oxo-ethyl 4-(2-oxo-1,2,4,5-tetrahydro-1,3-benzodiazepin-3-yl)-piperidine-1-carboxylate

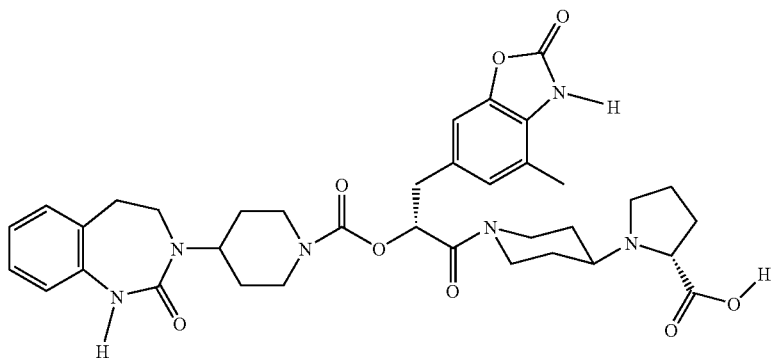

Prepared analogously to Example 3.1 from 265 mg (0.37 mmol) (R)-2-[4-((R)-2-ethoxy-carbonyl-pyrrolidin-1-yl)-piperidin-1-yl]-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate and 22 mg (0.92 mmol) LiOH.

Yield: 85 mg (33% of theory)
ESI-MS: (M+H)$^+$=689
retention time (HPLC): 2.5 min (method A)

Example 4.2

(R)-2-[4-((R)-2-dimethylcarbamoylmethoxycarbonyl-pyrrolidin-1-yl)-piperid in-1-yl]-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate

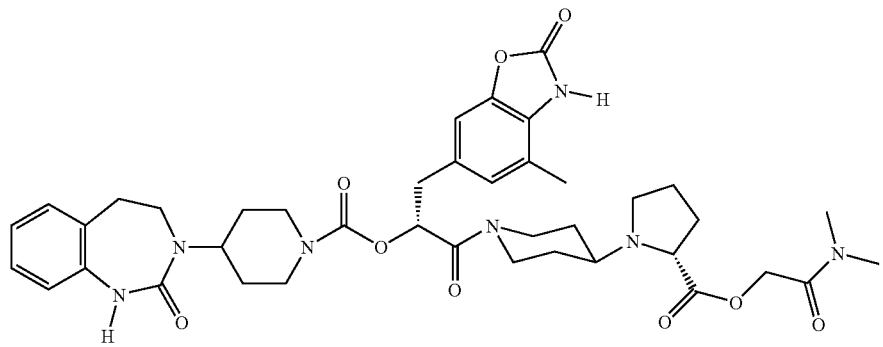

Prepared analogously to Example 3.2 from 85 mg (0.12 mmol) (R)-2-[4-((R)-2-carboxy-pyrrolidin-1-yl)-piperidin-1-yl]-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate and 15 mg (0.14 mmol) 2-hydroxy-N,N-dimethyl-acetamide. After purification by HPLC (solvent mixture contains 0.1% trifluoroacetic acid) the product was obtained as the trifluoroacetate salt.

Yield: 21 mg (19% of theory)
ESI-MS: (M+H)$^+$=774
retention time (HPLC): 2.5 min (method A)

Example 5

Ethyl 1'-{(R)-3-(4-methyl-2-oxo-2,3-dihydro-benzoxazol-6-yl)-2-[4-(2-oxo-1,2,4,5-tetrahydro-1,3-benzodiazepin-3-yl)-piperidine-1-carbonyloxy]-propionyl}-1,4'-bipiperidinyl-4-carboxylate

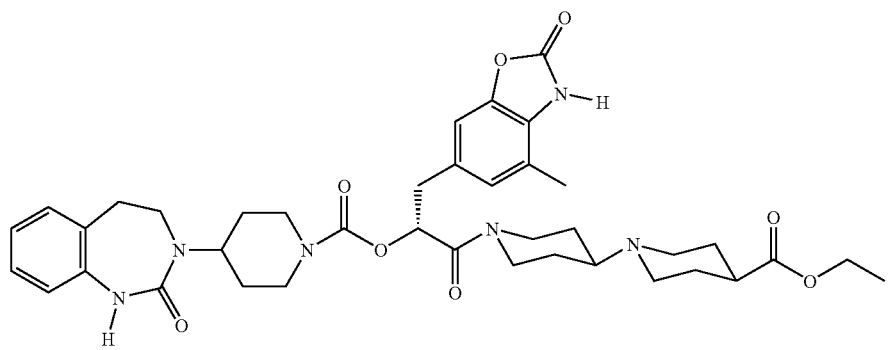

A solution of 300 mg (0.59 mmol) (R)-1-carboxy-2-(4-methyl-2-oxo-2,3-dihydrobenz-oxazol-6-yl)-ethyl 4-(2-oxo-1,2,4,5,-tetrahydro-1,3-benzodiazepin-3-yl)-piperidine-1-carboxylate, 210 mg (0.65 mmol) TBTU and 100 μL (0.72 mmol) triethylamine in 20 mL THF was stirred for 1 h at RT. Then 220 mg (0.70 mmol) ethyl [1,4']bipiperidinyl-4-carboxylate (used as the bis-hydrochloride salt) and 400 μL (2.87 mmol) triethylamine were added. The reaction mixture was stirred for 24 h at RT. The mixture was diluted with EtOAc, the organic phase was washed with saturated $NaHCO_3$ solution and dried on $Na_2SO_4$. After the desiccant and solvent had been eliminated the residue was purified by chromatography (Alox, activity grade II-III, gradient DCM/EtOH 20:1 to DCM/EtOH 10:1). The fractions containing the product were combined, evaporated down i. vac., the residue was triturated with diethyl ether, suction filtered and dried.

Yield: 240 mg (56% of theory)
ESI-MS: $(M+H)^+$=731
retention time (HPLC): 3.0 min (method B)

Example 5.1

1'-{(R)-3-(4-methyl-2-oxo-2,3-dihydro-benzoxazol-6-yl)-2-[4-(2-oxo-1,2,4,5-tetrahydro-1,3-benzodiazepin-3-yl)-piperidine-1-carbonyloxy]-propionyl}-1,4'-bipiperidinyl-4-carboxylic acid A solution of 12 mg (0.50 mmol) LiOH in 2 mL water was added to a solution of 190 mg (0.26 mmol) ethyl 1'-{(R)-3-(4-methyl-2-oxo-2,3-dihydro-benzoxazol-6-yl)-2-[4-(2-oxo-1,2,4,5-tetrahydro-1,3-benzodiazepin-3-yl)-piperidine-1-carbonyloxy]-propionyl}-1,4'-bipiperidinyl-4-carboxylate in 10 mL THF and the reaction solution was stirred for 3 h at RT. The mixture was diluted with water, the THF was eliminated i.vac., the aqueous phase was combined with 4 M HCl until a slightly acidic reaction was obtained, this was washed with DCM and the aqueous phase was saturated with solid NaCl, whereupon an oily precipitate settled out. The mixture was decanted to eliminate the solvent, the residue was taken up in DCM/MeOH and the organic phase was dried on $Na_2SO_4$. After the desiccant and solvent had been eliminated the product was obtained as the hydrochloride salt.

Yield: 175 mg (87% of theory)
ESI-MS: $(M-H)^-$=701
retention time (HPLC): 2.8 min (method B)

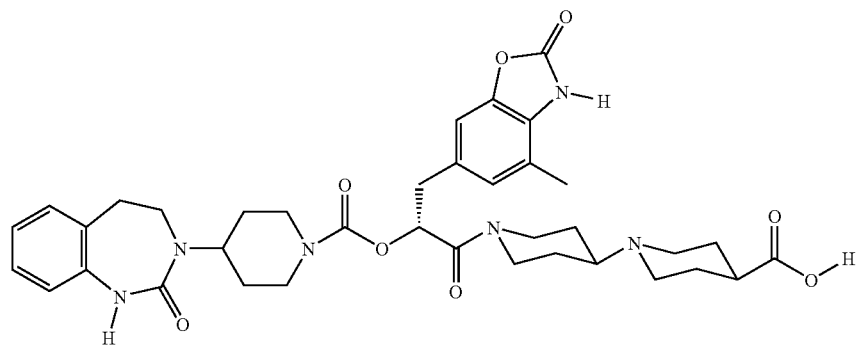

Example 6

(R)-1-(4-methyl-2-oxo-2,3-dihydro-benzoxazol-6-ylmethyl)-2-[1'-(2-morpholin-4-yl-ethoxycarbonylmethyl)-4,4'-bipiperidinyl-1-yl]-2-oxo-ethyl 4-(2-oxo-1,2,4,5-tetrahydro-1,3-benzodiazepin-3-yl)-piperidine-1-carboxylate

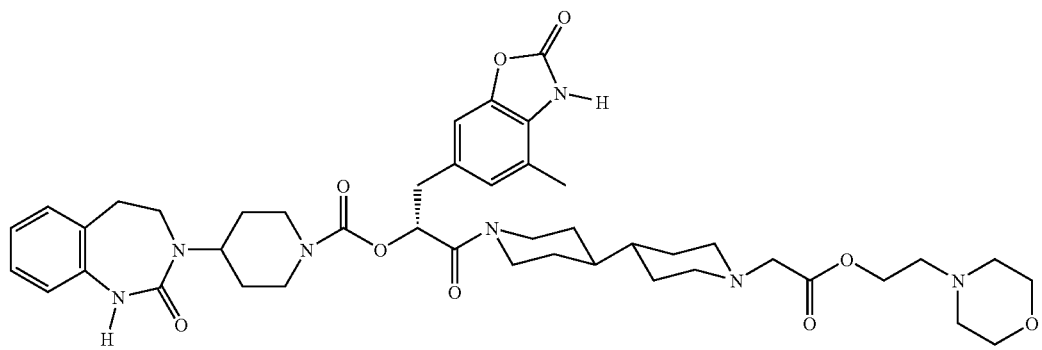

6a) (R)-2-(1'-ethoxycarbonylmethyl-4,4'-bipiperidinyl-1-yl)-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate A solution of 350 mg (0.69 mmol) (R)-1-carboxy-2-(4-methyl-2-oxo-2,3-dihydrobenz-oxazol-6-yl)-ethyl 4-(2-oxo-1,2,4,5,-tetrahydro-1,3-benzodiazepin-3-yl)-piperidine-1-carboxylate, 244 mg (0.76 mmol) TBTU and 138 µL (1.04 mmol) triethylamine in 15 mL THF was stirred for 1 h at RT. Then 175 mg (0.69 mmol) ethyl [4,4']bipiperidinyl-1-yl-acetate were added. The reaction mixture was stirred for 4 h at RT. The solvent was eliminated i.vac., the residue was taken up in 30 mL EtOAc, the organic phase was washed with 30 mL 5% NaHCO₃ solution and dried on Na₂SO₄. After the desiccant and solvent had been eliminated the residue was purified by chromatography (silica gel, gradient DCM/EtOH 19:1 to DCM/EtOH 9:1). The fractions containing the product were combined and evaporated down i. vac.

Yield: 240 mg (47% of theory)
ESI-MS: (M+H)⁺=745
retention time (HPLC): 3.1 min (method B)

6b) (R)-2-(1'-carboxymethyl-4,4'-bipiperidinyl-1-yl)-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate A solution of 39 mg (1.61 mmol) LiOH in 5 mL water was added to a solution of 240 mg (0.32 mmol) (R)-2-(1'-ethoxycarbonylmethyl-4,4'-bipiperidinyl-1-yl)-1-(4-methyl-2-oxo-2,3-dihydrobenzoxazol-6-ylmethyl)-2-oxo-ethyl 4-(2-oxo-1,2,4,5-tetrahydro-1,3-benzodiazepin-3-yl)-piperidine-1-carboxylate in 10 mL THF and the reaction solution was stirred for 1 h at RT. 1.61 mL of 1 M HCl was added and the mixture was evaporated down i.vac. The residue was combined with a little water, stirred, the water was decanted off and the residue was dried in the air.

Yield: 240 mg (47% of theory)
ESI-MS: (M+H)⁺=717
retention time (HPLC): 2.9 min (method B)

6c) (R)-1-(4-methyl-2-oxo-2,3-dihydro-benzoxazol-6-ylmethyl)-2-[1'-(2-morpholin-4-yl-ethoxycarbonylmethyl)-4,4'-bipiperidinyl-1-yl]-2-oxo-ethyl 4-(2-oxo-1,2,4,5-tetrahydro-1,3-benzodiazepin-3-yl)-piperidine-1-carboxylate A solution of 90 mg (0.13 mmol) (R)-2-(1'-carboxymethyl-4,4'-bipiperidinyl-1-yl)-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate, 48 mg (0.15 mmol) TBTU and 26 µL (0.19 mmol) triethylamine in 1.4 mL DMF was stirred for 1 h at RT. Then 18 µL (0.15 mmol) 2-morpholin-4-yl-ethanol was added. The reaction mixture was stirred for 16 h at RT. 4 drops of formic acid were added, the mixture was filtered through a syringe filter and purified by HPLC. The fractions containing the product were combined, made alkaline with 5% NaHCO₃ solution, extracted with 50 mL EtOAc and the organic phase was dried on Na₂SO₄. After the desiccant and solvent had been eliminated the residue was triturated with DIPE, suction filtered and dried.

Yield: 47 mg (45% of theory)
ESI-MS: (M+H)⁺=830
retention time (HPLC): 2.6 min (method B)

Example 7

(R)-1-(2-methoxy-7-methyl-1H-benzimidazol-5-ylmethyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate

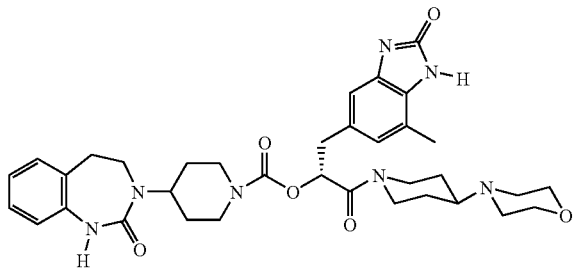

7a) methyl (Z,E)-2-acetylamino-3-(4-amino-methyl-5-nitro-phenyl)-acrylate

Under an argon atmosphere 0.7 g (2.9 mmol) Pd(OAc)₂ and 0.9 g (2.9 mmol) tri-o-tolyl-phosphane were added to a solution of 9.0 g (39.0 mmol) 4-bromo-2-methyl-6-nitro-phenylamine and 10.0 g (69.9 mmol) methyl 2-acetylamino-acrylate in 100 mL acetonitrile and 100 mL triethylamine. The reaction mixture was stirred for 24 h at a bath temperature of 90° C., evaporated down i. vac., the residue was combined with 200 mL water and 200 mL EtOAc and the precipitate was filtered off. The crystals were dissolved by refluxing in 500 mL MeOH, filtered off while hot and the filtrate was evaporated to dryness i.vac.

Yield: 8.0 g (70% of theory)
ESI-MS: (M+H)⁺=294

7b) 3-(4-amino-3-methyl-5-nitro-phenyl)-2-oxo-propionic acid 60 mL of a 4 M HCl were metered into a solution of 8.0 g (53.1 mmol) methyl (Z,E)-2-acetylamino-3-(4-amino-methyl-5-nitro-phenyl)-acrylate in 60 mL 1,4-dioxane, refluxed for 3 h with stirring, the reaction solution was concentrated by evaporation i.vac. and the residue was combined with ice. The precipitate was filtered off, washed with ice water and dried.

Yield: 6.5 g (95% of theory)
EI-MS: (M)⁺=238

7c) (R)-3-(4-amino-3-methyl-5-nitro-phenyl)-2-hydroxy-propionic acid

Under a nitrogen atmosphere a solution of 12.0 g (37.4 mmol) (1R)-B-chloro-diisopinocampheyl borane in 40 mL THF was added dropwise to a solution, cooled to −35° C., of 6.5 g (26.0 mmol) 3-(4-amino-3-methyl-5-nitro-phenyl)-2-oxo-propionic acid and 4.5 mL (32.4 mmol) triethylamine in 100 mL THF within 15 min and the reaction solution was stirred overnight at RT. Then the reaction solution was carefully combined at 5° C. with 60 mL of 1 M NaOH and 150 mL diethyl ether and stirred for 15 min. The organic phase was separated off, extracted three times with 40 mL of 1 M NaOH and once with 40 mL water. The combined aqueous phases were acidified with semiconc. HCl while cooling with an ice bath and extracted twice with in each case 120 mL EtOAc. The combined organic phases were dried on $Na_2SO_4$ and evaporated down i. vac. The crude product was obtained, which was reacted further without purification.

Yield: 6.0 g (67% of theory)

7d) methyl (R)-3-(4-amino-3-methyl-5-nitro-phenyl)-2-hydroxy-propionate 4.0 mL (54.8 mmol) $SOCl_2$ were slowly added dropwise to 90 mL MeOH while cooling with ice-acetone and 6.0 g (17.5 mmol) (R)-3-(4-amino-3-methyl-5-nitro-phenyl)-2-hydroxy-propionic acid in 10 mL MeOH were also added dropwise at 0° C. The reaction solution was stirred for 1 h at 0° C. and for 1 h at RT and then evaporated down i. vac. The residue was combined with EtOAc, washed with saturated $NaHSO_4$ solution and dried on $Na_2SO_4$. After the desiccant and solvent had been eliminated the residue was purified by chromatography (silica gel, gradient DCM/MeOH 100:1 to 50:1).

Yield: 3.4 g (76% of theory)

ESI-MS: $(M+H)^+=255$ $R_f=0.43$ (Polygram, DCM/MeOH 50:1)

7e) (R)-2-(4-amino-3-methyl-5-nitro-phenyl)-1-methoxycarbonyl-ethyl 4-(2-oxo-1,2,4,5-tetrahydro-1,3-benzodiazepin-3-yl)-piperidine-1-carboxylate Under a nitrogen atmosphere while cooling with an ice bath 1.8 g (14.7 mmol) 4-dimethylaminopyridine in 25 mL pyridine were combined first with 2.7 g (13.4 mmol) 4-nitrophenyl chloroformate, and stirred for 30 min at RT, then with 3.4 g (13.2 mmol) methyl (R)-3-(4-amino-3-methyl-5-nitrophenyl)-2-hydroxy-propionate in 15 mL pyridine, the mixture was stirred for another 2 h at RT, and then combined with 3.5 g (14.3 mmol) 3-piperidin-4-yl-1,3,4,5-tetrahydro-1,3-benzodiazepin-2-one and stirred for 5 h at RT. After the reaction had ended the reaction mixture was evaporated down i. vac., the residue was combined with EtOAc, the organic phase was washed with 10% $KHSO_4$ solution and saturated $NaHSO_4$ solution and dried on $Na_2SO_4$. After the desiccant and solvent had been eliminated the residue was purified by chromatography (silica gel, DCM/MeOH 25:1).

Yield: 3.7 g (50% of theory)

ESI-MS: $(M+H)^+=526$ $R_f=0.42$ (Polygram, DCM/MeOH 25:1)

7f) (R)-2-(3,4-diamino-5-methyl-phenyl)-1-methoxycarbonyl-ethyl 4-(2-oxo-1,2,4,5-tetrahydro-1,3-benzodiazepin-3-yl)-piperidine-1-carboxylate A suspension of 2.00 g (3.24 mmol) (R)-2-(4-amino-3-methyl-5-nitro-phenyl)-1-methoxycarbonyl-ethyl 4-(2-oxo-1,2,4,5-tetrahydro-1,3-benzodiazepin-3-yl)-piperidine-1-carboxylate and 300 mg 10% Pd/C in 100 mL MeOH was hydrogenated for 3.5 h at 50° C. and 50 psi hydrogen pressure. The catalyst was filtered off, the filtrate was evaporated down i. vac. and the residue was purified by chromatography (silica gel, gradient DCM/MeOH 30:1 to DCM/MeOH 15:1).

Yield: 1.35 g (84% of theory)

ESI-MS: $(M+H)^+=496$

7g) (R)-1-methoxycarbonyl-2-(2-methoxy-7-methyl-1H-benzimidazol-5-yl)-ethyl 4-(2-oxo-1,2,4,5-tetrahydro-1,3-benzodiazepin-3-yl)-piperidine-1-carboxylate A solution of 1.00 g (2.02 mmol) (R)-2-(3,4-diamino-5-methyl-phenyl)-1-methoxycarbonyl-ethyl 4-(2-oxo-1,2,4,5-tetrahydro-1,3-benzodiazepin-3-yl)-piperidine-1-carboxylate and 2.00 mL (15.01 mmol) tetramethoxymethane in 20 mL MeOH was refluxed for 1 h in the presence of 40 mg (0.21 mmol) toluenesulphonic acid hydrate. The mixture was evaporated down i.vac. and the residue was purified by chromatography (Alox, activity grade II-III, DCM/MeOH 20:1).

Yield: 0.99 g (92% of theory)

ESI-MS: $(M+H)^+=536$

7h) (R)-1-carboxy-2-(2-methoxy-7-methyl-1H-benzimidazol-5-yl)-ethyl 4-(2-oxo-1,2,4,5-tetrahydro-1,3-benzodiazepin-3-yl)-piperidine-1-carboxylate A solution of 0.10 g (4.18 mmol) LiOH in 6 mL water was added to a solution of 0.98 g (1.83 mmol) (R)-1-methoxycarbonyl-2-(2-methoxy-7-methyl-1H-benzimidazol-5-yl)-ethyl 4-(2-oxo-1,2,4,5-tetrahydro-1,3-benzodiazepin-3-yl)-piperidine-1-carboxylate in 18 mL THF and the reaction solution was stirred overnight at RT. 1.05 mL of 4 M HCl was added and the THF was eliminated i.vac. The mixture was decanted to separate off the oily residue, this was dissolved in DCM/MeOH and the organic phase was dried on $Na_2SO_4$. After the desiccant and solvent had been eliminated the desired product was obtained.

Yield: 0.80 g (80% of theory)

ESI-MS: $(M-H)^-=520$ retention time (HPLC): 2.7 min (method B)

7i) (R)-1-(2-methoxy-7-methyl-1H-benzimidazol-5-ylmethyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate 40 mg (0.24 mmol) 4-piperidin-4-yl-morpholine were added to a solution of 90 mg (0.16 mmol) (R)-1-carboxy-2-(2-methoxy-7-methyl-1H-benzimidazol-5-yl)-ethyl 4-(2-oxo-1,2,4,5-tetrahydro-1,3-benzodiazepin-3-yl)-piperidine-1-carboxylate, 60 mg (0.19 mmol) TBTU and 30 μL (0.22 mmol) triethylamine in 1 mL DMF and the reaction mixture was stirred overnight at RT. The reaction mixture was purified by HPLC without working up; the fractions containing the product were combined and lyophilised.

Yield: 44 mg (40% of theory)

ESI-MS: $(M+H)^+=674$ retention time (HPLC): 6.9 min (method C)

Example 7.1

(R)-2-(4,4-dimethyl-1,4'-bipiperidinyl-1'-yl)-1-(2-methoxy-7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate

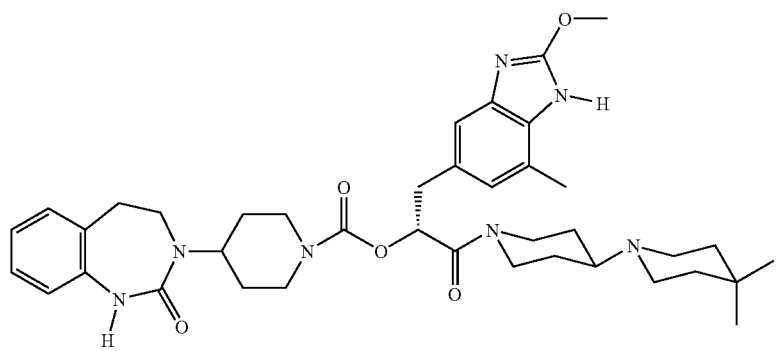

Prepared analogously to Example 7i from 90 mg (0.16 mmol) (R)-1-carboxy-2-(2-methoxy-7-methyl-1H-benzimidazol-5-yl)-ethyl 4-(2-oxo-1,2,4,5-tetrahydro-1,3-benzodiazepin-3-yl)-piperidine-1-carboxylate and 55 mg (0.20 mmol) 4,4-dimethyl-[1,4']bipiperidinyl (used as the bis-hydrochloride salt), using 100 μL (0.72 mmol) triethylamine.

Yield: 38 mg (33% of theory)

ESI-MS: (M+H)$^+$=700 retention time (HPLC): 7.4 min (method C)

Example 7.2

(R)-2-(4-methoxy-1,4'-bipiperidinyl-1'-yl)-1-(2-methoxy-7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate

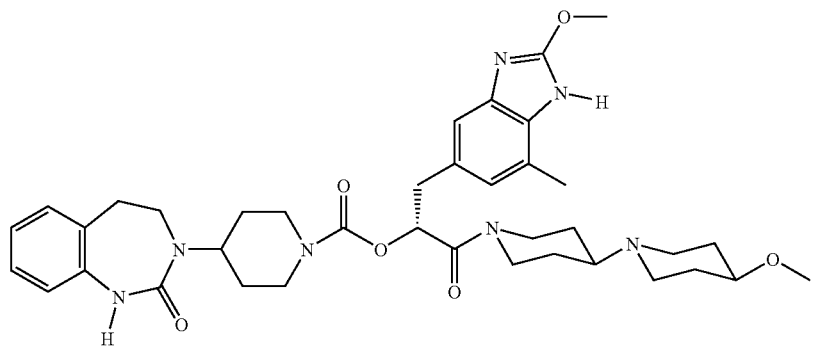

Prepared analogously to Example 7i from 90 mg (0.16 mmol) (R)-1-carboxy-2-(2-methoxy-7-methyl-1H-benzimidazol-5-yl)-ethyl 4-(2-oxo-1,2,4,5-tetrahydro-1,3-benzodiazepin-3-yl)-piperidine-1-carboxylate and 55 mg (0.20 mmol) 4-methoxy-[1,4']bipiperidinyl (used as the bis-hydrochloride salt), using 100 μL (0.72 mmol) triethylamine.

Yield: 44 mg (38% of theory)

ESI-MS: (M+H)$^+$=702 retention time (HPLC): 7.1 min (method C)

Example 7.3

(R)-2-[4-(4-ethoxycarbonylmethyl-piperazin-1-yl)-piperidin-1-yl]-1-(2-methoxy-7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate

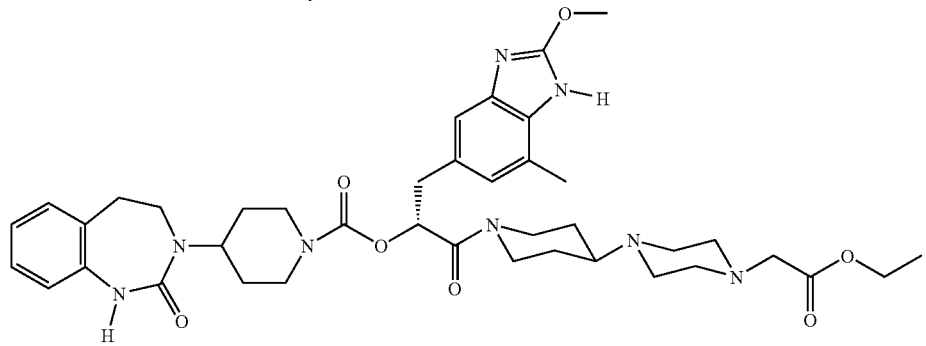

Prepared analogously to Example 7i from 150 mg (0.27 mmol) (R)-1-carboxy-2-(2-methoxy-7-methyl-1H-benzimidazol-5-yl)-ethyl 4-(2-oxo-1,2,4,5-tetrahydro-1,3-benzodiazepin-3-yl)-piperidine-1-carboxylate and 85 mg (0.33 mmol) ethyl (4-piperidin-4-yl-piperazin-1-yl)-acetate.

Yield: 21 mg (10% of theory)
ESI-MS: $(M+H)^+=759$
retention time (HPLC): 7.2 min (method C)

The Examples that follow describe the preparation of pharmaceutical formulations which contain as active substance any desired compound of general formula I:

Example I

Capsules for Powder Inhalation Containing 1 Mg of Active Ingredient

Composition:

| 1 capsule for powder inhalation contains: | |
|---|---|
| active ingredient | 1.0 mg |
| lactose | 20.0 mg |
| hard gelatine capsules | 50.0 mg |
| | 71.0 mg |

Method of Preparation:

The active ingredient is ground to the particle size required for inhaled substances. The ground active ingredient is homogeneously mixed with the lactose. The mixture is transferred into hard gelatine capsules.

Example II

Inhalable Solution for Respimat® Containing 1 mg of Active Ingredient

Composition:

| 1 puff contains: | |
|---|---|
| active ingredient | 1.0 mg |
| benzalkonium chloride | 0.002 mg |
| disodium edetate | 0.0075 mg |
| purified water ad | 15.0 µl |

Method of Preparation:

The active ingredient and benzalkonium chloride are dissolved in water and transferred into Respimat® cartridges.

Example III

Inhalable Solution for Nebulisers Containing 1 mg of Active Ingredient

Composition:

| 1 vial contains: | |
|---|---|
| active ingredient | 0.1 g |
| sodium chloride | 0.18 g |
| benzalkonium chloride | 0.002 g |
| purified water ad | 20.0 ml |

Method of Preparation:

The active ingredient, sodium chloride and benzalkonium chloride are dissolved in water.

Example IV

Propellant Gas-Operated Metered Dose Aerosol Containing 1 mg of Active Ingredient Composition:

| 1 puff contains: | |
|---|---|
| active ingredient | 1.0 mg |
| lecithin | 0.1% |
| propellant gas ad | 50.0 µl |

Method of Preparation:

The micronised active ingredient is homogeneously suspended in the mixture of lecithin and propellant gas. The suspension is transferred into a pressurised container with a metering valve.

Example V

Nasal Spray Containing 1 mg of Active Ingredient

Composition:

| | |
|---|---|
| active ingredient | 1.0 mg |
| sodium chloride | 0.9 mg |
| benzalkonium chloride | 0.025 mg |
| disodium edetate | 0.05 mg |
| purified water ad | 0.1 ml |

Method of Preparation:

The active ingredient and the excipients are dissolved in water and transferred into a suitable container.

Example VI

Injectable Solution Containing 5 mg of Active Substance per 5 ml

Composition:

| | |
|---|---|
| active substance | 5 mg |
| glucose | 250 mg |
| human serum albumin | 10 mg |
| glycofurol | 250 mg |
| water for injections ad | 5 ml |

Preparation:

Glycofurol and glucose are dissolved in water for injections (Wfl); human serum albumin is added; active ingredient is dissolved with heating; made up to specified volume with Wfl; transferred into ampoules under nitrogen gas.

Example VII

Injectable Solution Containing 100 mg of Active Substance Per 20 ml

Composition:

| | |
|---|---|
| active substance | 100 mg |
| monopotassium dihydrogen phosphate = $KH_2PO_4$ | 12 mg |
| disodium hydrogen phosphate = $Na_2HPO_4 \cdot 2H_2O$ | 2 mg |
| sodium chloride | 180 mg |
| human serum albumin | 50 mg |
| Polysorbate 80 | 20 mg |
| water for injections ad | 20 ml |

Preparation:

Polysorbate 80, sodium chloride, monopotassium dihydrogen phosphate and disodium hydrogen phosphate are dissolved in water for injections (Wfl); human serum albumin is added; active ingredient is dissolved with heating; made up to specified volume with Wfl; transferred into ampoules.

Example VIII

Lyophilisate Containing 10 mg of Active Substance

Composition:

| | |
|---|---|
| Active substance | 10 mg |
| Mannitol | 300 mg |
| human serum albumin | 20 mg |
| water for injections ad | 2 ml |

Preparation:

Mannitol is dissolved in water for injections (Wfl); human serum albumin is added; active ingredient is dissolved with heating; made up to specified volume with Wfl; transferred into vials; freeze-dried.

| Solvent for lyophilisate: | |
|---|---|
| Polysorbate 80 = Tween 80 | 20 mg |
| mannitol | 200 mg |
| water for injections ad | 10 ml |

Preparation:

Polysorbate 80 and mannitol are dissolved in water for injections (Wfl); transferred into ampoules.

Example IX

Tablets Containing 20 mg of Active Substance

Composition:

| | |
|---|---|
| active substance | 20 mg |
| lactose | 120 mg |
| corn starch | 40 mg |
| magnesium stearate | 2 mg |
| Povidone K 25 | 18 mg |

Preparation:

Active substance, lactose and corn starch are homogeneously mixed; granulated with an aqueous solution of Povidone; mixed with magnesium stearate; compressed in a tablet press; weight of tablet 200 mg.

Example X

Capsules Containing 20 mg Active Substance

Composition:

| | |
|---|---|
| active substance | 20 mg |
| corn starch | 80 mg |
| highly dispersed silica | 5 mg |
| magnesium stearate | 2.5 mg |

205

Preparation:

Active substance, corn starch and silica are homogeneously mixed; mixed with magnesium stearate; the mixture is packed into size for 3 hard gelatine capsules in a capsule filling machine.

Example XI

Suppositories Containing 50 mg of Active Substance

Composition:

| active substance | 50 mg |
| hard fat (Adeps solidus) q.s. ad | 1700 mg |

Preparation:

Hard fat is melted at about 38° C.; ground active substance is homogeneously dispersed in the molten hard fat; after cooling to about 35° C. it is poured into chilled moulds.

Example XII

Injectable Solution Containing 10 mg of Active Substance Per 1 ml

Composition:

| active substance | 10 mg |
| mannitol | 50 mg |
| human serum albumin | 10 mg |
| water for injections ad | 1 ml |

Preparation:

Mannitol is dissolved in water for injections (Wfl); human serum albumin is added; active ingredient is dissolved with heating; made up to specified volume with Wfl; transferred into ampoules under nitrogen gas.

The invention claimed is:

1. A compound selected from the group consisting of:

| No. | Structure |
|---|---|
| (1) | 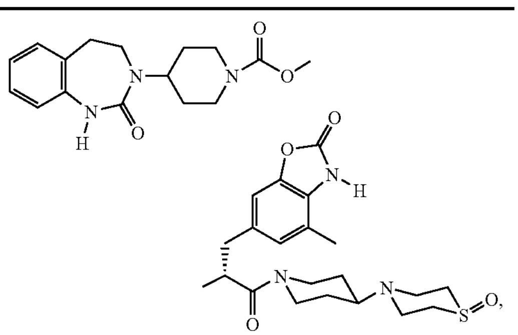 |

-continued

| No. | Structure |
|---|---|
| (2) | 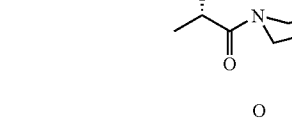 |
| (3) | 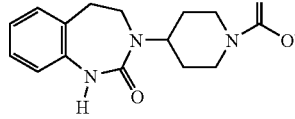 |
| (4) | 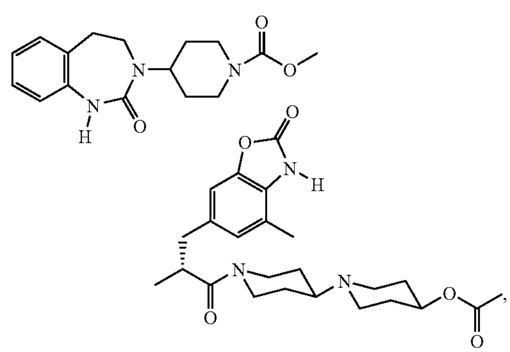 |
| (5) | 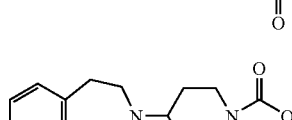 |
| (6) | 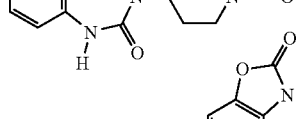 |

-continued
| No. | Structure |
|---|---|
| (7) | 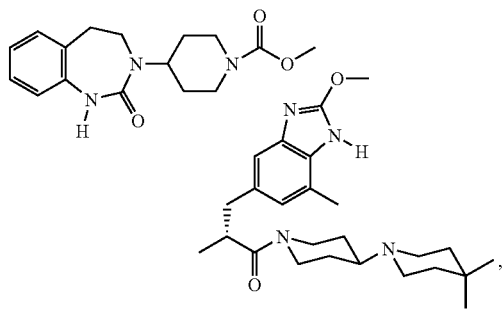 |
| (8) | 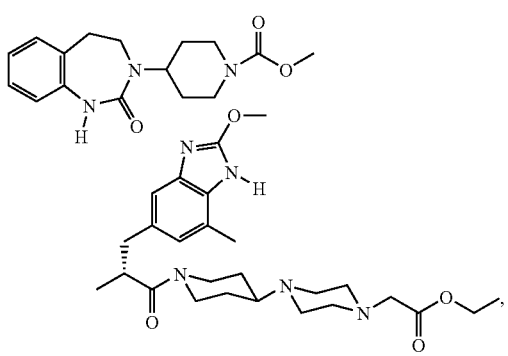 |
| (9) | 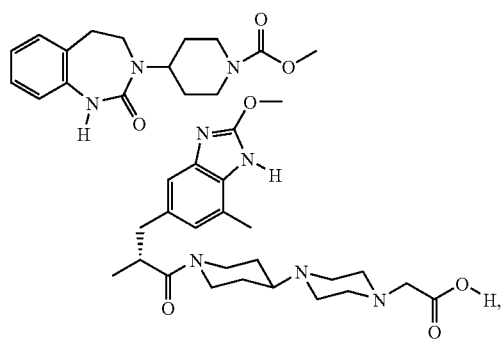 |
| (10) | 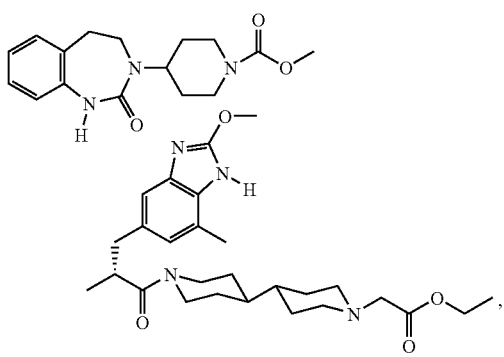 |
-continued
| No. | Structure |
|---|---|
| (11) | 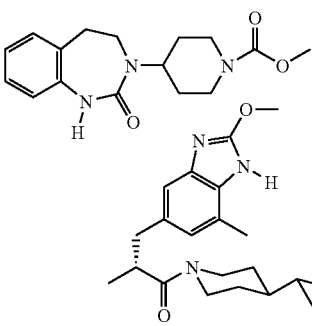 |
| (12) | 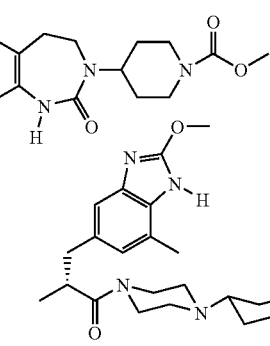 |
| (13) | 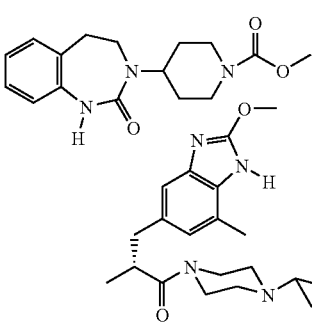 |
| (14) | 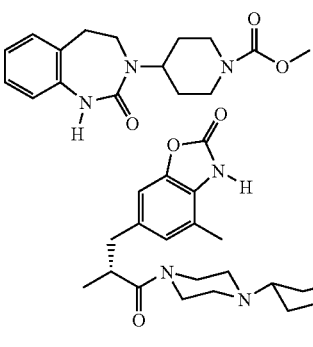 |

| No. | Structure |
|---|---|
| (15) | 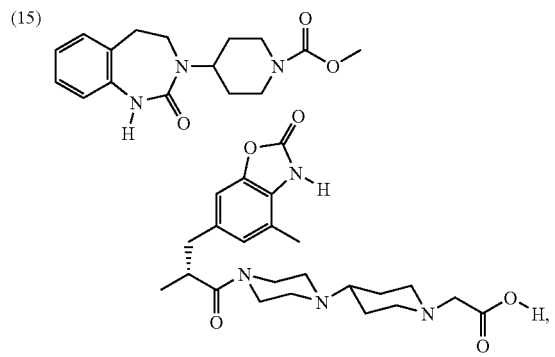 |
| (16) | 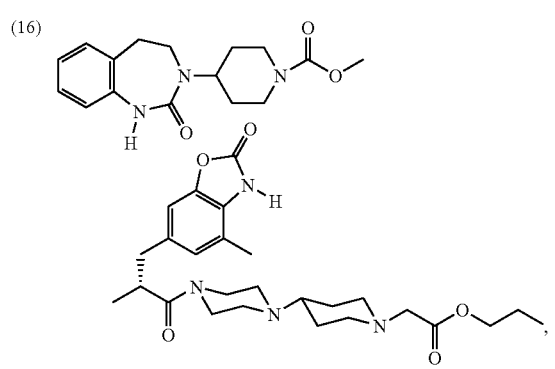 |
| (17) | 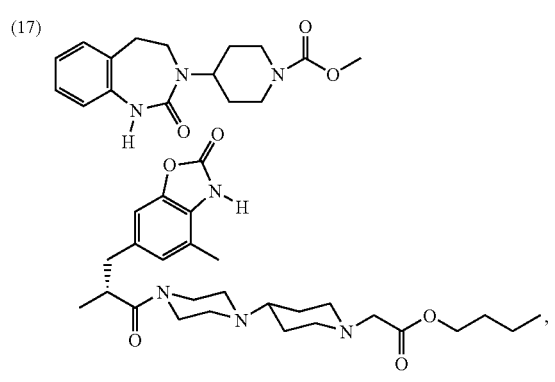 |
| (18) | 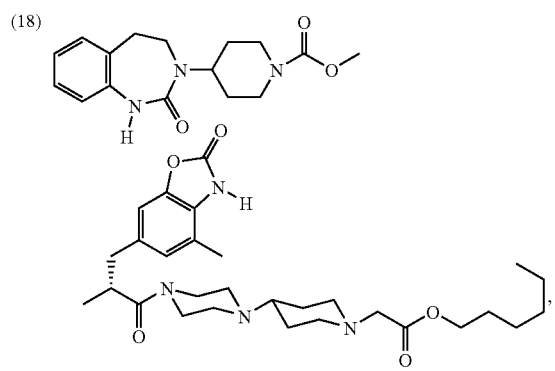 |
| No. | Structure |
|---|---|
| (19) | 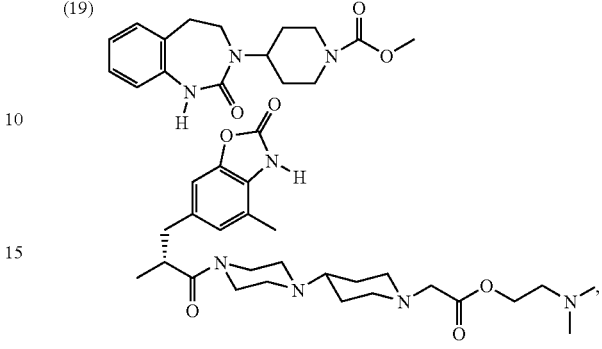 |
| (20) | 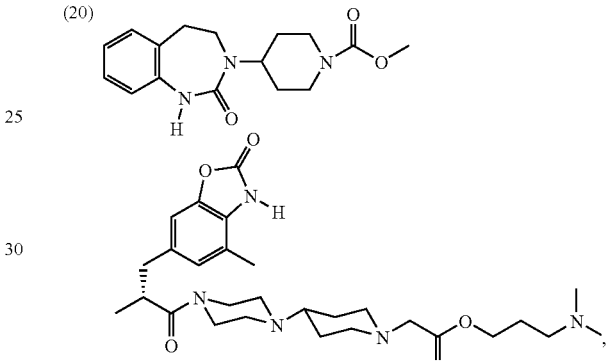 |
| (21) | 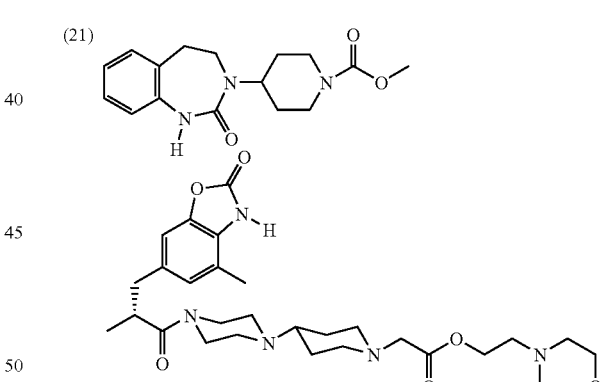 |
| (22) | 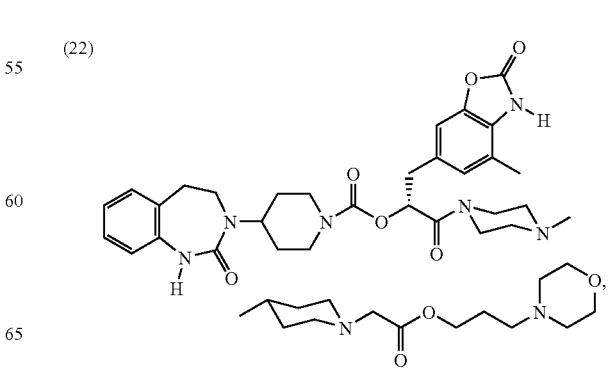 |

|     | -continued |
| --- | --- |
| No. | Structure |

(23), (24), (25), (26)

|     | -continued |
| --- | --- |
| No. | Structure |

(27), (28), (29), (30)

-continued
| No. | Structure |
|---|---|
| (31) | 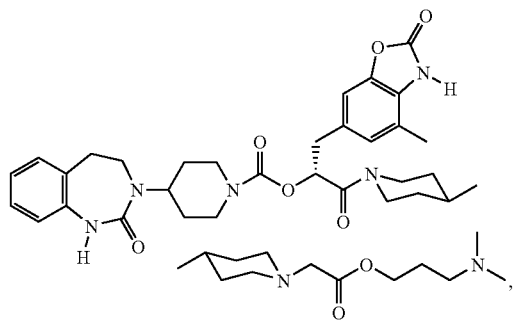 |
| (32) | 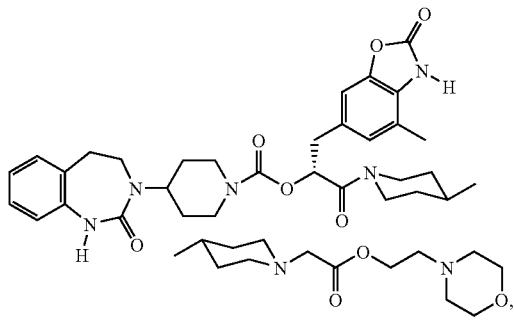 |
| (33) | 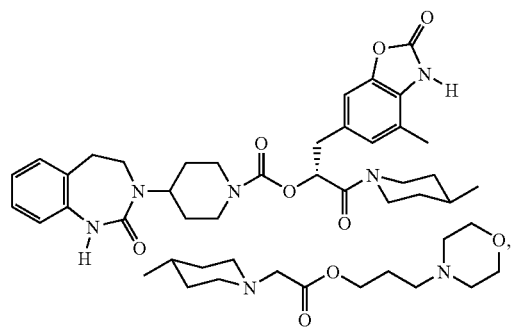 |
| (34) | 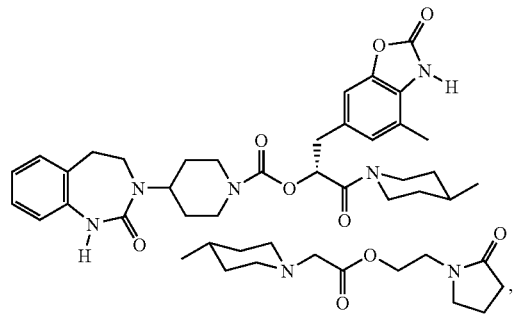 |
-continued
| No. | Structure |
|---|---|
| (35) | 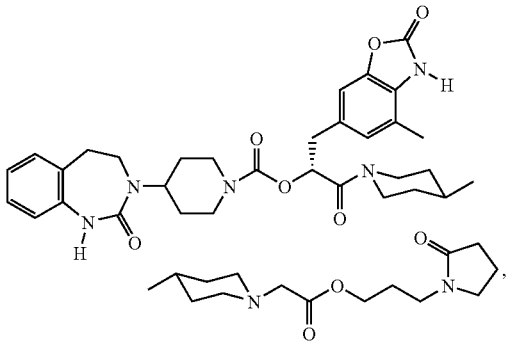 |
| (36) | 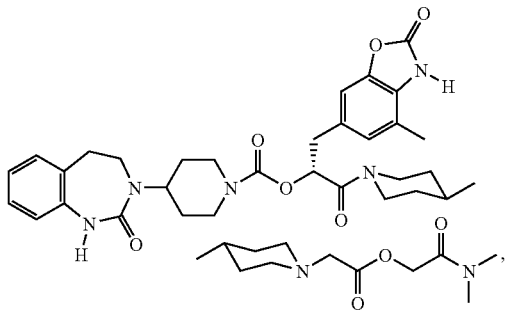 |
| (37) | 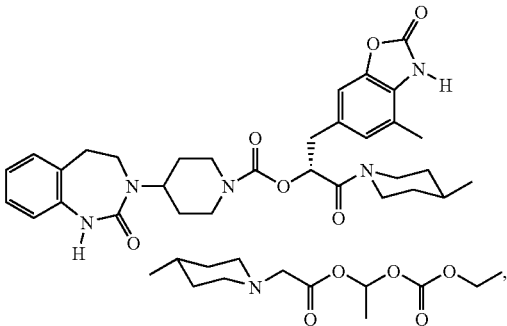 |
| (38) | 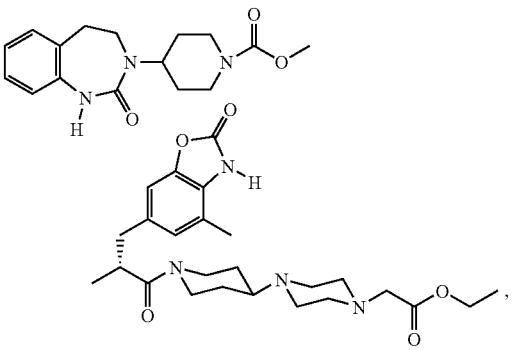 |

-continued
| No. | Structure |
|---|---|
| (39) | 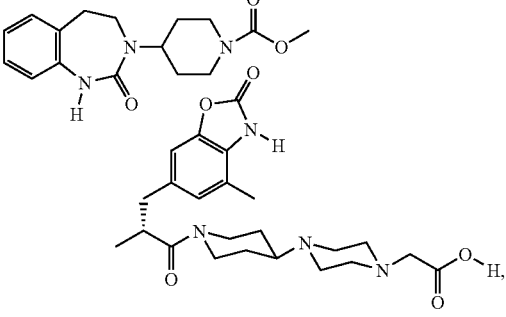 |
| (40) | 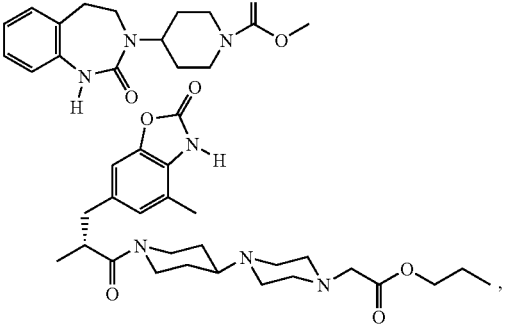 |
| (41) | 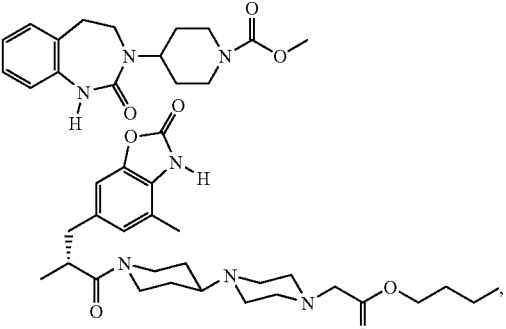 |
| (42) | 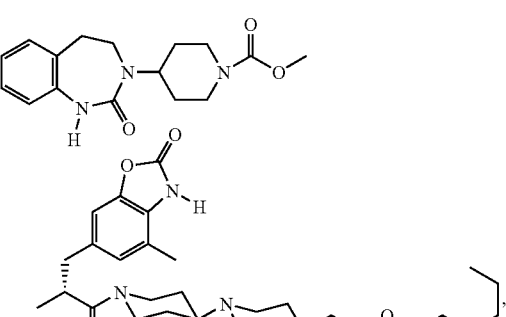 |
-continued
| No. | Structure |
|---|---|
| (43) | 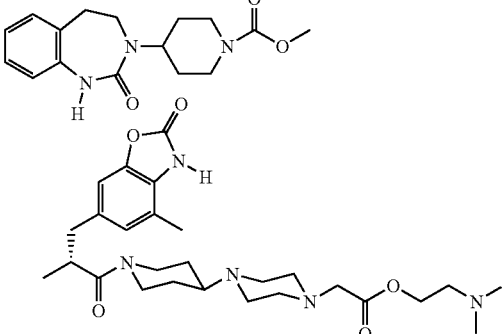 |
| (44) | 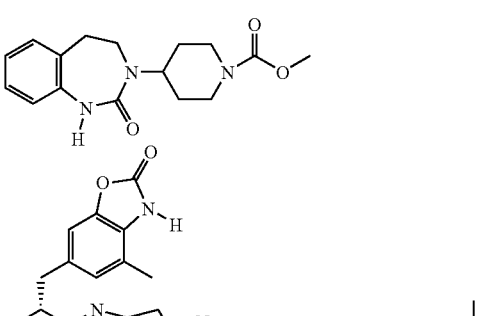 |
| (45) | 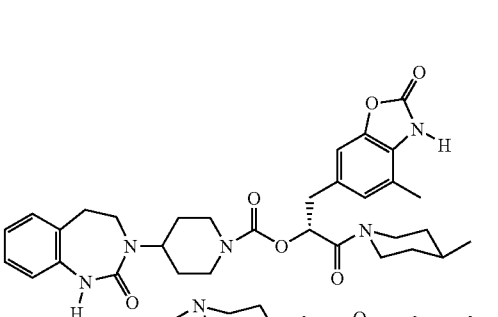 |
| (46) | 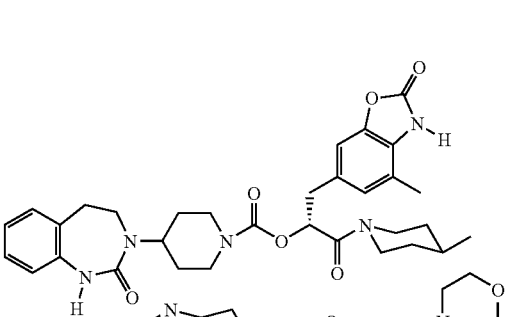 |

| No. | Structure |
|---|---|
| (47) | 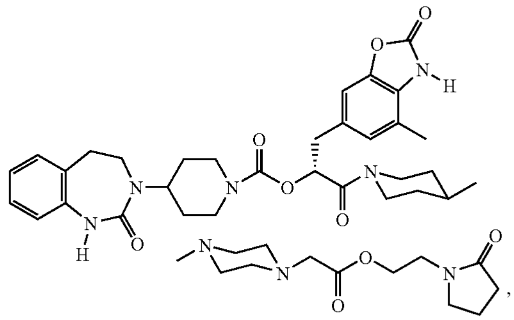 |
| (48) | 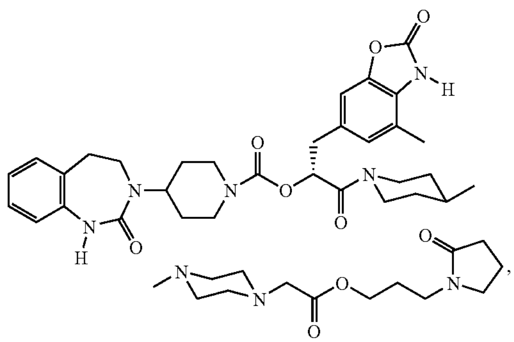 |
| (49) | 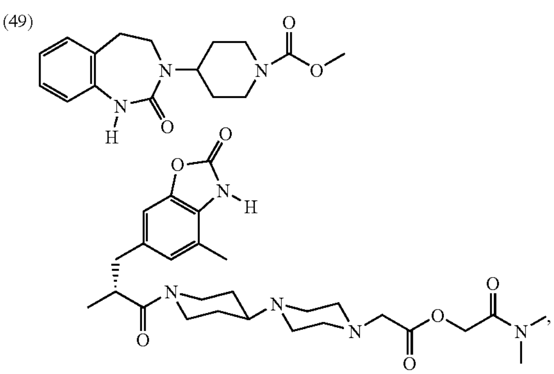 |
| (50) | 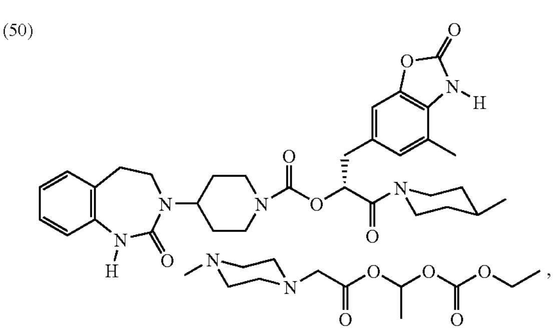 |

| No. | Structure |
|---|---|
| (51) | 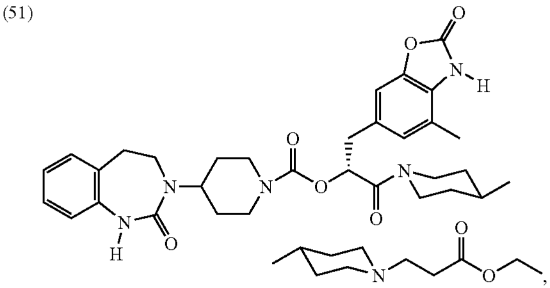 |
| (52) | 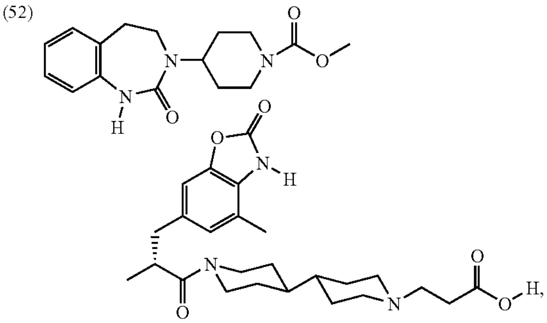 |
| (53) | 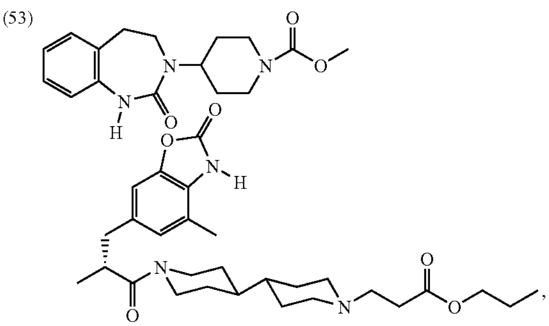 |
| (54) | 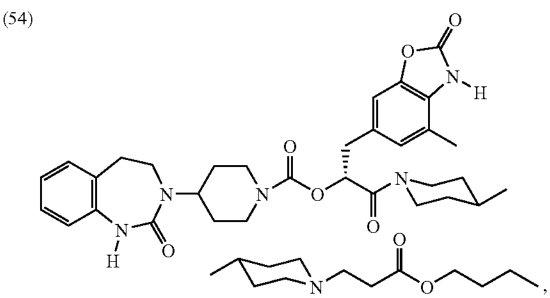 |
| (55) | 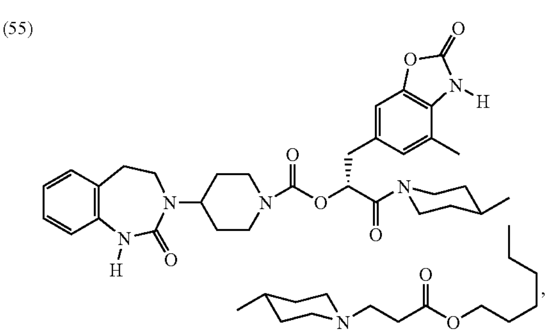 |

| No. | Structure |
|---|---|
| (56) | 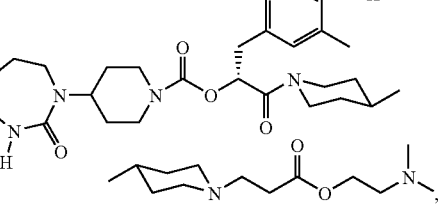 |
| (57) | 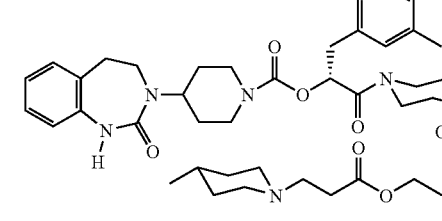 |
| (58) | 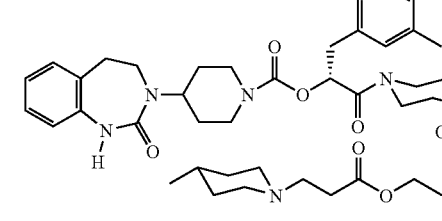 |
| (59) | 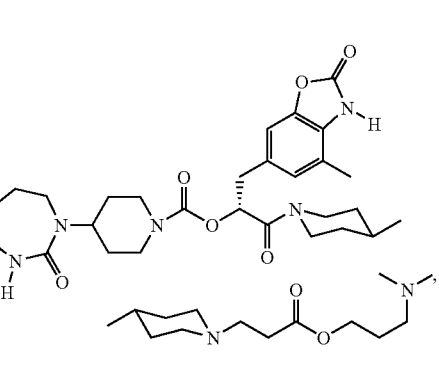 |
| No. | Structure |
|---|---|
| (60) | 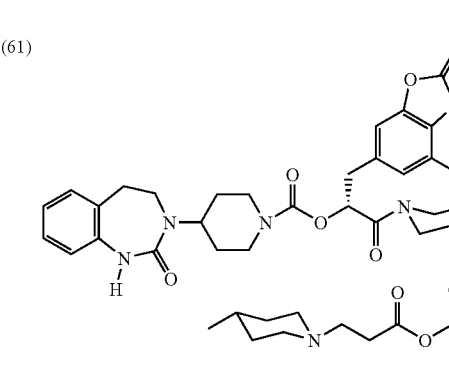 |
| (61) | 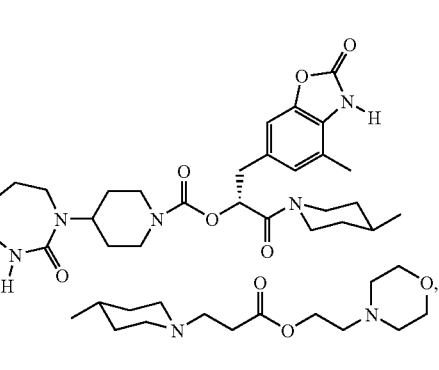 |
| (62) | 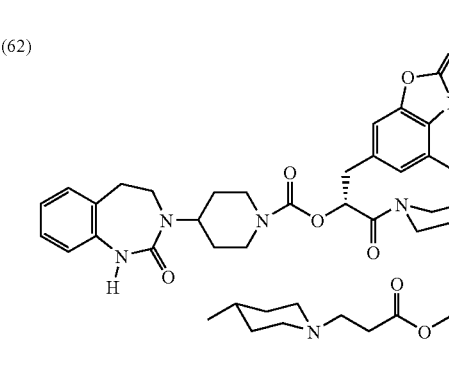 |
| (16) | 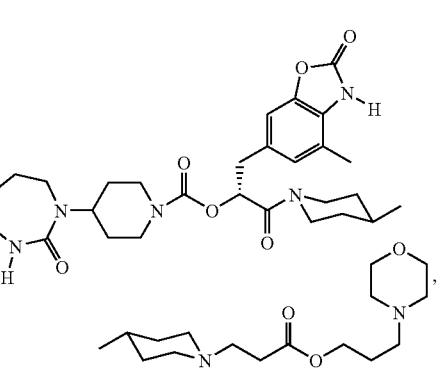 |

| No. | Structure |
|---|---|
| (63) | 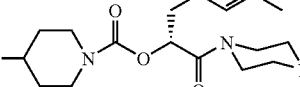 |
| (64) |  |
| (65) |  |
| (66) | 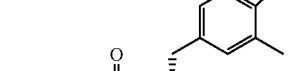 |
| (67) | |
| No. | Structure |
|---|---|
| (68) | 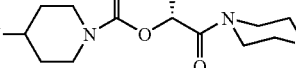 |
| (69) | 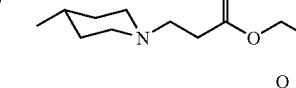 |
| (70) |  |
| (71) | 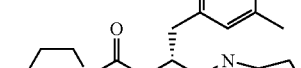 |
| (72) | |

| No. | Structure |
|---|---|
| (73) | 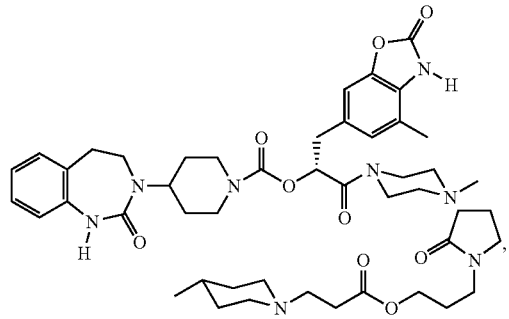 |
| (74) | 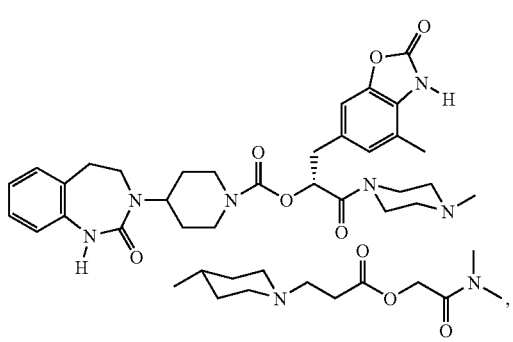 |
| (75) | 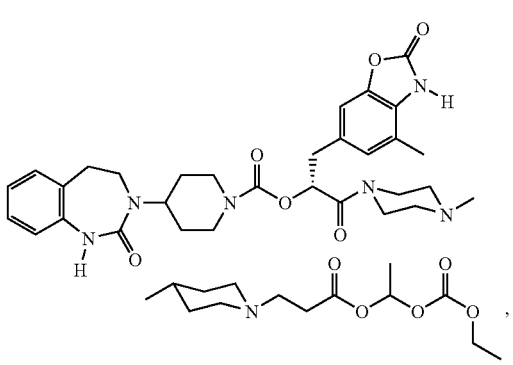 |
| (76) | 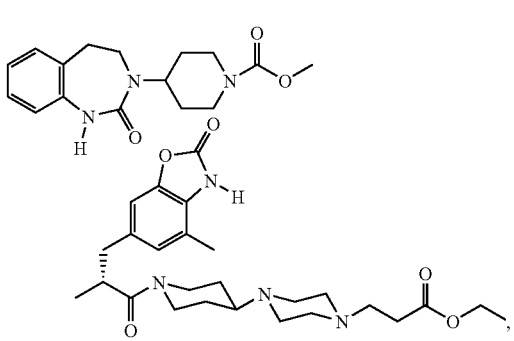 |
| No. | Structure |
|---|---|
| (77) | 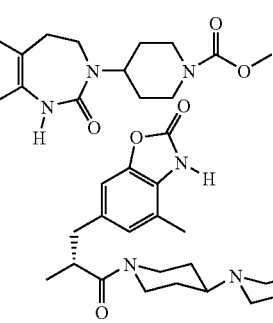 |
| (78) | 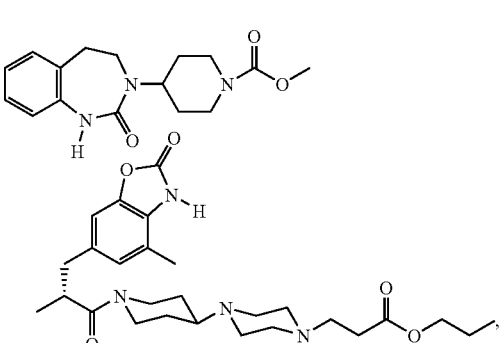 |
| (79) | 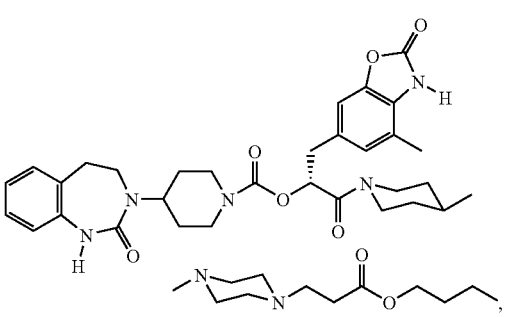 |
| (80) | 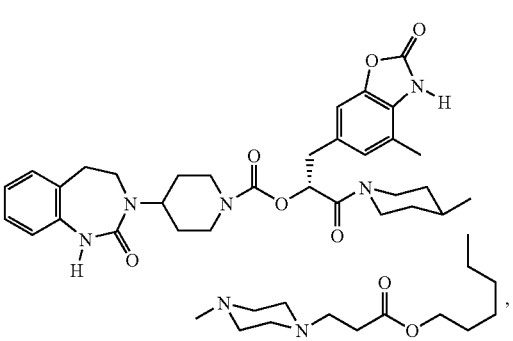 |

| No. | Structure |
|---|---|
| (81) | 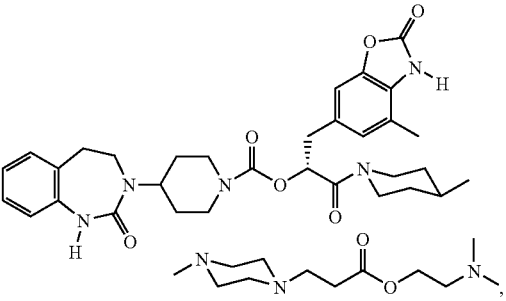 |
| (82) | 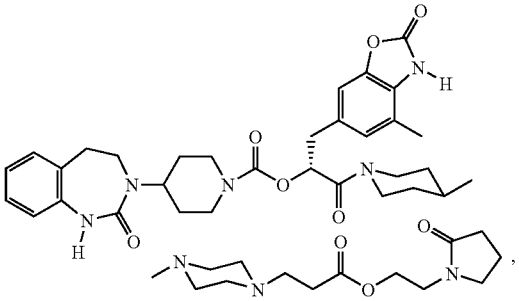 |
| (83) | 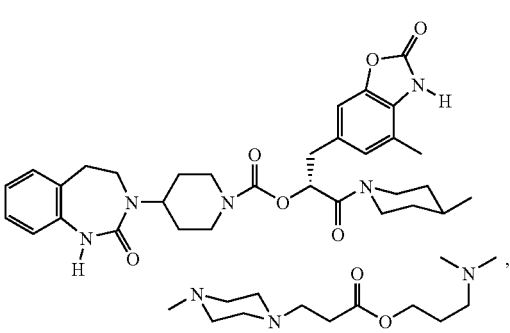 |
| (84) | 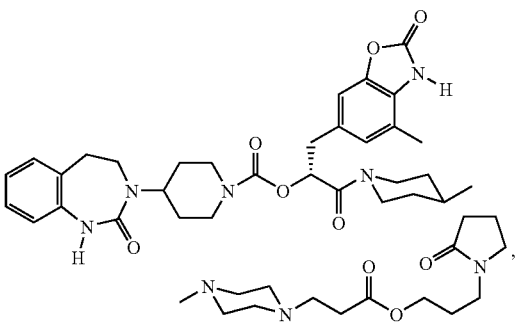 |
| No. | Structure |
|---|---|
| (85) | 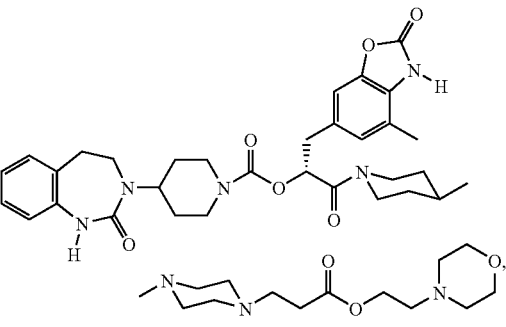 |
| (86) | 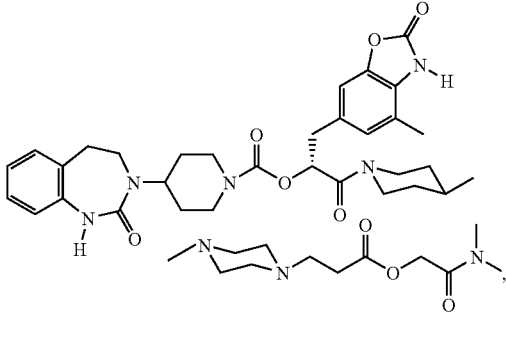 |
| (87) | 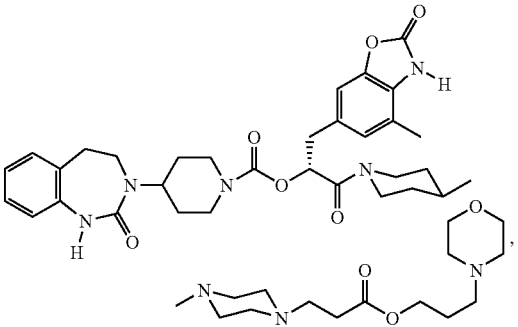 |
| (88) | 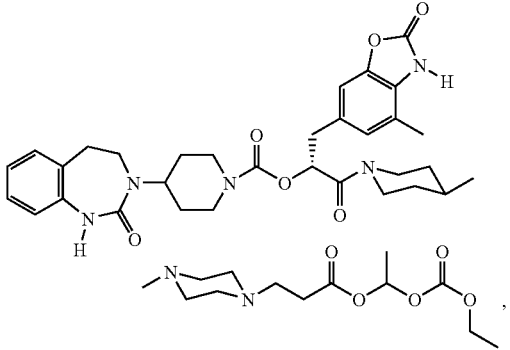 |

-continued
| No. | Structure |
|---|---|
| (89) | 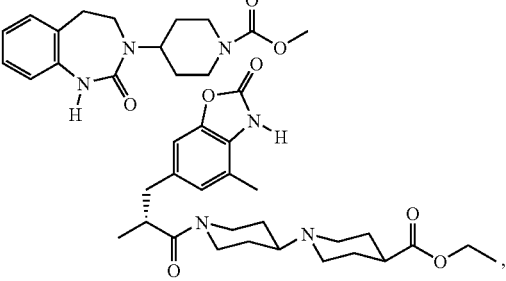 |
| (90) | 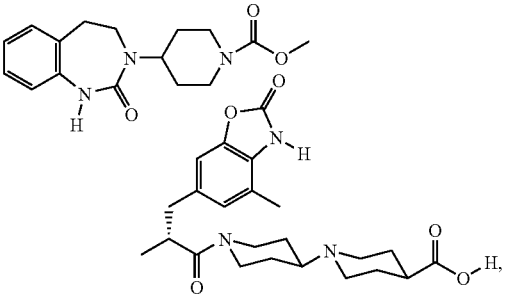 |
| (91) | 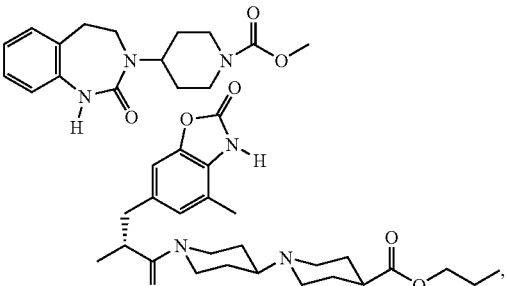 |
| (92) | 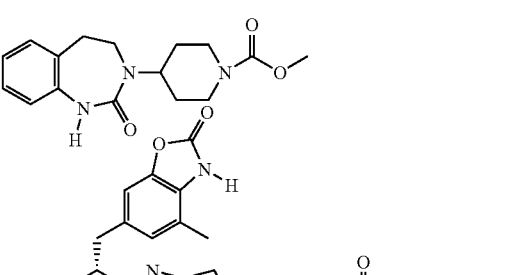 |
| (93) | 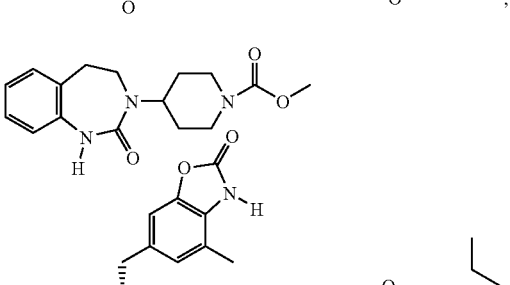 |
-continued
| No. | Structure |
|---|---|
| (94) | 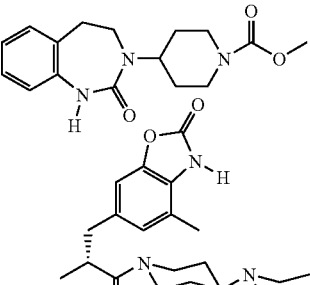 |
| (95) | 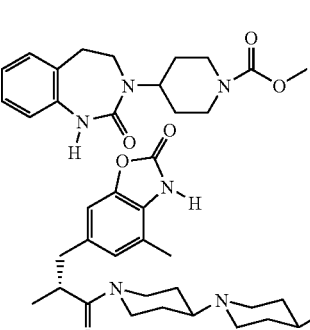 |
| (96) | 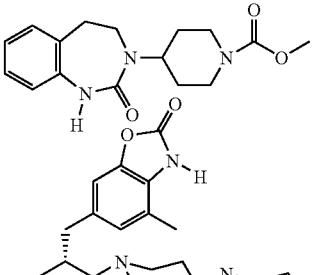 |
| (97) | 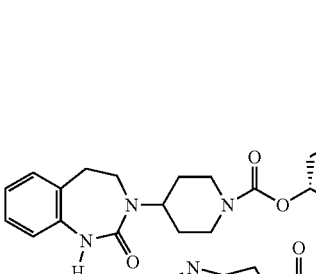 |

-continued

| No. | Structure |
|---|---|
| (98) | 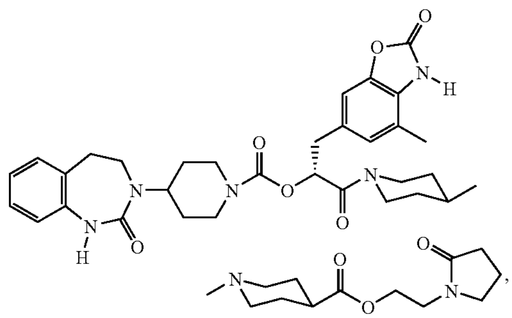 |
| (99) | 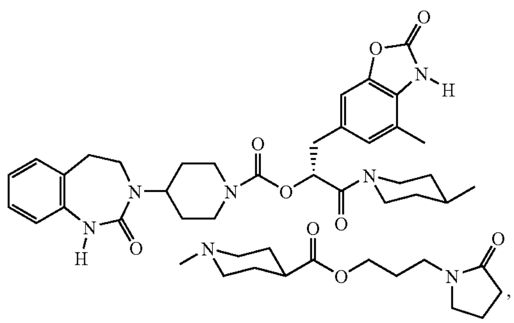 |
| (100) | 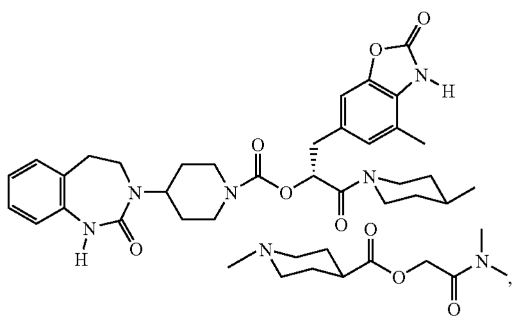 |
| (101) | 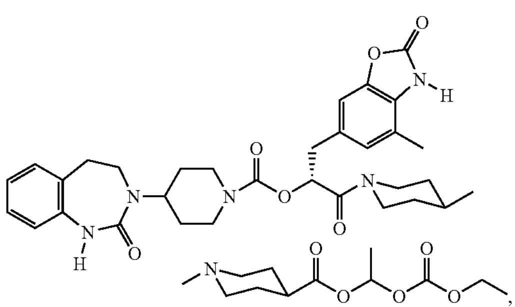 |
| (102) | 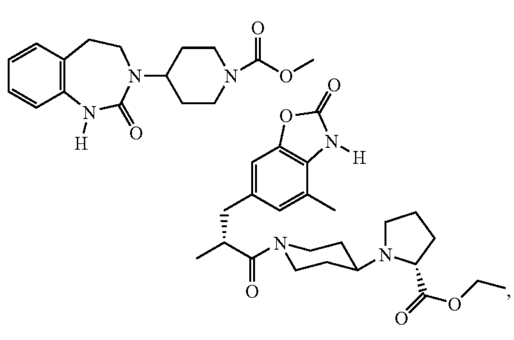 |

-continued

| No. | Structure |
|---|---|
| (103) | |
| (104) | |
| (105) | |
| (106) | |

| No. | Structure |
|---|---|
| (107) | 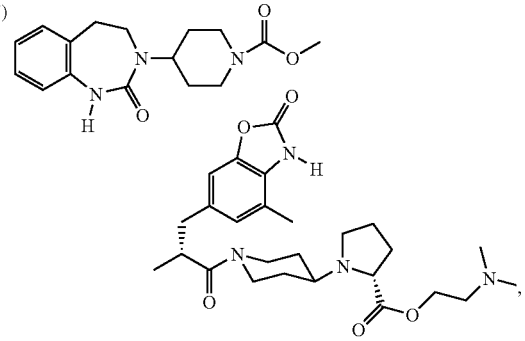 |
| (108) | 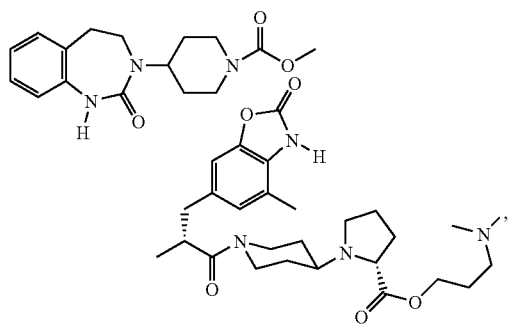 |
| (109) | 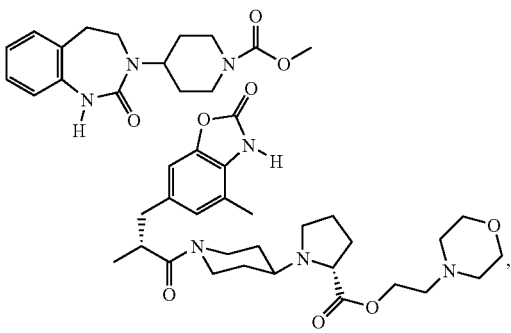 |
| (110) | 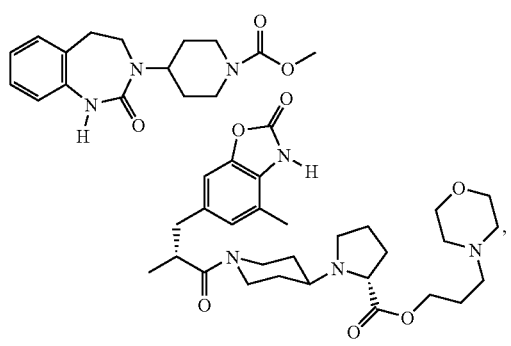 |
| No. | Structure |
|---|---|
| (111) | 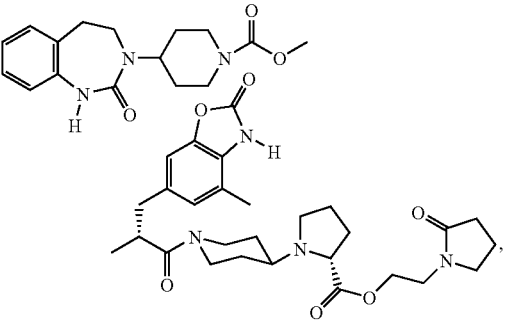 |
| (112) | 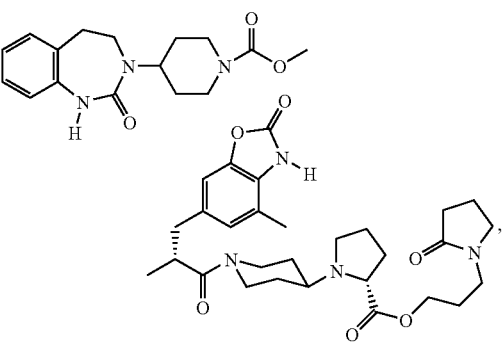 |
| (113) | 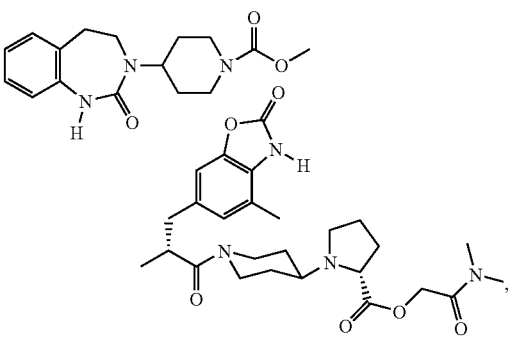 |
| (114) | 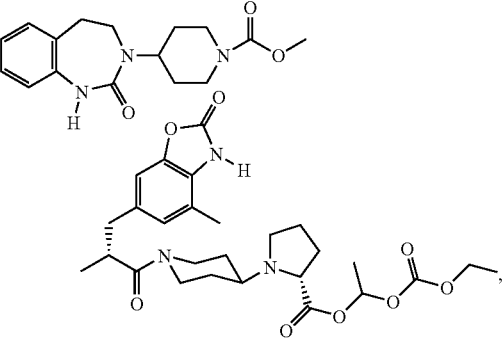 |

-continued
| No. | Structure |
|---|---|
| (115) | 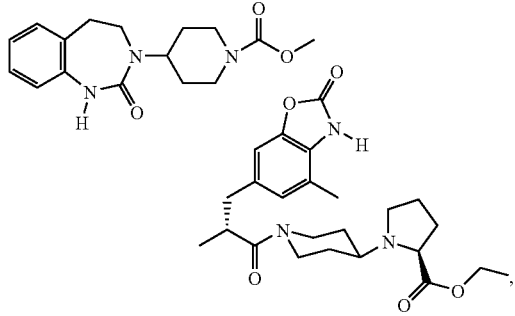 |
| (116) | 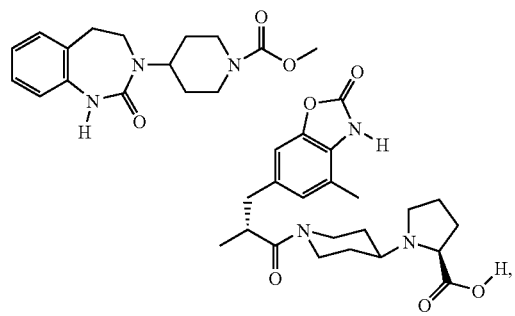 |
| (117) | 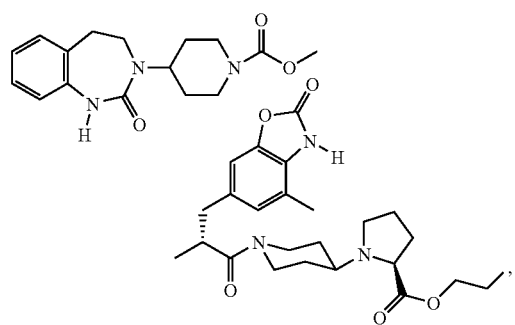 |
| (118) | 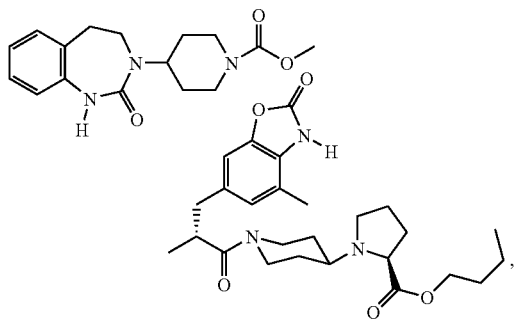 |
-continued
| No. | Structure |
|---|---|
| (119) | 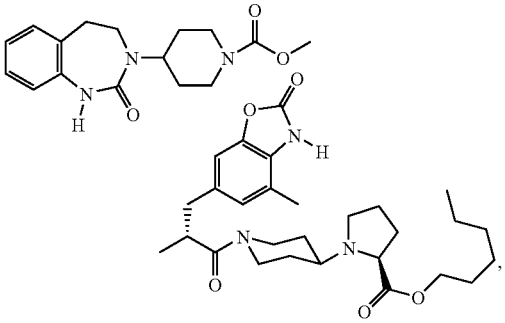 |
| (120) | 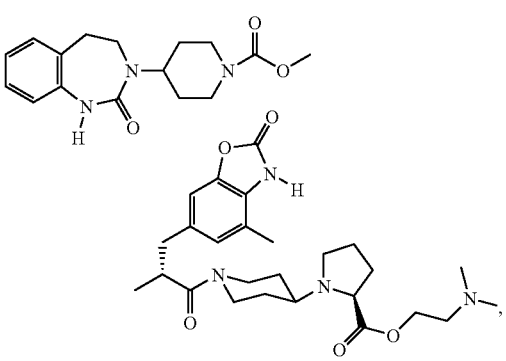 |
| (121) | 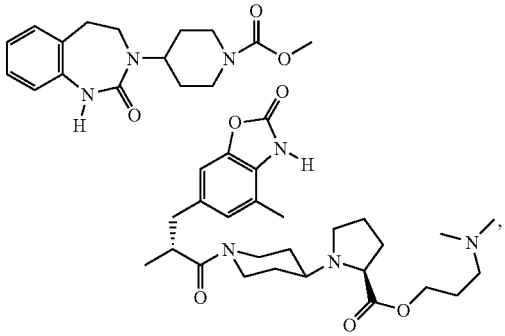 |
| (122) | 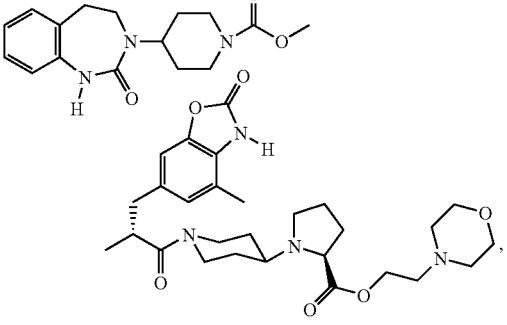 |

| No. | Structure |
|---|---|
| (123) | 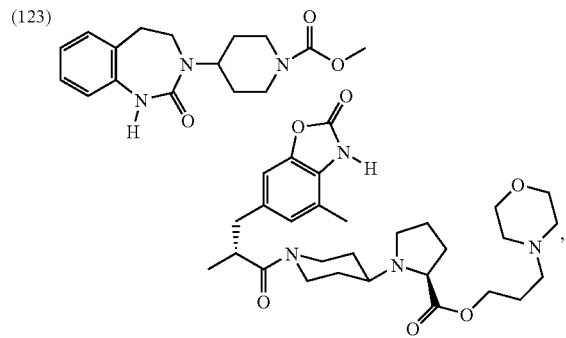 |
| (124) | 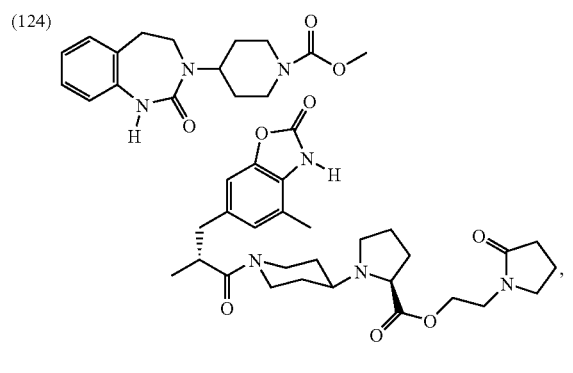 |
| (125) | 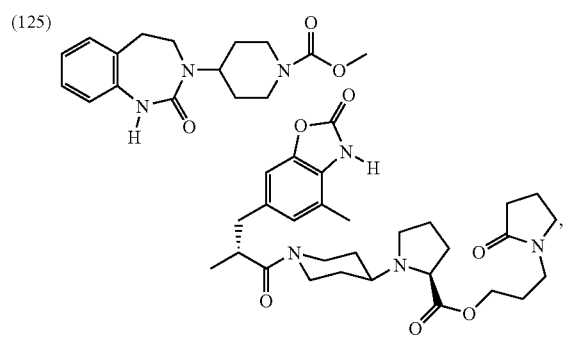 |
| (126) | 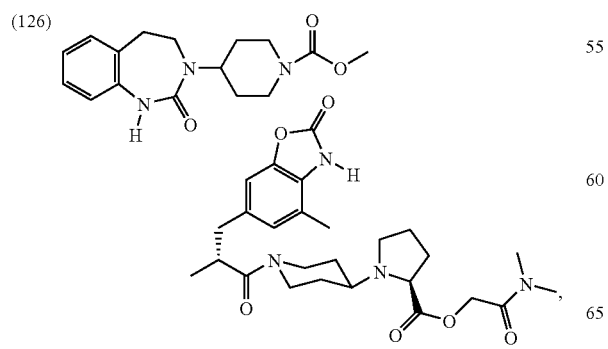 |
| No. | Structure |
|---|---|
| (127) | 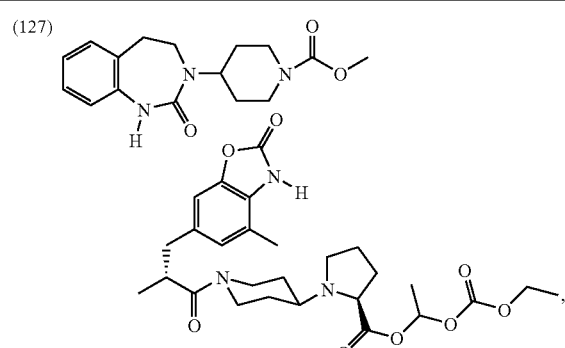 |
| (128) | 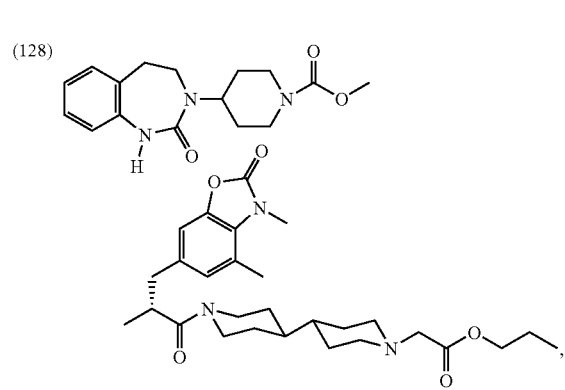 |
| (129) | 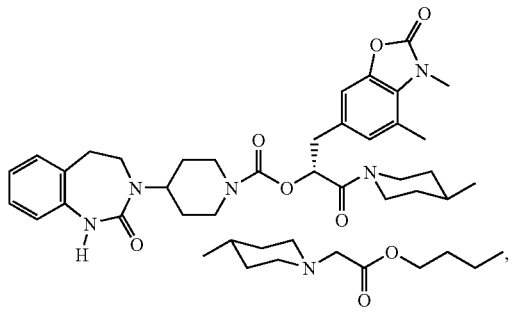 |
| (130) | 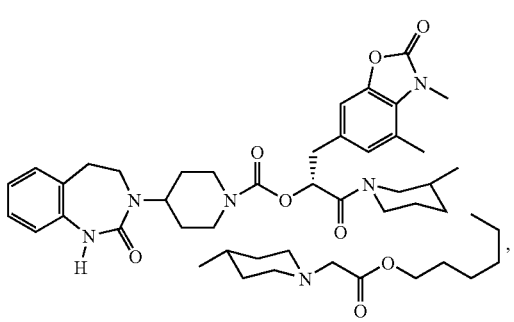 |

| No. | Structure |
|---|---|
| (131) | 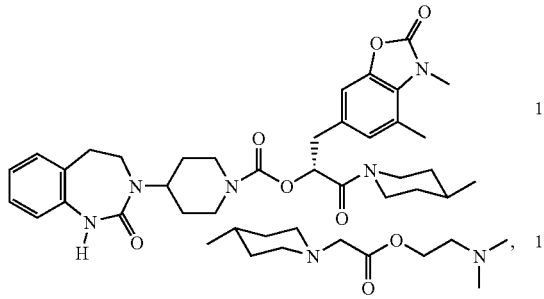 |
| (132) | 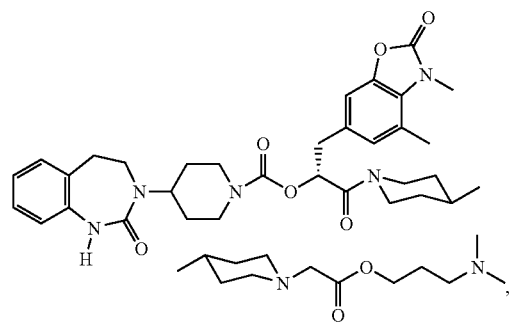 |
| (133) | 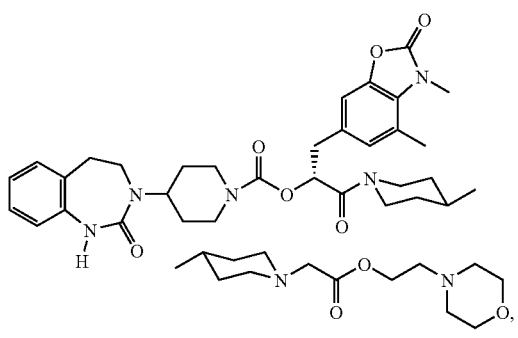 |
| (134) | 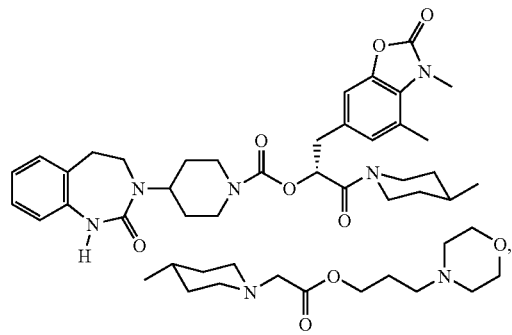 |
| No. | Structure |
|---|---|
| (135) | 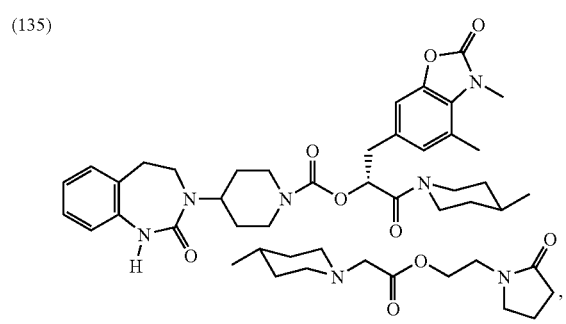 |
| (136) | 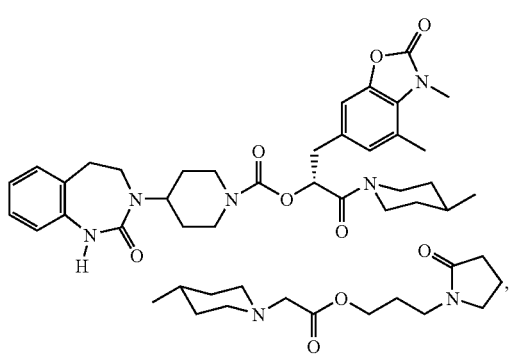 |
| (137) | 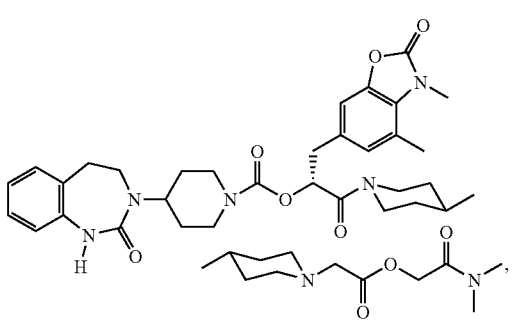 |
| (138) | 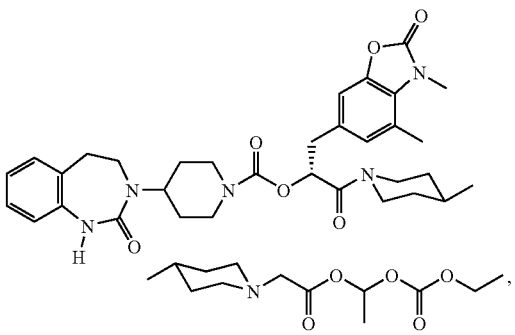 |

| No. | Structure |
|---|---|
| (139) | 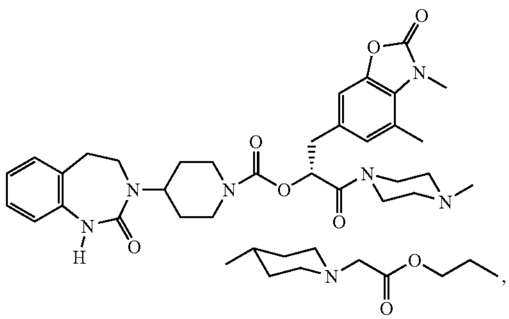 |
| (140) | 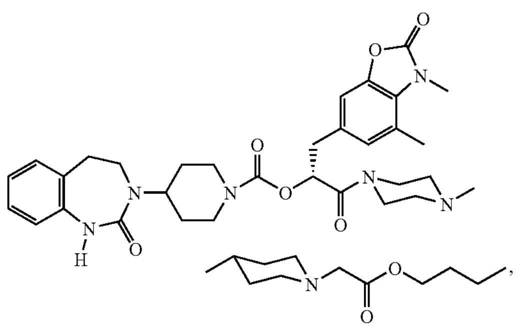 |
| (141) | 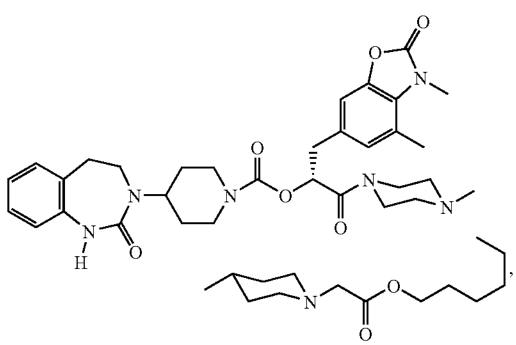 |
| (142) | 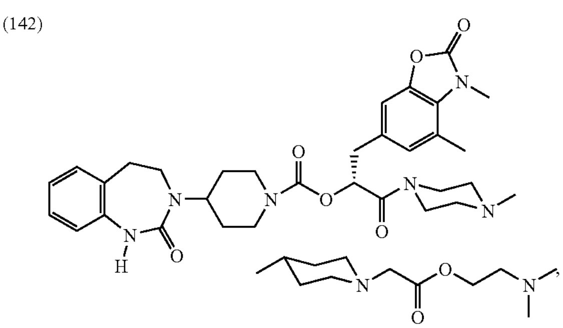 |
| (143) | |
| (144) | |
| (145) | |
| (146) | |

| No. | Structure |
|---|---|
| (147) | 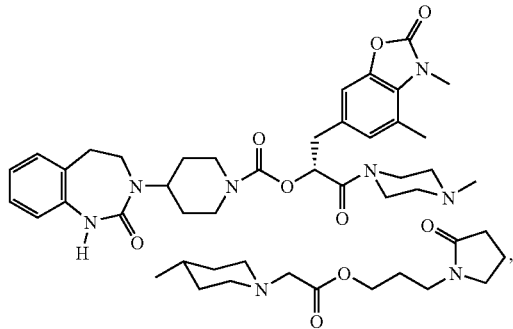 |
| (148) | 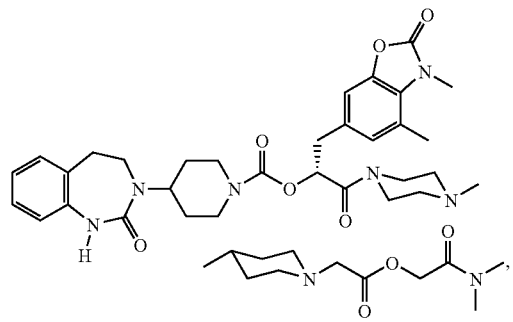 |
| (149) | 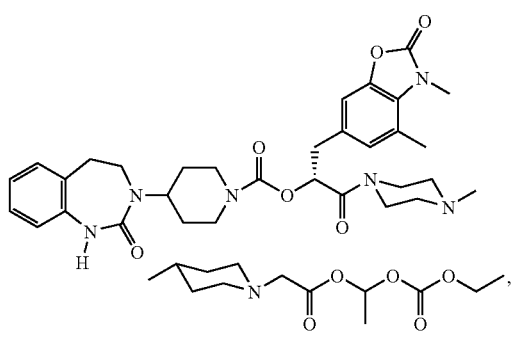 |
| (150) | 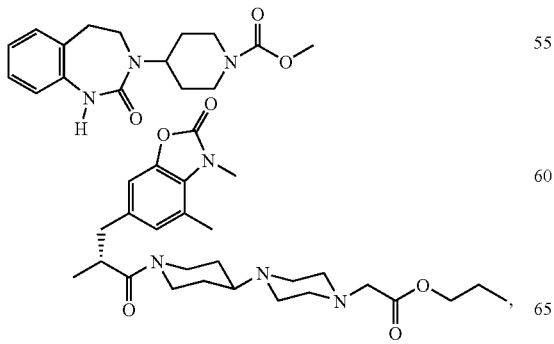 |
| No. | Structure |
|---|---|
| (151) | 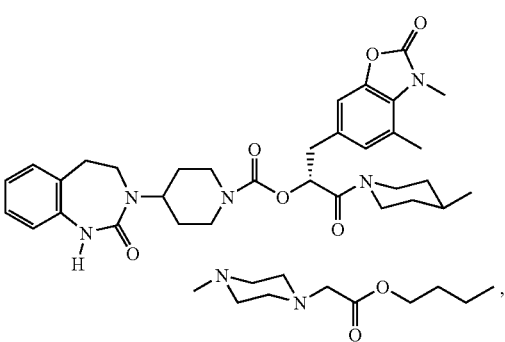 |
| (152) | 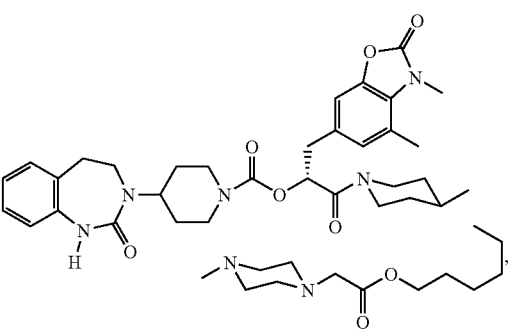 |
| (153) | 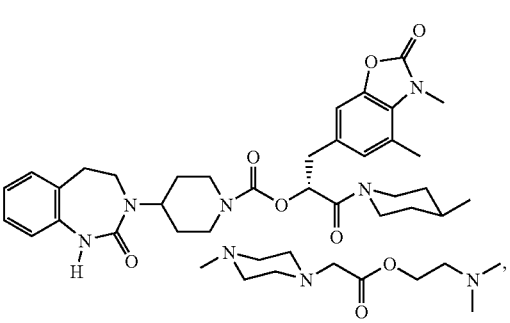 |
| (154) | 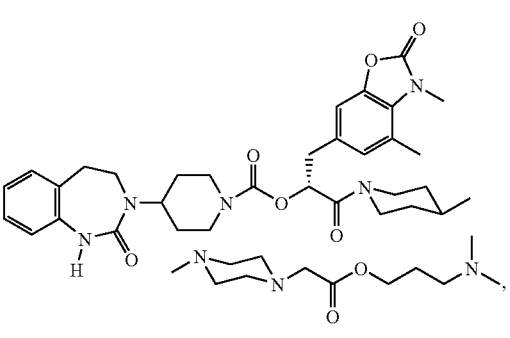 |

-continued

| No. | Structure |
|-----|-----------|
| (155) | 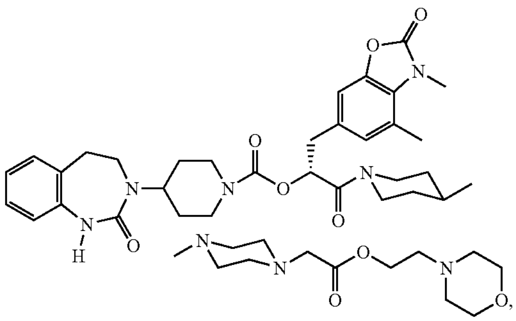 |
| (156) | 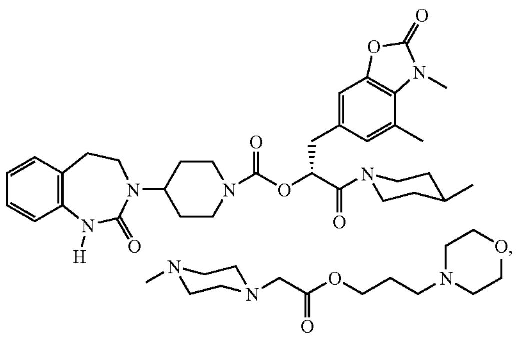 |
| (157) | 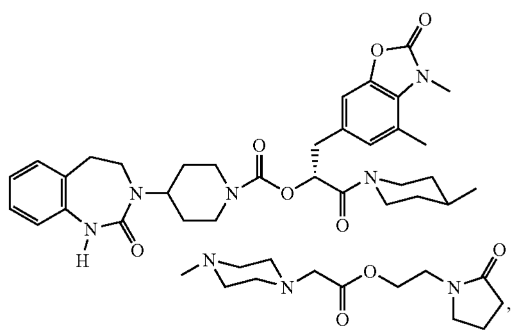 |
| (158) | 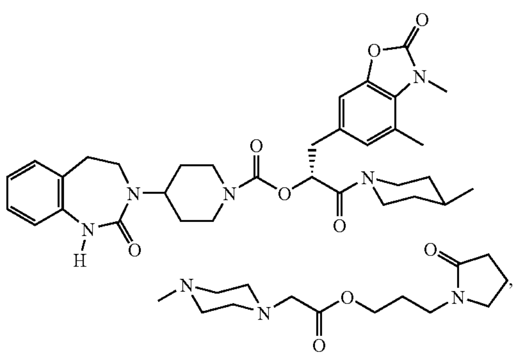 |

-continued

| No. | Structure |
|-----|-----------|
| (159) | 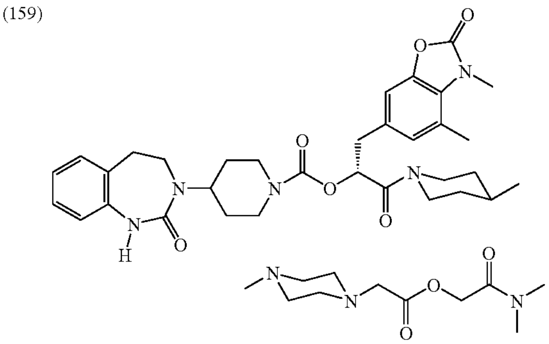 |
| (160) | 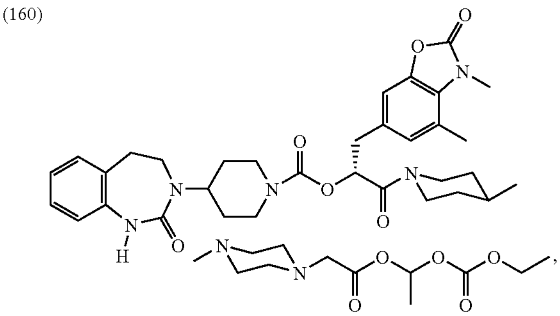 |
| (161) | 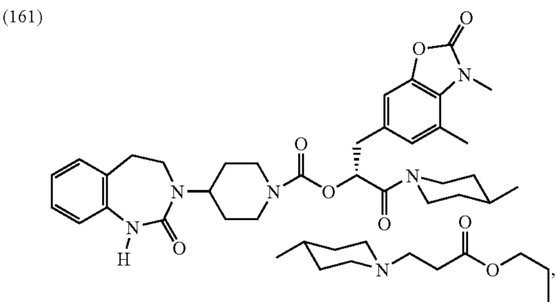 |
| (162) | 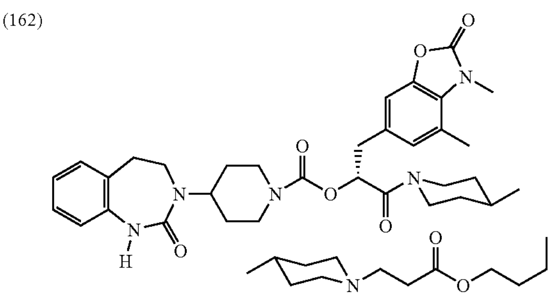 |
| (163) | 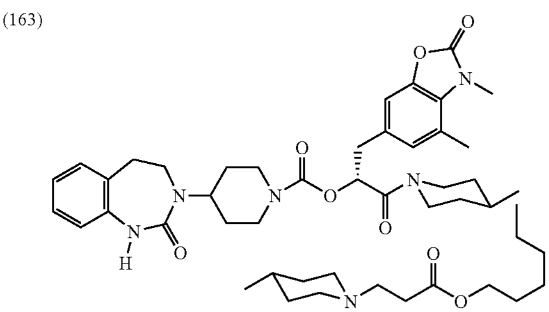 |

-continued

| No. | Structure |
|---|---|
| (164) | 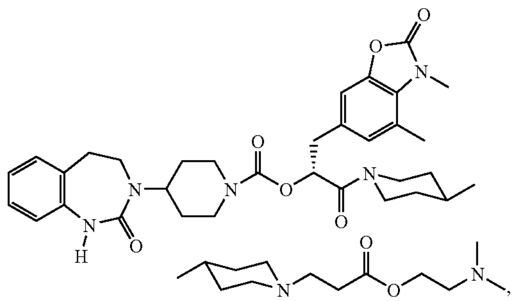 |
| (165) | 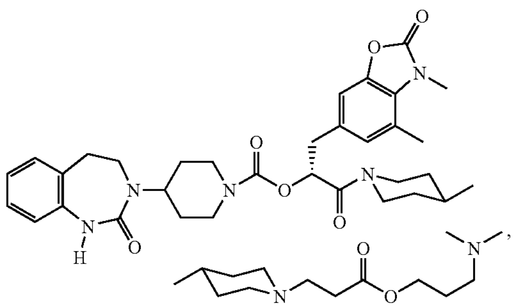 |
| (166) | 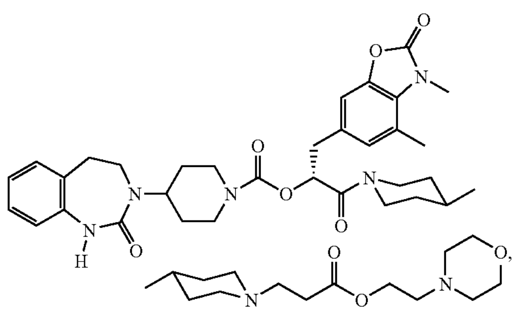 |
| (167) | 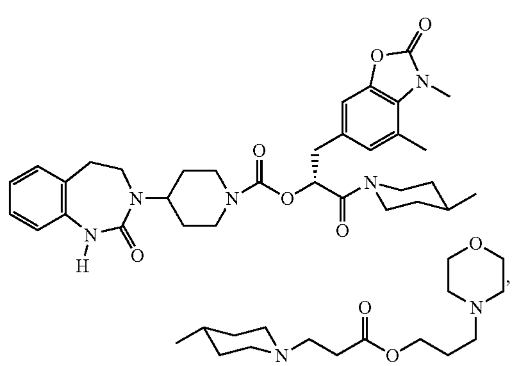 |

-continued

| No. | Structure |
|---|---|
| (168) | 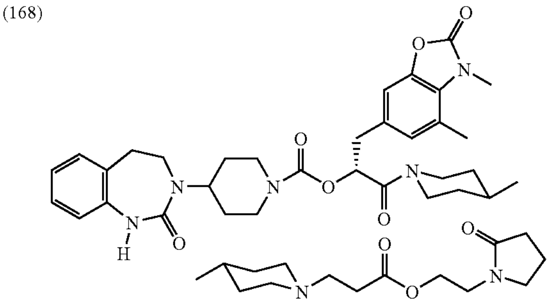 |
| (169) | 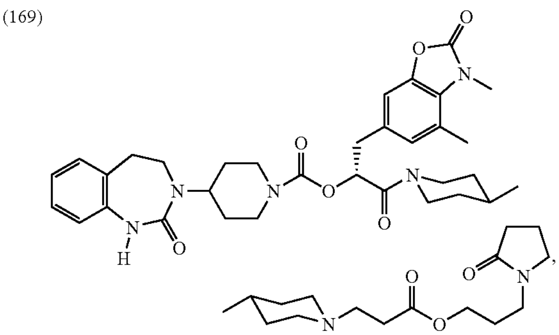 |
| (170) | 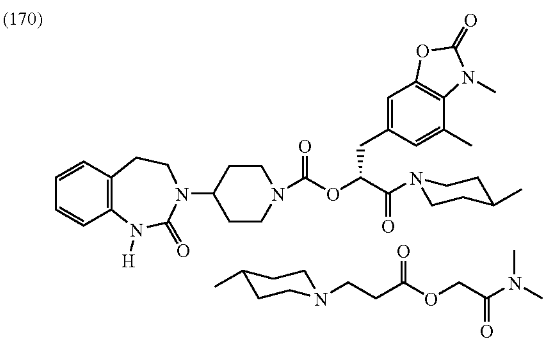 |
| (171) | 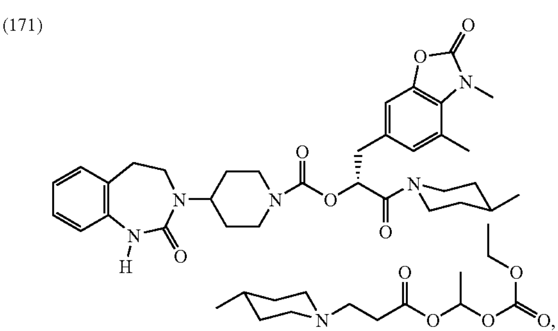 |

-continued

| No. | Structure |
|---|---|
| (172) | 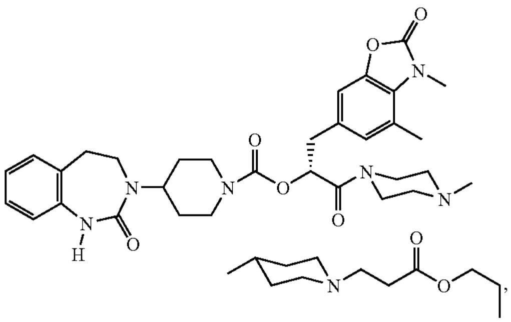 |
| (173) | 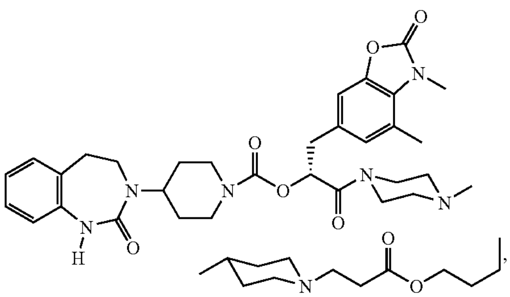 |
| (174) | 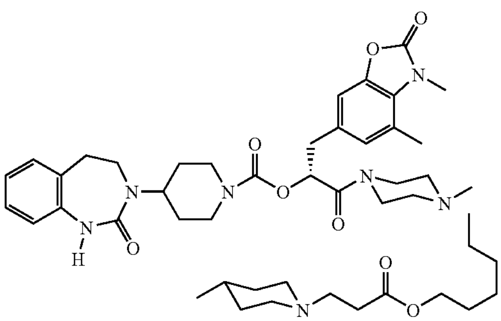 |
| (175) | 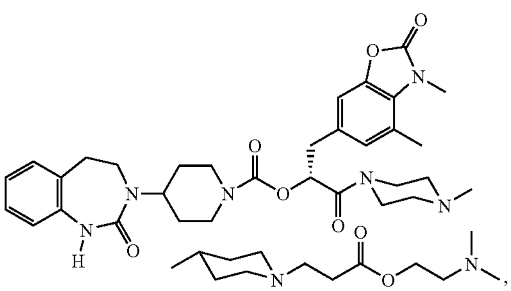 |
| (176) | 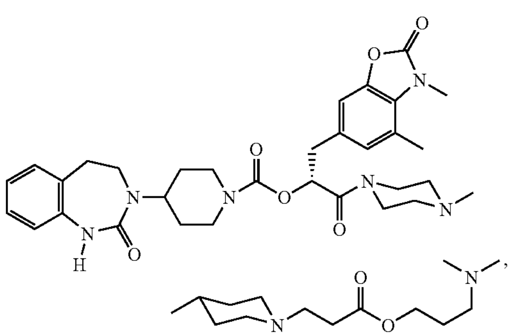 |

-continued

| No. | Structure |
|---|---|
| (177) | 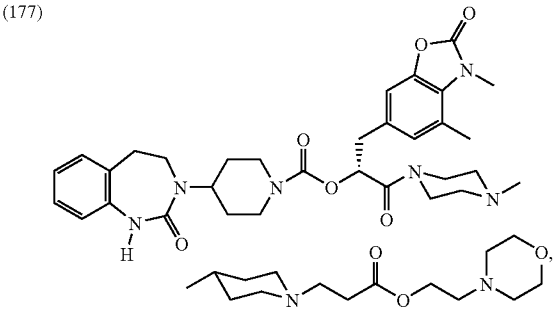 |
| (178) | 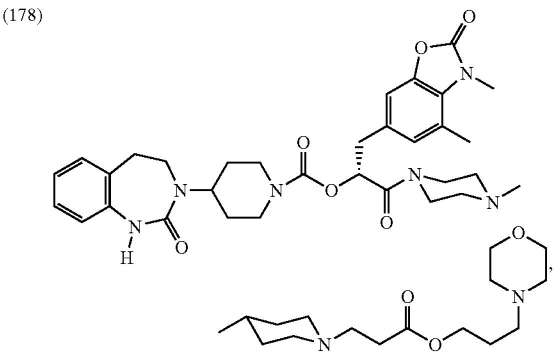 |
| (179) | 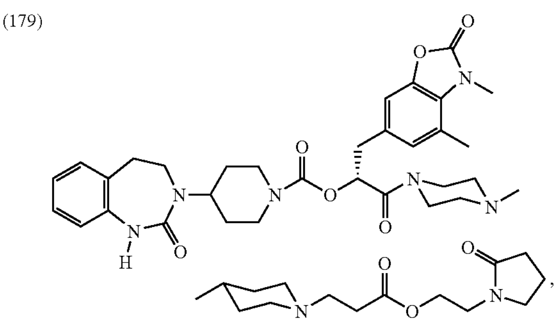 |
| (180) | 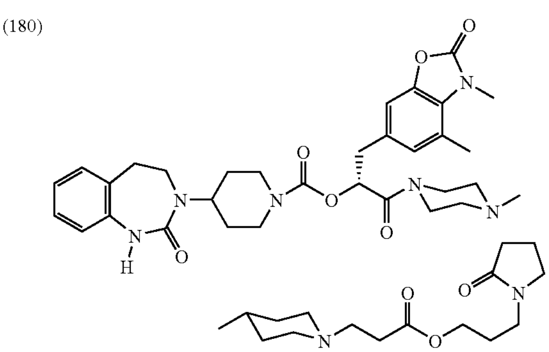 |

-continued

| No. | Structure |
|---|---|
| (181) | 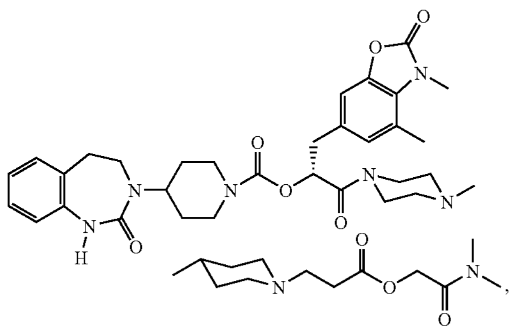 |
| (182) | 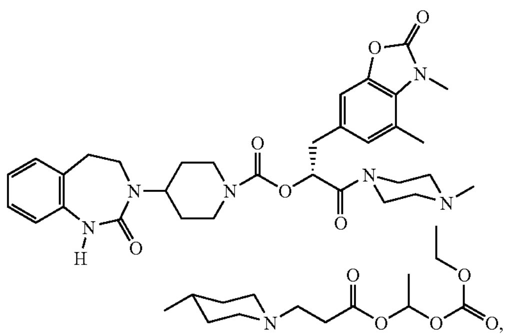 |
| (183) | 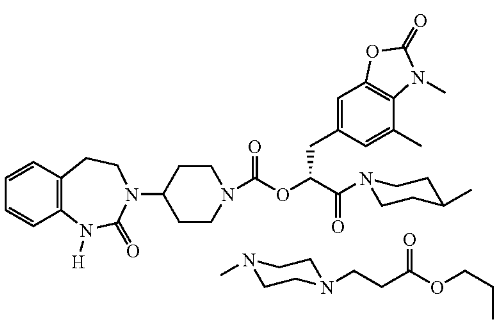 |
| (184) | 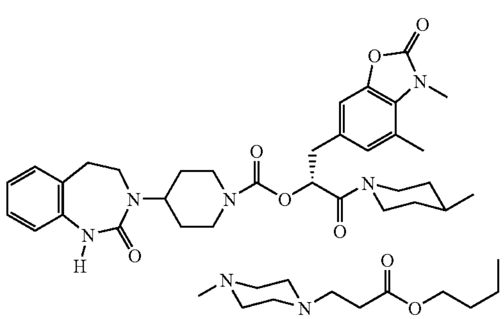 |

-continued

| No. | Structure |
|---|---|
| (185) | 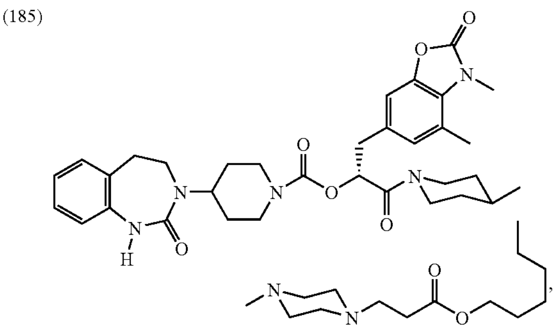 |
| (186) | 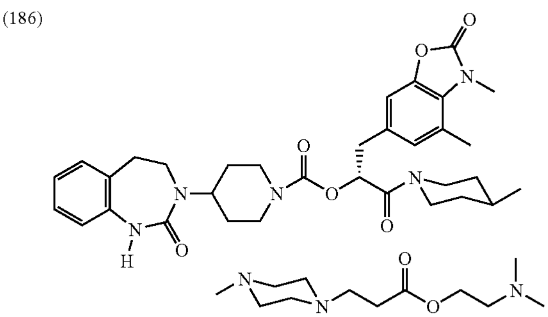 |
| (187) | 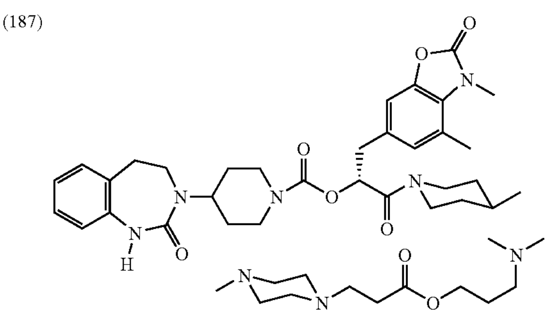 |
| (188) | 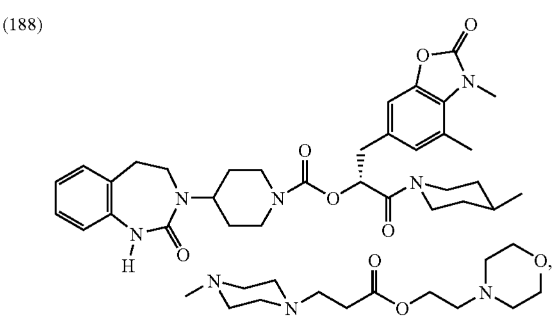 |

-continued
| No. | Structure |
|---|---|
| (189) | 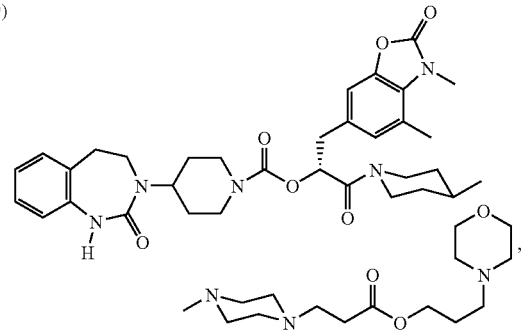 |
| (190) | 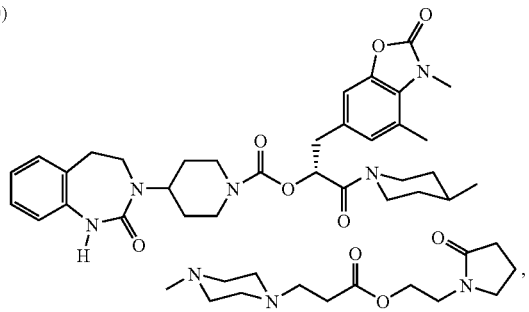 |
| (191) | 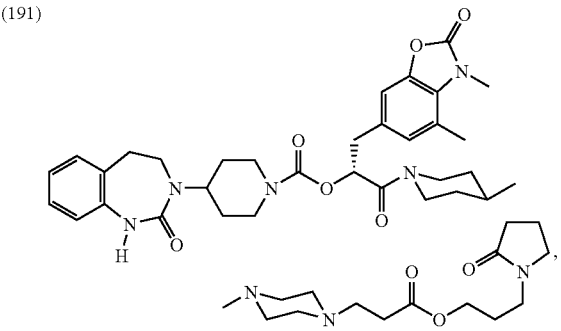 |
| (192) | 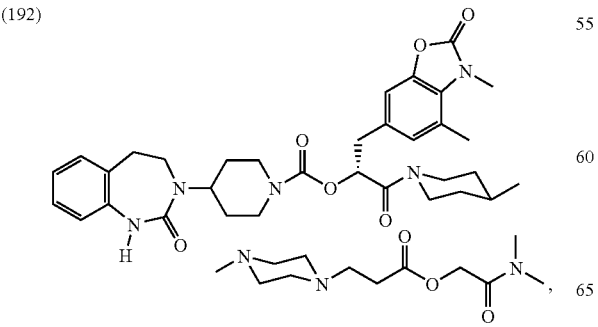 |
-continued
| No. | Structure |
|---|---|
| (193) | 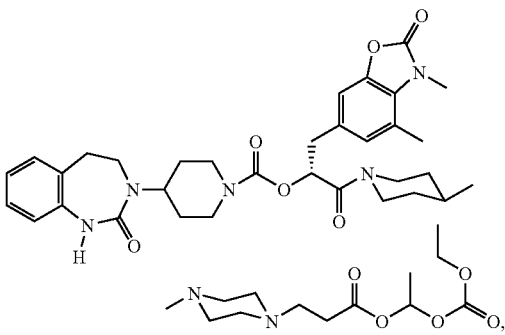 |
| (194) | 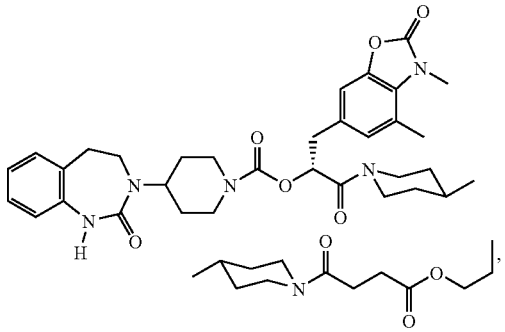 |
| (195) | 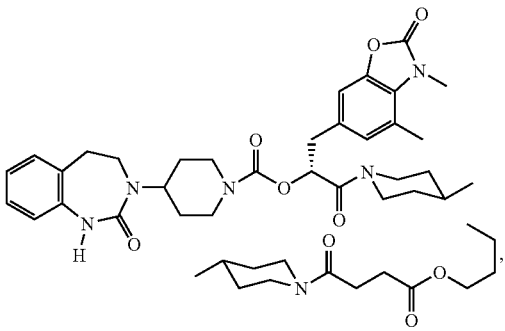 |
| (196) | 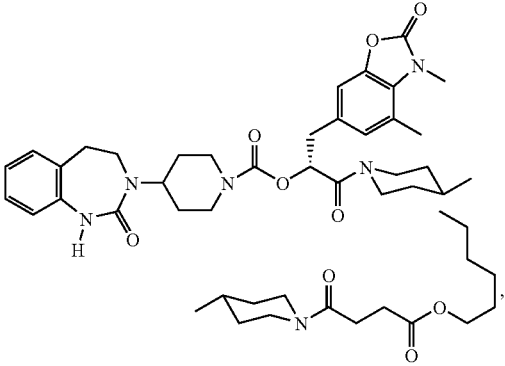 |

-continued
| No. | Structure |
|---|---|
| (197) | 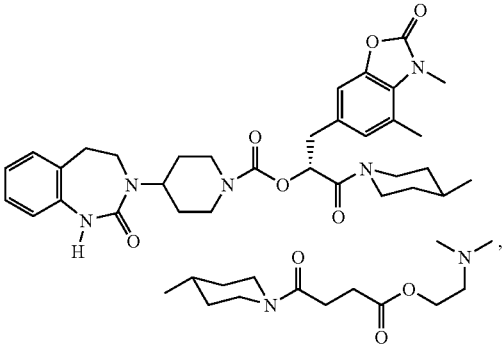 |
| (198) | 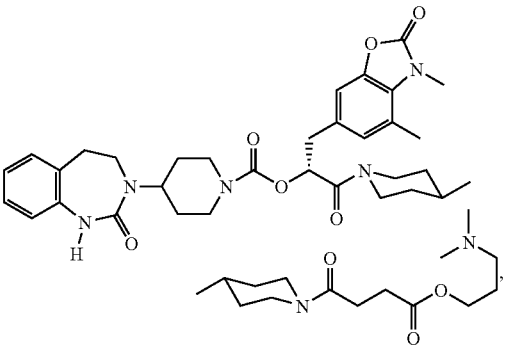 |
| (199) | 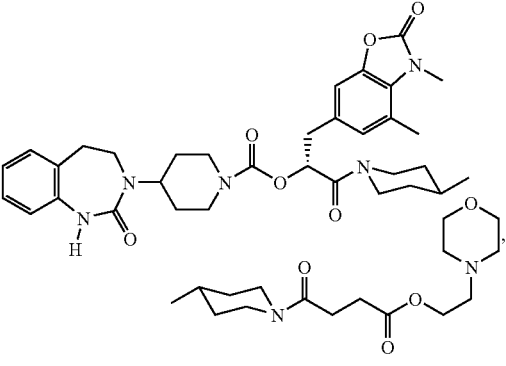 |
| (200) | 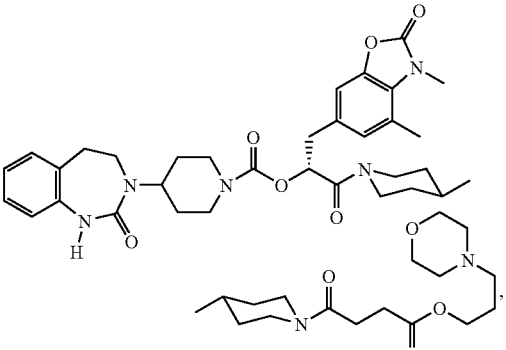 |
-continued
| No. | Structure |
|---|---|
| (201) | 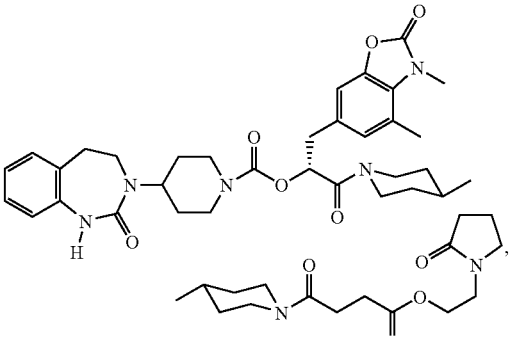 |
| (202) | 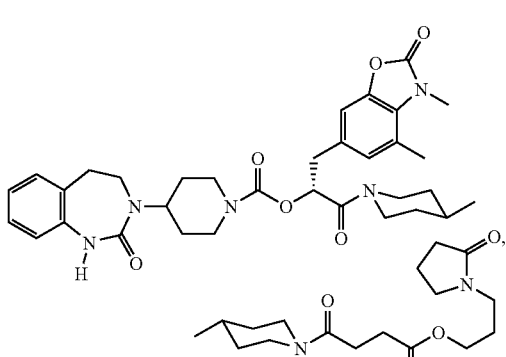 |
| (203) | 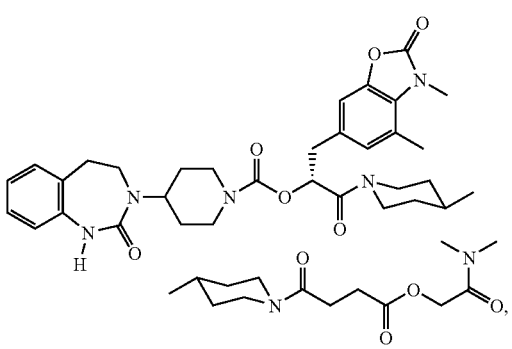 |
| (204) | 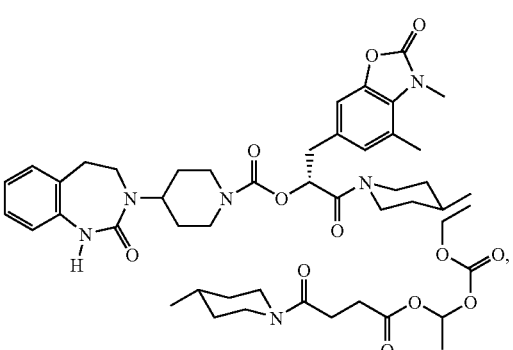 |

-continued
| No. | Structure |
|---|---|
| (205) | 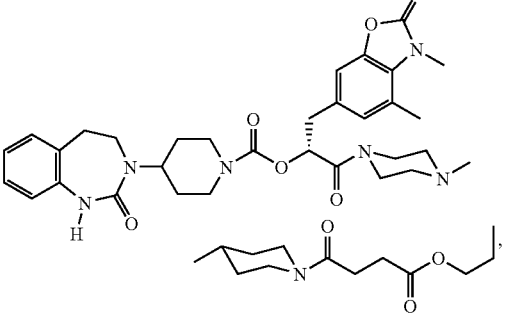 |
| (206) | 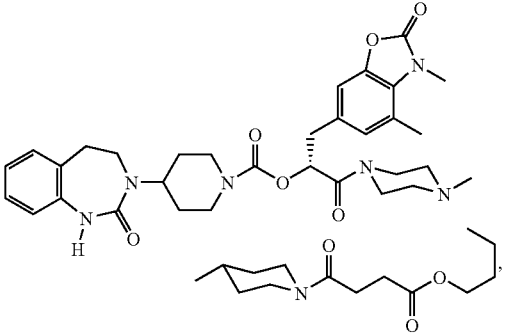 |
| (207) | 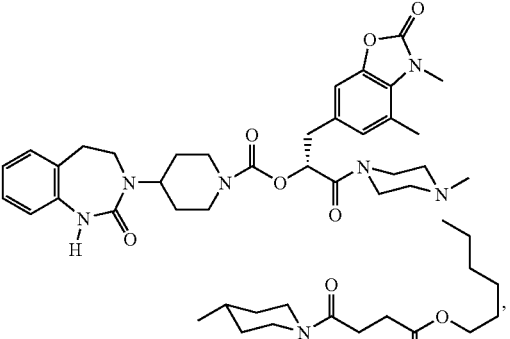 |
| (208) | 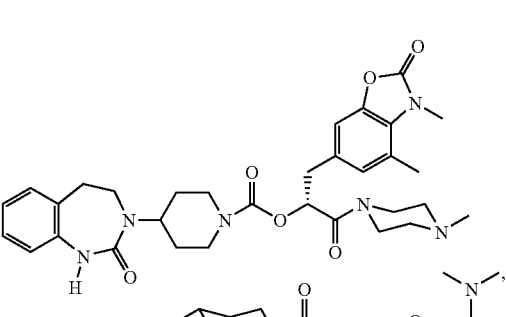 |
-continued
| No. | Structure |
|---|---|
| (209) | 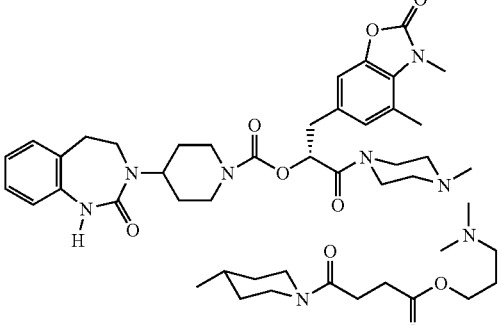 |
| (210) | 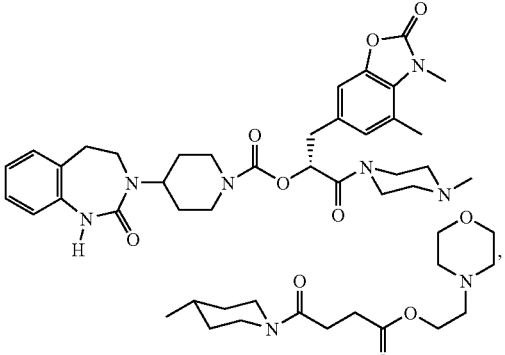 |
| (211) | 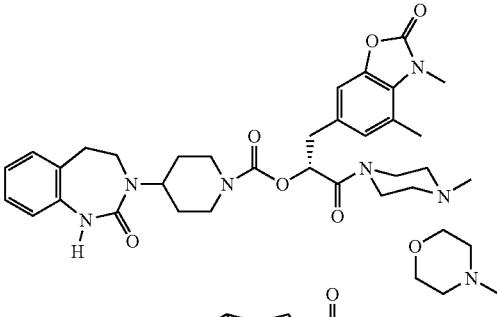 |
| (212) | 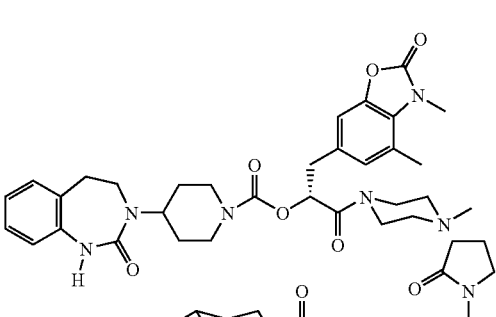 |

| No. | Structure |
|---|---|
| (213) | 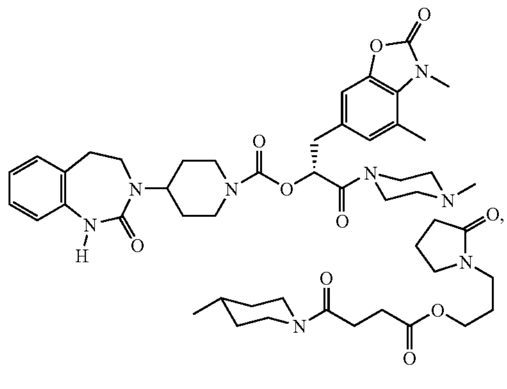 |
| (214) | 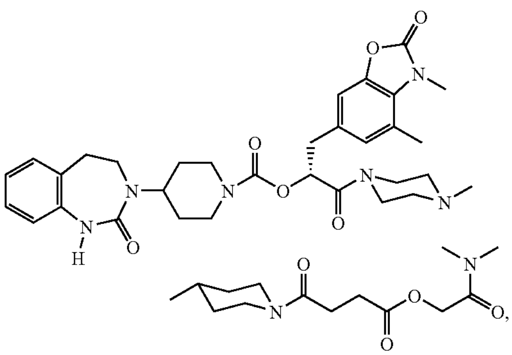 |
| (215) | 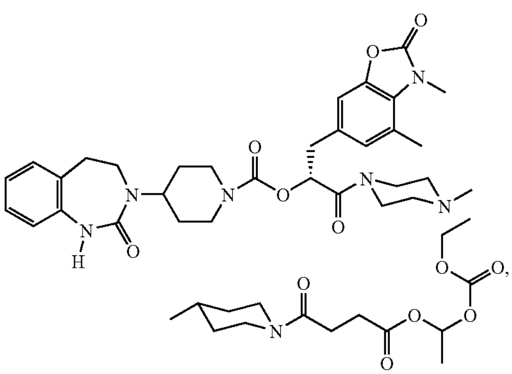 |
| (216) | 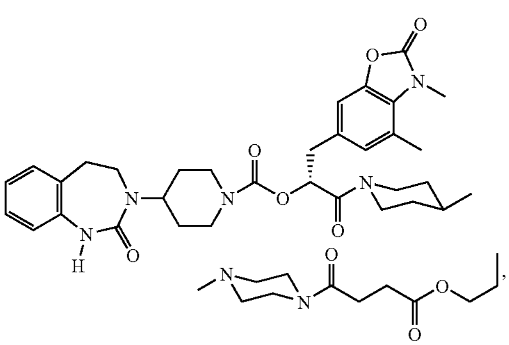 |

| No. | Structure |
|---|---|
| (217) | 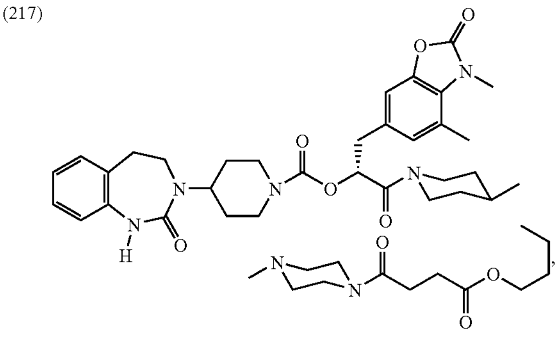 |
| (218) | 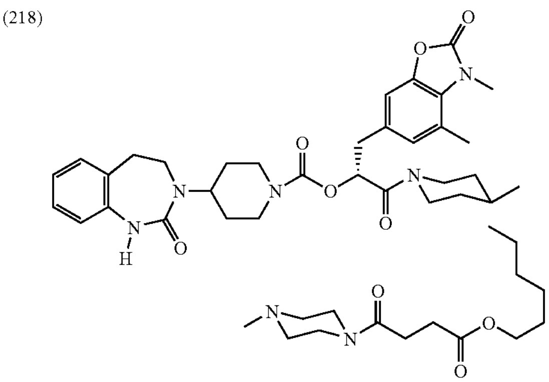 |
| (219) | 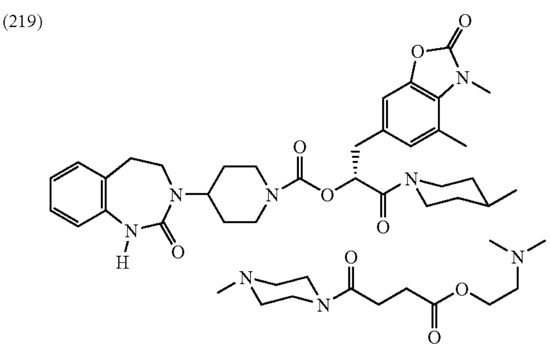 |
| (220) | 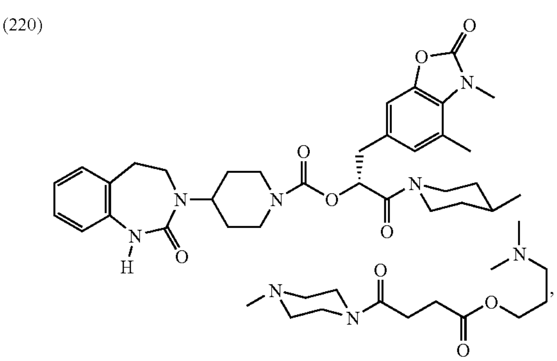 |

-continued
| No. | Structure |
|-----|-----------|
| (221) | 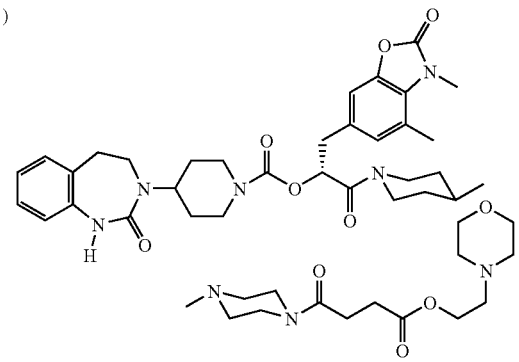 |
| (222) | 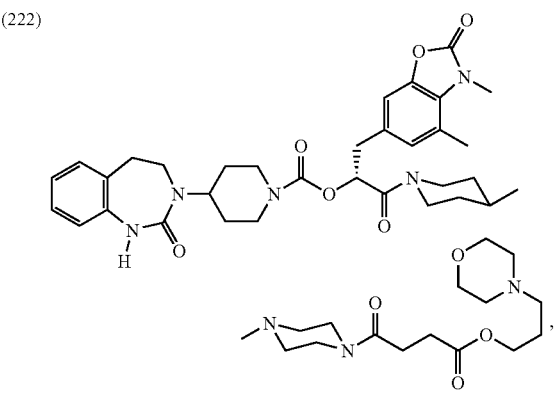 |
| (223) | 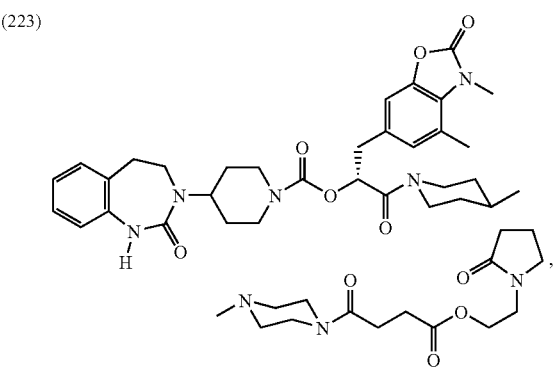 |
| (224) | 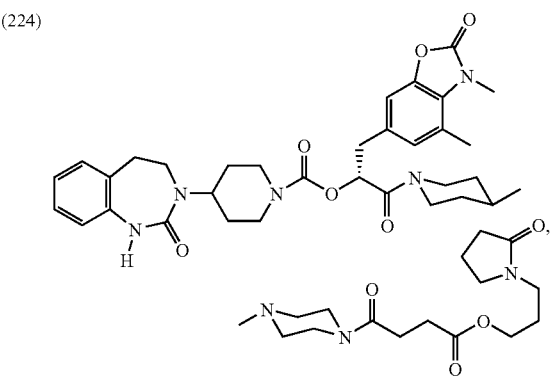 |
-continued
| No. | Structure |
|-----|-----------|
| (225) | 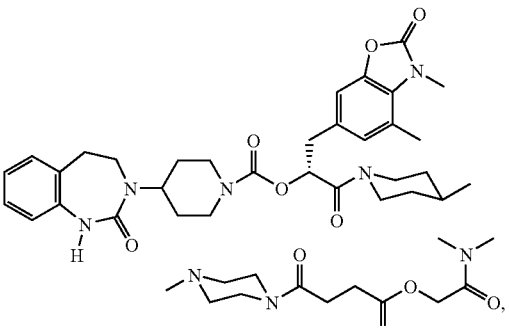 |
| (226) | 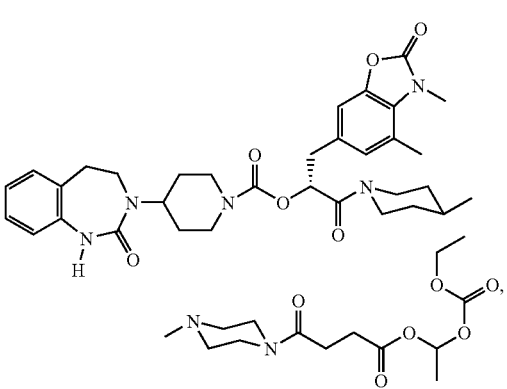 |
| (227) | 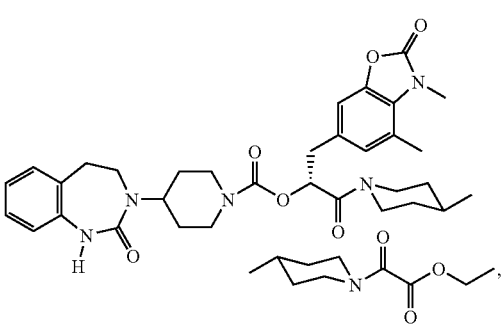 |
| (228) | 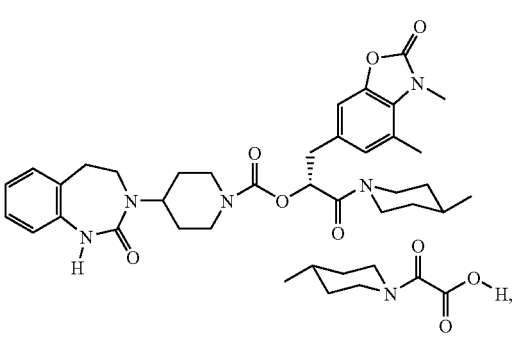 |

-continued
| No. | Structure |
|---|---|
| (229) | 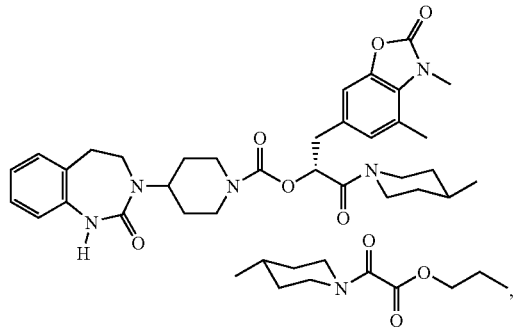 |
| (230) | 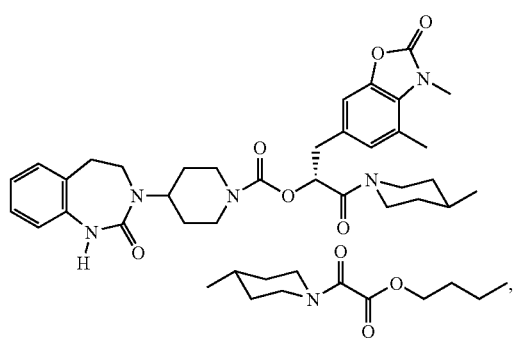 |
| (231) | 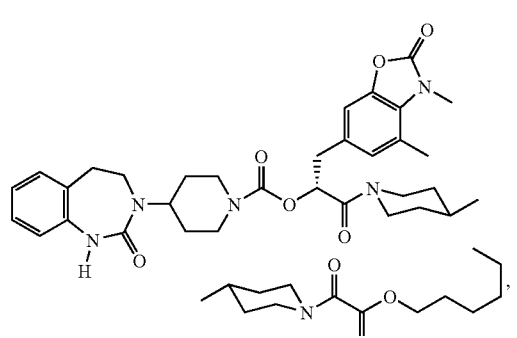 |
| (232) | 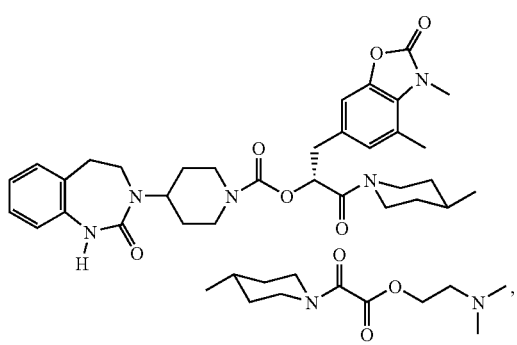 |
-continued
| No. | Structure |
|---|---|
| (233) | 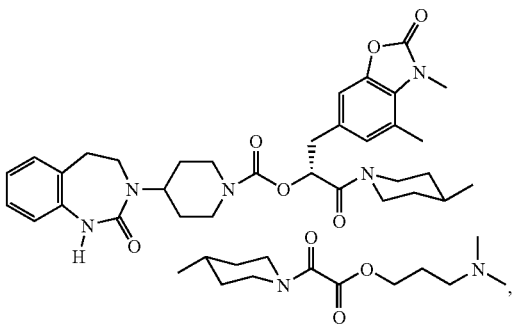 |
| (234) | 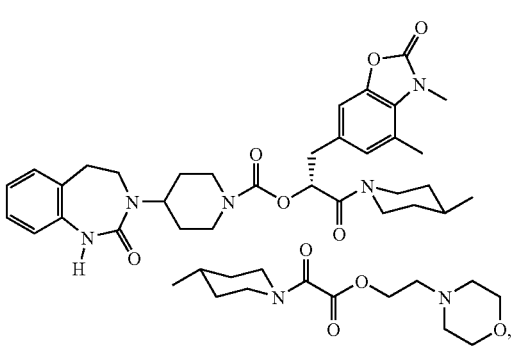 |
| (235) | 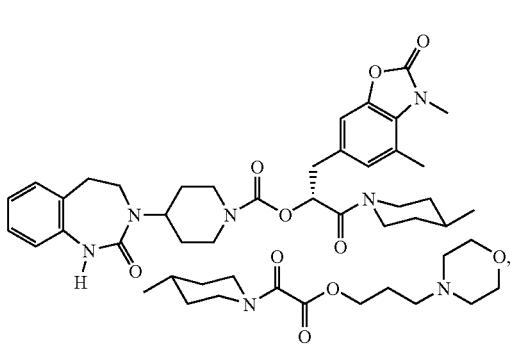 |
| (236) | 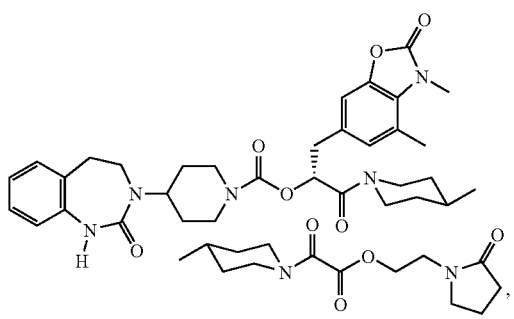 |

-continued

| No. | Structure |
|---|---|
| (237) | 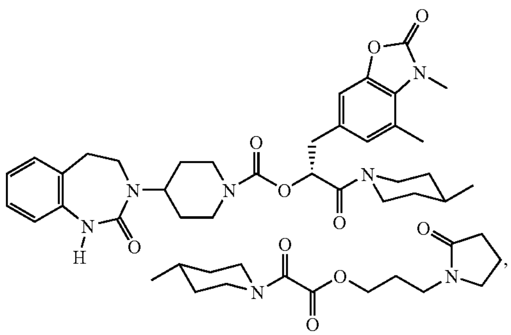 |
| (238) | 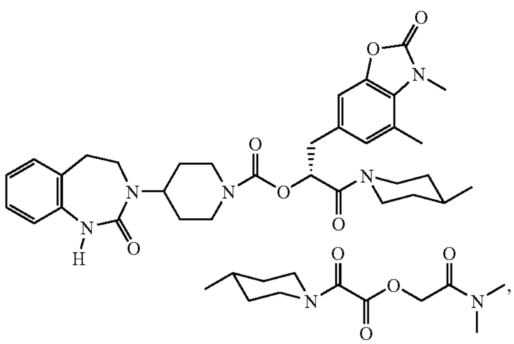 |
| (239) | 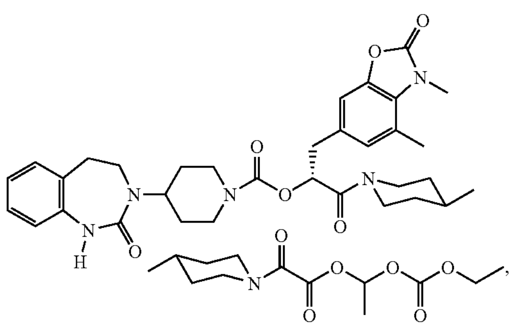 |
| (240) | 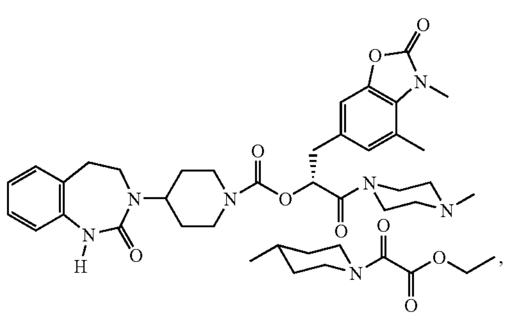 |

-continued

| No. | Structure |
|---|---|
| (241) | 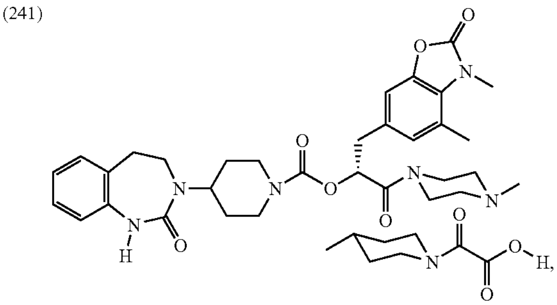 |
| (242) | 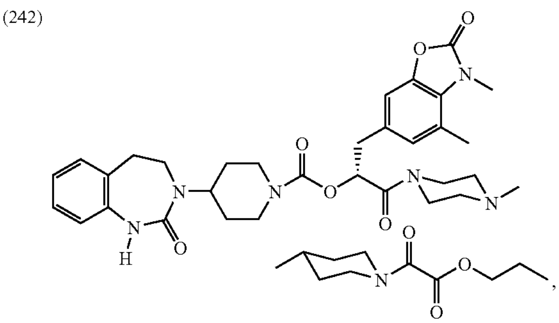 |
| (243) | 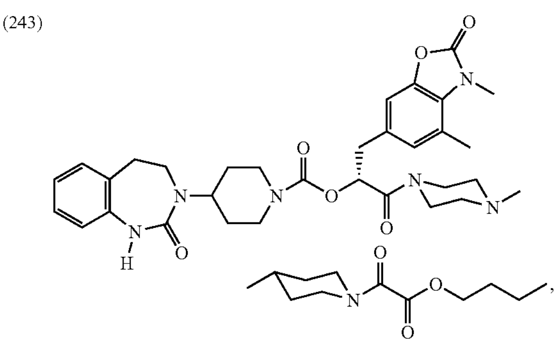 |
| (244) | 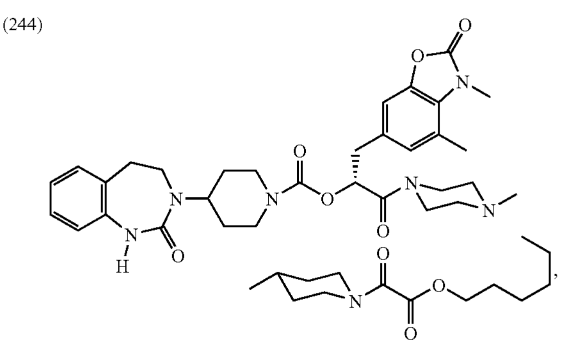 |

-continued

| No. | Structure |
|---|---|
| (245) | 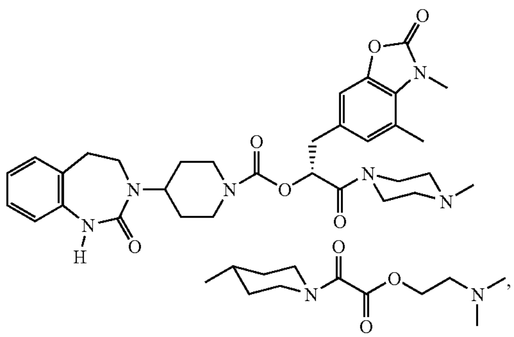 |
| (246) | 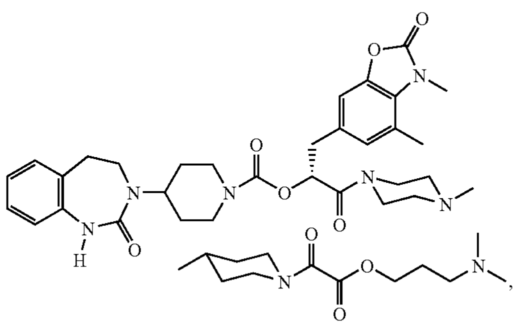 |
| (247) | 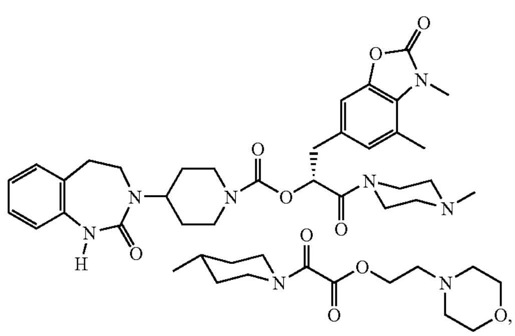 |
| (248) | 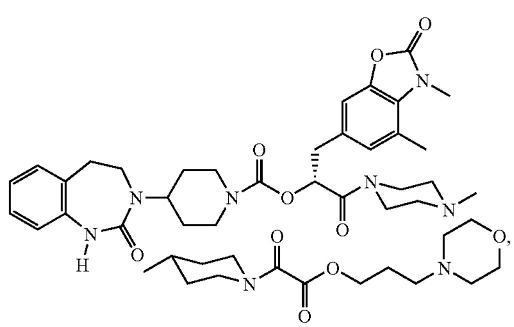 |

-continued

| No. | Structure |
|---|---|
| (249) | 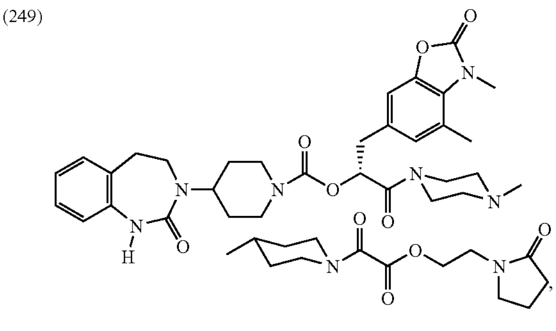 |
| (250) | 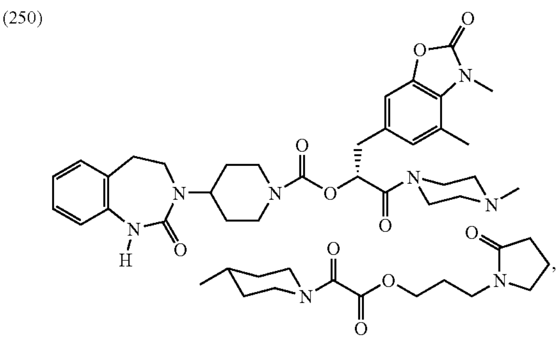 |
| (251) | 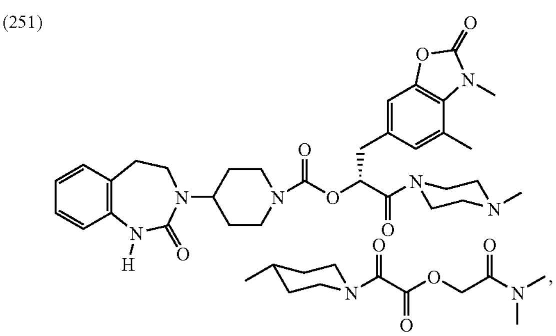 |
| (252) | 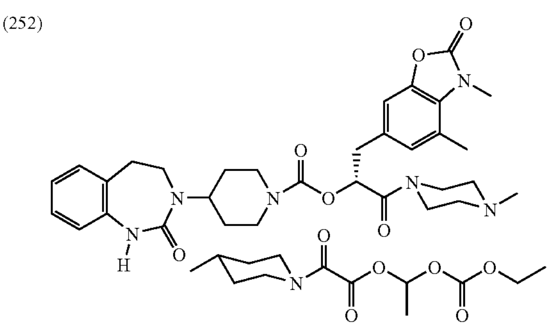 |

| No. | Structure |
|---|---|
| (253) | 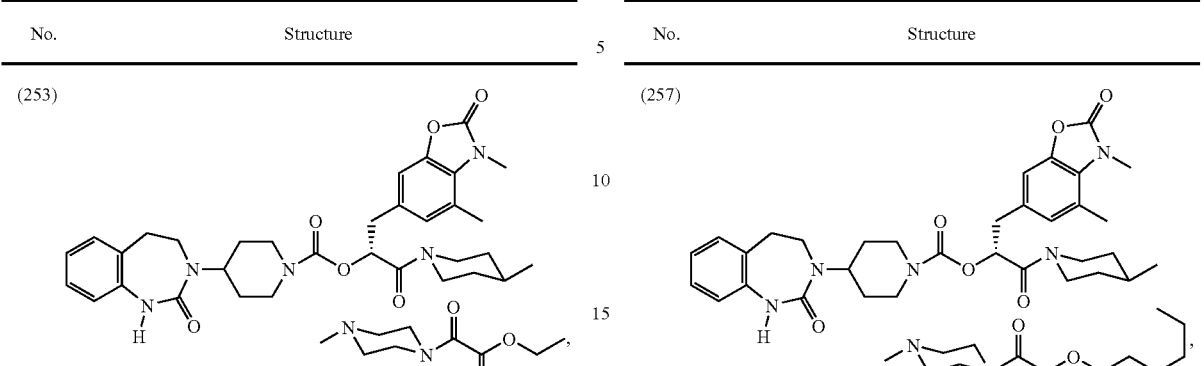 |
| (254) | 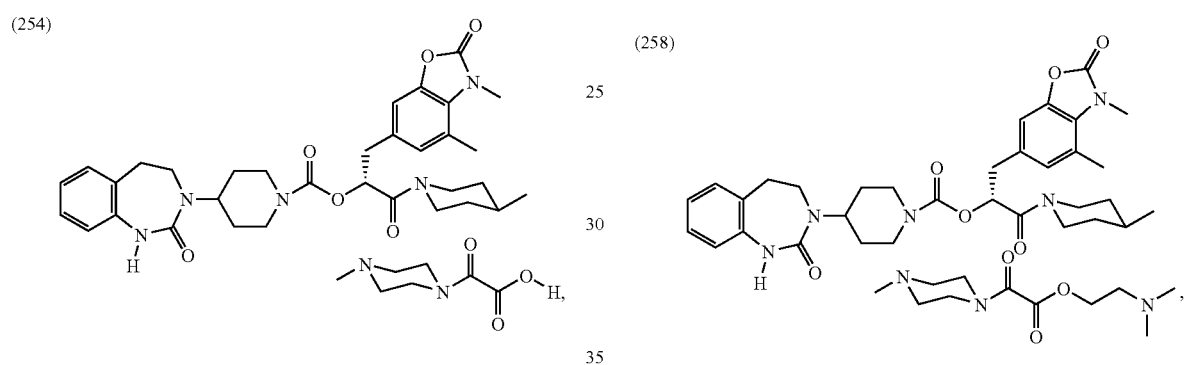 |
| (255) | 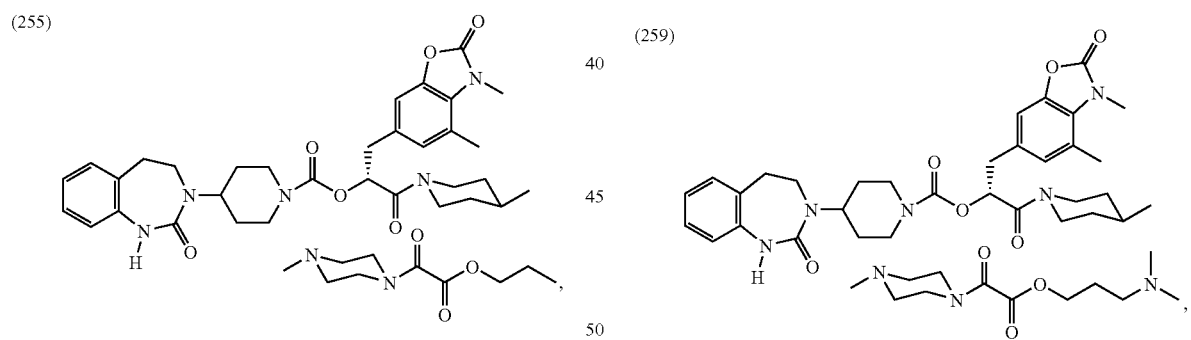 |
| (256) | 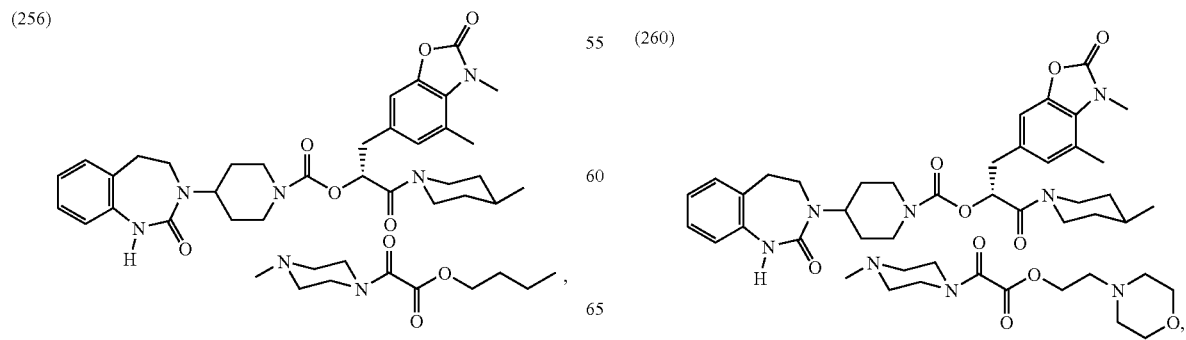 |
| No. | Structure |
|---|---|
| (257) | 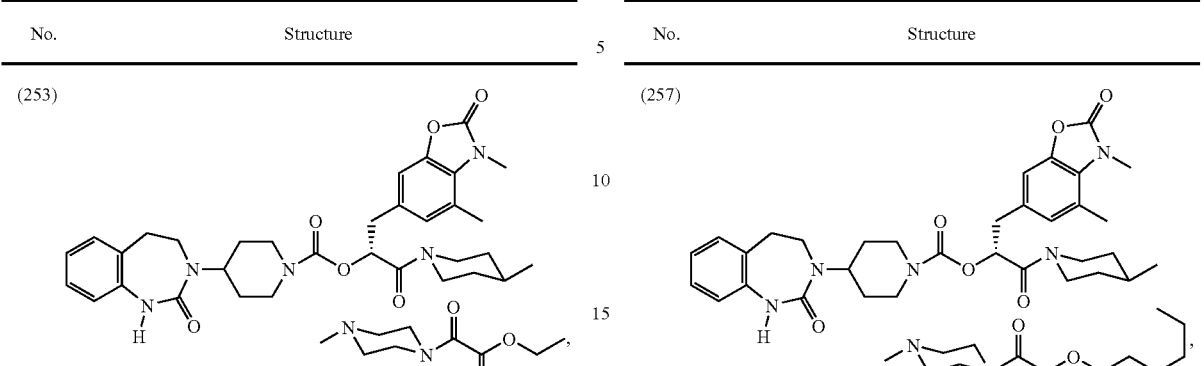 |
| (258) | |
| (259) | |
| (260) | |

-continued

| No. | Structure |
|-----|-----------|
| (261) | 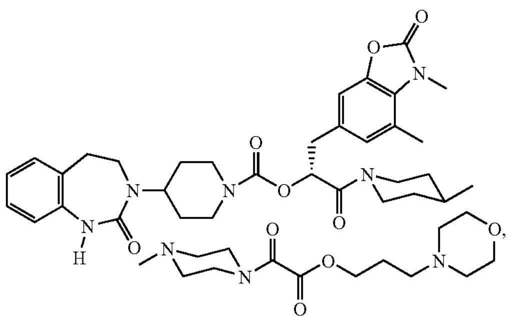 |
| (262) | 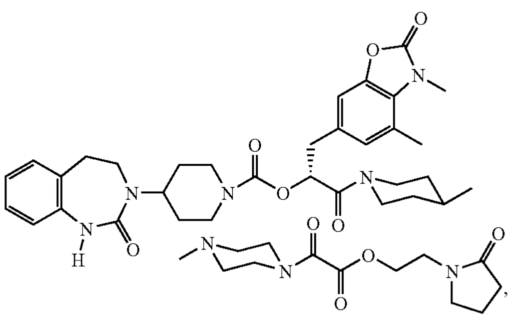 |
| (263) | 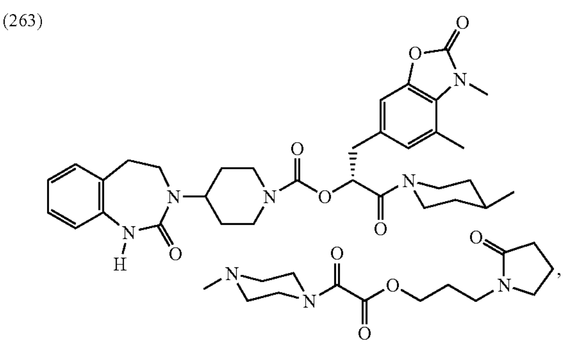 |
| (264) | 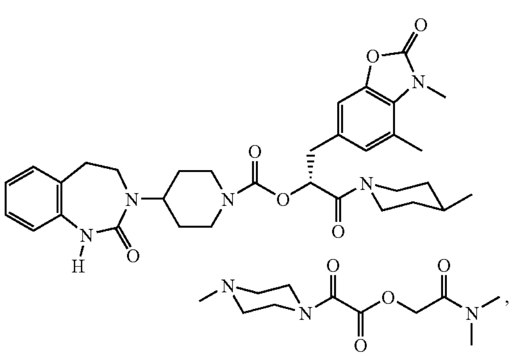 |

-continued

| No. | Structure |
|-----|-----------|
| (265) | 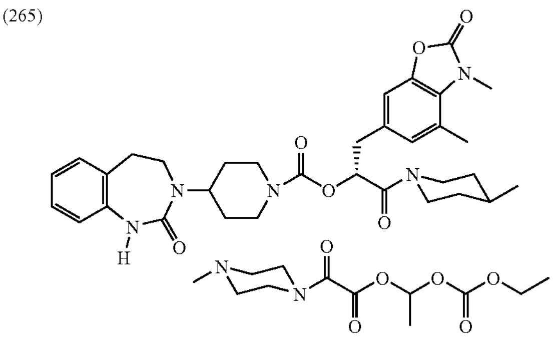 |
| (266) | 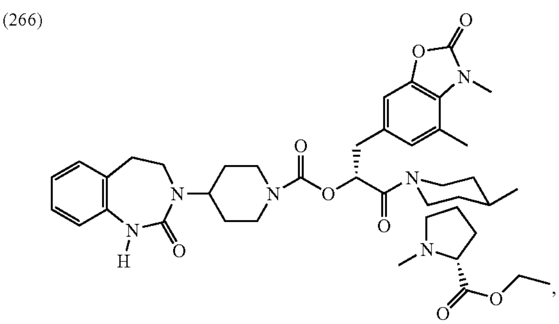 |
| (267) | 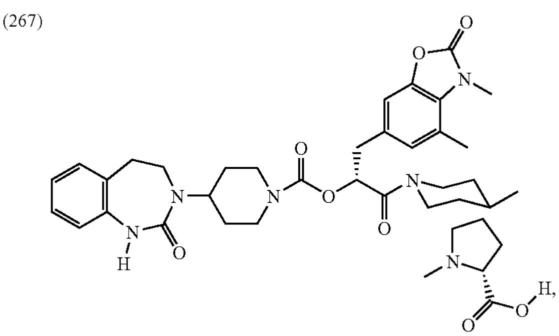 |
| (268) | 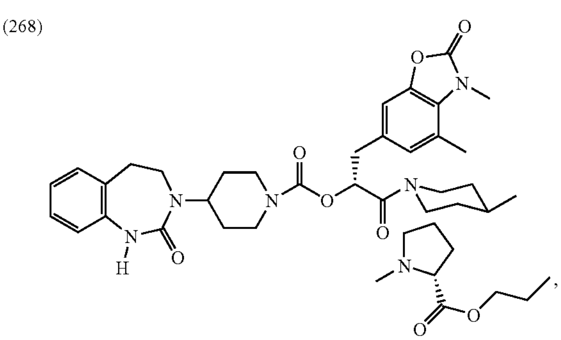 |

-continued

| No. | Structure |
|---|---|
| (269) | 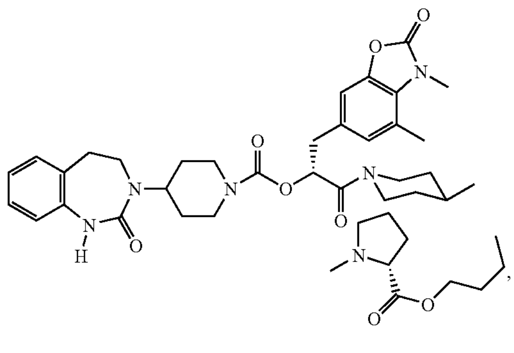 |
| (270) | 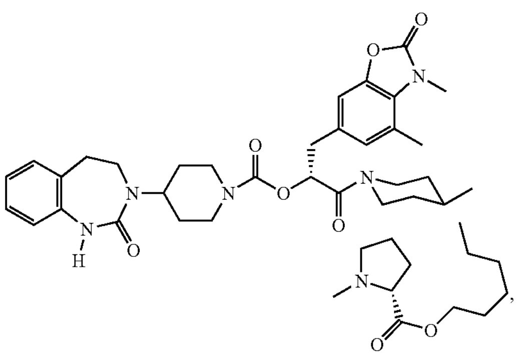 |
| (271) | 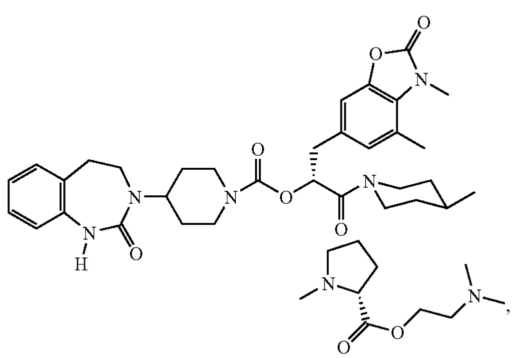 |
| (272) | 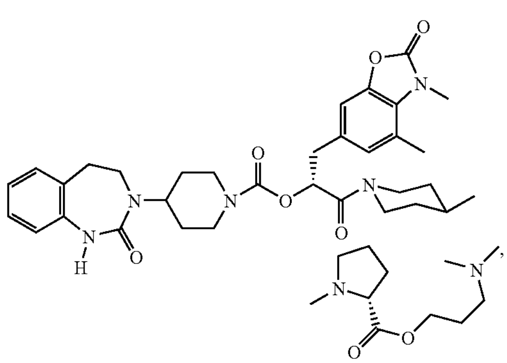 |

-continued

| No. | Structure |
|---|---|
| (273) | 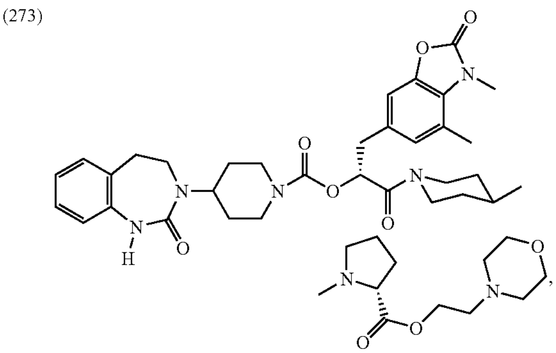 |
| (274) | 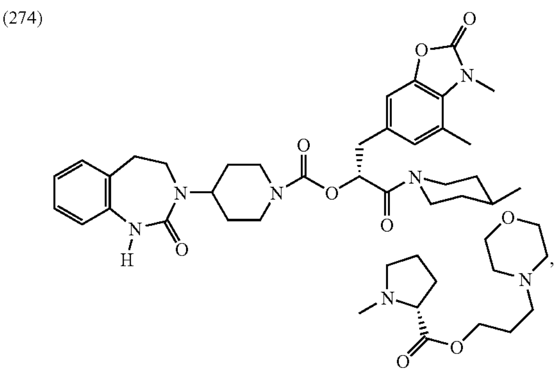 |
| (275) | 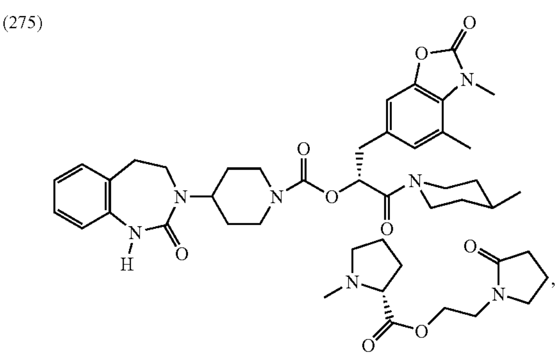 |
| (276) | 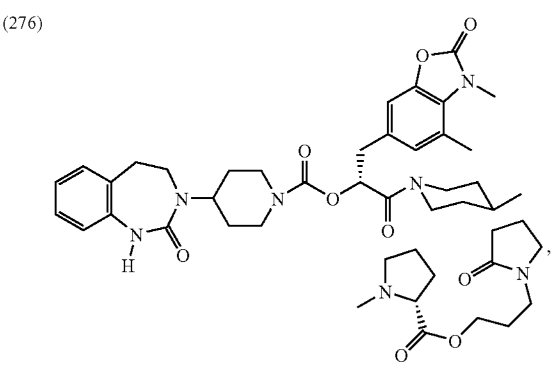 |

-continued
| No. | Structure |
|---|---|
| (277) | 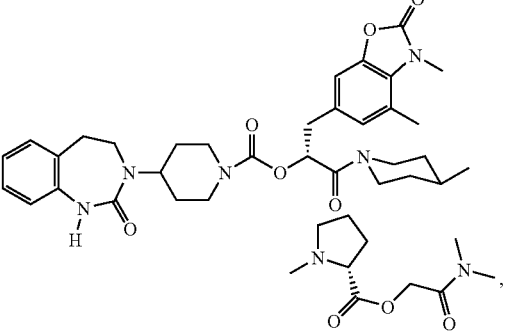 |
| (278) | 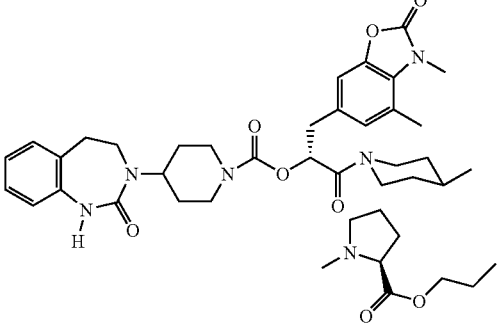 |
| (279) | 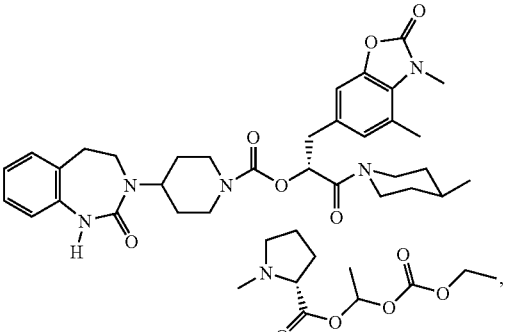 |
| (280) | 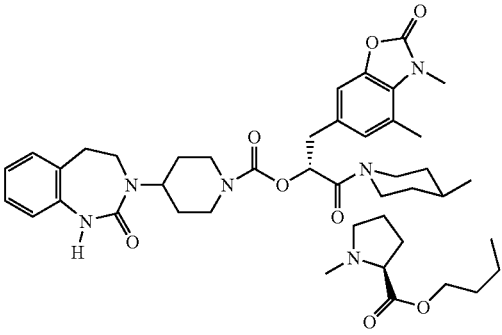 |
-continued
| No. | Structure |
|---|---|
| (281) | 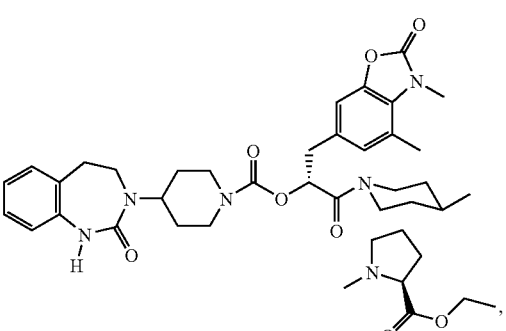 |
| (282) | 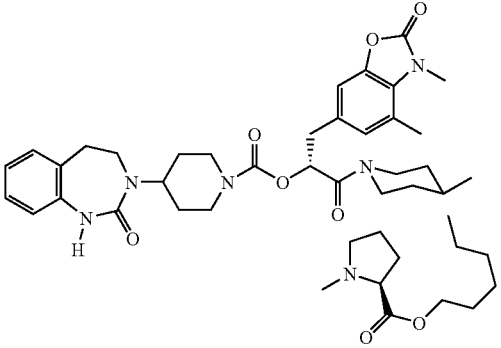 |
| (283) | 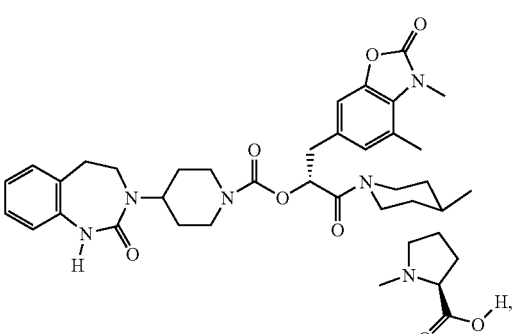 |
| (284) | 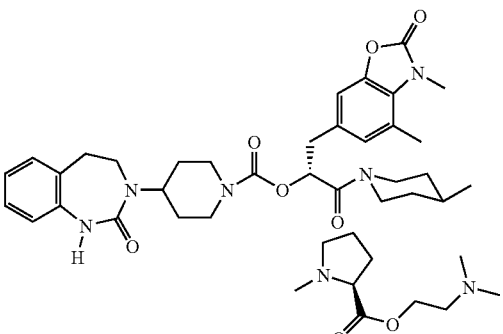 |

| No. | Structure |
|---|---|
| (285) | 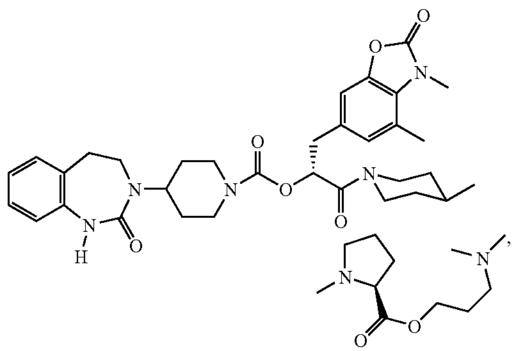 |
| (286) | 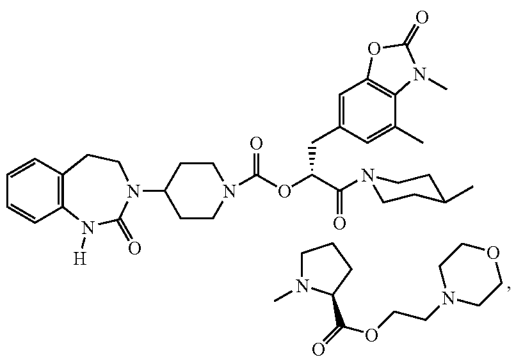 |
| (287) | 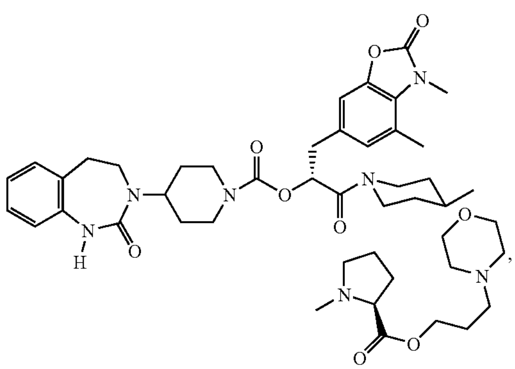 |
| (288) | 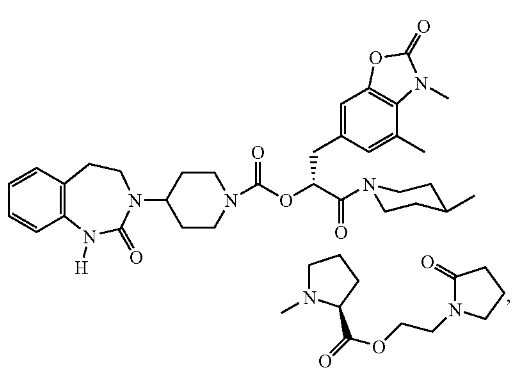 |

| No. | Structure |
|---|---|
| (289) | 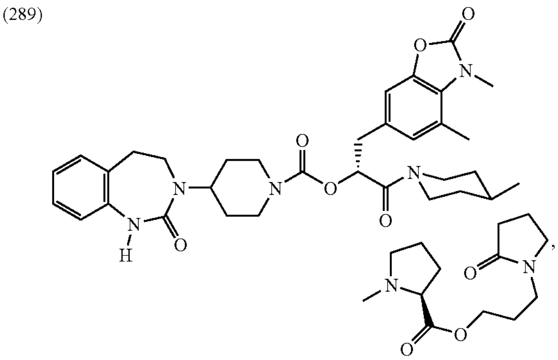 |
| (290) | 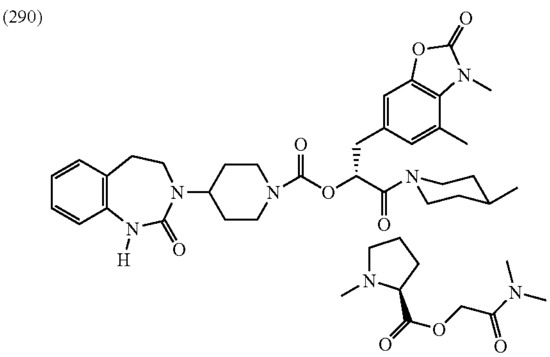 |
| (291) | 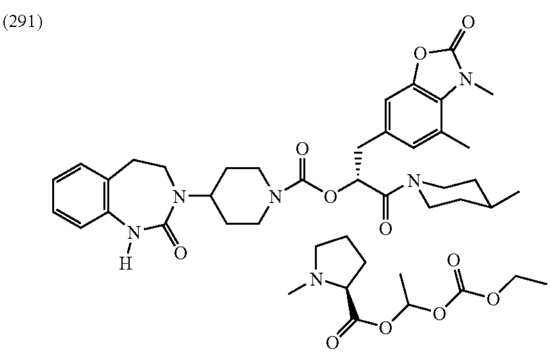 |
| (292) | 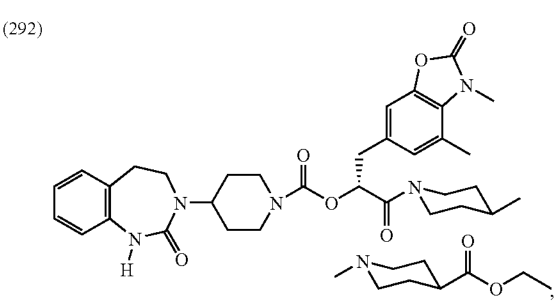 |

-continued
| No. | Structure |
|---|---|
| (293) | 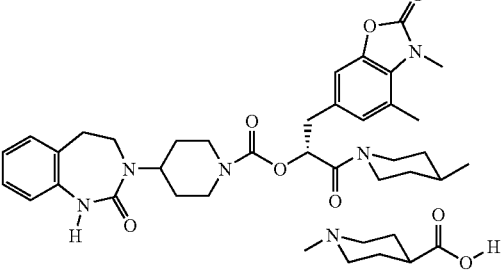 |
| (294) | 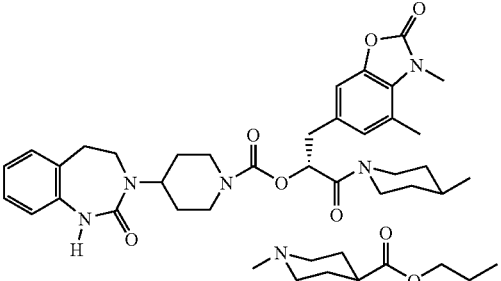 |
| (295) | 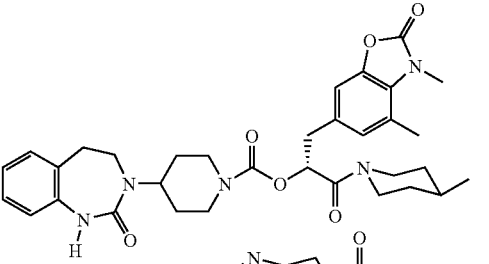 |
| (296) | 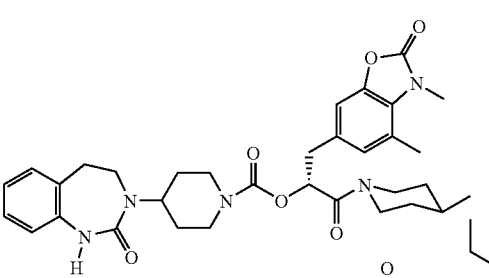 |
| (297) | 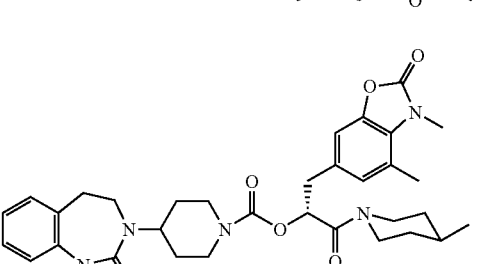 |
-continued
| No. | Structure |
|---|---|
| (298) | 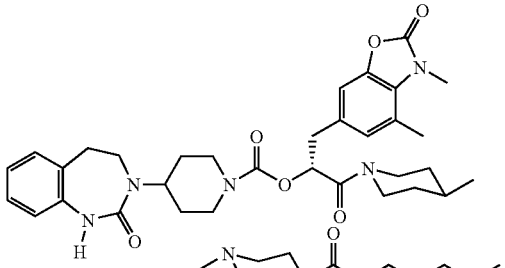 |
| (299) | 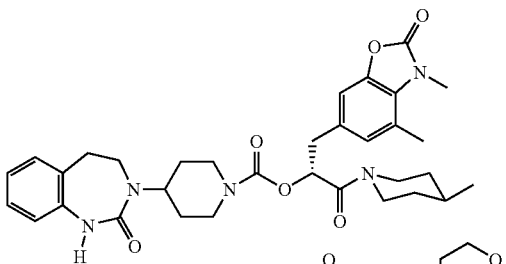 |
| (300) | 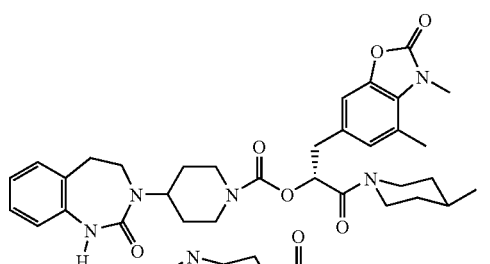 |
| (301) | 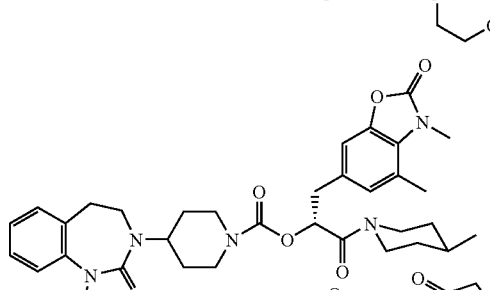 |
| (302) | 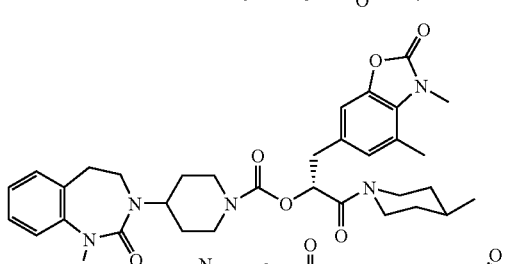 |

| No. | Structure |
|---|---|
| (303) | 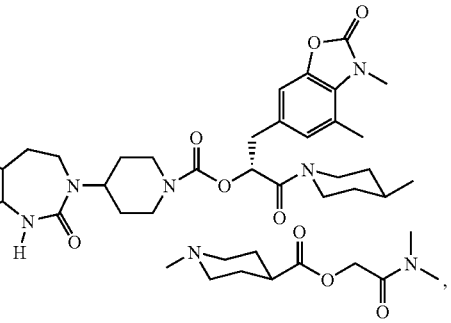 |
| (304) | 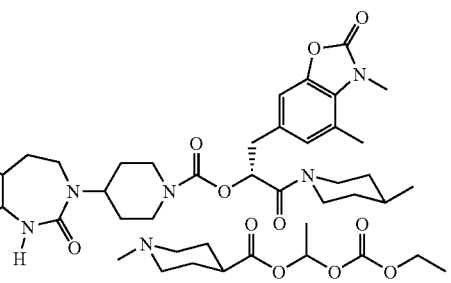 |
| No. | Structure |
|---|---|
| | and |
| (305) | 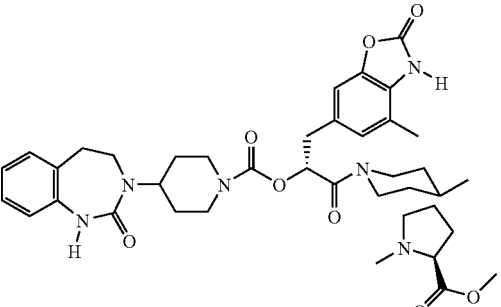 |
or a tautomer or salt thereof.
2. A physiologically acceptable salt of a compound according to claim 1.
3. A pharmaceutical composition comprising a compound of the formula I, according to claim 1 or a physiologically acceptable salt thereof, and a pharmaceutically acceptable carrier or diluent.
* * * * *